United States Patent
Nazare et al.

(10) Patent No.: US 9,718,825 B2
(45) Date of Patent: Aug. 1, 2017

(54) N-(4-(AZAINDAZOL-6-YL)-PHENYL)-SULFONAMIDES AND THEIR USE AS PHARMACEUTICALS

(71) Applicant: SANOFI, Paris (FR)

(72) Inventors: Marc Nazare, Frankfurt am Main (DE); Nis Halland, Frankfurt am Main (DE); Friedemann Schmidt, Frankfurt am Main (DE); Heinz-Werner Kleemann, Frankfurt am Main (DE); Tilo Weiss, Frankfurt am Main (DE); Joachim Saas, Frankfurt am Main (DE); Carsten Struebing, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/775,620

(22) PCT Filed: Mar. 12, 2014

(86) PCT No.: PCT/EP2014/054770
§ 371 (c)(1),
(2) Date: Sep. 11, 2015

(87) PCT Pub. No.: WO2014/140065
PCT Pub. Date: Sep. 18, 2014

(65) Prior Publication Data
US 2016/0024097 A1    Jan. 28, 2016

(30) Foreign Application Priority Data
Mar. 13, 2013   (EP) ..................... 13305283

(51) Int. Cl.
C07D 471/04   (2006.01)
C07D 487/04   (2006.01)
A61K 31/4162  (2006.01)

(52) U.S. Cl.
CPC ........ C07D 487/04 (2013.01); A61K 31/4162 (2013.01); C07D 471/04 (2013.01)

(58) Field of Classification Search
CPC . C07D 471/04; C07D 487/04; A61K 31/4162
USPC .......... 544/262; 546/119; 514/252.16, 262.1, 514/303
See application file for complete search history.

(56) References Cited

U.S. PATENT DOCUMENTS

| | | |
|---|---|---|
| 2,824,121 A | 2/1958 | Leonard et al. |
| 2008/0274487 A1 | 11/2008 | Bartnik et al. |
| 2010/0063115 A1 | 3/2010 | Klein et al. |

FOREIGN PATENT DOCUMENTS

| | | |
|---|---|---|
| WO | WO-2005/121107 A1 | 12/2005 |
| WO | WO-2006/061130 A2 | 6/2006 |
| WO | WO-2006/061130 A3 | 6/2006 |
| WO | WO-2008/086854 A1 | 7/2008 |
| WO | WO-2008/115974 A2 | 9/2008 |
| WO | WO-2008/115974 A3 | 9/2008 |
| WO | WO-2010/118367 A2 | 10/2010 |
| WO | WO-2010/118367 A3 | 10/2010 |

OTHER PUBLICATIONS

Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, 20th Edition, vol. 1, pp. 1004-1101 O, 1996.*
Alvarez De La Rosa, D. et al. (Feb. 2003). "Role of SGK in Hormonal Regulation of Epithelial Sodium Channel in A6 Cells," *Am. J. Physiol. Cell Physiol.* 284:C404-C414.
Alvarez De La Rosa, D. et al. (Oct. 2004). "Mechanisms of Regulation of Epithelial Sodium Channel by SGK1 in A6 Cells," *J. Gen. Physiol.* 124(4):395-407.
Atsumi, T. et al. (May 1990). "A Chondrogenic Cell Line Derived from a Differentiating Culture of AT805 Teratocarcinoma Cells," *Cell Differ. Dev.* 30(2):109-116.
Boehmer, C. et al. (Jun. 20, 2003). "Properties and Regulation of Glutamine Transporter SN1 by Protein Kinases SGK and PKB," *Biochem. Biophys. Res. Commun.* 306(1):156-162.

(Continued)

*Primary Examiner* — Deepak Rao
(74) *Attorney, Agent, or Firm* — Morrison & Foerster LLP

(57) ABSTRACT

The present invention relates to N-(4-(azaindazol-6-yl)-phenyl)-sulfonamides of the formula I,

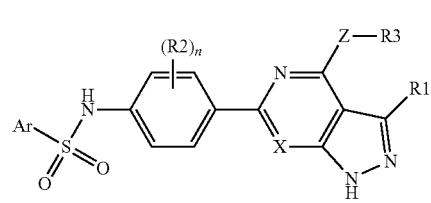

wherein Ar, n, X, Z, R1, R2 and R3 have the meanings indicated in the claims. The compounds of the formula I are valuable pharmacologically active compounds which modulate protein kinase activity, specifically the activity of serum and glucocorticoid regulated kinase (SGK), in particular of serum and glucocorticoid regulated kinase isoform 1 (SGK-1, SGK1), and are suitable for the treatment of diseases in which SGK activity is inappropriate, for example degenerative joint disorders or inflammatory processes such as osteoarthritis or rheumatism. The invention furthermore relates to processes for the preparation of the compounds of the formula I, their use as pharmaceuticals, and pharmaceutical compositions comprising them.

20 Claims, No Drawings

(56) References Cited

OTHER PUBLICATIONS

Debonneville, C. et al. (Dec. 17, 2001). "Phosphorylation of Nedd4-2 by Sgk1 Regulates Epithelial Na(+) Channel Cell Surface Expression," *EMBO J.* 20(24):7052-7059.
Extended European Search Report mailed on Jun. 11, 2013, for EP Application No. 13 305 283.7, filed on Mar. 13, 2013, four pages.
Faletti, C.J. et al. (Mar. 2002). "sgk: An Essential Convergence Point for Peptide and Steroid Hormone Regulation of ENaC-Mediated Na+ Transport," *Am. J. Physiol. Cell. Physiol.* 282(3):C494-C500.
Feng, Y. et al. (2005). "SGK1-Mediated Fibronectin Formation in Diabetic Nephropathy," *Cell. Physiol. Biochem.* 16(4-6):237-244.
Firestone, G.L. et al. (2003). "Stimulus-Dependent Regulation of Serum and Glucocorticoid Inducible Protein Kinase (SGK) Transcription, Subcellular Localization and Enzymatic Activity," *Cell Physiol. Biochem.* 13(1):1-12.
Friedrich, B. et al. (Mar. 2003). "The Serine/Threonine Kinases SGK2 and SGK3 are Potent Stimulators of the Epithelial Na+ Channel $\alpha,\beta,\gamma$-ENaC," *Eur. J. Physiol.* 445(6):693-696.
Funder, J. (2001). "Mineralocorticoids and Cardiac Fibrosis: The Decade in Review," *Clin. Exp. Pharmacol. Physiol.* 28(12):1002-1006.
Gamper, N. et al. (Feb. 2002). "IGF-1 Up-Regulates K+ Channels via PI3-Kinase, PDK1 and SGK1," *Pflugers Arch.* 443(4):625-634.
Hartwig, J.F. (1998). "Transition Metal Catalyzed Synthesis of Arylamines and Aryl Ethers from Aryl Halides and Triflates: Scope and Mechanism," *Angew. Chem. Int. Ed.* 37:2046-2067.
Imaizumi, K. et al. (1994). "Differential Expression of sgk mRNA, a Member of the Ser/Thr Protein Kinase Gene Family, in Rat Brain After CNS Injury," *Mol. Brain Research* 26(1-2):189-196.
International Search Report mailed on May 9, 2014, for PCT Patent Application No. PCT/EP2014/054770, filed on Mar. 12, 2014, three pages.
Klapars, A. et al. (2001). "A General and Efficient Copper Catalyst for the Amidation of Aryl Halides and the N-Arylation of Nitrogen Heterocycles," *J. Am. Chem. Soc.* 123(31):7727-7729.
Kobayashi, T. et al. (1999). "Characterization of the Structure and Regulation of Two Novel Isoforms of Serum- and Glucocorticoid-Induced Protein Kinase," *Biochem. J.* 344(Pt. 1):189-197.
Kwong, F.Y. et al. (Feb. 21, 2002). "Copper-Catalyzed Coupling of Alkylamines and Aryl Iodides: An Efficient System Even in an Air Atmosphere," *Organic Letters* 4(4):581-584.
Lang, F. et al. (2003). "Regulation of Channels by the Serum and Glucocorticoid-Inducible Kinase—Implications for Transport, Excitability and Cell Proliferation," *Cell. Physiol. Biochem.* 13(1):41-50.
Lang, F. et al. (Oct. 2006). "(Patho)Physiological Significance of the Serum- and Glucocorticoid-Inducible Kinase Isoforms," *Physiol. Rev.* 86(4):1151-1178.
Lidstrom, P. et al. (2001). "Microwave Assisted Organic Synthesis—A Review," *Tetrahedron* 57:9225-9283.
Littke, A.F. et al. (2002). "Palladium-Catalyzed Coupling Reactions of Aryl Chlorides," *Angew. Chem. Int. Ed.* 41:4176-4211.
Mitsunobu, O. (Jan. 1981). "The Use of Diethyl Azodicarboxylate and Triphenylphosphine in Synthesis and Transformation of Natural Products," *Synthesis*, pp. 1-28.
Muci, A.R. et al. (2002). "Practical Palladium Catalysts for C—N and C—O Bond Formation," *Topics Curr. Chem.* 219:131-209.
Netherton, M.R. et al. (2005). "Palladium-Catalyzed Cross-Coupling Reactions of Unactivated Alkyl Electrophiles with Organometallic Compounds," *Top Organomet Chem.* 14:85-108.
Perrin, D. et al. (Jan. 2010). "Capillary Microfluidic Electrophoretic Mobility Shift Assays: Application to Enzymatic Assays in Drug Discovery," *Expert Opinion Drug Disc.* 5(1):51-63.
Robson, H. et al. (Oct. 2000). "Thyroid hormone Acts Directly on Growth Plate Chondrocytes to Promote Hypertrophic Differentiation and Inhibit Clonal Expansion and Cell Proliferation," *Endocrinology* 141(10):3887-3897.
Sakoda, H. et al. (Jul. 11, 2003). "Differing Roles of Akt and Serum- and Glucocorticoid-Regulated Kinase in Glucose Metabolism, DNA Synthesis, and Oncogenic Activity," *J. Biol. Chem.* 278(28):25802-25807.
Shukunami, C. et al. (May 25, 1998). "Sequential Progression of the Differentiation Program by Bone Morphogenetic Protein-2 in Chondrogenic Cell Line ATDC5," *Exp. Cell Res.* 241(1):1-11.
Shukunami, C. et al. (Apr. 1996). "Chondrogenic Differentiation of Clonal Mouse Embryonic Cell Line ATDC5 In Vitro: Differentiation-Dependent Gene Expression of Parathyroid Hormone (PTH)/PTH-Related Peptide Receptor," *J. Cell Biol.* 133(2):457-468.
Singh, P.K. et al. (Dec. 2013). "Activation of Serum/Glucocorticoid-Induced Kinase 1 (SGK1) Underlies Increased Glycogen Levels, mTOR Activation, and Autophagy Defects in Lafora Disease," *Mol. Biol. Cell.* 24(24):3776-3786.
Staub, O. et al. (1997). "Regulation of Stability and Function of the Epithelial Na+ Channel (ENaC) by Ubiquitination," *EMBO J.* 16(21):6325-6336.
Vallon, V. et al. (Jan. 2005). "New Insights Into the Role of Serum- and Glucocorticoid-Inducible Kinase SGK1 in the Regulation of Renal Function and Blood Pressure," *Curr. Opin. Nephrol. Hypertens.* 14(1):59-66.
Wagner, C.A. et al. (2000). "The Heterodimeric Amino Acid Transporter 4F2hc/LAT1 is Associated in *Xenopus* Oocytes with a Non-Selective Cation Channel that is Regulated by the Serine/Threonine Kinase sgk-1," *J. Physiol.* 526(Pt. 1):35-46.
Warntges, S. et al. (2002). "Excessive Transcription of the Human Serum and Glucocorticoid Dependent Kinase hSGK1 in Lung Fibrosis," *Cell. Physiol. Biochem.* 12:135-142.
Webster, M.K. et al. (1993). "Immediate-Early Transcriptional Regulation and Rapid mRNA Turnover of a Putative Serine/Threonine Protein Kinase," *J. Biol. Chem.* 268(16):11482-11485.
Yun, C.C. et al. (Mar. 8, 2002). "Glucocorticoid Activation of Na(+)/H(+) Exchanger Isoform 3 Revisited. The Roles of SGK1 and NHERF2," *J. Biol. Chem.* 277(10):7676-7683.
Yun, C.C. (2003). "Concerted Roles of SGK1 and the Na+/H+ Exchanger Regulatory Factor 2 (NHERF2) in Regulation of NHE3," *Cell. Physiol. Biochem.* 13(1):29-40.

* cited by examiner

N-(4-(AZAINDAZOL-6-YL)-PHENYL)-SULFONAMIDES AND THEIR USE AS PHARMACEUTICALS

CROSS REFERENCE TO RELATED APPLICATIONS

This application is a National Phase application under 35 U.S.C. §371 of International Application No. PCT/EP2014/054770 filed Mar. 12, 2014, which claims priority benefit to EP Application No. 13305283.7 filed Mar. 13, 2013, the disclosures of which are herein incorporated by reference in their entirety.

The present invention relates to N-(4-(azaindazol-6-yl)-phenyl)-sulfonamides of the formula I,

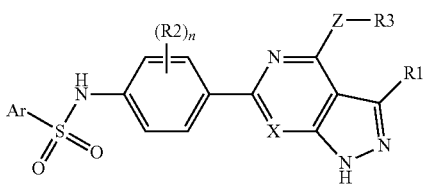

wherein Ar, n, X, Z, R1, R2 and R3 have the meanings indicated below. The compounds of the formula I are valuable pharmacologically active compounds which modulate protein kinase activity, specifically the activity of serum and glucocorticoid regulated kinase (SGK), in particular of serum and glucocorticoid regulated kinase isoform 1 (SGK-1, SGK1), and are suitable for the treatment of diseases in which SGK activity is inappropriate, for example degenerative joint disorders or inflammatory processes such as osteoarthritis or rheumatism. The invention furthermore relates to processes for the preparation of the compounds of the formula I, their use as pharmaceuticals, and pharmaceutical compositions comprising them.

Due to their physiologic importance, variety, and ubiquity, protein kinases have become one of the most important and widely-studied family of enzymes in biochemical and medical research. Studies have shown that the currently known about 500 different protein kinases are key regulators of many cell functions, including signal transduction, transcriptional regulation, cell motility, growth, differentiation, division and destruction. They act through reversible phosphorylation of the hydroxyl groups of distinct amino acids in proteins. Several oncogenes have been shown to encode protein kinases, suggesting that kinases play a role also in oncogenesis. These processes are highly regulated, often by complex intermeshed pathways where each kinase itself will be regulated by one or more kinases.

Consequently, aberrant or inappropriate protein kinase activity can contribute to the rise of disease states associated with such aberrant kinase activity.

The protein kinase family is typically classified into two main subfamilies, protein tyrosine kinases, which phosphorylate tyrosine residues, and protein serine/threonine kinases (PSTK) which phosphorylate serine and threonine residues. The PSTK subfamily is usually cytoplasmic or associated with the particulate fractions of cells, possibly by anchoring proteins. Aberrant PSTK activity has been implicated or is suspected in a number of pathologies such as rheumatoid arthritis, psoriasis, septic shock, bone loss, many cancers and other proliferative diseases. Accordingly, PSTKs and their associated signal transduction pathways are important targets for drug design.

Serum and glucocorticoid regulated kinases, also designated as serum/glucocorticoid regulated kinase, serum and glucocorticoid induced kinase, serum and glucocorticoid inducible kinase or serum and glucocorticoid dependent kinase, form a family of PSTKs. Currently three members are known, designated as SGK-1, SGK-2 and SGK-3. They are also designated as SGKL (SGK-like) and CISK (cytokine-independent survival kinase). At the protein level the three isoforms show a homology of at least 80% in their catalytic domain. SGK-1 was described in 1993 for the first time as an "immediate early gene" in a rat mammary cancer cell line (Webster, M. K. et al., Immediate-early Transcriptional Regulation and Rapid mRNA Turnover of a Putative Serine/Threonine Protein Kinase, J. Biol. Chem. 1993, 268, 11482-11485). SGK-1 mRNA is expressed ubiquitously in almost all adult tissues and in several embryonic tissues. SGK-2 is expressed with greatest abundance in epithelial tissues, such as in the kidney, liver, pancreas, and specific areas of the brain, whereas SGK-3 was detected in all tested tissues, especially in the adult heart and spleen (Kobayashi, T. et al., Characterization of the structure and regulation of two novel isoforms of serum and glucocorticoid induced protein kinase, Biochem. J. 1999, 344, 189-197).

A distinguishing feature of SGK to many other kinases is based on the stringent stimulus-dependent regulation of transcription, cellular localization and enzymatic activation of the molecule (Firestone, G. L. et al., Stimulus-Dependent Regulation of Serum and Glucocorticoid Inducible Protein Kinase (SGK) Transcription, Subcellular Localization and Enzymatic Activity, Cell. Physiol. Biochem. 2003, 13, 1-12). A variety of stimuli are known which induce and activate SGK-1. These include mineralocorticoids, gonadotropins, 1,25(OH)2D3, p53, osmotic, hypotonic and cellular volume changes, and cytokines such as GM-CSF, TNF-alpha and TGF-beta (reviewed in Lang, F. et al., (Patho)physiological Significance of the Serum- and Glucocorticoid-Inducible Kinase Isoforms, Physiol. Rev. 2006, 86, 1151-1178). In further growth-dependent signaling pathways SGK is induced by serum, insulin and IGF-1, FSH, Fibroblast and Platelet-derived growth factor, activators of the Erk signaling cascade and TPA (reviewed in Lang, F. et al., Physiol. Rev. 2006, 86, 1151-1178). SGK-1 is also known to be activated in pathological changes such as ischemic brain injury (Imaizumi, K. et al., Differential expression of sgk mRNA, a member of the Ser/Thr protein kinase gene family, in rat brain after CNS injury, Mol. Brain Res. 1994, 26, 189-196), pulmonary fibrosis (Warntges, S. et al., Excessive Transcription of the Human Serum and Glucocorticoid Dependent Kinase hSGK1 in Lung Fibrosis, Cell. Physiol. Biochem. 2002, 12, 135-142) or cardiac fibrosis (Funder, J., Mineralocorticoids and Cardiac Fibrosis: The Decade in Review, Clin. Exp. Pharmacol. Physiol. 2001, 28, 1002-1006).

In order to be converted into its functional form, SGK-1 requires activation by phosphorylation. This is mediated by a signaling cascade involving the phosphatidylinositol 3 (PI-3) kinase and phosphoinositide 3-dependent kinases PDK1 and PDK2. The activation of SGK-1 through the PI-3 kinase signaling pathway is known to be a response to insulin, IGF and growth factors. For activation the phosphorylation of two amino acid residues is necessary, threonine$^{256}$ on the T-loop (mediated by PDK1) and serine$^{422}$ at the hydrophobic motif of the protein (catalyzed by a putative PDK2) (reviewed in Lang, F. et al., Physiol. Rev. 2006, 86, 1151-1178).

For the function of SGK, there are a series of studies that show regulatory influence of SGK-1, SGK-2 and SGK-3 on cell membrane channels. It was shown that the epithelial Na$^+$ channel (ENaC), the main transporter for the mineralocorticoid-regulated Na$^+$ reabsorption in the renal tubule, is a target of SGK-1, SGK-2 and SGK-3 (Faletti, C. J. et al., sgk: an essential convergence point for peptide and steroid hormone regulation of ENaCmediated Na$^+$ transport, Am. J. Physiol. Cell Physiol. 2002, 282, C494-C500; Friedrich, B. et al., The serine/threonine kinases SGK2 and SGK3 are potent stimulators of the epithelial Na$^+$ Channel alpha, beta, gamma-ENaC, Pflugers Arch.—Eur. J. Physiol. 2003, 445, 693-696). The interaction of ENaC and SGK is not by direct phosphorylation, but due to the inactivation of the ubiquitin ligase Nedd4-2 (Debonneville, C. et al., Phosphorylation of Nedd4-2 by Sgk1 regulates epithelial Na$^+$ channel cell surface expression, EMBO J. 2001, 20, 7052-7059) as a result of phosphorylation by SGK. As a result, the amount and residence time of ENaC in the cell membrane is increased (Staub, O. et al., Regulation of stability and function of the epithelial Na$^+$ channel (ENaC) by ubiquitination, EMBO J. 1997, 16, 6325-6336). It has also been shown that the renal outer medullary potassium channel (ROMK1) and the sodium-hydrogen exchanger 3 (NHE3) are indirectly regulated by SGK, via the Na$^+$/H$^+$ exchange regulating factor 2 (NHERF2) as an intermediary molecule (Yun, C. C. et al., Glucocorticoid Activation of Na$^+$/H+ Exchanger Isoform 3 Revisited. The Roles of SGK1 and NHERF2, J. Biol. Chem. 2002, 277, 7676-7683; Yun, C. C., Concerted Roles of SGK1 and the Na$^+$/H$^+$ Exchanger Regulatory Factor 2 (NHERF2) in Regulation of NHE3, Cell. Physiol, Biochem. 2003, 13, 29-40). In addition it has also been shown that SGK influences the Kv1.3 channel-dependent K$^+$ current (Gamper, N. et al., IGF-1 up-regulates K$^+$ Channels via PI3-kinase, PDK1 and SGK1, Pflugers Arch. 2002, 443, 625-634) and regulates the amino acid transporter SN1 and 4F2/LAT (Wagner, C. A. et al., The heterodimeric amino acid transporter 4F2hc/LAT1 is associated in *Xenopus* oocytes with a non-selective cation channel that is regulated by the serine/threonine kinase sgk-1, J. Physiol. 2000, 526.1, 35-46; Boehmer, C. et al., Properties and regulation of glutamine transporter SN1 by protein kinases SGK and PKB, Biochem. Biophys. Res. Commun. 2003, 306, 156-162). SGK-1 has also been shown to play a role in cell proliferation and electrolyte homeostasis (Vallon, V. et al., New insights into the role of serum- and glucocorticoid-inducible kinase SGK1 in the regulation of renal function and blood pressure, Curr. Opin. Nephrol. Hypertens. 2005, 14, 59-66; Lang, F. et al., Regulation of Channels by the Serum and Glucocorticoid-Inducible Kinase—Implications for Transport, Excitability and Cell Proliferation, Cell. Physiol. Biochem. 2003, 13, 41-50). SGK-1 is thought to regulate several cellular mechanisms that contribute to disease states. For example, SGK-1 has been shown to mediate fibronectin formation in diabetic nephropathy (Feng, Y. et al., SGK1-mediated Fibronectin Formation in Diabetic Nephropathy, Cell. Physiol. Biochem. 2005, 16, 237-244). SGK1 has also been shown to mediate insulin, IGF-1, and aldosterone-induced Na$^+$ retention in renal and cardiovascular disease (Vallon, V. et al., Curr. Opin. Nephrol. Hypertens. 2005, 14, 59-66; Lang, F. et al., Cell. Physiol. Biochem. 2003, 13, 41-50). SGK1 has furthermore been shown to be activated by loss of laforin in Lafora disease, a genetic form of myoclonic epilepsy, SGK1 inhibition resulting in a reduction of abnormal glycogen accumulation and offering a way of treating Lafora disease (Singh, P. K. et al., Activation of serum/glucocorticoid-induced kinase 1 (SGK1) underlies increased glycogen levels, mTOR activation, and autophagy defects in Lafora disease, Mol. Biol. Cell 2013, 24, 3776-3786).

Osteoarthritis (OA) is one of the most common degenerative joint diseases and leads in an advanced stage to a loss of joint function. During the chronic course of illness, there is a destruction of the articular cartilage down to the underlying bone tissue, which makes a joint replacement surgery in affected patients necessary. In addition to the destruction of the cartilage, pathological changes in the synovial membrane and the ligaments can also be observed. The disease is temporarily accompanied by inflammatory processes like in rheumatoid arthritis, but differs from it. The exact causes of the disease are still unknown, however, several factors come into question, such as metabolic changes, mechanical stress, genetic disorders or joint injuries. Regardless of the original trigger, the degradation of articular cartilage occurs as a common pathological feature of OA. A key feature of the pathological condition of OA is the proteolytic cleavage of collagens and proteoglycans. Simultaneously a number of other processes occur such as anabolic repair mechanisms, redifferentiation of the cells or cell death. The precise molecular mechanisms underlying these processes are still poorly understood.

The healthy functioning of the adult cartilage is created by its unique biomechanical properties, providing both the resistance against high pressure as well as the necessary elasticity of the tissue. The decisive factor is the special organization of the cartilage tissue. Unlike most other tissues, the cartilage cells are not in direct contact but are embedded separately from each other in an extracellular matrix (ECM). The macromolecules of this ECM guarantee the viability of the articular cartilage and joints. The basic structure of the ECM consists of a network that is formed by fibrils of collagen types II, IX and XI. Proteoglycans, mainly aggrecan, are embedded in the ECM producing an extremely high osmotic water binding capacity. The water pressure generated in connection with the properties of the collagen backbone guarantees the specific properties of the cartilage. A main feature of the pathogenesis of OA is the loss of the ECM of the cartilage and the articular cartilage tissue. The function of the affected joint is restricted by or lost by this mechanism. In addition, various symptomatic parameters such as pain appear during symptomatic progression of the disease. Current treatments for osteoarthritis are limited mostly to the alleviation of symptomatic complaints. A causal therapy based on drugs, which leads to the decrease of cartilage degeneration, is not possible to current knowledge. Therefore, there is a considerable need for novel drugs for the prevention and/or therapy of osteoarthritis.

It has been shown, through comparative gene expression analysis of samples of total-cellular RNA from healthy and degenerated/degenerating cartilage that SGK-1 is expressed in degenerated/degenerating osteoarthritic cartilage, while it is not detectable in healthy articular cartilage (Bartnik, E. et al., Use of a Serum/Glucocorticoid-regulated Kinase, WO 2006/061130). Moreover, further experiments gave evidence of the causal implication of SGK in the pathogenesis of degenerative cartilage changes (Bartnik, E. et al., WO 2006/061130). As a conclusion of these studies, SGK-1 is specifically involved in pathological conditions of the cartilage, for example in the context of rheumatoid arthritis or osteoarthritis, in particular in the context of osteoarthritis, and thus represents a key molecule inducing cartilage degradative processes. Due to the high homology between the SGK family members, it is assumed that this also applies to the SGK-2 and SGK-3.

The identification of these relationships allows the discovery of drugs for the prevention or therapy of degenerative cartilage changes by determining the effect of potential drugs on the activity of SGK and/or the levels of SGK by known test methods. The causal implication of SGK in the pathogenesis of degenerative joint disease allows a focused search for therapeutic agents that target regulatory mechanisms for the restoration of normal cell physiology of cartilage. In the joints of mouse embryos SGK-1 mRNA was detected specifically in hypertrophic chondrocytes but not in proliferative cells. The role of SGK-1 in this model of skeletal development and endochondral ossification shows that the natural occurrence of SGK-1 in cartilage is not associated with the synthesis and maintenance of cartilage, but exerts its function in the conversion (hypertrophy) and degradation. The expression of SGK-1 in osteoarthritic cartilage is thus a process that causes or promotes the pathology of OA. Due to its regulatory properties SGK-1 could be a key molecule for the induction of early pathological changes in cartilage as well as for the later degradative activities. Therefore, SGK-1 is a very relevant target for the pharmacological intervention in osteoarthritis.

To specifically study the function of SGK-1 during differentiation of cartilage, human SGK-1 was overexpressed in murine ATDC5 cells. In these experiments, it was clearly demonstrated that overexpression of SGK-1 causes inhibition of cartilage synthesis. Both the amount of Alcian blue stained proteoglycan as well as aggrecan mRNA was significantly reduced. A kinase deficient SGK-1 form, however, had no negative effect on these parameters. Regarding the effect of SGK-1 in OA-diseased articular cartilage, several conclusions can be drawn from these experiments. On the one hand, SGK-1 expressing chondrocytes are no longer able to synthesize sufficient extracellular matrix such as proteoglycans, which are essential for the function of the tissue. On the other hand, the cartilage cells are inhibited to compensate for, or repair, degradation processes by increasing the expression of genes such as aggrecan. Therefore a function of SGK-1 as a potential cause and central factor of OA pathology is confirmed. SGK-1 thus represents a highly relevant target molecule for the development of novel drugs for the treatment of degenerative cartilage changes, especially osteoarthritis.

In view of the relevance of SGK-1 for various physiological processes outlined above, inhibitors of SGK-1 such as the compounds of the present invention can be used in the treatment, including therapy and prophylaxis, of various disease states in which SGK-1 activity plays a role or which are associated with an inappropriate SGK-1 activity, or in which an inhibition, regulation or modulation of signal transduction by SGK-1 is desired by the physician, for example degenerative joint disorders and degenerative cartilage changes including osteoarthritis, osteoarthrosis, rheumatoid arthritis, spondylosis, chondrolysis following joint trauma and prolonged joint immobilization after meniscus or patella injuries or ligament tears, connective tissue disorders such as collagenoses, periodontal disorders, wound-healing disturbances, diabetes including diabetes mellitus, diabetic nephropathy, diabetic neuropathy, diabetic angiopathy and microangiopathy, obesity, metabolic syndrome (dyslipidaemia), systemic and pulmonary hypertension, cerebral infarctions, cardiovascular diseases including cardiac fibrosis after myocardial infarction, cardiac hypertrophy and heart failure, arteriosclerosis, renal diseases including glomerulosclerosis, nephrosclerosis, nephritis, nephropathy and electrolyte excretion disorder, and any type of fibrosis and inflammatory processes including liver cirrhosis, lung fibrosis, fibrosing pancreatitis, rheumatism, arthritis, gout, Crohn's disease, chronic bronchitis, radiation fibrosis, sclerodermatitis, cystic fibrosis, scar formation and Alzheimer's disease. Inhibitors of SGK-1 such as the compounds of the present invention can also be used in the treatment of pain including acute pain like pain following injuries, post-operative pain, pain in association with an acute attack of gout and acute pain following jaw-bone surgery interventions, and chronic pain like pain associated with chronic musculoskeletal diseases, back pain, pain associated with osteoarthritis or rheumatoid arthritis, pain associated with inflammation, amputation pain, pain associated with multiple sclerosis, pain associated with neuritis, pain associated with carcinomas and sarcomas, pain associated with AIDS, pain associated with chemotherapy, trigeminus neuralgia, headache, migraine, cephalalgia, neuropathic pains and post-herpes zoster neuralgia. Inhibitors of SGK-1 such as the compounds of the present invention can also be used in tumor therapy for inhibiting the growth of tumor cells and tumor metastases, and for the treatment of chronic disorders of the locomotor system such as inflammatory, immunologically or metabolically-related acute and chronic arthritides, arthropathies, myalgias and disturbances of bone metabolism. Further, inhibitors of SGK-1 such as the compounds of the present invention can be used in the treatment of peptic ulcers, especially in forms that are triggered by stress, in the treatment of tinnitus, in the treatment of bacterial infections and in anti-infective therapy, for increasing the learning ability and attention, for counteracting cellular aging and stress and thus increasing life expectancy and fitness in the elderly, in states of neuronal excitability including epilepsy and progressive myoclonic epilepsy of the Lafora type (Lafora disease), in the treatment of glaucoma or cataracts, and in the treatment of coagulopathies including dysfibrinogenaemia, hypoproconvertinaemia, haemophilia B, Stuart-Prower defect, prothrombin complex deficiency, consumption coagulopathy, fibrinolysis, immunokoagulopathy or complex coagulopathies. Further details about the physiological role of SGK are found in the literature, for example in the mentioned literature articles and others.

The identification of small compounds that specifically inhibit, regulate or modulate signal transduction by SGK, is therefore desirable and an object of the present invention. But besides being effective SGK inhibitors, it is desirable that such inhibitors also have further advantageous properties, for example high bioavailability, stability in plasma and liver, and selectivity versus other kinases or receptors whose inhibition or activation is not intended. Thus, it is an object of the present invention to provide SGK inhibitors which effectively inhibit an aberrant activity of SGK in a pathological context and which have further advantageous properties, for example high bioavailability, stability in plasma and liver, and selectivity versus other kinases and receptors which are not intended to be influenced in an agonistic or antagonistic manner. This object is achieved by providing the novel compounds of the formula I which exhibit excellent SGK-1 inhibitory activity and are favorable agents with high bioavailability and stability in plasma and liver.

Thus, a subject of the present invention are the compounds of the formula I, in any of their stereoisomeric forms or a mixture of stereoisomeric forms in any ratio, and the pharmaceutically acceptable salts thereof,

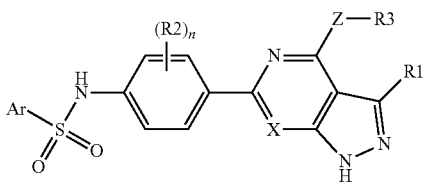

wherein
Ar is selected from the series consisting of phenyl and a 5-membered or 6-membered, monocyclic, aromatic, heterocyclic group which comprises 1, 2 or 3 identical or different ring heteroatoms selected from the series consisting of nitrogen, oxygen and sulfur, and is bonded via a ring carbon atom, which all are unsubstituted or substituted by one or more identical or different substituents R5;
n is selected from the series consisting of 0, 1 and 2;
X is selected from the series consisting of N and CH;
Z is selected from the series consisting of a direct bond, O, S and N(R10);
R1 is selected from the series consisting of H, —N(R11)-R12, —N(R13)-C(O)—R14, —N(R13)-S(O)$_2$—R15, —N(R13)-C(O)—NH—R16, ($C_1$-$C_4$)-alkyl and —($C_1$-$C_4$)-alkyl-O—R17;
R2 is selected from the series consisting of halogen, ($C_1$-$C_4$)-alkyl, —O—($C_1$-$C_4$)-alkyl and —CN;
R3 is selected from the series consisting of H, ($C_1$-$C_8$)-alkyl, R30 and —($C_1$-$C_4$)-alkyl-R30, wherein ($C_1$-$C_8$)-alkyl is unsubstituted or substituted by one or more identical or different substituents R31;
R5 is selected from the series consisting of halogen, ($C_1$-$C_4$)-alkyl, ($C_3$-$C_7$)-cycloalkyl, —($C_1$-$C_4$)-alkyl-($C_3$-$C_7$)-cycloalkyl, —O—($C_1$-$C_4$)-alkyl, —O—($C_3$-$C_7$)-cycloalkyl, —O—($C_1$-$C_4$)-alkyl-($C_3$-$C_7$)-cycloalkyl, —C(O)—N(R6)-R7 and —CN,
and two groups R5 bonded to adjacent ring carbon atoms in Ar, together with the carbon atoms carrying them, can form a 5-membered to 8-membered, monocyclic, unsaturated ring which comprises 0, 1 or 2 identical or different ring heteroatoms selected from the series consisting of nitrogen, oxygen and sulfur, and which is unsubstituted or substituted by one or more identical or different substituents R8;
R6 and R7 are independently of one another selected from the series consisting of H and ($C_1$-$C_4$)-alkyl;
R8 is selected from the series consisting of halogen, ($C_1$-$C_4$)-alkyl, —O—($C_1$-$C_4$)-alkyl and —CN;
R10 is selected from the series consisting of H and ($C_1$-$C_4$)-alkyl;
R11 and R12 are independently of one another selected from the series consisting of H, ($C_1$-$C_4$)-alkyl, ($C_3$-$C_7$)-cycloalkyl, —($C_1$-$C_4$)-alkyl-($C_3$-$C_7$)-cycloalkyl, Het1, —($C_1$-$C_4$)-alkyl-Het1 and —($C_1$-$C_4$)-alkyl-phenyl, wherein phenyl is unsubstituted or substituted by one or more identical or different substituents R50,
or R11 and R12, together with the nitrogen atom carrying them, form a 4-membered to 7-membered, monocyclic, saturated, heterocyclic group which, in addition to the nitrogen atom carrying R11 and R12, comprises 0 or 1 further ring heteroatom selected from the series consisting of nitrogen, oxygen and sulfur, and which is unsubstituted or substituted by one or more identical or different substituents selected from the series consisting of fluorine and ($C_1$-$C_4$)-alkyl;
R13 is selected from the series consisting of H, ($C_1$-$C_4$)-alkyl and ($C_3$-$C_7$)-cycloalkyl;

R14 and R16 are independently of one another selected from the series consisting of ($C_1$-$C_8$)-alkyl, ($C_3$-$C_7$)-cycloalkyl, —($C_1$-$C_4$)-alkyl-($C_3$-$C_7$)-cycloalkyl, phenyl, —($C_1$-$C_4$)-alkyl-phenyl, Het2 and —($C_1$-$C_4$)-alkyl-Het2, wherein ($C_1$-$C_8$)-alkyl and ($C_3$-$C_7$)-cycloalkyl all are unsubstituted or substituted by one or more identical or different substituents selected from the series consisting of —OH and —O—($C_1$-$C_4$)-alkyl, and wherein phenyl and Het2 all are unsubstituted or substituted by one or more identical or different substituents R50;
R15 is selected from the series consisting of ($C_1$-$C_8$)-alkyl, phenyl and Het3, wherein phenyl and Het3 all are unsubstituted or substituted by one or more identical or different substituents R50;
R17 is selected from the series consisting of H and ($C_1$-$C_4$)-alkyl;
R30 is a 3-membered to 12-membered, monocyclic or bicyclic, saturated, partially unsaturated or aromatic, cyclic group which comprises 0, 1, 2 or 3 identical or different ring heteroatoms selected from the series consisting of nitrogen, oxygen and sulfur, which is unsubstituted or substituted by one or more identical or different substituents R32;
R31 is selected from the series consisting of halogen, —OH, —O—($C_1$-$C_4$)-alkyl, —O—($C_3$-$C_7$)-cycloalkyl, —O—($C_1$-$C_4$)-alkyl-($C_3$-$C_7$)-cycloalkyl, —N(R33)-R34, —CN and —C(O)—N(R35)-R36;
R32 is selected from the series consisting of halogen, ($C_1$-$C_4$)-alkyl, ($C_3$-$C_7$)-cycloalkyl, —($C_1$-$C_4$)-alkyl-($C_3$-$C_7$)-cycloalkyl, —($C_1$-$C_4$)-alkyl-O—R37, —($C_1$-$C_4$)-alkyl-N(R38)-R39, —($C_1$-$C_4$)-alkyl-CN, —C(O)—($C_1$-$C_4$)-alkyl, —CN, —OH, =O, —O—($C_1$-$C_4$)-alkyl, —N(R40)-R41, —C(O)—O—($C_1$-$C_4$)-alkyl and —C(O)—N(R42)-R43;
R33, R34, R35, R36, R37, R38, R39, R40, R41, R42 and R43 are independently of one another selected from the series consisting of H and ($C_1$-$C_4$)-alkyl;
R50 is selected from the series consisting of halogen, ($C_1$-$C_4$)-alkyl, —O—($C_1$-$C_4$)-alkyl and —CN;
Het1 is a 4-membered to 7-membered, monocyclic, saturated, heterocyclic group which comprises 1 or 2 identical or different ring heteroatoms selected from the series consisting of nitrogen, oxygen and sulfur, and is bonded via a ring carbon atom, and which is unsubstituted or substituted by one or more identical or different substituents selected from the series consisting of fluorine and ($C_1$-$C_4$)-alkyl;
Het2 is a 4-membered to 7-membered, monocyclic, saturated, partially unsaturated or aromatic, heterocyclic group which comprises 1 or 2 identical or different ring heteroatoms selected from the series consisting of nitrogen, oxygen and sulfur, and is bonded via a ring carbon atom;
Het3 is a 5-membered or 6-membered, monocyclic, aromatic, heterocyclic group which comprises 1, 2 or 3 identical or different ring heteroatoms selected from the series consisting of nitrogen, oxygen and sulfur, and is bonded via a ring carbon atom;
wherein all cycloalkyl groups, independently of any other substituents which can be present on a cycloalkyl group, can be substituted by one or more identical or different substituents selected from the series consisting of fluorine and ($C_1$-$C_4$)-alkyl;
wherein all alkyl groups, independently of any other substituents which can be present on an alkyl group, can be substituted by one or more fluorine substituents.

If structural elements such as groups, substituents or numbers, for example, can occur several times in the compounds of the formula I, they are all independent of each other and can in each case have any of the indicated meanings, and they can in each case be identical to or different from any other such element. In a dialkylamino group, for example, the alkyl groups can be identical or different.

Alkyl groups, i.e. saturated hydrocarbon residues, can be linear (straight-chain) or branched. This also applies if these groups are substituted or are part of another group, for example an —O-alkyl group (alkyloxy group, alkoxy group) or an HO-substituted alkyl group (-alkyl-OH, hydroxyalkyl group). Depending on the respective definition, the number of carbon atoms in an alkyl group can be 1, 2, 3, 4, 5, 6, 7 or 8, or 1, 2, 3, 4, 5 or 6, or 1, 2, 3 or 4, or 1, 2 or 3, or 1 or 2, or 1. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, hexyl including n-hexyl, 2,2-dimethylbutyl, 3,3-dimethylbutyl, 2-methylpentyl, 3-methylpentyl and isohexyl, heptyl including n-heptyl, and octyl including n-octyl and 2,2-dimethylhexyl. Examples of —O-alkyl groups are methoxy, ethoxy, n-propoxy, isopropoxy, n-butoxy, isobutoxy, tert-butoxy, n-pentoxy.

A substituted alkyl group can be substituted in any positions, provided that the respective compound is sufficiently stable and is suitable as a pharmaceutical active compound. The prerequisite that a specific group and a compound of the formula I are sufficiently stable and suitable as a pharmaceutical active compound, applies in general with respect to the definitions of all groups in the compounds of the formula I. Independently of any other substituents which can be present on an alkyl group, and unless specified otherwise, alkyl groups can be substituted by one or more fluorine substituents, for example by 1, 2, 3, 4, 5, 6, 7, 8, 9, 10 or 11 fluorine substituents, or by 1, 2, 3, 4 or 5 fluorine substituents, or by 1, 2 or 3 fluorine substituents, which can be located in any positions. I.e., independently of any other substituents which can be present on an alkyl group, an alkyl group can be unsubstituted by fluorine substituents, i.e. not carry fluorine substituents, or substituted by fluorine substituents, wherein all alkyl groups in the compounds of the formula I are independent of one another with regard to the optional substitution by fluorine substituents. For example, in a fluoro-substituted alkyl group one or more methyl groups can carry three fluorine substituents each and be present as trifluoromethyl groups, and/or one or more methylene groups ($CH_2$) can carry two fluorine substituents each and be present as difluoromethylene groups. The explanations with respect to the substitution of a group by fluorine also apply if the group additionally carries other substituents and/or is part of another group, for example of an —O-alkyl group. Examples of fluoro-substituted alkyl groups are —$CF_3$ (trifluoromethyl), —$CHF_2$, —$CH_2F$, —CHF—$CF_3$, —CHF—$CHF_2$, —CHF—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—CHF—$CF_3$, —$CH_2$—CHF—$CHF_2$, —$CH_2$—CHF—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$, or —$CF_2$—$CF_2$—$CH_2F$. Examples of fluoro-substituted —O-alkyl groups are trifluoromethoxy (—O—$CF_3$), 2,2,2-trifluoroethoxy, pentafluoroethoxy and 3,3,3-trifluoropropoxy. With respect to all groups or substituents in the compounds of the formula I which can be an alkyl group which can generally contain one or more fluorine substituents, as an example of groups or substituents containing fluorine-substituted alkyl, which may be included in the definition of the group or substituent, the group $CF_3$ (trifluoromethyl), or a respective group such as —O—$CF_3$, may be mentioned.

The above explanations with respect to alkyl groups apply correspondingly to alkyl groups which in the definition of a group in the compounds of the formula I are bonded to two adjacent groups, or linked to two groups, and may be regarded as divalent alkyl groups (alkanediyl groups), like in the case of the alkyl part of a substituted alkyl group. Thus, such groups can also be linear or branched, the bonds to the adjacent groups can be located in any positions and can start from the same carbon atom or from different carbon atoms, and they can be unsubstituted or substituted by fluorine substituents independently of any other substituents. Examples of such divalent alkyl groups are —$CH_2$—, —$CH_2$—$CH_2$—, —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH_2$—$CH_2$—$CH_2$—$CH_2$—$CH_2$—$CH_2$—, —CH($CH_3$)—, —C($CH_3$)$_2$—, —CH($CH_3$)—$CH_2$—, —$CH_2$—CH($CH_3$)—, —C($CH_3$)$_2$—$CH_2$—, —$CH_2$—C($CH_3$)$_2$—. Examples of fluoro-substituted alkanediyl groups, which can contain 1, 2, 3, 4, 5 or 6 fluorine substituents, or 1, 2, 3 or 4 fluorine substituents, or 1 or 2 fluorine substituents, for example, are —$CF_2$—, —CHF—, —CHF—$CHF_2$—, —CHF—CHF—, —$CH_2$—$CF_2$—, —$CH_2$—CHF—, —$CF_2$—$CF_2$—, —$CF_2$—CHF—, —$CH_2$—CHF—$CF_2$—, —$CH_2$—CHF—CHF—, —$CH_2$—$CH_2$—$CF_2$—, —$CH_2$—$CH_2$—CHF, —$CH_2$—$CF_2$—$CF_2$—, —$CH_2$—$CF_2$—CHF—, —CHF—CHF—$CF_2$—, —CHF—CHF—CHF—, —CHF—$CH_2$—$CF_2$—, —CHF—$CH_2$—CHF—, —CHF—$CF_2$—$CF_2$—, —CHF—$CF_2$—CHF—, —$CF_2$—CHF—$CF_2$—, —$CF_2$—CHF—CHF—, —$CF_2$—$CH_2$—$CF_2$—, —$CF_2$—$CH_2$—CHF—, —$CF_2$—$CF_2$—$CF_2$—, or —$CF_2$—$CF_2$—CHF—.

The number of ring carbon atoms in a ($C_3$-$C_7$)-cycloalkyl group can be 3, 4, 5, 6 or 7. Examples of cycloalkyl are cyclopropyl, cyclobutyl, cyclopentyl, cyclohexyl and cycloheptyl. Independently of any other substituents which can be present on a cycloalkyl group, and unless specified otherwise, cycloalkyl groups can be substituted by one or more ($C_1$-$C_4$)-alkyl substituents, for example by 1, 2, 3 or 4 identical or different ($C_1$-$C_4$)-alkyl substituents, for example by methyl groups, which can be located in any positions. I.e., independently of any other substituents which can be present on a cycloalkyl group, a cycloalkyl group can be unsubstituted by ($C_1$-$C_4$)-alkyl substituents, i.e. not carry ($C_1$-$C_4$)-alkyl substituents, or substituted by ($C_1$-$C_4$)-alkyl substituents, wherein all cycloalkyl groups in the compounds of the formula I are independent of one another with regard to the optional substitution by ($C_1$-$C_4$)-alkyl substituents. Examples of such alkyl-substituted cycloalkyl groups are 1-methylcyclopropyl, 2,2-dimethylcyclopropyl, 1-methylcyclopentyl, 2,3-dimethylcyclopentyl, 1-methylcyclohexyl, 4-methylcyclohexyl, 4-isopropylcyclohexyl, 4-tert-butylcyclohexyl, 3,3,5,5-tetramethylcyclohexyl. Independently of any other substituents including ($C_1$-$C_4$)-alkyl substituents which can be present on a cycloalkyl group, and unless specified otherwise, cycloalkyl groups can further be substituted by one or more fluorine substituents, for example by 1, 2, 3, 4, 5, 6, 7, 8, 9, 10 or 11 fluorine substituents, or by 1, 2, 3, 4 or 5 fluorine substituents, or by 1, 2 or 3 fluorine substituents, which can be located in any positions and can also be present in a $(C_1-C_4)$-alkyl substituent. I.e., independently of any other substituents which can be present on a cycloalkyl group, a cycloalkyl group can be unsubstituted by fluorine substituents, i.e. not carry fluorine substituents, or substituted by fluorine substituents, wherein all cycloalkyl groups in the compounds of the formula I are independent of one another with regard to the optional substitution by fluorine substituents. Examples of fluoro-substituted cycloalkyl groups are 1-fluorocyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl. Cycloalkyl groups can also be substituted simultaneously by fluorine and alkyl. Examples of the group $—(C_1-C_4)$-alkyl-$(C_3-C_7)$-cycloalkyl are cyclopropylmethyl-, cyclobutylmethyl-, cyclopentylmethyl-, cyclohexylmethyl-, cycloheptylmethyl-, 1-cyclopropylethyl-, 2-cyclopropylethyl-, 1-cyclobutylethyl-, 2-cyclobutylethyl-, 1-cyclopentylethyl-, 2-cyclopentylethyl-, 1-cyclohexylethyl-, 2-cyclohexylethyl-, 1-cycloheptylethyl-, 2-cycloheptylethyl-. In one embodiment of the invention, a $—(C_1-C_4)$-alkyl-$(C_3-C_7)$-cycloalkyl group in any one or more occurrences of such a group, independently of any other occurrences, is a $—(C_1-C_2)$-alkyl-$(C_3-C_7)$-cycloalkyl group, in another embodiment a $—CH_2—(C_3-C_7)$-cycloalkyl group. In the group $—(C_1-C_4)$-alkyl-$(C_3-C_7)$-cycloalkyl, and likewise in all other groups, the terminal hyphen denotes the free bond via which the group is bonded, and thus indicates via which subgroup a group composed of subgroups is bonded.

In substituted phenyl groups, including phenyl groups representing Ar, for example, the substituents can be located in any positions. In monosubstituted phenyl groups, the substituent can be located in position 2, in position 3 or in position 4. In disubstituted phenyl groups, the substituents can be located in positions 2 and 3, in positions 2 and 4, in positions 2 and 5, in positions 2 and 6, in positions 3 and 4, or in positions 3 and 5. In trisubstituted phenyl groups, the substituents can be located in positions 2, 3 and 4, in positions 2, 3 and 5, in positions 2, 3 and 6, in positions 2, 4 and 5, in positions 2, 4 and 6, or in positions 3, 4 and 5. If a phenyl group carries four substituents, some of which can be fluorine atoms, for example, the substituents can be located in positions 2, 3, 4 and 5, in positions 2, 3, 4 and 6, or in positions 2, 3, 5 and 6. If a polysubstituted phenyl group or any other polysubstituted group carries different substituents, each substituent can be located in any suitable position, and the present invention comprises all positional isomers. The number of substituents in a substituted phenyl group can be 1, 2, 3, 4 or 5. In one embodiment of the invention, the number of substituents in a substituted phenyl group, is 1, 2, 3 or 4, in another embodiment 1, 2 or 3, in another embodiment 1 or 2, in another embodiment 1, wherein the number of substituents in any occurrence of such a substituted group is independent of the number of substituents in other occurrences.

In heterocyclic groups, including the groups Het1, Het2, Het3, heterocyclic groups representing Ar, heterocyclic groups R30 and other heterocyclic rings which can be present in the compounds of the formula I, such as rings formed by two group together with the atom or atoms carrying them, the hetero ring members can be present in any combination and located in any suitable ring positions, provided that the resulting group and the compound of the formula I are suitable and sufficiently stable as a pharmaceutical active compound. In one embodiment of the invention, two oxygen atoms in any heterocyclic ring in the compounds of the formula I cannot be present in adjacent ring positions. In another embodiment of the invention, two hetero ring members selected from the series consisting of oxygen atoms and sulfur atoms cannot be present in adjacent ring positions in any heterocyclic ring in the compounds of the formula I. In another embodiment of the invention, two hetero ring members selected from the series consisting of nitrogen atoms carrying an exocyclic group like a hydrogen atom or a substituent, sulfur atoms and oxygen atoms cannot be present in adjacent ring positions in any heterocyclic ring in the compounds of the formula I. The choice of hetero ring members in an aromatic heterocyclic ring is limited by the prerequisite that the ring is aromatic, i.e. it comprises a cyclic system of six delocalized pi electrons in case of a monocycle or 10 delocalized pi electrons in case of a bicycle. Monocyclic aromatic heterocycles are 5-membered or 6-membered rings and, in the case of a 5-membered ring, comprise one ring heteroatom selected from the series consisting of oxygen, sulfur and nitrogen, wherein this ring nitrogen carries an exocyclic group like a hydrogen atom or a substituent, and optionally one or more further ring nitrogen atoms, and, in the case of a 6-membered ring, comprise one or more nitrogen atoms as ring heteroatoms, but no oxygen atoms and sulfur atoms as ring heteroatoms. Heterocyclic groups in the compounds of the formula I can be bonded via a ring carbon atom or a ring nitrogen atom, unless specified otherwise in the definition of the respective group, wherein a heterocyclic group can be bonded via any suitable carbon atom or nitrogen atom, respectively, in the ring. In substituted heterocyclic groups, the substituents can be located in any positions.

The number of ring heteroatoms which can be present in a heterocyclic group in the compounds of the formula I, the number of ring members which can be present, and the degree of saturation, or hydrogenation, i.e. whether the heterocyclic group is saturated and does not contain a double bond within the ring, or whether it is partially unsaturated and contains one or more, for example one or two, double bonds within the ring but is not aromatic, or whether it is aromatic and thus contains two double bonds within the ring in the case of a 5-membered monocyclic aromatic heterocycle and three double bonds within the ring in the case of a 6-membered monocyclic aromatic heterocycle, for example, is specified in the definitions of the individual groups in the compounds of the formula I. Examples of heterocyclic ring systems, from which heterocyclic groups in the compounds of the formula I including, for example, Het1, Het2, Het3, heterocyclic groups representing Ar, heterocyclic groups R30 and rings formed by two groups together with the atom or atoms carrying them, can be derived, and from any one or more of which any of the heterocyclic groups in the compounds of the formula I is selected in one embodiment of the invention, provided that the ring system is comprised by the definition of the group, are oxetane, thietane, azetidine, furan, tetrahydrofuran, thiophene, tetrahydrothiophene, pyrrole, pyrroline, pyrrolidine, [1,3]dioxole, [1,3]dioxolane, isoxazole ([1,2]oxazole), isoxazoline, isoxazolidine, oxazole ([1,3]oxazole), oxazoline, oxazolidine, isothiazole ([1,2]thiazole), isothiazoline, isothiazolidine, thiazole ([1,3]thiazole), thiazoline, thiazolidine, pyrazole, pyrazoline, pyrazolidine, imidazole, imidazoline, imidazolidine, [1,2,3]triazole, [1,2,4]triazole, [1,2,4]oxadiazole, [1,3,4]oxadiazole, [1,2,5]oxadiazole, [1,2,4]thiadiazole, pyran, tetrahydropyran, thiopyran, tetrahydrothiopyran, 2,3-dihydro[1,4]dioxine, 1,4-dioxane, pyridine, 1,2,5,6-tetrahydropyridine, piperidine, morpholine, thiomorpholine, piperazine, pyridazine, pyrimidine, pyrazine, [1,2,4]triazine, oxepane, thiepane, azepane, [1,3]diazepane, [1,4]diazepane,

[1,4]oxazepane, [1,4]thiazepane, benzofuran, isobenzofuran, benzothiophene (benzo[b]thiophene), 1H-indole, 2,3-dihydro-1H-indole, 2H-isoindole, 2-aza-spiro[4.4]nonane, 2-aza-spiro[4.5]decane, 2-aza-spiro[4.6]undecane, 2-aza-spiro[5.5]undecane, 3-aza-spiro[5.5]undecane, 6-aza-spiro[2.5]octane, 7-aza-spiro[3.5]nonane, 8-aza-spiro[4.5]decane, benzo[1,3]dioxole, benzoxazole, benzthiazole, 1H-benzimidazole, chroman, isochroman, thiochroman, benzo[1,4]dioxane, 3,4-dihydro-2H-benzo[b][1,4]dioxepine (3,4-dihydro-2H-1,5-benzodioxepine), 3,4-dihydro-2H-benzo[1,4]oxazine, 1-oxa-8-aza-spiro[4.5]decane, 2-oxa-6-aza-spiro[3,3]heptane, 2-oxa-6-aza-spiro[3.4]octane, 2-oxa-6-aza-spiro[3.5]nonane, 2-oxa-7-aza-spiro[3,5]nonane, 8-oxa-2-aza-spiro[4.5]decane, 3,4-dihydro-2H-benzo[1,4]thiazine, quinoline, 5,6,7,8-tetrahydroquinoline, isoquinoline, 5,6,7,8-tetrahydroisoquinoline, cinnoline, quinazoline, quinoxaline, phthalazine and [1,8]naphthyridine, which can all be unsubstituted or substituted in any suitable positions as specified in the definition of the respective group in the compounds of the formula I, wherein the given degree of unsaturation is by way of example only, and in the individual groups also ring systems with a higher or lower degree of saturation or unsaturation can be present as specified in the definition of the group. Ring sulfur atoms, in particular in saturated and partially unsaturated heterocycles, can generally carry one or two oxo groups, i.e. doubly bonded oxygen atoms (═O), and in such heterocycles, besides a ring sulfur atom, also an S(O) group (S(═O)) and an S(O)$_2$ group (S(═O)$_2$) can be present as hetero ring member.

As mentioned, unless specified otherwise in the definition of the respective group in the compounds of the formula I, heterocyclic groups can be bonded via any suitable ring carbon atom and ring nitrogen atom, for example in the case of heterocyclic groups representing R30. Thus, for example, among others can an oxetane and a thietane ring be bonded via positions 2 and 3, an azetidine ring via positions 1, 2 and 3, a furan ring, a tetrahydrofuran ring, a thiophene ring and a tetrahydrothiophene ring via positions 2 and 3, a pyrrole ring and a pyrrolidine ring via positions 1, 2 and 3, an isoxazole ring and an isothiazole ring via positions 3, 4 and 5, a pyrazole ring via positions 1, 3, 4 and 5, an oxazole ring and a thiazole ring via positions 2, 4 and 5, an imidazole ring and an imidazolidine ring via positions 1, 2, 4 and 5, a tetrahydropyran ring and a tetrahydrothiopyran ring via positions 2, 3 and 4, a 1,4-dioxane ring via position 2, a pyridine ring via positions 2, 3 and 4, a piperidine ring via positions 1, 2, 3 and 4, a morpholine ring and a thiomorpholine ring via positions 2, 3 and 4, a piperazine ring via positions 1 and 2, a pyrimidine ring via positions 2, 4 and 5, a pyrazine ring via position 2, an azepane ring via positions 1, 2, 3 and 4, a benzofuran ring and a benzothiophene ring via positions 2, 3, 4, 5, 6 and 7, a 1H-indole ring and a 2,3-dihydro-1H-indole ring via positions 1, 2, 3, 4, 5, 6 and 7, a benzo[1,3]dioxole ring via positions 4, 5, 6 and 7, a benzoxazole ring and a benzthiazole ring via positions 2, 4, 5, 6 and 7, a 1H-benzimidazole ring via positions 1, 2, 4, 5, 6 and 7, a benzo[1,4]dioxane ring via positions 5, 6, 7 and 8, a quinoline ring via positions 2, 3, 4, 5, 6, 7 and 8, a 5,6,7,8-tetrahydroquinoline ring via positions 2, 3 and 4, an isoquinoline ring via positions 1, 3, 4, 5, 6, 7 and 8, a 5,6,7,8-tetrahydroisoquinoline ring via positions 1, 3 and 4, wherein the resulting residues of the heterocyclic groups can all be unsubstituted or substituted in any suitable positions as specified in the definition of the respective group in the compounds of the formula I.

Halogen is fluorine, chlorine, bromine or iodine. In one embodiment of the invention, halogen is in any of its occurrences fluorine, chlorine or bromine, in another embodiment fluorine or chlorine, in another embodiment fluorine, in another embodiment chlorine, wherein all occurrences of halogen are independent of each other.

The present invention comprises all stereoisomeric forms of the compounds of the formula I, for example all enantiomers and diastereomers including cis/trans isomers. The invention likewise comprises mixtures of two or more stereoisomeric forms, for example mixtures of enantiomers and/or diastereomers including cis/trans isomers, in all ratios. Asymmetric centers contained in the compounds of the formula I can all independently of each other have S configuration or R configuration. The invention relates to enantiomers, both the levorotatory and the dextrorotatory antipode, in enantiomerically pure form and essentially enantiomerically pure form, and in the form of their racemate, i.e. a mixture of the two enantiomers in molar ratio of 1:1, and in the form of mixtures of the two enantiomers in all ratios. The invention likewise relates to diastereomers in the form of pure and essentially pure diastereomers and in the form of mixtures of two or more diastereomers in all ratios. The invention also comprises all cis/trans isomers of the compounds of the formula I in pure form and essentially pure form, and in the form of mixtures of the cis isomer and the trans isomer in all ratios. Cis/trans isomerism can occur in substituted rings. The preparation of individual stereoisomers, if desired, can be carried out by resolution of a mixture according to customary methods, for example, by chromatography or crystallization, or by use of stereochemically uniform starting compounds in the synthesis, or by stereoselective reactions. Optionally, before a separation of stereoisomers a derivatization can be carried out. The separation of a mixture of stereoisomers can be carried out at the stage of the compound of the formula I or at the stage of an intermediate in the course of the synthesis. For example, in the case of a compound of the formula I containing an asymmetric center the individual enantiomers can be prepared by preparing the racemate of the compound of the formula I and resolving it into the enantiomers by high pressure liquid chromatography on a chiral phase according to standard procedures, or resolving the racemate of any intermediate in the course of its synthesis by such chromatography or by crystallization of a salt thereof with an optically active amine or acid and converting the enantiomers of the intermediate into the enantiomeric forms of the final compound of the formula I, or by performing an enantioselective reaction in the course of the synthesis. The invention also comprises all tautomeric forms of the compounds of the formula I.

Besides the free compounds of the formula I, i.e. compounds in which acidic and basic groups are not present in the form of a salt, the present invention comprises also salts of the compounds of the formula I, in particular their physiologically acceptable salts, or toxicologically acceptable salts, or pharmaceutically acceptable salts, which can be formed on one or more acidic or basic groups in the compounds of the formula I, for example on basic heterocyclic moieties. The compounds of the formula I may thus be deprotonated on an acidic group by an inorganic or organic base and be used, for example, in the form of the alkali metal salts. Compounds of the formula I comprising at least one basic group may also be prepared and used in the form of their acid addition salts, for example in the form of pharmaceutically acceptable salts with inorganic acids and organic acids, such as salts with hydrochloric acid and thus be present in the form of the hydrochlorides, for example. Salts can in general be prepared from acidic and basic compounds of the formula I by reaction with an acid or base in a solvent or diluent according to customary procedures. If the compounds of the formula I simultaneously contain an acidic and a basic group in the molecule, the invention also includes internal salts (betaines, zwitterions) in addition to the salt forms mentioned. The present invention also comprises all salts of the compounds of the formula I which, because of low physiological tolerability, are not directly suitable for use as a pharmaceutical, but are suitable as intermediates for chemical reactions or for the preparation of physiologically acceptable salts, for example by means of anion exchange or cation exchange.

In one embodiment of the invention, an aromatic heterocycle representing the group Ar comprises 1 or 2 identical or different ring heteroatoms, in another embodiment 1 or 2 identical or different ring heteroatoms which are selected from the series consisting of nitrogen and sulfur. In another embodiment, an aromatic heterocycle representing Ar is a 5-membered heterocycle which comprises 1 or 2 identical or different ring heteroatoms which are selected from the series consisting of nitrogen and sulfur, or it is a 6-membered heterocycle which comprises 1 or 2 ring heteroatoms which are nitrogen atoms, in another embodiment it is a 5-membered heterocycle which comprises 1 or 2 identical or different ring heteroatoms which are selected from the series consisting of nitrogen and sulfur, which heterocycles are all unsubstituted or substituted by one or more substituents identical or different R5. In another embodiment, an aromatic heterocycle representing Ar is selected from the series consisting of thiophene, thiazole, pyrazole, imidazole, pyridine, pyridazine, pyrimidine and pyrazine, in another embodiment from the series consisting of thiophene, thiazole, pyrazole, imidazole and pyridine, in another embodiment from the series consisting of thiophene, thiazole, pyrazole and imidazole, in another embodiment from the series consisting of thiophene and pyrazole, in another embodiment it is thiophene, and in another embodiment it is pyrazole, which heterocycles are all unsubstituted or substituted by one or more identical or different substituents R5. In one embodiment of the invention, Ar is phenyl which is unsubstituted or substituted by one or more identical or different substituents R5, in another embodiment Ar is phenyl which is substituted by one or more identical or different substituents R5, in another embodiment Ar is a 5-membered or 6-membered aromatic heterocycle which is unsubstituted or substituted by one or more identical or different substituents R5, and in another embodiment Ar is a 5-membered or 6-membered aromatic heterocycle which is substituted by one or more identical or different substituents R5. In one embodiment, Ar is substituted by one or more identical or different substituents R5. In one embodiment of the invention, the number of identical or different substituents R5 which can be present in the group Ar is 1, 2, 3 or 4, in another embodiment it is 1, 2 or 3, in another embodiment it is 1 or 2, in another embodiment it is 1, in another embodiment it is 2, 3 or 4, in another embodiment it is 2 or 3, in another embodiment it is 3, in another embodiment it is 2.

In one embodiment of the invention, the number n is selected from the series consisting of 0 and 1, in another embodiment from the series consisting of 1 and 2, in another embodiment it is 1, in another embodiment it is 0.

In one embodiment of the invention, X is N, and the compounds of the formula I thus are N-[4-(1H-pyrazolo[3,4-d]pyrimidin-6-yl)-phenyl]-sulfonamides. In another embodiment of the invention, X is CH, and the compounds of the formula I thus are N-[4-(1H-pyrazolo[4,3-c]pyridin-6-yl)-phenyl]-sulfonamides.

In case the divalent group Z is a direct bond, the group R3 is directly bonded via a single bond to the ring carbon in position 4 of the bicyclic ring system depicted in formula I which carries Z, and the compound of the formula I thus is a compound of the formula Ia, wherein Ar, n, X, R1, R2 and R3 are defined as in the compounds of the formula I. In one embodiment of the invention, Z is selected from the series

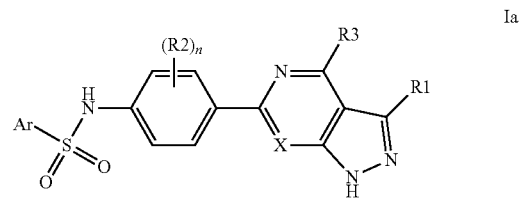

Ia consisting of a direct bond, O and N(R10), in another embodiment from the series consisting of a direct bond and O, in another embodiment from the series consisting of a direct bond and N(R10), in another embodiment from the series consisting of O, S and N(R10), in another embodiment from the series consisting of O and N(R10), in another embodiment Z is a direct bond, in another embodiment Z is O, i.e. an oxygen atom, in another embodiment Z is S, i.e. a sulfur atom, and in another embodiment Z is N(R10), i.e. a nitrogen atom carrying the atom or group R10.

In one embodiment of the invention, R1 is selected from the series consisting of H, —N(R11)-R12, —N(R13)-C(O)—R14, —N(R13)-S(O)$_2$—R15, —N(R13)-C(O)—NH—R16 and ($C_1$-$C_4$)-alkyl, in another embodiment from the series consisting of H, —N(R11)-R12, —N(R13)-C(O)—R14, —N(R13)-S(O)$_2$—R15 and —N(R13)-C(O)—NH—R16, in another embodiment from the series consisting of —N(R11)-R12, —N(R13)-C(O)—R14, —N(R13)-S(O)$_2$—R15, —N(R13)-C(O)—NH—R16 and ($C_1$-$C_4$)-alkyl, in another embodiment from the series consisting of —N(R11)-R12, —N(R13)-C(O)—R14, —N(R13)-S(O)$_2$—R15 and —N(R13)-C(O)—NH—R16, in another embodiment from the series consisting of —N(R11)-R12 and N(R13)-C(O)—R14, and in another embodiment R1 is —N(R11)-R12. In another embodiment, R1 is selected from the series consisting of H, —N(R11)-R12, —N(R13)-C(O)—R14 and ($C_1$-$C_4$)-alkyl, in another embodiment from the series consisting of H, —N(R11)-R12 and ($C_1$-$C_4$)-alkyl, and in another embodiment from the series consisting of —N(R11)-R12 and ($C_1$-$C_4$)-alkyl. In another embodiment, R1 is selected from the series consisting of H, ($C_1$-$C_4$)-alkyl and —($C_1$-$C_4$)-alkyl-O—R17, in another embodiment from the series consisting of H and ($C_1$-$C_4$)-alkyl, in another embodiment R1 is H, in another embodiment R1 is ($C_1$-$C_4$)-alkyl, and in another embodiment R1 is —($C_1$-$C_4$)-alkyl-O—R17. In one embodiment, a ($C_1$-$C_4$)-alkyl group representing R1 or present in —($C_1$-$C_4$)-alkyl-O—R17 is ($C_1$-$C_3$)-alkyl, in another embodiment it is ($C_1$-$C_2$)-alkyl, in another embodiment it is methyl. As applies to alkyl groups in general, in all these embodiments an alkyl group representing R1 or present in R1, for example the group ($C_1$-$C_4$)-alkyl representing R1, can be substituted by one or more fluorine substituents, i.e., independently of any other substituents on the alkyl group it is unsubstituted by fluorine substituents or it is substituted by fluorine substituents. In one embodiment, an alkyl group representing R1 or present in R1, for example the group $(C_1-C_4)$-alkyl representing R1, independently of any other substituents on the alkyl group, is unsubstituted by fluorine substituents. In another embodiment, an alkyl group representing R1 or present in R1, for example the group $(C_1-C_4)$-alkyl representing R1, independently of any other substituents on the alkyl group, is substituted by one or more fluorine substituents, for example by 1, 2, 3, 4 or 5 fluorine substituents or by 1, 2 or 3 fluorine substituents.

In one embodiment of the invention, R2 is selected from the series consisting of halogen, $(C_1-C_4)$-alkyl and —O—$(C_1-C_4)$-alkyl, in another embodiment from the series consisting of halogen and $(C_1-C_4)$-alkyl, in another embodiment from the series consisting of halogen and —O—$(C_1-C_4)$-alkyl, in another embodiment from the series consisting of halogen, —O—$(C_1-C_4)$-alkyl and —CN, in another embodiment from the series consisting of halogen and —CN, in another embodiment from the series consisting of halogen, wherein in all these embodiments alkyl can be substituted by one or more, for example by 1, 2, 3, 4 or 5, or by 1, 2 or 3, fluorine substituents, as applies to alkyl groups in general. In one embodiment, a $(C_1-C_4)$-alkyl group representing R2 or present in R2 is $(C_1-C_3)$-alkyl, in another embodiment it is $(C_1-C_2)$-alkyl, in another embodiment it is methyl. In one embodiment, halogen representing R2 is selected from the series consisting of fluorine and chlorine, in another embodiment it is fluorine. Ring carbon atoms in the divalent phenyl group depicted in formula I which are not bonded to adjacent groups depicted in formula I, and which do not carry a group R2, carry hydrogen atoms. Thus, in case the number n is 0 and hence no group R2 is present, all four carbon atoms in the ring positions of the divalent phenyl group depicted in formula I, which in formula I' are designated as positions 2', 3', 5' and 6', carry hydrogen atoms. In case the number n is 1 and hence one group R2 is present, one of the four carbon atoms in the ring positions of the divalent phenyl group depicted in formula I, which in formula I' are designated as 2', 3', 5' and 6', carries the group R2 and the other three said carbon atoms carry hydrogen atoms. In case the number n is 2 and hence two groups R2 are present, two of the four carbon atoms in the ring positions of the divalent phenyl group depicted in formula I, which in formula I' are designated as positions 2', 3', 5' and 6', carry the groups R2 and the other two said carbon atoms carry hydrogen atoms.

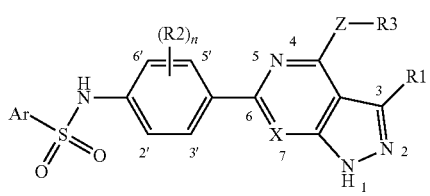

Groups R2 can be present in any positions of the divalent phenyl group depicted in formula I which in formula I' are designated as 2', 3', 5' and 6'. If one group R2 is present, in one embodiment of the invention the group R2 is present in the position which in formula I' is designated as position 2', which is equivalent to position 6', and in another embodiment it is present in the position which in formula I' is designated as position 3', which is equivalent to position 5'. If two groups R2 are present, in one embodiment of the invention the groups R2 are present in the positions which in formula I' are designated as positions 2' and 3', in another embodiment in the positions which in formula I' are designated as positions 2' and 5', in another embodiment in the positions which in formula I' are designated as positions 2' and 6', in another embodiment in the positions which in formula I' are designated as positions 3' and 5'.

In one embodiment of the invention, R3 is selected from the series consisting of H, $(C_1-C_8)$-alkyl and R30, in another embodiment from the series consisting of H, $(C_1-C_8)$-alkyl and —$(C_1-C_4)$-alkyl-R30, in another embodiment from the series consisting of H and $(C_1-C_8)$-alkyl, in another embodiment from the series consisting of H and R30, in another embodiment from the series consisting of $(C_1-C_8)$-alkyl, R30 and —$(C_1-C_4)$-alkyl-R30, in another embodiment from the series consisting of $(C_1-C_8)$-alkyl and R30, in another embodiment from the series consisting of R30 and —$(C_1-C_4)$-alkyl-R30, in another embodiment R3 is H, in another embodiment R3 is $(C_1-C_8)$-alkyl, in another embodiment R3 is R30, and in another embodiment R3 is —$(C_1-C_4)$-alkyl-R30, wherein in all these embodiments $(C_1-C_8)$-alkyl is unsubstituted or substituted by one or more identical or different substituents R31, and wherein in one embodiment of the invention all these embodiments independently apply to compounds of the formula I in which Z is a direct bond on the one hand, and to compounds of the formula I in which Z is selected from the series consisting of O, S and N(R10) on the other hand, and R3 can thus be defined differently for such compounds. For example, in one embodiment R3 is selected from the series consisting of H, $(C_1-C_8)$-alkyl and R30 in case Z is a direct bond, and R3 is selected from the series consisting of H, $(C_1-C_8)$-alkyl, R30 and —$(C_1-C_4)$-alkyl-R30 in case Z is selected from the series consisting of O, S and N(R10), in another embodiment R3 is selected from the series consisting of H, $(C_1-C_8)$-alkyl and R30 in case Z is a direct bond, and R3 is selected from the series consisting of H, $(C_1-C_8)$-alkyl and R30 in case Z is selected from the series consisting of O, S and N(R10), in another embodiment R3 is selected from the series consisting of H, $(C_1-C_8)$-alkyl and R30 in case Z is a direct bond, and R3 is selected from the series consisting of $(C_1-C_8)$-alkyl, R30 and —$(C_1-C_4)$-alkyl-R30 in case Z is selected from the series consisting of O, S and N(R10), in another embodiment R3 is selected from the series consisting of H, $(C_1-C_8)$-alkyl and R30 in case Z is a direct bond, and R3 is selected from the series consisting of $(C_1-C_8)$-alkyl and R30 in case Z is selected from the series consisting of O, S and N(R10), in another embodiment R3 is selected from the series consisting of H and R30 in case Z is a direct bond, and R3 is selected from the series consisting of $(C_1-C_8)$-alkyl, R30 and —$(C_1-C_4)$-alkyl-R30 in case Z is selected from the series consisting of O, S and N(R10), and in another embodiment R3 is selected from the series consisting of H and R30 in case Z is a direct bond, and R3 is selected from the series consisting of $(C_1-C_8)$-alkyl and R30 in case Z is selected from the series consisting of O, S and N(R10), wherein in all these embodiments $(C_1-C_8)$-alkyl is unsubstituted or substituted by one or more identical or different substituents R31. In one embodiment, the number of substituents R31 which is optionally present in alkyl groups representing R3, is 1, 2, 3, 4 or 5, in another embodiment it is 1, 2, 3 or 4, in another embodiment it is 1, 2 or 3, in another embodiment it is 1 or 2, in another embodiment it is 1, wherein independently of substituents R31 an alkyl group representing R3 can be substituted by one or more fluorine substituents, as applies to alkyl groups in general. In one embodiment, a $(C_1-C_8)$-alkyl group representing R3 is $(C_1-C_6)$-alkyl, in another embodiment it is $(C_1-C_4)$-alkyl, in another embodiment it is $(C_1-C_3)$-alkyl, in another embodiment it is $(C_1-C_2)$-alkyl, which groups all are unsubstituted or substituted by one or more identical or different substituents R31 and/or fluorine substituents. In one embodiment, the ($C_1$-$C_4$)-alkyl moiety in the group —($C_1$-$C_4$)-alkyl-R30 representing R3 is ($C_1$-$C_3$)-alkyl, in another embodiment it is ($C_1$-$C_2$)-alkyl, in another embodiment it is methyl.

If two groups R5 bonded to adjacent ring carbon atoms in Ar together with the ring carbon atoms carrying them form a 5-membered to 8-membered ring, this ring is at least mono-unsaturated, i.e., the resulting ring contains at least one double bond within the ring, which double bond is present between the said two adjacent ring carbon in the aromatic ring Ar which are common to the ring Ar and the ring formed by the two groups R5, and because of the rules of nomenclature for fused rings is regarded as a double bond present in both rings. The ring formed by two groups R5 together with the carbon atoms carrying them can contain 1, 2 or 3 double bonds within the ring. In one embodiment, the formed ring contains 1 or 2 double bonds, in another embodiment 1 double bond within the ring. In the case of a 6-membered carbocyclic or heterocyclic ring or a 5-membered heterocyclic ring the formed ring can be aromatic and, together with the aromatic ring Ar, form a bicyclic aromatic ring system, for example a naphthalene ring system, a quinoline ring system, an isoquinoline ring system or a benzothiophene ring system. In one embodiment of the invention, not more than two substituents R5 on Ar, together with the ring carbon atoms in Ar carrying them, form a ring, i.e., in this embodiment not more than one ring formed by two groups R5 together with the ring carbon atoms in Ar carrying them is fused to Ar. If paired groups R5 forming a ring are present, further individual groups R5 can additionally be present on Ar, for example groups like halogen, ($C_1$-$C_4$)-alkyl or —O—($C_1$-$C_4$)-alkyl.

The case that two groups R5 bonded to adjacent ring carbon atoms in Ar together with the carbon atoms carrying them form a 5-membered to 8-membered unsaturated ring, can in other terms be regarded as two groups R5 together forming a divalent residue comprising a chain of 3 to 6 atoms of which 0, 1 or 2 are identical or different heteroatoms selected from the series consisting of nitrogen, oxygen and sulfur, the terminal atoms of which are bonded to the two adjacent ring carbon atoms in Ar. Examples of such divalent residues, from any one or more of which two groups R5 bonded to adjacent ring carbon atoms in Ar are selected in one embodiment of the invention, are the residues —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —CH=CH—CH=CH—, —N=CH—CH=CH—, —CH=CH—CH=N—, —CH=N—CH=CH—, —CH=CH—N=CH—, —O—$CH_2$—$CH_2$—, —$CH_2$—$CH_2$—O—, —O—$CH_2$—O—, —O—$CH_2$—$CH_2$—O—, —O—$CH_2$—$CH_2$—$CH_2$—O—, —O—$CH_2$—$CH_2$—$CH_2$—$CH_2$—O—, —S—CH=CH—, —CH=CH—S—, =CH—S—CH=, —N=CH—S—, —S—CH=N—, —N=CH—O—, —O—CH=N—, —NH—$CH_2$—$CH_2$—O—, —O—$CH_2$—$CH_2$—NH—, —S—$CH_2$—$CH_2$—NH— and —NH—$CH_2$—$CH_2$—S—, which can all be substituted by one or more identical or different substituents R8, and can thus also be present, for example, as the divalent residues —O—$CF_2$—O—, —O—C($CH_3$)$_2$—O—, —S—C(Cl)=CH—, —CH=C(Cl)—S—, —N($CH_3$)—$CH_2$—$CH_2$—O—, —O—$CH_2$—$CH_2$—N($CH_3$)—, —S—$CH_2$—$CH_2$—N($CH_3$)— and —N($CH_3$)—$CH_2$—$CH_2$—S—. In one embodiment of the invention, the ring heteroatoms which are optionally present in a ring formed by two groups R5 bonded to adjacent ring carbon atoms in Ar together with the carbon atoms carrying them, are selected from the series consisting of nitrogen and oxygen, in another embodiment from the series consisting of oxygen and sulfur, and in another embodiment they are oxygen atoms. In one embodiment of the invention, the ring which can be formed by two groups R5 bonded to adjacent ring carbon atoms in Ar together with the ring carbon atoms carrying them, is a 5-membered to 7-membered, in another embodiment a 5-membered to 6-membered, in another embodiment a 6-membered to 7-membered, in another embodiment a 5-membered, in another embodiment a 6-membered ring, in another embodiment a 7-membered ring. In one embodiment of the invention, the ring which can be formed by two groups R5 bonded to adjacent carbon atoms in Ar together with the carbon atoms carrying them, comprises 0 ring heteroatoms, i.e. it is a carbocyclic ring, and in another embodiment it comprises 1 or 2 identical or different ring heteroatoms. In one embodiment of the invention, the number of substituents R8 which can be present in a ring formed by two groups R5 bonded to adjacent ring carbon atoms in Ar together with the carbon atoms carrying them, is 1, 2, 3 or 4, in another embodiment 1, 2 or 3, in another embodiment 1 or 2, in another embodiment 1, in another embodiment it is 0.

In one embodiment of the invention, R5 is selected from the series consisting of halogen, ($C_1$-$C_4$)-alkyl, ($C_3$-$C_7$)-cycloalkyl, —O—($C_1$-$C_4$)-alkyl, —O—($C_3$-$C_7$)-cycloalkyl, —C(O)—N(R6)-R7 and —CN, in another embodiment from the series consisting of halogen, ($C_1$-$C_4$)-alkyl, ($C_3$-$C_7$)-cycloalkyl, —O—($C_1$-$C_4$)-alkyl, —C(O)—N(R6)-R7 and —CN, in another embodiment from the series consisting of halogen, ($C_1$-$C_4$)-alkyl, —O—($C_1$-$C_4$)-alkyl, —O—($C_3$-$C_7$)-cycloalkyl, —C(O)—N(R6)-R7 and —CN, in another embodiment from the series consisting of halogen, ($C_1$-$C_4$)-alkyl, —O—($C_1$-$C_4$)-alkyl, —C(O)—N(R6)-R7 and —CN, in another embodiment from the series consisting of halogen, ($C_1$-$C_4$)-alkyl, —O—($C_1$-$C_4$)-alkyl and —CN, in another embodiment from the series consisting of halogen, —($C_1$-$C_4$)-alkyl and —CN, in another embodiment from the series consisting of halogen, —O—($C_1$-$C_4$)-alkyl and —CN, in another embodiment from the series consisting of —O—($C_1$-$C_4$)-alkyl and —CN, in another embodiment from the series consisting of halogen and —CN, in another embodiment from the series consisting of halogen, and in all these embodiments two groups R5 bonded to adjacent ring carbon atoms in Ar, together with the carbon atoms carrying them, can form a 5-membered to 8-membered unsaturated ring which comprises 0, 1 or 2 identical or different ring heteroatoms selected from the series consisting of nitrogen, oxygen and sulfur, and which is unsubstituted or substituted by one or more identical or different substituents R8.

In one embodiment of the invention, R5 is selected from the series consisting of halogen, ($C_1$-$C_4$)-alkyl, ($C_3$-$C_7$)-cycloalkyl, —O—($C_1$-$C_4$)-alkyl, —O—($C_3$-$C_7$)-cycloalkyl, —C(O)—N(R6)-R7 and —CN, in another embodiment from the series consisting of halogen, ($C_1$-$C_4$)-alkyl, ($C_3$-$C_7$)-cycloalkyl, —O—($C_1$-$C_4$)-alkyl, —C(O)—N(R6)-R7 and —CN, in another embodiment from the series consisting of halogen, ($C_1$-$C_4$)-alkyl, —O—($C_1$-$C_4$)-alkyl, —O—($C_3$-$C_7$)-cycloalkyl, —C(O)—N(R6)-R7 and —CN, in another embodiment from the series consisting of halogen, ($C_1$-$C_4$)-alkyl, —O—($C_1$-$C_4$)-alkyl, —C(O)—N(R6)-R7 and —CN, in another embodiment from the series consisting of halogen, ($C_1$-$C_4$)-alkyl, —O—($C_1$-$C_4$)-alkyl and —CN, in another embodiment from the series consisting of halogen, —($C_1$-$C_4$)-alkyl and —CN, in another embodiment from the series consisting of halogen, —O—($C_1$-$C_4$)-alkyl and —CN, in another embodiment from the series consisting of —O—($C_1$-$C_4$)-alkyl and —CN, in another embodiment from the series consisting of halogen and —CN, in another embodiment from the series consisting of halogen.

In one embodiment, substituents R5 which are bonded to a ring nitrogen atom in Ar, such as in the case of a pyrrole, pyrazole or imidazole ring representing Ar, are selected from the series consisting of ($C_1$-$C_4$)-alkyl, ($C_3$-$C_7$)-cycloalkyl, —($C_1$-$C_4$)-alkyl-($C_3$-$C_7$)-cycloalkyl and —C(O)—N(R6)-R7, in another embodiment from the series consisting of ($C_1$-$C_4$)-alkyl, ($C_3$-$C_7$)-cycloalkyl and —($C_1$-$C_4$)-alkyl-($C_3$-$C_7$)-cycloalkyl, in another embodiment from the series consisting of ($C_1$-$C_4$)-alkyl.

In one embodiment of the invention, a ($C_1$-$C_4$)-alkyl group which represents R5 or is present in the group —O—($C_1$-$C_4$)-alkyl representing R5, is a ($C_1$-$C_3$)-alkyl group, in another embodiment a ($C_1$-$C_2$)-alkyl group, in another embodiment a methyl group, wherein all these alkyl groups can optionally be substituted by fluorine substituents as applies to alkyl groups in general, and also occur as a trifluoromethyl group, for example. In one embodiment, an alkyl group representing R5 or present in a group representing R5 is, independently of any other alkyl group occurring in R5, not substituted by fluorine substituents. In one embodiment, a ($C_3$-$C_7$)-cycloalkyl group representing R5 or present in a group representing R5, is a ($C_3$-$C_6$)-cycloalkyl group, in another embodiment a ($C_3$-$C_4$)-cycloalkyl group, in another embodiment a cyclopropyl group. In one embodiment, halogen representing R5 is selected from the series consisting of fluorine and chlorine.

Examples of groups Ar, including the optional substituents R5 on Ar, from any one or more of which Ar is selected in one embodiment of the invention, are 2-chloro-phenyl, 2-fluoro-phenyl, 3-fluoro-phenyl, 2,3-dichloro-phenyl, 2,5-dichloro-phenyl, 2,5-difluoro-phenyl, 2-chloro-3-fluoro-phenyl, 2-chloro-4-fluoro-phenyl, 3-chloro-2-fluoro-phenyl, 5-chloro-2-fluoro-phenyl, 2,3,5-trifluoro-phenyl, 2,4,5-trifluoro-phenyl, 2-chloro-3,5-difluoro-phenyl, 2-chloro-4,5-difluoro-phenyl, 3-chloro-2,5-difluoro-phenyl, 3-chloro-2,6-difluoro-phenyl, 5-chloro-2,4-difluoro-phenyl, 2-fluoro-5-methyl-phenyl, 2-fluoro-5-methoxy-phenyl, 2-chloro-5-methoxy-phenyl, 2-bromo-4,5-dimethoxy-phenyl, 2-fluoro-4,5-dimethoxy-phenyl, 4,5-dimethoxy-2-methyl-phenyl, 2-cyano-phenyl, 3-cyano-phenyl, 2-cyano-3-fluoro-phenyl, 2-cyano-5-fluoro-phenyl, 3-cyano-4-fluoro-phenyl, 5-cyano-2-fluoro-phenyl, 3-chloro-2-cyano-phenyl, 5-chloro-2-cyano-phenyl, 2-cyano-5-methyl-phenyl, 5-cyano-2-methyl-phenyl, 2-cyano-5-methoxy-phenyl, 2-carbamoyl-phenyl, 4-bromo-thiophen-2-yl, 4-chloro-thiophen-3-yl, 5-bromo-thiophen-2-yl, 5-chloro-thiophen-2-yl, 2,5-dichloro-thiophen-3-yl, 4,5-dichloro-thiophen-2-yl, 5-chloro-1,3-dimethyl-pyrazol-4-yl, 7-chloro-2,3-dihydro-benzo[1,4]dioxin-6-yl, 8-bromo-3,4-dihydro-2H-benzo[b][1,4]dioxepin-7-yl, 8-chloro-3,4-dihydro-2H-benzo[b][1,4]dioxepin-7-yl.

In one embodiment of the invention, R6 and R7 are independently of one another selected from the series consisting of hydrogen and ($C_1$-$C_3$)-alkyl, in another embodiment from the series consisting of hydrogen and ($C_1$-$C_2$)-alkyl, in another embodiment from the series consisting of hydrogen and methyl, and in another embodiment R6 and R7 are hydrogen.

In one embodiment of the invention, substituents R8 which can be present in a ring formed by two groups R5 bonded to adjacent ring carbon atoms in Ar together with the carbon atoms carrying them, are selected from the series consisting of halogen, ($C_1$-$C_4$)-alkyl and —CN, in another embodiment from the series consisting of halogen, —O—($C_1$-$C_4$)-alkyl and —CN, in another embodiment from the series consisting of halogen and ($C_1$-$C_4$)-alkyl, in another embodiment from the series consisting of ($C_1$-$C_4$)-alkyl. In one embodiment, substituents R8 which are bonded to a ring nitrogen atom in a ring from by two groups R5 bonded to adjacent ring carbon atoms in Ar together with the carbon atoms carrying them, are selected from the series consisting of ($C_1$-$C_4$)-alkyl.

In one embodiment of the invention, R10 is selected from the series consisting of hydrogen and ($C_1$-$C_3$)-alkyl, in another embodiment from the series consisting of hydrogen and ($C_1$-$C_2$)-alkyl, in another embodiment from the series consisting of hydrogen and methyl, and in another embodiment R10 is hydrogen.

The monocyclic heterocycle which can be formed by the groups R11 and R12 together with the nitrogen atom carrying them, which heterocycle is thus bonded via a ring nitrogen atom, can be 4-membered, 5-membered, 6-membered or 7-membered. In one embodiment of the invention, the heterocycle formed by the groups R11 and R12 together with the nitrogen atom carrying them, is 4-membered to 6-membered, in another embodiment it is 5-membered or 6-membered, in another embodiment it is 6-membered. In one embodiment, the further ring heteroatom which is optionally present in a heterocycle formed by the groups R11 and R12 together with the nitrogen atom carrying them, is selected from the series consisting of nitrogen and oxygen, in another embodiment it is a nitrogen atom, and in another embodiment it is an oxygen atom, and in another embodiment no further ring heteroatom is present. In one embodiment of the invention, the number of substituents selected from the series consisting of fluorine and ($C_1$-$C_4$)-alkyl, which can be present in a ring formed by the groups R11 and R12 together with the nitrogen atom carrying them, is 1, 2 or 3, in another embodiment it is 1 or 2, in another embodiment it is 1. In one embodiment of the invention, substituents which can be present in a ring formed by the groups R11 and R12 together with the nitrogen atom carrying them, are fluorine substituents, and in another embodiment they are ($C_1$-$C_4$)-alkyl substituents, for example methyl substituents. In one embodiment are substituents in a ring formed by the groups R11 and R12 together with the nitrogen atom carrying them, which are bonded to a ring nitrogen atom, selected from the series consisting of ($C_1$-$C_4$)-alkyl. Examples of heterocyclic groups, from any one or more of which the heterocyclic group formed by the groups R11 and R12 together with the nitrogen atom carrying them is selected in one embodiment of the invention, are azetidin-1-yl, pyrrolidin-1-yl, piperidin-1-yl, morpholin-4-yl, thiomorpholin-4-yl, and 4-methylpiperazin-1-yl.

In one embodiment of the invention, one of the groups R11 and R12 is selected from the series consisting of hydrogen and ($C_1$-$C_4$)-alkyl, and the other of the groups R11 and R12 is selected from the series consisting of hydrogen, ($C_1$-$C_4$)-alkyl, ($C_3$-$C_7$)-cycloalkyl, —($C_1$-$C_4$)-alkyl-($C_3$-$C_7$)-cycloalkyl, Het1, —($C_1$-$C_4$)-alkyl-Het1 and —($C_1$-$C_4$)-alkyl-phenyl, in another embodiment the other of the groups R11 and R12 is selected from the series consisting of hydrogen, ($C_1$-$C_4$)-alkyl, —($C_1$-$C_4$)-alkyl-($C_3$-$C_7$)-cycloalkyl and —($C_1$-$C_4$)-alkyl-Het1, in another embodiment the other of the groups R11 and R12 is selected from the series consisting of hydrogen, ($C_1$-$C_4$)-alkyl and —($C_1$-$C_4$)-alkyl-Het1, in another embodiment the groups R11 and R12 are independently of one another selected from the series consisting of hydrogen, ($C_1$-$C_4$)-alkyl, —($C_1$-$C_4$)-alkyl-($C_3$-$C_7$)-cycloalkyl and —($C_1$-$C_4$)-alkyl-Het1, in another embodiment the groups R11 and R12 are independently of one another selected from the series consisting of hydrogen, $(C_1-C_4)$-alkyl and —$(C_1-C_4)$-alkyl-Het1, in another embodiment the groups R11 and R12 are independently of one another selected from the series consisting of hydrogen and $(C_1-C_4)$-alkyl, and in another embodiment the groups R11 and R12 are both hydrogen, i.e., in this latter embodiment the group —N(R11)-R12 representing R1 is the group —NH$_2$ (amino), or in all these embodiments R11 and R12, together with the nitrogen atom carrying them, form a monocyclic, 4-membered to 7-membered, saturated heterocycle which, in addition to the nitrogen atom carrying R11 and R12, comprises 0 or 1 further ring heteroatom selected from the series consisting of nitrogen, oxygen and sulfur, and which is unsubstituted or substituted by one or more identical or different substituents selected from the series consisting of fluorine and $(C_1-C_4)$-alkyl.

In one embodiment of the invention, R11 and R12 are independently of one another selected from the series consisting of hydrogen (H), $(C_1-C_4)$-alkyl, $(C_3-C_7)$-cycloalkyl, —$(C_1-C_4)$-alkyl-$(C_3-C_7)$-cycloalkyl, Het1, —$(C_1-C_4)$-alkyl-Het1 and —$(C_1-C_4)$-alkyl-phenyl, wherein phenyl is unsubstituted or substituted by one or more identical or different substituents R50. In another embodiment, one of the groups R11 and R12 is selected from the series consisting of hydrogen and $(C_1-C_4)$-alkyl, and the other of the groups R11 and R12 is selected from the series consisting of hydrogen, $(C_1-C_4)$-alkyl, $(C_3-C_7)$-cycloalkyl, —$(C_1-C_4)$-alkyl-$(C_3-C_7)$-cycloalkyl, Het1, —$(C_1-C_4)$-alkyl-Het1 and —$(C_1-C_4)$-alkyl-phenyl, in another embodiment the other of the groups R11 and R12 is selected from the series consisting of hydrogen, $(C_1-C_4)$-alkyl, —$(C_1-C_4)$-alkyl-$(C_3-C_7)$-cycloalkyl and —$(C_1-C_4)$-alkyl-Het1, and in another embodiment the other of the groups R11 and R12 is selected from the series consisting of hydrogen, $(C_1-C_4)$-alkyl and —$(C_1-C_4)$-alkyl-Het1. In one embodiment, the groups R11 and R12 are independently of one another selected from the series consisting of hydrogen, $(C_1-C_4)$-alkyl, —$(C_1-C_4)$-alkyl-$(C_3-C_7)$-cycloalkyl and —$(C_1-C_4)$-alkyl-Het1, in another embodiment the groups R11 and R12 are independently of one another selected from the series consisting of hydrogen, $(C_1-C_4)$-alkyl and —$(C_1-C_4)$-alkyl-Het1, in another embodiment the groups R11 and R12 are independently of one another selected from the series consisting of hydrogen and $(C_1-C_4)$-alkyl, and in another embodiment the groups R11 and R12 are both hydrogen, i.e., in this latter embodiment the group —N(R11)-R12 representing R1 is the group —NH$_2$.

In one embodiment, one of the groups R11 and R12 is hydrogen, and the other of the groups R11 and R12 is selected from the series consisting of hydrogen, $(C_1-C_4)$-alkyl, $(C_3-C_7)$-cycloalkyl, —$(C_1-C_4)$-alkyl-$(C_3-C_7)$-cycloalkyl, Het1, —$(C_1-C_4)$-alkyl-Het1 and —$(C_1-C_4)$-alkyl-phenyl, in another embodiment the other of the groups R11 and R12 is selected from the series consisting of hydrogen, $(C_1-C_4)$-alkyl, —$(C_1-C_4)$-alkyl-$(C_3-C_7)$-cycloalkyl and —$(C_1-C_4)$-alkyl-Het1, in another embodiment the other of the groups R11 and R12 is selected from the series consisting of hydrogen, $(C_1-C_4)$-alkyl and —$(C_1-C_4)$-alkyl-Het1, and in another embodiment the other of the groups R11 and R12 is selected from the series consisting of hydrogen and $(C_1-C_4)$-alkyl.

In one embodiment of the invention, R13 is selected from the series consisting of hydrogen and $(C_1-C_4)$-alkyl, in another embodiment from the series consisting of hydrogen and $(C_1-C_3)$-alkyl, in another embodiment from the series consisting of hydrogen and $(C_1-C_2)$-alkyl, in another embodiment from the series consisting of hydrogen and methyl, and in another embodiment R13 is hydrogen.

In one embodiment of the invention, R14 is selected from the series consisting of $(C_3-C_7)$-cycloalkyl, —$(C_1-C_4)$-alkyl-$(C_3-C_7)$-cycloalkyl, phenyl, —$(C_1-C_4)$-alkyl-phenyl, Het2 and —$(C_1-C_4)$-alkyl-Het2, in another embodiment from the series consisting of $(C_3-C_7)$-cycloalkyl, —$(C_1-C_4)$-alkyl-$(C_3-C_7)$-cycloalkyl, phenyl, —$(C_1-C_4)$-alkyl-phenyl and Het2, in another embodiment from the series consisting of $(C_3-C_7)$-cycloalkyl, phenyl, —$(C_1-C_4)$-alkyl-phenyl, Het2 and —$(C_1-C_4)$-alkyl-Het2, in another embodiment from the series consisting of $(C_3-C_7)$-cycloalkyl, phenyl, —$(C_1-C_4)$-alkyl-phenyl and Het2, in another embodiment from the series consisting of $(C_3-C_7)$-cycloalkyl, phenyl and Het2, in another embodiment from the series consisting of $(C_3-C_7)$-cycloalkyl and Het2, in another embodiment R14 is $(C_3-C_7)$-cycloalkyl, in another embodiment R14 is Het2, and in another embodiment R14 is phenyl, wherein in all these embodiments $(C_3-C_7)$-cycloalkyl groups all are unsubstituted or substituted by one or more identical or different substituents selected from the series consisting of —OH and —O—$(C_1-C_4)$-alkyl and, independently thereof, one or more identical or different substituents selected from the series consisting of fluorine and $(C_1-C_4)$-alkyl as applies to cycloalkyl groups in general, and phenyl and Het2 groups all are unsubstituted or substituted by one or more identical or different substituents R50. In one embodiment, the number of substituents selected from the series consisting of —OH and —O—$(C_1-C_4)$-alkyl, which can be present in a $(C_1-C_8)$-alkyl group representing R14 or a $(C_3-C_7)$-cycloalkyl group occurring in R14, is 1, 2 or 3, in another embodiment it is 1 or 2, in another embodiment it is 1. In one embodiment, the number of substituents R50 which can be present in a phenyl group or Het2 group representing R14 or occurring in R14, is 1, 2 or 3, in another embodiment it is 1 or 2, in another embodiment it is 1.

In one embodiment of the invention, R15 is selected from the series consisting of phenyl and Het3, in another embodiment from the series consisting of $(C_1-C_8)$-alkyl and phenyl, and in another embodiment R15 is phenyl, wherein in all these embodiments phenyl and Het3 all are unsubstituted or substituted by one or more identical or different substituents R50. In one embodiment, the number of substituents R50 which can be present in a phenyl group or Het3 group representing R15 is 1, 2, 3 or 4, in another embodiment it is 1, 2 or 3, in another embodiment it is 1 or 2, in another embodiment it is 1.

In one embodiment of the invention, R16 is selected from the series consisting of $(C_1-C_8)$-alkyl, $(C_3-C_7)$-cycloalkyl, —$(C_1-C_4)$-alkyl-$(C_3-C_7)$-cycloalkyl, —$(C_1-C_4)$-alkyl-phenyl, Het2 and —$(C_1-C_4)$-alkyl-Het2, in another embodiment from the series consisting of $(C_3-C_7)$-cycloalkyl, —$(C_1-C_4)$-alkyl-$(C_3-C_7)$-cycloalkyl, —$(C_1-C_4)$-alkyl-phenyl, Het2 and —$(C_1-C_4)$-alkyl-Het2, in another embodiment from the series consisting of —$(C_1-C_4)$-alkyl-phenyl, Het2 and —$(C_1-C_4)$-alkyl-Het2, in another embodiment from the series consisting of —$(C_1-C_4)$-alkyl-phenyl and —$(C_1-C_4)$-alkyl-Het2, wherein $(C_1-C_8)$-alkyl and $(C_3-C_7)$-cycloalkyl all are unsubstituted or substituted by one or more identical or different substituents selected from the series consisting of —OH and —O—$(C_1-C_4)$-alkyl and, independently thereof, fluorine substituents and, in case of cycloalkyl groups, $(C_1-C_4)$-alkyl substituents, and wherein phenyl and Het2 all are unsubstituted or substituted by one or more identical or different substituents R50. In one embodiment, the number of substituents selected from the series consisting of —OH and —O—$(C_1-C_4)$-alkyl, which can be present in a $(C_1-C_8)$-alkyl group representing R16 or a $(C_3-C_7)$-cycloalkyl group occurring in R16, is 1 or 2, in another embodiment it is 1, and in another embodiment it is 0. In one embodiment, the number of substituents R50 which can be present in a phenyl group or Het2 group representing R16 or occurring in R16, is 1, 2 or 3, in another embodiment it is 1 or 2, in another embodiment it is 1, and in another embodiment it is 0.

In one embodiment of the invention, R17 is $(C_1-C_4)$-alkyl, in another embodiment R17 is hydrogen. In one embodiment, a $(C_1-C_4)$-alkyl group representing R17 is $(C_1-C_3)$-alkyl, in another embodiment it is $(C_1-C_2)$-alkyl, in another embodiment it is methyl.

The cyclic group R30, which can be monocyclic and bicyclic, can contain 3, 4, 5, 6, 7, 8, 9, 10, 11 or 12 ring members. In one embodiment of the invention, R30 contains 3, 4, 5, 6, 7, 8, 9, 10 or 11 ring members, in another embodiment 3, 4, 5, 6, 7, 8, 9 or 10 ring members, in another embodiment 3, 4, 5, 6, 7, 8 or 9 ring members. In one embodiment, the number of ring members in a monocyclic group R30 is 3, 4, 5, 6 or 7, in another embodiment 3, 4, 5 or 6, in another embodiment 3 or 4, in another embodiment 5, 6 or 7, in another embodiment 5 or 6, in another embodiment 3, in another embodiment 4, in another embodiment 5, in another embodiment 6, and the number of ring members in a bicyclic group R30 is 6, 7, 8, 9, 10, 11 or 12, in another embodiment 6, 7, 8, 9, 10 or 11, in another embodiment 6, 7, 8, 9 or 10, in another embodiment 7, 8, 9, 10 or 11, in another embodiment 7, 8, 9 or 10, in another embodiment 7, 8 or 9, in another embodiment 8, 9 or 10. In one embodiment, the number of ring members of the cyclic group R30 is from 3 to 12 in the case of a carbocyclic ring, and from 4 to 12 in the case of a heterocyclic ring. In one embodiment, the cyclic group R30 is monocyclic, in another embodiment it is bicyclic. A bicyclic group R30 can be a fused ring system or a bridged ring system or a spirocyclic ring system. In one embodiment, a bicyclic group R30 is a fused or bridged ring system, in another embodiment it is a fused or spirocyclic ring system, in another embodiment it is a bridged or spirocyclic ring system, in another embodiment it is a fused ring system, in another embodiment it is a bridged ring system, and in another embodiment it is a spirocyclic ring system. In one embodiment, the cyclic group R30 is a saturated group, i.e. it does not contain a double bond within the ring, or it is an aromatic group, i.e. it contains two double bonds within the ring in the case of a 5-membered monocyclic aromatic heterocycle which double bonds, together with an electron pair on a ring heteroatom, form a delocalized cyclic system of six pi electrons, and three double bonds within the ring in the case of a phenyl group or a 6-membered monocyclic aromatic heterocycle, or two, three, four or five double bonds within two fused rings in the case of a bicyclic group comprising one or two aromatic rings. In another embodiment, R30 is a partially unsaturated group, i.e. it contains one or more, for example one or two, double bonds within the ring via which it is bonded, but is not aromatic within this ring. In another embodiment, R30 is a saturated group or it is a partially unsaturated group, in another embodiment R30 is an aromatic group or it is a partially unsaturated group, in another embodiment R30 is a saturated group, and in another embodiment R30 is an aromatic group.

The cyclic group R30 can be a carbocyclic group, i.e. comprise 0 (zero) ring heteroatoms, or a heterocyclic group, i.e. comprise 1, 2 or 3 identical or different ring heteroatoms. In one embodiment, R30 comprises 0, 1 or 2 identical or different ring heteroatoms, in another embodiment 0 or 1 ring heteroatom. In another embodiment, R30 comprises 0 ring heteroatoms, i.e. R30 is a carbocyclic group. In another embodiment R30 is a heterocyclic group which comprises 1, 2 or 3 identical or different ring heteroatoms, in another embodiment 1 or 2 identical or different ring heteroatoms, in another embodiment 1 ring heteroatom. In one embodiment, the ring heteroatoms in R30 are selected from the series consisting of nitrogen and oxygen, in another embodiment from the series consisting of oxygen and sulfur, in another embodiment they are nitrogen atoms, and in another embodiment they are oxygen atoms. Heterocyclic groups representing R30 can be bonded to the group Z via a ring carbon atom or a ring nitrogen atom. In one embodiment, a heterocyclic group representing R30 is bonded via a ring carbon atom, in another embodiment it is bonded via a ring nitrogen atom.

Examples of carbocyclic groups, which may represent R30 and any one or more of which may be included in the definition of R30 in one embodiment of the invention, and from any one or more of which R30 is selected in another embodiment, are cycloalkyl groups such as $(C_3-C_7)$-cycloalkyl, including cyclopropyl, cyclobutyl, cyclopentyl, cyclohexyl and cycloheptyl, cycloalkenyl groups such as $(C_5-C_7)$-cycloalkenyl, including cyclopentenyl, cyclohexenyl and cycloheptenyl, bicycloalkyl groups such as $(C_6-C_{12})$-bicycloalkyl, phenyl groups, indanyl groups, including indan-1-yl and indan-2-yl, and naphthyl groups, including naphthalen-1-yl and naphthalen-2-yl, for example, which can all be unsubstituted or substituted by one or more identical or different substituents R32. The explanations given above, for example with respect to cycloalkyl groups and phenyl groups, apply also to such groups representing R30.

Examples of heterocyclic groups, which may represent R30 and any one or more of which may be included in the definition of R30 in one embodiment of the invention, and from any one or more of which R30 is selected in another embodiment, are 4-membered to 7-membered, monocyclic, saturated, partially unsaturated or aromatic, heterocyclic groups which comprise 1, 2 or 3 identical or different ring heteroatoms selected from the series consisting of nitrogen, oxygen and sulfur and are bonded via a nitrogen atom, 6-membered to 12-membered, bicyclic, saturated or partially unsaturated, heterocyclic groups which comprise 1, 2 or 3 identical or different ring heteroatoms selected from the series consisting of nitrogen, oxygen and sulfur and are bonded via a nitrogen atom, and the groups Het1, Het2 and Het3, and more specifically oxetanyl including oxetan-2-yl and oxetan-3-yl, tetrahydrofuranyl including tetrahydrofuran-2-yl and tetrahydrofuran-3-yl, tetrahydropyranyl including tetrahydropyran-2-yl, tetrahydropyran-3-yl and tetrahydropyran-4-yl, oxepanyl including oxepan-2-yl, oxepan-3-yl and oxepan-4-yl, azetidinyl including azetidin-1-yl, azetidin-2-yl and azetidin-3-yl, pyrrolidinyl including pyrrolidin-1-yl, pyrrolidin-2-yl and pyrrolidin-3-yl, piperidinyl including piperidin-1-yl, piperidin-2-yl, piperidin-3-yl and piperidin-4-yl, azepanyl including azepan-1-yl, azepan-2-yl, azepan-3-yl and azepan-4-yl, morpholinyl including morpholin-2-yl, morpholin-3-yl and morpholin-4-yl, thiomorpholinyl including thiomorpholin-2-yl, thiomorpholin-3-yl and thiomorpholin-4-yl, piperazinyl including piperazin-1-yl and piperazin-2-yl, furanyl including furan-2-yl and furan-3-yl, thiophenyl (thienyl) including thiophen-2-yl and thiophen-3-yl, pyrrolyl including pyrrol-1-yl, pyrrol-2-yl and pyrrol-3-yl, isoxazolyl including isoxazol-3-yl, isoxazol-4-yl and isoxazol-5-yl, oxazolyl including oxazol-2-yl, oxazol-4-yl and oxazol-5-yl, thiazolyl including thiazol-2-yl, thiazol-4-yl and thiazol-5-yl, pyrazolyl including pyrazol-1-yl, pyrazol-3-yl, pyrazol-4-yl and pyrazol-5-yl, imidazolyl including imidazolyl-1-yl, imidazol-2-yl, imidazol-4-yl and imidazol-5-yl, [1,2,4]triazolyl including [1,2,4]triazol-1-yl, [1,2,4]triazol-3-yl and [1,2,4]triazol-5-yl, pyridinyl (pyridyl) including pyridin-2-yl, pyridin-3-yl and pyridin-4-yl, pyrazinyl including pyrazin-2-yl, for example, which can all be unsubstituted or substituted by one or more identical or different substituents R32. The explanations given above and below, for example with respect to heterocyclic groups in general and the groups Het1, Het2 and Het3, apply also to such groups representing R30.

In one embodiment of the invention, the number of substituents R32 which can be present in R30, is 1, 2, 3, 4, 5 or 6, in another embodiment it is 1, 2, 3, 4 or 5, in another embodiment it is 1, 2, 3 or 4, in another embodiment it is 1, 2 or 3, in another embodiment it is 1 or 2, in another embodiment it is 1. In another embodiment, R30 is unsubstituted.

In one embodiment of the invention, R31 is selected from the series consisting of halogen, —OH, —O—($C_1$-$C_4$)-alkyl, —O—($C_3$-$C_7$)-cycloalkyl, —O—($C_1$-$C_4$)-alkyl-($C_3$-$C_7$)-cycloalkyl, —N(R33)-R34 and —CN, in another embodiment from the series consisting of halogen, —OH, —O—($C_1$-$C_4$)-alkyl, —O—($C_3$-$C_7$)-cycloalkyl, —N(R33)-R34 and —CN, in another embodiment from the series consisting of halogen, —OH, —O—($C_1$-$C_4$)-alkyl, —O—($C_3$-$C_7$)-cycloalkyl, —N(R33)-R34, —CN and —C(O)—N(R35)-R36, in another embodiment from the series consisting of halogen, —OH, —O—($C_1$-$C_4$)-alkyl, —O—($C_3$-$C_7$)-cycloalkyl, —O—($C_1$-$C_4$)-alkyl-($C_3$-$C_7$)-cycloalkyl and —N(R33)-R34, in another embodiment from the series consisting of halogen, —OH, —O—($C_1$-$C_4$)-alkyl, —O—($C_3$-$C_7$)-cycloalkyl, —O—($C_1$-$C_4$)-alkyl-($C_3$-$C_7$)-cycloalkyl, —N(R33)-R34 and —C(O)—N(R35)-R36, in another embodiment from the series consisting of halogen, —OH, —O—($C_1$-$C_4$)-alkyl, —O—($C_3$-$C_7$)-cycloalkyl and —N(R33)-R34, in another embodiment from the series consisting of halogen, —OH, —O—($C_1$-$C_4$)-alkyl, —O—($C_3$-$C_7$)-cycloalkyl, —N(R33)-R34 and —C(O)—N(R35)-R36, in another embodiment from the series consisting of halogen, —OH, —O—($C_1$-$C_4$)-alkyl and —N(R33)-R34, in another embodiment from the series consisting of halogen, —OH, —O—($C_1$-$C_4$)-alkyl, —N(R33)-R34 and —C(O)—N(R35)-R36, in another embodiment from the series consisting of halogen, —OH, —O—($C_1$-$C_4$)-alkyl, —N(R33)-R34 and —CN, in another embodiment from the series consisting of halogen, —OH, —O—($C_1$-$C_4$)-alkyl, —N(R33)-R34, —CN and —C(O)—N(R35)-R36, in another embodiment from the series consisting of halogen, —OH, —O—($C_1$-$C_4$)-alkyl, —O—($C_3$-$C_7$)-cycloalkyl and —O—($C_1$-$C_4$)-alkyl-($C_3$-$C_7$)-cycloalkyl, in another embodiment from the series consisting of halogen, —OH, —O—($C_1$-$C_4$)-alkyl and —O—($C_3$-$C_7$)-cycloalkyl, in another embodiment from the series consisting of halogen, —OH and —O—($C_1$-$C_4$)-alkyl, in another embodiment from the series consisting of halogen and —N(R33)-R34, in another embodiment from the series consisting of —OH, —O—($C_1$-$C_4$)-alkyl and —N(R33)-R34, in another embodiment from the series consisting of —OH, —O—($C_1$-$C_4$)-alkyl, —N(R33)-R34 and —C(O)—N(R35)-R36, in another embodiment from the series consisting of —OH, —O—($C_1$-$C_4$)-alkyl, —O—($C_3$-$C_7$)-cycloalkyl and —O—($C_1$-$C_4$)-alkyl-($C_3$-$C_7$)-cycloalkyl, in another embodiment from the series consisting of —OH, —O—($C_1$-$C_4$)-alkyl and —O—($C_3$-$C_7$)-cycloalkyl. In one embodiment, halogen representing R31 is selected from the series consisting of fluorine and chlorine, in another embodiment halogen representing R31 is fluorine.

In one embodiment of the invention, R32 is selected from the series consisting of halogen, ($C_1$-$C_4$)-alkyl, ($C_3$-$C_7$)-cycloalkyl, —($C_1$-$C_4$)-alkyl-($C_3$-$C_7$)-cycloalkyl, —($C_1$-$C_4$)-alkyl-O—R37, —($C_1$-$C_4$)-alkyl-N(R38)-R39, —C(O)—($C_1$-$C_4$)-alkyl, —OH, =O, —O—($C_1$-$C_4$)-alkyl, —N(R40)-R41, —C(O)—O—($C_1$-$C_4$)-alkyl and —C(O)—N(R42)-R43, in another embodiment from the series consisting of halogen, ($C_1$-$C_4$)-alkyl, ($C_3$-$C_7$)-cycloalkyl, —($C_1$-$C_4$)-alkyl-($C_3$-$C_7$)-cycloalkyl, —($C_1$-$C_4$)-alkyl-O—R37, —($C_1$-$C_4$)-alkyl-N(R38)-R39, —OH, =O, —O—($C_1$-$C_4$)-alkyl, —N(R40)-R41, —C(O)—O—($C_1$-$C_4$)-alkyl and —C(O)—N(R42)-R43, in another embodiment from the series consisting of halogen, ($C_1$-$C_4$)-alkyl, ($C_3$-$C_7$)-cycloalkyl, —($C_1$-$C_4$)-alkyl-($C_3$-$C_7$)-cycloalkyl, —($C_1$-$C_4$)-alkyl-O—R37, —($C_1$-$C_4$)-alkyl-N(R38)-R39, —OH, =O, —O—($C_1$-$C_4$)-alkyl and —N(R40)-R41, in another embodiment from the series consisting of halogen, ($C_1$-$C_4$)-alkyl, ($C_3$-$C_7$)-cycloalkyl, —($C_1$-$C_4$)-alkyl-O—R37, —($C_1$-$C_4$)-alkyl-N(R38)-R39, —OH, =O, —O—($C_1$-$C_4$)-alkyl and —N(R40)-R41, in another embodiment from the series consisting of halogen, ($C_1$-$C_4$)-alkyl, ($C_3$-$C_7$)-cycloalkyl, —($C_1$-$C_4$)-alkyl-O—R37, —($C_1$-$C_4$)-alkyl-N(R38)-R39, —OH, =O and —O—($C_1$-$C_4$)-alkyl, in another embodiment from the series consisting of halogen, ($C_1$-$C_4$)-alkyl, ($C_3$-$C_7$)-cycloalkyl, —($C_1$-$C_4$)-alkyl-O—R37, —OH, =O and —O—($C_1$-$C_4$)-alkyl, in another embodiment from the series consisting of halogen, ($C_1$-$C_4$)-alkyl, ($C_3$-$C_7$)-cycloalkyl, —($C_1$-$C_4$)-alkyl-O—R37, —($C_1$-$C_4$)-alkyl-N(R38)-R39, —OH and —O—($C_1$-$C_4$)-alkyl, in another embodiment from the series consisting of halogen, ($C_1$-$C_4$)-alkyl, ($C_3$-$C_7$)-cycloalkyl, —($C_1$-$C_4$)-alkyl-O—R37, —($C_1$-$C_4$)-alkyl-N(R38)-R39, —OH and =O, in another embodiment from the series consisting of halogen, ($C_1$-$C_4$)-alkyl, ($C_3$-$C_7$)-cycloalkyl, —($C_1$-$C_4$)-alkyl-O—R37 and —OH, in another embodiment from the series consisting of halogen, ($C_1$-$C_4$)-alkyl, ($C_3$-$C_7$)-cycloalkyl and —OH, in another embodiment from the series consisting of halogen, ($C_1$-$C_4$)-alkyl and ($C_3$-$C_7$)-cycloalkyl, in another embodiment from the series consisting of —OH and —O—($C_1$-$C_4$)-alkyl, in another embodiment from the series consisting of halogen and —OH, in another embodiment from the series consisting of halogen, ($C_1$-$C_4$)-alkyl, ($C_3$-$C_7$)-cycloalkyl, —($C_1$-$C_4$)-alkyl-O—R37, —OH and —O—($C_1$-$C_4$)-alkyl, in another embodiment from the series consisting of halogen, ($C_1$-$C_4$)-alkyl, ($C_3$-$C_7$)-cycloalkyl, —OH and —O—($C_1$-$C_4$)-alkyl, in another embodiment from the series consisting of halogen, ($C_1$-$C_4$)-alkyl, —OH and —O—($C_1$-$C_4$)-alkyl, in another embodiment from the series consisting of halogen, —OH and —O—($C_1$-$C_4$)-alkyl, in another embodiment from the series consisting of —OH and —O—($C_1$-$C_4$)-alkyl, and in another embodiment R32 is —OH. In another embodiment R32 is selected from the series of halogen, ($C_1$-$C_4$)-alkyl, ($C_3$-$C_7$)-cycloalkyl, —($C_1$-$C_4$)-alkyl-($C_3$-$C_7$)-cycloalkyl, —($C_1$-$C_4$)-alkyl-O—R37, —($C_1$-$C_4$)-alkyl-N(R38)-R39, —C(O)—($C_1$-$C_4$)-alkyl, —OH, =O, —O—($C_1$-$C_4$)-alkyl, —N(R40)-R41, —C(O)—O—($C_1$-$C_4$)-alkyl and —C(O)—N(R42)-R43, in another embodiment from the series consisting of halogen, ($C_1$-$C_4$)-alkyl, ($C_3$-$C_7$)-cycloalkyl, —($C_1$-$C_4$)-alkyl-($C_3$-$C_7$)-cycloalkyl, —($C_1$-$C_4$)-alkyl-O—R37, —($C_1$-$C_4$)-alkyl-N(R38)-R39, —C(O)—($C_1$-$C_4$)-alkyl, —OH, =O, —O—($C_1$-$C_4$)-alkyl and —N(R40)-R41, in another embodiment from the series consisting of halogen, ($C_1$-$C_4$)-alkyl, ($C_3$-$C_7$)-cycloalkyl, —($C_1$-$C_4$)-alkyl-O—R37, —($C_1$-$C_4$)-alkyl- N(R38)-R39, —C(O)—($C_1$-$C_4$)-alkyl, —OH, =O, —O—($C_1$-$C_4$)-alkyl and —N(R40)-R41, in another embodiment from the series consisting of halogen, ($C_1$-$C_4$)-alkyl, ($C_3$-$C_7$)-cycloalkyl, —($C_1$-$C_4$)-alkyl-O—R37, —($C_1$-$C_4$)-alkyl-N(R38)-R39, —C(O)—($C_1$-$C_4$)-alkyl, —OH, =O and —O—($C_1$-$C_4$)-alkyl, in another embodiment from the series consisting of halogen, ($C_1$-$C_4$)-alkyl, ($C_3$-$C_7$)-cycloalkyl, —($C_1$-$C_4$)-alkyl-O—R37, —OH, =O and —O—($C_1$-$C_4$)-alkyl, in another embodiment from the series consisting of halogen, ($C_1$-$C_4$)-alkyl, ($C_3$-$C_7$)-cycloalkyl, —($C_1$-$C_4$)-alkyl-O—R37, —($C_1$-$C_4$)-alkyl-N(R38)-R39, —C(O)—($C_1$-$C_4$)-alkyl, —OH and —O—($C_1$-$C_4$)-alkyl, in another embodiment from the series consisting of halogen, ($C_1$-$C_4$)-alkyl, ($C_3$-$C_7$)-cycloalkyl, —($C_1$-$C_4$)-alkyl-O—R37, —($C_1$-$C_4$)-alkyl-N(R38)-R39, —C(O)—($C_1$-$C_4$)-alkyl, —OH and =O, in another embodiment from the series consisting of halogen, ($C_1$-$C_4$)-alkyl, ($C_3$-$C_7$)-cycloalkyl, —($C_1$-$C_4$)-alkyl-O—R37, —C(O)—($C_1$-$C_4$)-alkyl and —OH, in another embodiment from the series consisting of halogen, ($C_1$-$C_4$)-alkyl, ($C_3$-$C_7$)-cycloalkyl, —C(O)—($C_1$-$C_4$)-alkyl and —OH, in another embodiment from the series consisting of halogen, ($C_1$-$C_4$)-alkyl and ($C_3$-$C_7$)-cycloalkyl and —C(O)—($C_1$-$C_4$)-alkyl, in another embodiment from the series consisting of halogen, ($C_1$-$C_4$)-alkyl, ($C_3$-$C_7$)-cycloalkyl, —($C_1$-$C_4$)-alkyl-O—R37, —C(O)—($C_1$-$C_4$)-alkyl, —OH and —O—($C_1$-$C_4$)-alkyl, and in another embodiment from the series consisting of halogen, ($C_1$-$C_4$)-alkyl, ($C_3$-$C_7$)-cycloalkyl, —C(O)—($C_1$-$C_4$)-alkyl, —OH and —O—($C_1$-$C_4$)-alkyl.

In one embodiment, substituents R32 which are bonded to ring nitrogen atoms in R30, are selected from the series consisting of ($C_1$-$C_4$)-alkyl, ($C_3$-$C_7$)-cycloalkyl, —($C_1$-$C_4$)-alkyl-($C_3$-$C_7$)-cycloalkyl, —($C_1$-$C_4$)-alkyl-O—R37, —($C_1$-$C_4$)-alkyl-N(R38)-R39, —($C_1$-$C_4$)-alkyl-CN, —C(O)—($C_1$-$C_4$)-alkyl, —C(O)—O—($C_1$-$C_4$)-alkyl and —C(O)—N(R42)-R43, in another embodiment from the series consisting of ($C_1$-$C_4$)-alkyl, ($C_3$-$C_7$)-cycloalkyl, —($C_1$-$C_4$)-alkyl-($C_3$-$C_7$)-cycloalkyl, —($C_1$-$C_4$)-alkyl-O—R37, —($C_1$-$C_4$)-alkyl-N(R38)-R39 and —($C_1$-$C_4$)-alkyl-CN, in another embodiment from the series consisting of ($C_1$-$C_4$)-alkyl, ($C_3$-$C_7$)-cycloalkyl, —($C_1$-$C_4$)-alkyl-($C_3$-$C_7$)-cycloalkyl and —($C_1$-$C_4$)-alkyl-O—R37, in another embodiment from the series consisting of ($C_1$-$C_4$)-alkyl, ($C_3$-$C_7$)-cycloalkyl and —($C_1$-$C_4$)-alkyl-O—R37. In one embodiment, the number of oxo substituents (=O) occurring in the cyclic group R30 is not greater than two, in another embodiment it is not greater than one. In one embodiment, halogen representing R32 is selected from the series consisting of fluorine and chlorine, in another embodiment halogen representing R32 is fluorine. In another embodiment, substituents R32 which are bonded to ring nitrogen atoms in R30, are selected from the series consisting of ($C_1$-$C_4$)-alkyl, ($C_3$-$C_7$)-cycloalkyl, —($C_1$-$C_4$)-alkyl-($C_3$-$C_7$)-cycloalkyl, —($C_1$-$C_4$)-alkyl-O—R37, —($C_1$-$C_4$)-alkyl-N(R38)-R39 and —C(O)—($C_1$-$C_4$)-alkyl, in another embodiment from the series consisting of ($C_1$-$C_4$)-alkyl, ($C_3$-$C_7$)-cycloalkyl, —($C_1$-$C_4$)-alkyl-($C_3$-$C_7$)-cycloalkyl, —($C_1$-$C_4$)-alkyl-O—R37 and —C(O)—($C_1$-$C_4$)-alkyl, in another embodiment from the series consisting of ($C_1$-$C_4$)-alkyl, ($C_3$-$C_7$)-cycloalkyl, —($C_1$-$C_4$)-alkyl-O—R37 and —C(O)—($C_1$-$C_4$)-alkyl, in another embodiment from the series consisting of ($C_1$-$C_4$)-alkyl, ($C_3$-$C_7$)-cycloalkyl and —C(O)—($C_1$-$C_4$)-alkyl. In one embodiment, the number of oxo (=O) substituents R32 occurring in the cyclic group R30 is not greater than two, in another embodiment it is not greater than one. In one embodiment, halogen representing R32 is selected from the series consisting of fluorine and chlorine, in another embodiment halogen representing R32 is fluorine.

In one embodiment of the invention, R33, R34, R35, R36, R37, R38, R39, R40, R41, R42 and R43 are independently of one another selected from the series consisting of hydrogen and ($C_1$-$C_3$)-alkyl, in another embodiment from the series consisting of hydrogen and ($C_1$-$C_2$)-alkyl, in another embodiment from the series consisting of hydrogen and methyl. In another embodiment, any of the groups R33, R34, R35, R36, R37, R38, R39, R40, R41, R42 and R43 is independently of any other group hydrogen, in another embodiment it is ($C_1$-$C_4$)-alkyl, in another embodiment ($C_1$-$C_3$)-alkyl, in another embodiment ($C_1$-$C_2$)-alkyl, and in another embodiment methyl.

In one embodiment of the invention, R50 is in any of its occurrences, independently of its other occurrences, selected from the series consisting of halogen, ($C_1$-$C_4$)-alkyl and —CN; in another embodiment from the series consisting of halogen, ($C_1$-$C_4$)-alkyl and —O—($C_1$-$C_4$)-alkyl, in another embodiment from the series consisting of halogen and ($C_1$-$C_4$)-alkyl, in another embodiment from the series consisting of halogen and —CN, in another embodiment from the series consisting of halogen. In one embodiment, a group R50 which is bonded to ring nitrogen atom in a group Het2 or Het3, is selected from the series consisting of ($C_1$-$C_4$)-alkyl. In one embodiment, a ($C_1$-$C_4$)-alkyl group representing R50 or occurring in R50 is in any occurrence of R50, independently of other occurrences, selected from ($C_1$-$C_3$)-alkyl, in another embodiment from ($C_1$-$C_2$)-alkyl, and in another embodiment it is methyl.

The group Het1 can contain 4, 5, 6 or 7 ring members. In one embodiment of the invention, Het1 is 4-membered to 6-membered, in another embodiment 5-membered or 6-membered, in another embodiment 6-membered. In one embodiment, Het1 comprises 1 ring heteroatom. In one embodiment, the ring heteroatoms in Het1 are selected from the series consisting of nitrogen and oxygen, in another embodiment from the series consisting of oxygen and sulfur, in another embodiment they are nitrogen atoms, and in another embodiment they are oxygen atoms. Examples of heterocycles, from any one or more of which Het1 is chosen in one embodiment, are oxetanyl, tetrahydrofuranyl, tetrahydropyranyl, oxepanyl, tetrahydrothiophenyl, tetrahydrothiopyranyl, azetidinyl, pyrrolidinyl, piperidinyl, azepanyl, morpholinyl, thiomorpholinyl and piperazinyl. In one embodiment, the number of optional substituents in a group Het1 is 1, 2, 3 or 4, in another embodiment it is 1, 2 or 3, in another embodiment it is 1 or 2, in another embodiment it is 1, and in another embodiment Het1 is unsubstituted. In one embodiment, substituents which are bonded to a ring nitrogen atom in Het1, are selected from the series consisting of ($C_1$-$C_4$)-alkyl.

The group Het2 can contain 4, 5, 6 or 7 ring members. In one embodiment of the invention, Het2 is 4-membered to 6-membered, in another embodiment 5-membered or 6-membered, in another embodiment 5-membered, in another embodiment 6-membered. In one embodiment, Het2 is a saturated or aromatic group, in another embodiment a saturated group, in another embodiment an aromatic group. In one embodiment, Het2 comprises 1 ring heteroatom. In one embodiment, the ring heteroatoms in Het2 are selected from the series consisting of nitrogen and oxygen, in another embodiment from the series consisting of nitrogen and sulfur, in another embodiment from the series consisting of oxygen and sulfur, in another embodiment they are nitrogen atoms, in another embodiment they are oxygen atoms, and in another embodiment they are sulfur atoms. Examples of heterocycles, from any one or more of which Het2 is chosen in one embodiment, are oxetanyl, tetrahydrofuranyl, furanyl, tetrahydropyranyl, oxepanyl, tetrahydrothiophenyl, thiophenyl, tetrahydrothiopyranyl, azetidinyl, pyrrolidinyl, pyrrolyl, piperidinyl, pyridinyl, azepanyl, pyrazolyl, imidazolyl, oxazolyl, isoxazolyl, thiazolyl, morpholinyl, thiomorpholinyl and piperazinyl.

In one embodiment of the invention, the group Het3 is 5-membered, in another embodiment it is 6-membered. In one embodiment, Het3 comprises 1 or 2 identical or different ring heteroatoms, in another embodiment 1 ring heteroatom. In one embodiment, the ring heteroatoms in Het3 are selected from the series consisting of nitrogen and oxygen, in another embodiment from the series consisting of nitrogen and sulfur, in another embodiment they are nitrogen atoms, and in another embodiment they are sulfur atoms. Examples of heterocycles, from any one or more of which Het3 is chosen in one embodiment, are furanyl, thiophenyl, pyrrolyl, pyridinyl, pyrazolyl, imidazolyl, [1,2,4]triazolyl, oxazolyl, isoxazolyl and thiazolyl.

A subject of the invention are all compounds of the formula I wherein any one or more structural elements such as groups, residues, substituents and numbers are defined as in any of the specified embodiments or definitions of the elements, or have one or more of the specific meanings which are mentioned herein as examples of elements, wherein all combinations of one or more definitions of compounds or elements and/or specified embodiments and/or specific meanings of elements are a subject of the present invention. Also with respect to all such compounds of the formula I, all their stereoisomeric forms and mixtures of stereoisomeric forms in any ratio, and their pharmaceutically acceptable salts are a subject of the present invention.

As an example of compounds of the invention which with respect to any structural elements are defined as in specified embodiments of the invention or definitions of such elements, compounds of the formula I may be mentioned, in any of their stereoisomeric forms or a mixture of stereoisomeric forms in any ratio, and the pharmaceutically acceptable salts thereof, wherein Ar is selected from the series consisting of phenyl and a 5-membered or 6-membered, monocyclic, aromatic, heterocyclic group which comprises 1 or 2 identical or different ring heteroatoms selected from the series consisting of nitrogen, oxygen and sulfur, and is bonded via a ring carbon atom, which all are unsubstituted or substituted by one or more identical or different substituents R5;

n is selected from the series consisting of 0, 1 and 2;

X is selected from the series consisting of N and CH;

Z is selected from the series consisting of a direct bond, O, S and N(R10);

R1 is selected from the series consisting of H, —N(R11)-R12, —N(R13)-C(O)—R14, —N(R13)-S(O)$_2$—R15, —N(R13)-C(O)—NH—R16 and ($C_1$-$C_4$)-alkyl;

R2 is selected from the series consisting of halogen, ($C_1$-$C_4$)-alkyl, —O—($C_1$-$C_4$)-alkyl and —CN;

R3 is selected from the series consisting of H, ($C_1$-$C_8$)-alkyl, R30 and —($C_1$-$C_4$)-alkyl-R30, wherein ($C_1$-$C_8$)-alkyl is unsubstituted or substituted by one or more identical or different substituents R31;

R5 is selected from the series consisting of halogen, ($C_1$-$C_4$)-alkyl, ($C_3$-$C_7$)-cycloalkyl, —O—($C_1$-$C_4$)-alkyl, —O—($C_3$-$C_7$)-cycloalkyl, —C(O)—N(R6)-R7 and —CN, and two groups R5 bonded to adjacent ring carbon atoms in Ar, together with the carbon atoms carrying them, can form a 5-membered to 8-membered, monocyclic, unsaturated ring which comprises 0, 1 or 2 identical or different ring heteroatoms selected from the series consisting of nitrogen, oxygen and sulfur, and which is unsubstituted or substituted by one or more identical or different substituents R8;

R6 and R7 are independently of one another selected from the series consisting of H and ($C_1$-$C_4$)-alkyl;

R8 is selected from the series consisting of halogen and ($C_1$-$C_4$)-alkyl;

R10 is selected from the series consisting of H and ($C_1$-$C_4$)-alkyl;

R11 and R12 are independently of one another selected from the series consisting of H, ($C_1$-$C_4$)-alkyl, ($C_3$-$C_7$)-cycloalkyl, —($C_1$-$C_4$)-alkyl-($C_3$-$C_7$)-cycloalkyl, Het1, —($C_1$-$C_4$)-alkyl-Het1 and —($C_1$-$C_4$)-alkyl-phenyl, wherein phenyl is unsubstituted or substituted by one or more identical or different substituents R50;

R13 is selected from the series consisting of H and ($C_1$-$C_4$)-alkyl;

R14 and R16 are independently of one another selected from the series consisting of ($C_1$-$C_8$)-alkyl, ($C_3$-$C_7$)-cycloalkyl, —($C_1$-$C_4$)-alkyl-($C_3$-$C_7$)-cycloalkyl, phenyl, —($C_1$-$C_4$)-alkyl-phenyl, Het2 and —($C_1$-$C_4$)-alkyl-Het2, wherein ($C_1$-$C_8$)-alkyl and ($C_3$-$C_7$)-cycloalkyl all are unsubstituted or substituted by one or more identical or different substituents selected from the series consisting of —OH and —O—($C_1$-$C_4$)-alkyl, and wherein phenyl and Het2 all are unsubstituted or substituted by one or more identical or different substituents R50;

R15 is selected from the series consisting of phenyl and Het3, wherein phenyl and Het3 all are unsubstituted or substituted by one or more identical or different substituents R50;

R30 is a 3-membered to 12-membered, monocyclic or bicyclic, saturated, partially unsaturated or aromatic, cyclic group which comprises 0, 1, 2 or 3 identical or different ring heteroatoms selected from the series consisting of nitrogen, oxygen and sulfur, which is unsubstituted or substituted by one or more identical or different substituents R32;

R31 is selected from the series consisting of halogen, —OH, —O—($C_1$-$C_4$)-alkyl, —O—($C_3$-$C_7$)-cycloalkyl, —O—($C_1$-$C_4$)-alkyl-($C_3$-$C_7$)-cycloalkyl, —N(R33)-R34 and —CN;

R32 is selected from the series consisting of halogen, ($C_1$-$C_4$)-alkyl, ($C_3$-$C_7$)-cycloalkyl, —($C_1$-$C_4$)-alkyl-($C_3$-$C_7$)-cycloalkyl, —($C_1$-$C_4$)-alkyl-O—R37, —($C_1$-$C_4$)-alkyl-N(R38)-R39, —($C_1$-$C_4$)-alkyl-CN, —C(O)—($C_1$-$C_4$)-alkyl, —CN, —OH, =O, —O—($C_1$-$C_4$)-alkyl, —N(R40)-R41, —C(O)—O—($C_1$-$C_4$)-alkyl and —C(O)—N(R42)-R43;

R33, R34, R37, R38, R39, R40, R41, R42 and R43 are independently of one another selected from the series consisting of H and ($C_1$-$C_4$)-alkyl;

R50 is selected from the series consisting of halogen, ($C_1$-$C_4$)-alkyl, —O—($C_1$-$C_4$)-alkyl and —CN;

Het1 is a 4-membered to 7-membered, monocyclic, saturated, heterocyclic group which comprises 1 or 2 identical or different ring heteroatoms selected from the series consisting of nitrogen, oxygen and sulfur, and is bonded via a ring carbon atom, and which is unsubstituted or substituted by one or more identical or different substituents selected from the series consisting of fluorine and ($C_1$-$C_4$)-alkyl;

Het2 is a 4-membered to 7-membered, monocyclic, saturated, partially unsaturated or aromatic, heterocyclic group which comprises 1 or 2 identical or different ring heteroatoms selected from the series consisting of nitrogen, oxygen and sulfur, and is bonded via a ring carbon atom;

Het3 is a 5-membered or 6-membered, monocyclic, aromatic, heterocyclic group which comprises 1 or 2 identical or different ring heteroatoms selected from the series consisting of nitrogen, oxygen and sulfur, and is bonded via a ring carbon atom;

wherein all cycloalkyl groups, independently of any other substituents which can be present on a cycloalkyl group, can be substituted by one or more identical or different substituents selected from the series consisting of fluorine and $(C_1-C_4)$-alkyl;

wherein all alkyl groups, independently of any other substituents which can be present on an alkyl group, can be substituted by one or more fluorine substituents.

As another such example, compounds of the formula I may be mentioned, in any of their stereoisomeric forms or a mixture of stereoisomeric forms in any ratio, and the pharmaceutically acceptable salts thereof, wherein Ar is selected from the series consisting of phenyl and a 5-membered monocyclic, aromatic, heterocyclic group which comprises 1 or 2 identical or different ring heteroatoms selected from the series consisting of nitrogen and sulfur, and is bonded via a ring carbon atom, which all are unsubstituted or substituted by one or more identical or different substituents R5;

n is selected from the series consisting of 0, 1 and 2;

X is selected from the series consisting of N and CH;

Z is selected from the series consisting of a direct bond, O, S and N(R10);

R1 is selected from the series consisting of H, —N(R11)-R12, —N(R13)-C(O)—R14, —N(R13)-S(O)$_2$—R15, —N(R13)-C(O)—NH—R16 and $(C_1-C_4)$-alkyl;

R2 is selected from the series consisting of halogen, $(C_1-C_4)$-alkyl and —O—$(C_1-C_4)$-alkyl;

R3 is selected from the series consisting of H, $(C_1-C_8)$-alkyl, R30 and —$(C_1-C_4)$-alkyl-R30, wherein $(C_1-C_8)$-alkyl is unsubstituted or substituted by one or more identical or different substituents R31;

R5 is selected from the series consisting of halogen, $(C_1-C_4)$-alkyl, $(C_3-C_7)$-cycloalkyl, —O—$(C_1-C_4)$-alkyl, —O—$(C_3-C_7)$-cycloalkyl and —CN, and two groups R5 bonded to adjacent ring carbon atoms in Ar, together with the carbon atoms carrying them, can form a 5-membered to 7-membered, monocyclic, unsaturated ring which comprises 0, 1 or 2 oxygen atoms as ring heteroatoms, and which is unsubstituted or substituted by one or more identical or different substituents R8;

R8 is selected from the series consisting of halogen and $(C_1-C_4)$-alkyl;

R10 is selected from the series consisting of H and $(C_1-C_4)$-alkyl;

one of the groups R11 and R12 is selected from the series consisting of hydrogen and $(C_1-C_4)$-alkyl, and the other of the groups R11 and R12 is selected from the series consisting of hydrogen, $(C_1-C_4)$-alkyl, $(C_3-C_7)$-cycloalkyl, —$(C_1-C_4)$-alkyl-$(C_3-C_7)$-cycloalkyl, Het1, —$(C_1-C_4)$-alkyl-Het1 and —$(C_1-C_4)$-alkyl-phenyl;

R13 is selected from the series consisting of H and $(C_1-C_4)$-alkyl;

R14 and R16 are independently of one another selected from the series consisting of $(C_1-C_8)$-alkyl, $(C_3-C_7)$-cycloalkyl, —$(C_1-C_4)$-alkyl-$(C_3-C_7)$-cycloalkyl, phenyl, —$(C_1-C_4)$-alkyl-phenyl, Het2 and —$(C_1-C_4)$-alkyl-Het2, wherein $(C_1-C_8)$-alkyl and $(C_3-C_7)$-cycloalkyl all are unsubstituted or substituted by one or more identical or different substituents selected from the series consisting of —OH and —O—$(C_1-C_4)$-alkyl, and wherein phenyl and Het2 all are unsubstituted or substituted by one or more identical or different substituents R50;

R15 is phenyl which is unsubstituted or substituted by one or more identical or different substituents R50;

R30 is a 3-membered to 12-membered, monocyclic or bicyclic, saturated, partially unsaturated or aromatic, cyclic group which comprises 0, 1, 2 or 3 identical or different ring heteroatoms selected from the series consisting of nitrogen and oxygen, which is unsubstituted or substituted by one or more identical or different substituents R32;

R31 is selected from the series consisting of halogen, —OH, —O—$(C_1-C_4)$-alkyl, —O—$(C_3-C_7)$-cycloalkyl, —O—$(C_1-C_4)$-alkyl-$(C_3-C_7)$-cycloalkyl and —N(R33)-R34;

R32 is selected from the series consisting of halogen, $(C_1-C_4)$-alkyl, $(C_3-C_7)$-cycloalkyl, —$(C_1-C_4)$-alkyl-$(C_3-C_7)$-cycloalkyl, —$(C_1-C_4)$-alkyl-O—R37, —$(C_1-C_4)$-alkyl-N(R38)-R39, —OH, =O, —O—$(C_1-C_4)$-alkyl and —N(R40)-R41;

R33, R34, R37, R38, R39, R40 and R41 are independently of one another selected from the series consisting of H and $(C_1-C_4)$-alkyl;

R50 is selected from the series consisting of halogen, $(C_1-C_4)$-alkyl, —O—$(C_1-C_4)$-alkyl and —CN;

Het1 is a 4-membered to 7-membered, monocyclic, saturated, heterocyclic group which comprises 1 or 2 identical or different ring heteroatoms selected from the series consisting of nitrogen and oxygen, and is bonded via a ring carbon atom, and which is unsubstituted or substituted by one or more identical or different substituents selected from the series consisting of fluorine and $(C_1-C_4)$-alkyl;

Het2 is a 4-membered to 7-membered, monocyclic, saturated, partially unsaturated or aromatic, heterocyclic group which comprises 1 or 2 identical or different ring heteroatoms selected from the series consisting of nitrogen, oxygen and sulfur, and is bonded via a ring carbon atom;

wherein all cycloalkyl groups, independently of any other substituents which can be present on a cycloalkyl group, can be substituted by one or more identical or different substituents selected from the series consisting of fluorine and $(C_1-C_4)$-alkyl;

wherein all alkyl groups, independently of any other substituents which can be present on an alkyl group, can be substituted by one or more fluorine substituents.

As another such example, compounds of the formula I may be mentioned, in any of their stereoisomeric forms or a mixture of stereoisomeric forms in any ratio, and the pharmaceutically acceptable salts thereof, wherein Ar is phenyl, which is unsubstituted or substituted by one or more identical or different substituents R5;

n is selected from the series consisting of 0 and 1;

X is selected from the series consisting of N and CH;

Z is selected from the series consisting of a direct bond, O and N(R10);

R1 is selected from the series consisting of H, —N(R11)-R12, —N(R13)-C(O)—R14 and $(C_1-C_4)$-alkyl;

R2 is selected from the series consisting of halogen and —O—$(C_1-C_4)$-alkyl;

R3 is selected from the series consisting of H, $(C_1-C_8)$-alkyl, R30 and —$(C_1-C_4)$-alkyl-R30, wherein $(C_1-C_8)$-alkyl is unsubstituted or substituted by one or more identical or different substituents R31;

R5 is selected from the series consisting of halogen, $(C_1-C_4)$-alkyl, —O—$(C_1-C_4)$-alkyl and —CN, and two groups R5 bonded to adjacent ring carbon atoms in Ar, together with the carbon atoms carrying them, can form a 5-membered to 7-membered, monocyclic, unsaturated ring which comprises 0, 1 or 2 oxygen atoms as ring heteroatoms, and which is unsubstituted or substituted by one or more identical or different substituents R8;

R8 is selected from the series consisting of halogen and $(C_1-C_4)$-alkyl;

R10 is selected from the series consisting of H and $(C_1-C_4)$-alkyl;

one of the groups R11 and R12 is selected from the series consisting of hydrogen and $(C_1-C_4)$-alkyl, and the other of the groups R11 and R12 is selected from the series consisting of hydrogen, $(C_1-C_4)$-alkyl, —$(C_1-C_4)$-alkyl-$(C_3-C_7)$-cycloalkyl and —$(C_1-C_4)$-alkyl-Het1;

R13 is selected from the series consisting of H and $(C_1-C_4)$-alkyl;

R14 is selected from the series consisting of $(C_3-C_7)$-cycloalkyl, phenyl and Het2, wherein $(C_3-C_7)$-cycloalkyl is unsubstituted or substituted by one or more identical or different substituents selected from the series consisting of —OH and —O—$(C_1-C_4)$-alkyl, and wherein phenyl and Het2 all are unsubstituted or substituted by one or more identical or different substituents R50;

R30 is a 3-membered to 10-membered, monocyclic or bicyclic, saturated, partially unsaturated or aromatic, cyclic group which comprises 0, 1, 2 or 3 identical or different ring heteroatoms selected from the series consisting of nitrogen and oxygen, which is unsubstituted or substituted by one or more identical or different substituents R32;

R31 is selected from the series consisting of halogen, —OH, —O—$(C_1-C_4)$-alkyl, —O—$(C_3-C_7)$-cycloalkyl and —N(R33)-R34;

R32 is selected from the series consisting of halogen, $(C_1-C_4)$-alkyl, $(C_3-C_7)$-cycloalkyl, —$(C_1-C_4)$-alkyl-O—R37, —$(C_1-C_4)$-alkyl-N(R38)-R39, —OH, =O, —O—$(C_1-C_4)$-alkyl and —N(R40)-R41;

R33, R34, R37, R38, R39, R40 and R41 are independently of one another selected from the series consisting of H and $(C_1-C_4)$-alkyl;

R50 is selected from the series consisting of halogen, $(C_1-C_4)$-alkyl, —O—$(C_1-C_4)$-alkyl and —CN;

Het1 is a 4-membered to 7-membered, monocyclic, saturated, heterocyclic group which comprises 1 or 2 identical or different ring heteroatoms selected from the series consisting of nitrogen and oxygen, and is bonded via a ring carbon atom, and which is unsubstituted or substituted by one or more identical or different substituents selected from the series consisting of fluorine and $(C_1-C_4)$-alkyl;

Het2 is a 4-membered to 7-membered, monocyclic, saturated or aromatic, heterocyclic group which comprises 1 or 2 identical or different ring heteroatoms selected from the series consisting of nitrogen, oxygen and sulfur, and is bonded via a ring carbon atom;

wherein all cycloalkyl groups, independently of any other substituents which can be present on a cycloalkyl group, can be substituted by one or more identical or different substituents selected from the series consisting of fluorine and $(C_1-C_4)$-alkyl;

wherein all alkyl groups, independently of any other substituents which can be present on an alkyl group, can be substituted by one or more fluorine substituents.

As another such example, compounds of the formula I may be mentioned, in any of their stereoisomeric forms or a mixture of stereoisomeric forms in any ratio, and the pharmaceutically acceptable salts thereof, wherein Ar is phenyl, which is unsubstituted or substituted by one or more identical or different substituents R5;

n is selected from the series consisting of 0 and 1;

X is selected from the series consisting of N and CH;

Z is selected from the series consisting of a direct bond and O;

R1 is selected from the series consisting of H, —N(R11)-R12 and $(C_1-C_4)$-alkyl;

R2 is selected from the series consisting of halogen;

R3 is selected from the series consisting of H, R30 and —$(C_1-C_4)$-alkyl-R30;

R5 is selected from the series consisting of halogen, $(C_1-C_4)$-alkyl, —O—$(C_1-C_4)$-alkyl and —CN;

R11 and R12 are independently of one another selected from the series consisting of hydrogen and $(C_1-C_4)$-alkyl;

R30 is a 3-membered to 7-membered, monocyclic saturated or aromatic, cyclic group which comprises 0, 1 or 2 identical or different ring heteroatoms selected from the series consisting of nitrogen and oxygen, which is unsubstituted or substituted by one or more identical or different substituents R32;

R32 is selected from the series consisting of halogen, $(C_1-C_4)$-alkyl, $(C_3-C_7)$-cycloalkyl, —$(C_1-C_4)$-alkyl-O—R37, —$(C_1-C_4)$-alkyl-N(R38)-R39, —OH and =O;

R37, R38 and R39 are independently of one another selected from the series consisting of H and $(C_1-C_4)$-alkyl;

wherein all cycloalkyl groups can be substituted by one or more identical or different substituents selected from the series consisting of fluorine and $(C_1-C_4)$-alkyl;

wherein all alkyl groups, independently of any other substituents which can be present on an alkyl group, can be substituted by one or more fluorine substituents.

A subject of the invention also is a compound of the formula I which is selected from any of the specific compounds of the formula I which are disclosed herein, or is any one of the specific compounds of the formula I which are disclosed herein, irrespective thereof whether they are disclosed as a free compound and/or as a specific salt, or a pharmaceutically acceptable salt thereof, wherein the compound of the formula I is a subject of the invention in any of its stereoisomeric forms or a mixture of stereoisomeric forms in any ratio, if applicable. For example, a subject of the invention is a compound of the formula I which is selected from the series consisting of:

N-[4-(3-Amino-4-cyclopropyl-1H-pyrazolo[3,4-d]pyrimidin-6-yl)-phenyl]-2-cyano-5-methoxy-benzenesulfonamide, N-[4-(3-Amino-1H-pyrazolo[3,4-d]pyrimidin-6-yl)-phenyl]-2,5-difluoro-benzenesulfonamide, N-[4-(3-Amino-1H-pyrazolo[3,4-d]pyrimidin-6-yl)-phenyl]-5-chloro-2-cyano-benzenesulfonamide, 2-Chloro-N-{4-[4-(1-ethyl-piperidin-3-yloxy)-3-methyl-1H-pyrazolo[3,4-d]pyrimidin-6-yl]-phenyl}-5-methoxy-benzenesulfonamide, 5-Chloro-N-{4-[4-(1-ethyl-piperidin-3-yloxy)-3-methyl-1H-pyrazolo[3,4-d]pyrimidin-6-yl]-phenyl}-2-fluoro-benzenesulfonamide, 4-{6-[4-(2,5-Difluoro-benzenesulfonylamino)-phenyl]-3-methyl-1H-pyrazolo[3,4-d]pyrimidin-4-yloxy}-piperidine-1-carboxylic acid ethyl ester, N-[4-(3-Amino-4-propoxy-1H-pyrazolo[3,4-d]pyrimidin-6-yl)-phenyl]-2,5-difluoro-benzenesulfonamide, N-[4-(3-Amino-4-ethoxy-1H-pyrazolo[3,4-d]pyrimidin-6-yl)-phenyl]-5-chloro-2-fluoro-benzenesulfonamide, N-[4-(3-Amino-4-propoxy-1H-pyrazolo[3,4-d]pyrimidin-6-yl)-phenyl]-5-chloro-2-fluoro-benzenesulfonamide, N-[4-(3-Amino-4-ethoxy-1H-pyrazolo[3,4-d]pyrimidin-6-yl)-phenyl]-2,5-difluoro-benzenesulfonamide, 2-Fluoro-N-(4-{4-[1-(2-methoxy-ethyl)-piperidin-4-yloxy]-3-methyl-1H-pyrazolo[3,4-d]pyrimidin-6-yl}-phenyl)-5-methyl-benzenesulfonamide, 2,5-Difluoro-N-(4-{4-[1-(2-methoxy-ethyl)-piperidin-4-yloxy]-3-methyl-1H-pyrazolo[3,4-d]pyrimidin-6-yl}-phenyl)-benzenesulfonamide,
5-Chloro-2-fluoro-N-(4-{4-[1-(2-methoxy-ethyl)-piperidin-4-yloxy]-3-methyl-1H-pyrazolo[3,4-d]pyrimidin-6-yl}-phenyl)-benzenesulfonamide,
N-{4-[4-(1-Ethyl-piperidin-4-yloxy)-3-methyl-1H-pyrazolo[3,4-d]pyrimidin-6-yl]-phenyl}-2-fluoro-5-methoxy-benzenesulfonamide,
2,5-Dichloro-N-{4-[4-(1-ethyl-piperidin-4-yloxy)-3-methyl-1H-pyrazolo[3,4-d]pyrimidin-6-yl]-phenyl}-benzenesulfonamide,
N-{4-[4-(1-Ethyl-piperidin-4-yloxy)-3-methyl-1H-pyrazolo[3,4-d]pyrimidin-6-yl]-phenyl}-2-fluoro-5-methyl-benzenesulfonamide,
N-{4-[4-(1-Ethyl-piperidin-4-yloxy)-3-methyl-1H-pyrazolo[3,4-d]pyrimidin-6-yl]-phenyl}-2-fluoro-benzenesulfonamide,
5-Chloro-N-{4-[4-(1-ethyl-piperidin-4-yloxy)-3-methyl-1H-pyrazolo[3,4-d]pyrimidin-6-yl]-phenyl}-2-fluoro-benzenesulfonamide,
N-{4-[4-(1-Cyclobutyl-piperidin-4-yloxy)-3-methyl-1H-pyrazolo[3,4-d]pyrimidin-6-yl]-phenyl}-2,5-difluoro-benzenesulfonamide,
2,5-Difluoro-N-(4-{4-[1-(3-methoxy-propyl)-piperidin-4-yloxy]-3-methyl-1H-pyrazolo[3,4-d]pyrimidin-6-yl}-phenyl)-benzenesulfonamide,
5-Chloro-2-fluoro-N-{4-[4-(3-hydroxy-propoxy)-3-methyl-1H-pyrazolo[3,4-d]pyrimidin-6-yl]-phenyl}-benzenesulfonamide,
2,5-Difluoro-N-{4-[4-(1-isopropyl-piperidin-4-yloxy)-3-methyl-1H-pyrazolo[3,4-d]pyrimidin-6-yl]-phenyl}-benzenesulfonamide,
2-Fluoro-N-(4-{4-[1-(2-fluoro-ethyl)-piperidin-4-yloxy]-3-methyl-1H-pyrazolo[3,4-d]pyrimidin-6-yl}-phenyl)-benzenesulfonamide,
5-Chloro-2-fluoro-N-{4-[4-(1-isopropyl-piperidin-4-yloxy)-3-methyl-1H-pyrazolo[3,4-d]pyrimidin-6-yl]-phenyl}-benzenesulfonamide,
2,5-Difluoro-N-(4-{4-[1-(2-fluoro-ethyl)-piperidin-4-yloxy]-3-methyl-1H-pyrazolo[3,4-d]pyrimidin-6-yl}-phenyl)-benzenesulfonamide,
N-[4-(3-Amino-4-isopropoxy-1H-pyrazolo[3,4-d]pyrimidin-6-yl)-phenyl]-2,5-dichloro-benzenesulfonamide,
N-[4-(3-Amino-4-isobutoxy-1H-pyrazolo[3,4-d]pyrimidin-6-yl)-phenyl]-2,5-difluoro-benzenesulfonamide,
N-[4-(3-Amino-4-isobutoxy-1H-pyrazolo[3,4-d]pyrimidin-6-yl)-phenyl]-2-fluoro-5-methoxy-benzenesulfonamide,
2,5-Dichloro-N-{4-[3-methyl-4-(piperidin-3-yloxy)-1H-pyrazolo[3,4-d]pyrimidin-6-yl]-phenyl}-benzenesulfonamide,
2,5-Difluoro-N-{4-[3-methyl-4-(piperidin-3-yloxy)-1H-pyrazolo[3,4-d]pyrimidin-6-yl]-phenyl}-benzenesulfonamide,
2-Fluoro-5-methyl-N-{4-[3-methyl-4-(morpholin-2-ylmethoxy)-1H-pyrazolo[3,4-d]pyrimidin-6-yl]-phenyl}-benzenesulfonamide,
N-{4-[4-(3-Aminomethyl-oxetan-3-ylmethoxy)-1H-pyrazolo[3,4-d]pyrimidin-6-yl]-phenyl}-5-chloro-2-fluoro-benzenesulfonamide,
N-[4-(3-Amino-4-ethoxymethyl-1H-pyrazolo[3,4-d]pyrimidin-6-yl)-phenyl]-2-fluoro-5-methyl-benzenesulfonamide,
N-[4-(3-Amino-4-trifluoromethyl-1H-pyrazolo[3,4-d]pyrimidin-6-yl)-phenyl]-2,5-difluoro-benzenesulfonamide,
2-Fluoro-N-{4-[4-(piperidin-4-yloxy)-1H-pyrazolo[3,4-d]pyrimidin-6-yl]-phenyl}-benzenesulfonamide,
N-[4-(3-Amino-1H-pyrazolo[3,4-d]pyrimidin-6-yl)-phenyl]-2-fluoro-5-methoxy-benzenesulfonamide,
N-[4-(3-Amino-4-methoxymethyl-1H-pyrazolo[3,4-d]pyrimidin-6-yl)-phenyl]-5-chloro-2-fluoro-benzenesulfonamide,
N-{4-[4-(3-Amino-propoxy)-3-methyl-1H-pyrazolo[3,4-d]pyrimidin-6-yl]-phenyl}-5-chloro-2-fluoro-benzenesulfonamide,
N-[4-(3-Amino-1H-pyrazolo[3,4-d]pyrimidin-6-yl)-phenyl]-2,5-difluoro-benzenesulfonamide,
N-[4-(3-Amino-1H-pyrazolo[3,4-d]pyrimidin-6-yl)-phenyl]-2,4,5-trifluoro-benzenesulfonamide,
N-[4-(3-Amino-1H-pyrazolo[3,4-d]pyrimidin-6-yl)-phenyl]-2-chloro-4,5-difluoro-benzenesulfonamide,
N-{4-[3-Amino-4-(2,2,2-trifluoro-ethoxy)-1H-pyrazolo[3,4-d]pyrimidin-6-yl]-phenyl}-2-cyano-5-methyl-benzenesulfonamide,
N-[4-(3-Amino-4-trifluoromethyl-1H-pyrazolo[3,4-d]pyrimidin-6-yl)-phenyl]-5-chloro-2-fluoro-benzenesulfonamide,
N-{4-[3-Amino-4-(2-methoxy-ethyl)-1H-pyrazolo[3,4-d]pyrimidin-6-yl]-phenyl}-2-cyano-5-methyl-benzenesulfonamide,
2-Cyano-5-methyl-N-{4-[4-(2,2,2-trifluoro-ethoxy)-1H-pyrazolo[3,4-d]pyrimidin-6-yl]-phenyl}-benzenesulfonamide,
N-[4-(3-Amino-4-cyclopropyl-1H-pyrazolo[3,4-d]pyrimidin-6-yl)-phenyl]-2,4,5-trifluoro-benzenesulfonamide,
N-[4-(3-Amino-4-cyclopropyl-1H-pyrazolo[3,4-d]pyrimidin-6-yl)-phenyl]-2-fluoro-benzenesulfonamide,
N-[4-(3-Amino-4-cyclopropyl-1H-pyrazolo[3,4-d]pyrimidin-6-yl)-phenyl]-2,5-difluoro-benzenesulfonamide,
N-[4-(3-Amino-4-methoxy-1H-pyrazolo[3,4-d]pyrimidin-6-yl)-phenyl]-5-chloro-2-fluoro-benzenesulfonamide,
N-[4-(3-Amino-4-methoxy-1H-pyrazolo[3,4-d]pyrimidin-6-yl)-phenyl]-5-chloro-2-cyano-benzenesulfonamide,
N-[4-(3-Amino-4-methyl-1H-pyrazolo[3,4-d]pyrimidin-6-yl)-phenyl]-2-chloro-3,5-difluoro-benzenesulfonamide,
2-Cyano-N-{4-[4-(4-hydroxy-cyclohexyloxy)-1H-pyrazolo[3,4-d]pyrimidin-6-yl]-phenyl}-5-methoxy-benzenesulfonamide,
N-[4-(3-Amino-1H-pyrazolo[4,3-c]pyridin-6-yl)-phenyl]-5-chloro-2,4-difluoro-benzenesulfonamide, and
5-Chloro-2-cyano-N-{4-[4-(4-hydroxy-cyclohexyloxy)-3-methyl-1H-pyrazolo[3,4-d]pyrimidin-6-yl]-phenyl}-benzenesulfonamide, and/or the series consisting of:
N-{4-[4-(1-Cyclopropyl-piperidin-4-yloxy)-3-methyl-1H-pyrazolo[3,4-d]pyrimidin-6-yl]-phenyl}-2,5-difluoro-benzenesulfonamide,
5-Chloro-N-{4-[4-(1-cyclopropyl-piperidin-4-yloxy)-3-methyl-1H-pyrazolo[3,4-d]pyrimidin-6-yl]-phenyl}-2-fluoro-benzenesulfonamide,
N-{4-[4-(1-Acetyl-piperidin-4-yloxy)-3-methyl-1H-pyrazolo[3,4-d]pyrimidin-6-yl]-phenyl}-2-fluoro-5-methoxy-benzenesulfonamide,
N-{4-[4-(1-Acetyl-piperidin-4-yloxy)-3-methyl-1H-pyrazolo[3,4-d]pyrimidin-6-yl]-phenyl}-2,5-difluoro-benzenesulfonamide,
N-{4-[4-(1-Acetyl-piperidin-4-yloxy)-3-methyl-1H-pyrazolo[3,4-d]pyrimidin-6-yl]-phenyl}-5-chloro-2-fluoro-benzenesulfonamide,
5-Chloro-2-fluoro-N-{4-[4-(6-hydroxy-pyridin-3-yloxy)-3-methyl-1H-pyrazolo[3,4-d]pyrimidin-6-yl]-phenyl}-benzenesulfonamide, and
2-Fluoro-N-{4-[4-(6-hydroxy-pyridin-3-yloxy)-3-methyl-1H-pyrazolo[3,4-d]pyrimidin-6-yl]-phenyl}-5-methyl-benzenesulfonamide, or which is any one of these compounds, and its pharmaceutically acceptable salts.

Another subject of the present invention are processes for the preparation of the compounds of the formula I which are outlined below and by which the compounds of the formula I and intermediates and occurring in the course of their synthesis, and salts thereof, are obtainable. The compounds of the formula I can be prepared by utilizing procedures and techniques which per se are known to a person skilled in the art. In general, pyrazolo[3,4-d]pyrimidine and pyrazolo[4,3-c]pyridine compounds of the formula I can be prepared, for example, in the course of a convergent synthesis, by linking two or more fragments which can be derived retrosynthetically from the formula I. More specifically, suitably substituted starting 1H-pyrazolo[3,4-d]pyrimidine and 1H-pyrazolo[4,3-c]pyridine derivatives can be employed as building blocks in the preparation of the compounds of formula I, which can be synthesized from suitable precursor compounds, which allow the introduction of a variety of substituents into the various positions of the 1H-pyrazolo[3,4-d]pyrimidine or 1H-pyrazolo[4,3-c]pyridine ring system and which can be chemically modified further in order to finally arrive at the compound of the formula I having the desired substituent pattern. For the synthesis of the 1H-pyrazolo[3,4-d]pyrimidine and 1H-pyrazolo[4,3-c]pyridine ring system, use can also be made of procedures and transformations which are described in the literature with respect to indazoles. As reviews in which numerous details and literature references on the chemistry of indazoles and on synthetic procedures for their preparation can be found, J. Eiguero in Comprehensive Heterocyclic Chemistry II, Eds. A. Katritzky, Ch. Rees, E. Scriven, Elsevier 1996, Vol. 3; W. Stadlbauer in Houben-Weyl, Methoden der Organischen Chemie (Methods of Organic Chemistry), Georg Thieme Verlag, Stuttgart, Germany, 1994, Vol. E8b, Hetarene; W. Stadlbauer in Houben-Weyl, Science of Synthesis, Georg Thieme Verlag, Stuttgart, Germany, 2002, vol. 12.2, 227-324, may be mentioned. The starting materials employed in the synthesis of the compounds of the formula I are commercially available or can be prepared according to procedures, or in analogy to procedures, described in the literature or herein.

In one synthetic approach for the preparation of compounds of the formula I, a compound of the formula II and a compound of the formula III are reacted to give a compound of the formula IV, which can already be the final compound of the formula I or which is then converted into the desired final compound of the formula I.

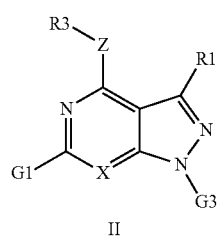

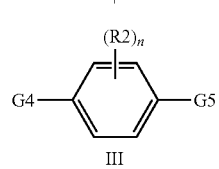

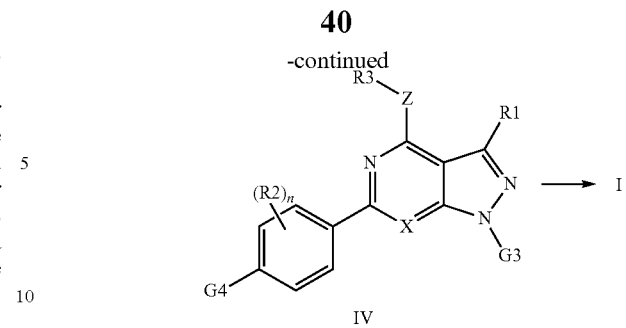

More specifically, in particular in case the group R1 in the compound of the formula I is hydrogen or an optionally substituted alkyl group, according to this approach a compound of the formula II is obtained by reacting a compound of the formula V with a hydrazine of the formula VI, reacting the obtained compound of the formula II with a compound of the formula III to give a compound of the formula IV, which can already be the final compound of the formula I, and optionally converting the compound of the formula IV into a compound of the formula I.

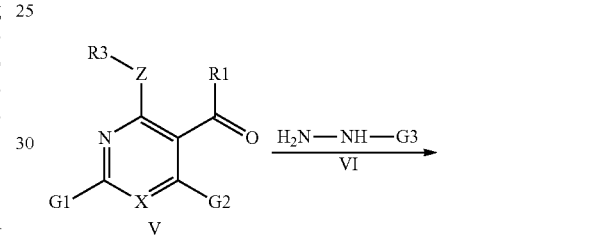

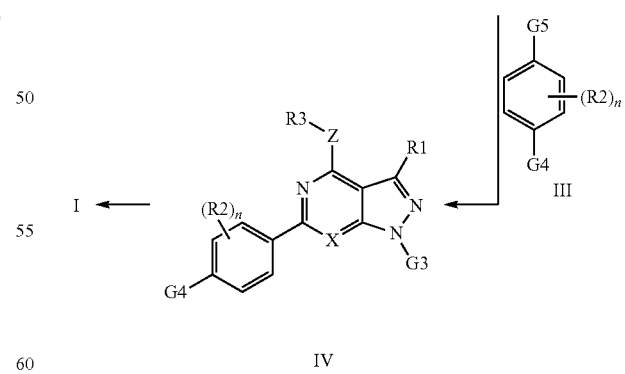

In an alternative approach for obtaining a compound of the formula IV, a compound of the formula V is first reacted with a compound of the formula III to give a compound of the formula VII, and the compound of the formula VII then reacted with a hydrazine of the formula VI.

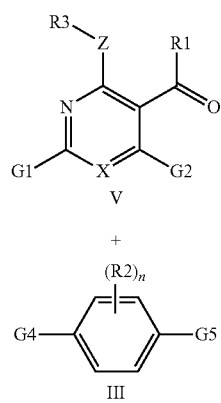

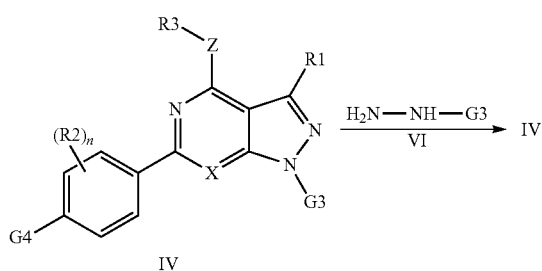

In another synthetic approach for the preparation of compounds of the formula I, in particular in case of compounds in which the group R1 is bonded via a nitrogen atom to the 1H-pyrazolo[3,4-d]pyrimidine or 1H-pyrazolo[4,3-c] pyridine ring system, specifically in case of the preparation of compounds in which R1 is an amino group, a compound of the formula X is obtained by reacting a compound of the formula VIII with a hydrazine of the formula VI, reacting the obtained compound of the formula IX with a compound of the formula III to give a compound of the formula X, which can already be the final compound of the formula I, and optionally converting the compound of the formula X into the compound of the formula I.

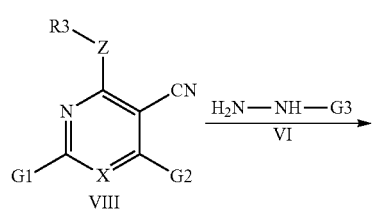

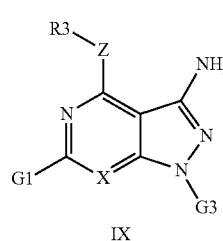

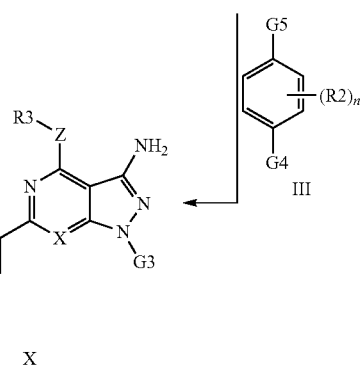
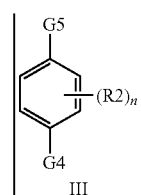

In an alternative approach for obtaining a compound of the formula X, a compound of the formula VIII is first reacted with a compound of the formula III to give a compound of the formula XI, and the compound of the formula XI then reacted with a hydrazine of the formula VI.

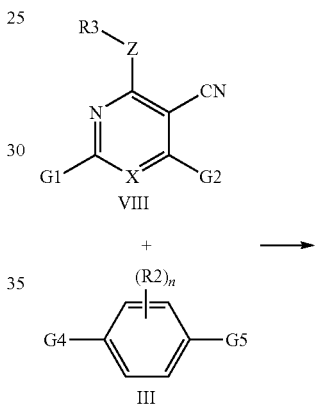

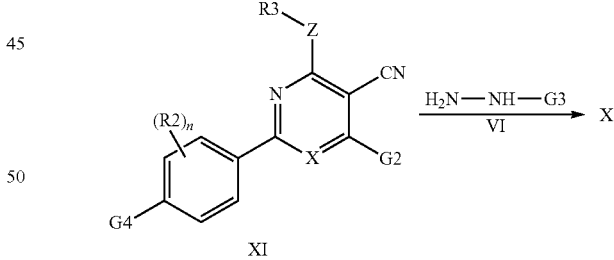

A compound of the formula XI in which X is N, i.e. a compound of the formula XV, can also be obtained, in particular in case of compounds in which the group —Z—R3 is hydrogen or a group which is bonded via a carbon atom to the 1H-pyrazolo[3,4-d]pyrimidine ring system, by reacting an amidine of the formula XII with a 2-cyano-acrylic acid ester of the formula XIII, in which R70 is an alkyl group such as ($C_1$-$C_2$)-alkyl like methyl or ethyl, to give a compound of the formula XIV, and converting the compound of the formula XIV into a compound of the formula XV.

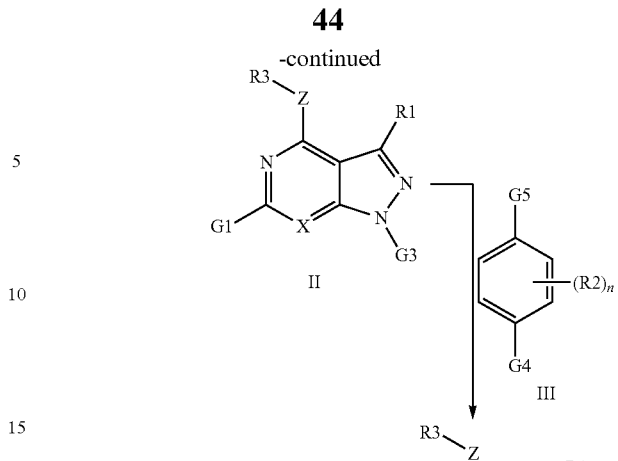

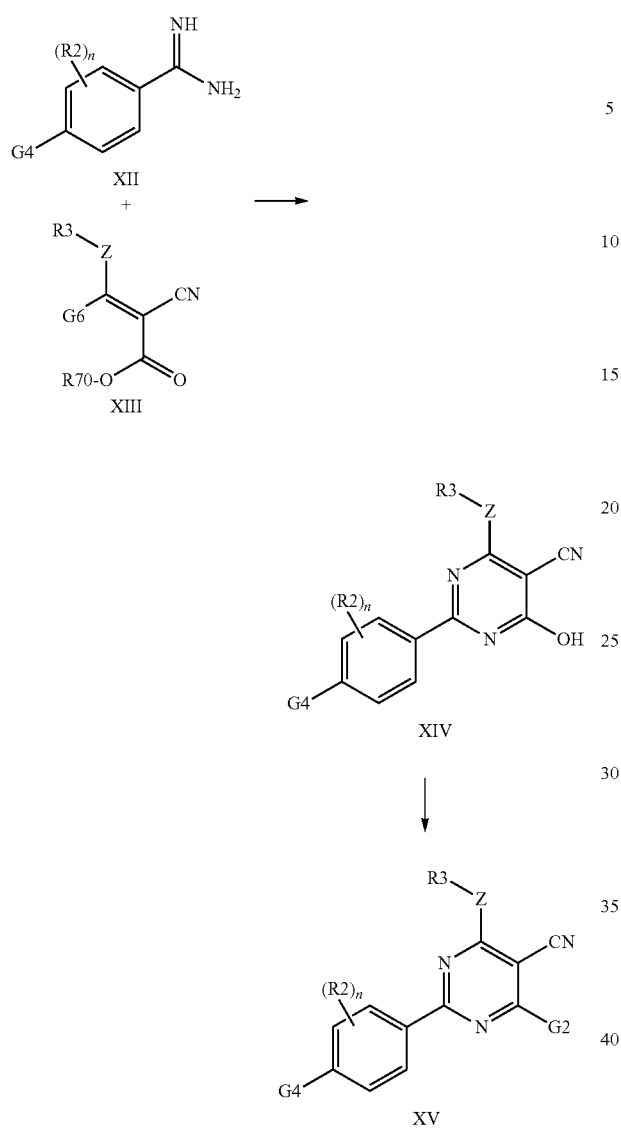

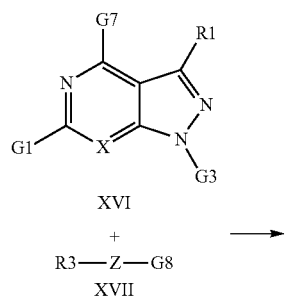

Another approach for the preparation of a compound of the formula I starts from a compound of the formula XVI, which is reacted with a compound of the formula XVII to give a compound of the formula II, which is then reacted with a compound of the formula III to give a compound of the formula IV, which can already be the final compound of the formula I or is optionally converted into the compound of the formula I.

The groups X, Z, R1, R2 and R3 and the number n in the compounds of the formulae II to XVII are defined as in the compounds of the formula I, wherein in certain cases their meanings may be more specific as also indicated above, and additionally can functional groups be present in protected form or in the form of a precursor group which is subsequently converted into the final group.

The group G1 in the compounds of the formulae II, V, VIII, IX and XVI is a leaving group which can be replaced in a Suzuki-type reaction or Stille-type reaction, such as a halogen atom, in particular bromine or chlorine, or a sulfonyloxy group, in particular trifluoromethanesulfonyloxy, methanesulfonyloxy, benzenesulfonyloxy or tosyloxy(4-methylbenzenesulfonyloxy).

The group G2 in the compounds of formulae V, VII, VIII, XI and XV can be identical to or different from the group G1 and is a leaving group, such as a halogen atom, in particular bromine or chlorine, or a sulfonyloxy group, in particular trifluoromethanesulfonyloxy, methanesulfonyloxy, benzenesulfonyloxy or tosyloxy, or an alkylsulfanyl group, in particular methylsulfanyl or ethylsulfanyl.

The group G3 in the compounds of formulae II, IV, VI, IX, X and XVI can be hydrogen, and in this case the compound of the formula VI thus be hydrazine, or it can be a protecting group which is suitable for protecting a ring nitrogen atom in the 1H-pyrazolo[3,4-d]pyrimidine or 1H-pyrazolo[4,3-c]pyridine ring system or similar ring systems such as the pyrazole ring system, for example, like a tetrahydropyran-2-yl group, a tert-butoxycarbonyl group, an ethoxycarbonyl group, a benzyl group or a substituted benzyl group like a 4-methoxybenzyl group or a 2,5-dimethoxybenzyl group.

The group G4 in the compounds of formulae III, IV, VII, X, XI, XII, XIV and XV can already be the desired final sulfonamide group of the formula Ar—S(O)$_2$—NH—, in which Ar is defined as in the compounds of the formula I and additionally can functional groups be present in protected form or in the form of a precursor group which is subsequently converted into the final group. G4 can also be a group which can be converted into the desired final sulfonamide group of the formula Ar—S(O)$_2$—NH— at an appropriate stage of the synthesis, for example in the compounds of the formulae IV and X, such as a precursor group like a nitro group which can be reduced to an amino group, or a protected amino group like a tert-butoxycarbonylamino group or a benzyloxycarbonylamino group which can be deprotected to an amino group, or a free amino group, and the amino group then be converted into the group Ar—S(O)$_2$—NH— by reaction with a sulfonyl chloride of the formula Ar—S(O)$_2$—Cl under standard conditions.

The group G5 in the compounds of formula III is a trialkylstannyl group, for example a tri((C$_1$-C$_4$)-alkyl)stannyl group, or a boronic acid group (—B(OH)$_2$) or a boronic acid ester group or cyclic boronic acid ester group, for example a —B(O—(C$_1$-C$_4$)-alkyl)$_2$ group or a 4,4,5,5-tetramethyl-[1,3,2]dioxaborolan-2-yl group, in particular a boronic acid group or a boronic acid ester group or cyclic boronic acid ester group, which allows performing a Suzuki-type reaction or Stille-type reaction for coupling the compounds of the formulae II, V, VIII and IX with the compounds of the formula III.

The group G6 in the compounds of the formula XIII is a leaving group such as a halogen atom, in particular chlorine, or an alkyloxy group, in particular a (C$_1$-C$_2$)-alkyloxy group like ethoxy or methoxy. The compounds of the formula XIII can be obtained from the respective compounds which contain a hydroxy group instead of the group G6 by halogenation, for example by treatment with a chlorinating agent such as oxalyl chloride or phosphorus oxychloride, or by alkylation, for example by treatment with a trifluoromethanesulfonic acid alkyl ester, or by condensation of a cyanoacetic acid alkyl ester with a carboxylic acid ortho ester, for example.

The group G7 in the compounds of formula XVI can be identical to or different from the group G1 in the compound of the formula XVI, and likewise is a leaving group, such as a halogen atom, in particular chlorine. The different reactivity of the groups G1 and G7 allows a selective reaction also in case they are identical and, for example, both are chlorine.

The group G8 in the compounds of the formula XVII can be hydrogen in case the group Z in the compound of the formula XVII is O, S or N(R10), and in such case the group Z replaces the group G7 in the compound of the formula XVI in a nucleophilic substitution, or it can be a metal-containing group such as a trialkylstannyl group, for example a tri((C$_1$-C$_4$)-alkyl)stannyl group, or a magnesium halide group ClMg or BrMg and the compound of the formula XVII thus be a Grignard compound, or lithium and the compound of the formula XVII thus be an organolithium compound, for example, in case the group Z in the compound of the formula XVII is a direct bond and R3 is different from hydrogen.

The starting compounds in the synthesis of the compounds of the formula I can also be employed, and the intermediates obtained and/or employed, in the form of salts, for example acid addition salts in case of basic compounds. The intermediates can also be present in another tautomeric form, for example in the case of the compounds of the formulae II or IX in which G3 is hydrogen, which can be present in the form of the respective 2H-pyrazolo[3,4-d]pyrimidine or 2H-pyrazolo[4,3-c]pyridine derivatives in which the mobile hydrogen atom, which in the compound of the formula II is bonded to the ring nitrogen atom in position 1 of the pyrazolo[3,4-d]pyrimidine or pyrazolo[4,3-c]pyridine ring system, is bonded to the ring nitrogen atom in position 2 of the pyrazolo[3,4-d]pyrimidine or pyrazolo[4,3-c]pyridine ring system.

The reaction of compounds of the formulae V, VII, VIII and XI with a hydrazine of the formula VI is generally carried out in a protic or aprotic solvent such as water, an alcohol like methanol, ethanol, trifluoroethanol, n-propanol, isopropanol, butanol, isobutanol, tert-butanol, 2-methylbutan-2-ol, 3-methyl-3-pentanol, 3-ethyl-3-pentanol, a hydrocarbon like benzene, toluene, xylene, mesitylene, a nitrile like acetonitrile, an ether like tetrahydrofuran or diglyme (di(2-methoxyethyl) ether), an amide like dimethylformamide, N-methylpyrrolidinone, dimethylacetamide, a sulfoxide like dimethylsulfoxide, or an amine like pyridine, or in a mixture of solvents, at temperatures from about 20° C. to about 200° C., for example at temperatures from about 80° C. to about 120° C. The reaction time generally is from about 30 minutes to about 48 hours, for example from about 5 hours to about 16 hours, depending on the particulars of the specific case and the chosen temperature range. Instead of using conventional heating, the reaction can also be carried out in a microwave oven utilizing microwave radiation at temperatures from about 60° C. to about 200° C., for example at temperatures from about 80° C. to about 120° C. In such case, the reaction time generally is from about 5 minutes to about 12 hours, for example from about 10 minutes to about 3 hours, depending on the particulars of the specific case and the chosen temperature range. The compound of the formula VI can be employed in free form, i.e., not in the form of a salt, for example in the form of a solution in a solvent like ethanol or isopropanol, or in the form of an acid addition salt, for example in the form of a salt with hydrochloric acid. In case a salt is employed, it can be transformed into the free form prior to the reaction or in situ with an organic or inorganic base such as an amine like triethylamine, ethyldiisopropylamine, N-methylmorpholine or 1,8-diazabicyclo[5.4.0]undec-7-ene, an alkoxide like sodium methoxide, sodium ethoxide, potassium methoxide, potassium tert-butoxide, an amide like lithium diisopropylamide or sodium amide, or an alkali metal carbonate like sodium carbonate, potassium carbonate or cesium carbonate, for example.

The reaction of compounds of the formulae II, V, VIII and IX with a compound of the formula III in which G5 is a boronic acid group or a boronic acid ester group or cyclic boronic acid ester group, is a Suzuki-type reaction, and is generally carried out in the presence of catalytic palladium compound, for example a palladium(II) salt like palladium(II) acetate or palladium(II) chloride, which can be employed in the presence of a phosphine such as 1,1'-bis(diphenylphosphino)ferrocene, tricyclohexylphosphine or triphenylphosphine, or a palladium complex such as tetrakis(triphenylphosphine)palladium(0), 1,1'-bis(diphenylphosphino)ferrocene-palladium(11) dichloride, palladium(0) bis(tri-tert-butylphosphine) or bis(triphenylphosphine)palladium(II) dichloride, and favorably in the presence of a base, for example an alkali metal carbonate or alkali metal phosphate like cesium carbonate, sodium carbonate or tripotassium phosphate, in an inert solvent, such as a hydrocarbon like benzene, toluene or xylene, or an ether like tetrahydrofuran (THF), dioxane or 1,2-dimethoxyethane (DME), or water, or a mixture of solvents, at temperatures from about 20° C. to about 200° C., for example at temperatures from about 80° C. to about 120° C. The reaction time generally is from about 30 minutes to about 48 hours, for example from 30 minutes to about 16 hours, depending on particulars of the specific case and the chosen temperature range. Except for the use of water as solvent, these explanations on the Suzuki-type reactions substantially apply also to reactions with compounds of the formula III in which G5 is a trialkylstannyl group, i.e. Stille-type reactions.

The reaction of compounds of the formula XII with compounds of the formula XIII to give a compound of the formula XIV is a standard reaction for the synthesis of pyrimidine derivatives and is generally performed in the presence of a base, for example an alkali metal alkoxide like sodium ethoxide or an alkali metal hydroxide like sodium hydroxide, in an inert solvent such as an alcohol like methanol or ethanol, or water, at temperatures from about 20° C. to about 100° C., depending on the particulars of the specific case such as the properties of the employed compound of the formula XIII. The conversion of the hydroxy group in the compound of the formula XIV, which may also be present in the tautomeric form of an oxo group, into a leaving group G2 in the compound of the formula XV likewise is a standard reaction and can be performed, for example in case G2 in the compound of the formula XV is chlorine, by treatment of the compound of the formula XIV with a chlorinating agent like phosphorus oxychloride, which is generally employed in excess and at reflux temperature, favorably in the presence of a tertiary amine like N,N-dimethylaniline.

The conditions of the reaction of compounds of the formula XVI with compounds of the formula XVII to give a compound of the formula IV depend on the specific case. If a compound of the formula XVII is employed in which Z is O, S or N(R10) and G8 is hydrogen, the reaction with a compound of the formula XVI is favorably performed in the presence of a base, for example a tertiary amine like ethyldiisopropylamine or triethylamine or an alkali metal hydride like sodium hydride or an alkali metal carbonate like cesium carbonate, in an inert solvent such as a chlorinated hydrocarbon like dichloromethane, an ether like THF or a nitrile like acetonitrile or in an excess of the compound of the formula XVII, at temperatures from about 0° C. to about 60° C., for example at temperatures from about 20° C. to about 40° C. If a compound of the formula XVII is employed in which Z is a direct bond, R3 is different from hydrogen and G8 is a metal-containing group such as a trialkylstannyl group or a magnesium halide group, and the reaction with the compound of the formula XVI thus is a Stille-type reaction or a Grignard-type reaction, respectively, the reaction can be performed under the general conditions for such types of reactions, for example in an inert solvent such as a hydrocarbon or an ether in the presence of a catalytic palladium compound as specified above for the reaction of the compounds of the formulae II and III in the case of a Stille-type reaction, or in an ether like THF at temperatures from about −80° C. to about 40° C. in the case of a Grignard-type reaction.

Further, in order to obtain the desired compound of the formula I, the functional groups introduced into the ring system during the 1H-pyrazolo[3,4-d]pyrimidine or 1H-pyrazolo[4,3-c]pyridine synthesis can be chemically modified by a variety of reactions and thus the desired groups obtained. For example, a compound of the formula I carrying a hydrogen atom in position 4 can also be obtained by saponification and subsequent decarboxylation of a respective compound carrying an ester group in this position. Halogen atoms can be introduced, for example, according to well-known procedures described in the literature. A fluorination of the aromatic substructures of compounds of the formula I can be carried out using a variety of reagents including, for example, N-fluoro-2,4,6-trimethylpyridinium triflate. A chlorination, bromination, or iodination can be accomplished by reaction with the elemental halogens or, for example, by use of N-bromosuccinimide, N-chlorosuccinimide or N-iodosuccinimide and many other reagents well known to the person skilled in the art. By selective halogen/metal exchange, or metalation by selective hydrogen/metal exchange, and subsequent reaction with a wide range of electrophiles, various substituents can be introduced using procedures which are known per se. Among others, halogen atoms, hydroxy groups after conversion into the triflate or nonaflate, for example, or primary amino groups after conversion into the diazonium salt, can directly, or after conversion to the corresponding stannane or boronic acid or boronic acid ester, converted into a variety of other groups like, for example, $-CN$, $-CF_3$, $-C_2F_5$ and ether, acid, amide, amine, alkyl or aryl groups. For such conversions, favorably use can also be made of reactions mediated by transition metals, such as palladium or nickel catalysts or copper salts, as are described in Diederich, F. et al., Metal-catalyzed Cross-coupling Reactions, Wiley-VCH, 1998; Beller, M. et al., Transition Metals for Organic Synthesis, Wiley-VCH, 1998; Tsuji, J., Palladium Reagents and Catalysts, Wiley, 1996; Hartwig, J., Angew. Chem. 1998, 110, 2154; Farina, V. et al., The Stille Reaction, Wiley, 1994; Buchwald, S. et al. J. Am. Chem. Soc. 2001, 123, 7727; Buchwald, S. et al., Organic Lett. 2002, 4, 581; Netherton, M. R. et al., Topics in Organometallic Chemistry 2005, 14, 85-108; Littke, A. F. et al., Angew. Chem. Int. Ed. 2002, 41, 4176-4211; Muci, A. R. et al., Topics in Current Chemistry 2002, 219, 131-209, for example. Nitro groups can be reduced to amino groups with various reducing agents, such as sulfides, dithionites, complex hydrides or by catalytic hydrogenation. A reduction of a nitro group may also be carried out simultaneously with a reaction performed on another functional group, for example when reacting a group like a cyano group with hydrogen sulfide or when hydrogenating a group. Amino groups, including an amino group representing R1, can be modified according to standard procedures, for example alkylated by reaction with optionally substituted alkyl halogenides like chlorides, bromides or iodides or sulfonyloxy compounds like tosyloxy, mesyloxy or trifluoromethylsulfonyloxy compounds, preferably in the presence of a base like potassium carbonate, cesium carbonate, sodium hydride or potassium tert-butoxide, or by reductive amination of carbonyl compounds, or acylated by reaction with activated carboxylic acid derivatives such as acid chlorides, anhydrides, activated esters or others or by reaction with carboxylic acids in the presence of an activating agent, or sulfonylated by reaction with sulfonyl chlorides. Ester groups can be hydrolyzed to the corresponding carboxylic acids which after activation can then be reacted with amines under standard conditions. Furthermore, ester or acid groups can be reduced to the corresponding alcohols by many standard procedures, and the resulting hydroxy compounds alkylated. Ether groups, for example benzyloxy groups or other easily cleavable ether groups, can be cleaved to give hydroxy groups which can then be reacted with a variety of agents, for example etherification agents or activating agents allowing replacement of the hydroxy group by other groups. A hydroxy group can also be converted into a leaving group and reacted with various reaction partners under the well-known conditions of the Mitsunobu reaction (Mitsunobu, O., Synthesis 1981, 1), or by further procedures known to the person skilled in the art.

The mentioned reactions for the conversion of functional groups are, in general, extensively described in textbooks of organic chemistry like M. Smith, J. March, March's Advanced Organic Chemistry, Wiley-VCH, 2001, and in Houben-Weyl, Methoden der Organischen Chemie (Methods of Organic Chemistry), Georg Thieme Verlag, Stuttgart, Germany; Organic Reactions, John Wiley & Sons, New York; R. C. Larock, Comprehensive Organic Transformations, Wiley-VCH, $2^{nd}$ ed (1999); B. Trost, I. Fleming (eds.), Comprehensive Organic Synthesis, Pergamon, 1991; A. Katritzky, C. Rees, E. Scriven, Comprehensive Heterocyclic Chemistry II, Elsevier Science, 1996; for example, in which details on the reactions and primary source literature can be found. Due to the fact that in the present case the functional groups occur in pyrazolo[3,4-d]pyrimidine or pyrazolo[4,3-c]pyridine compounds, it may in certain cases become necessary to specifically adapt reaction conditions or choose specific reagents from a variety of reagents that can in principle be employed in a conversion reaction, or otherwise take specific measures for achieving a desired conversion, for example to use protection group techniques, as applies in general and is known to the person skilled in the art.

In the course of the preparation of the compounds of the formula I it can generally be advantageous or necessary in order to reduce or prevent undesired reactions or side reactions in the respective synthesis steps, to block functional groups temporarily by protecting groups suited to the specific synthesis problem, or to have them present, or introduce them, in the form of precursor groups, and later convert them into the desired functional groups. Such strategies are well known to a person skilled in the art and are described, for example, in Greene and Wuts, Protective Groups in Organic Synthesis, Wiley, 1991, or P. Kocienski, Protecting Groups, Thieme 1994. Examples of precursor groups are cyano groups and nitro groups. The cyano group can, in a later step, be transformed by hydrolysis into carboxylic acid derivatives or by reduction into aminomethyl groups. Nitro groups can be transformed by reduction like catalytic hydrogenation into amino groups. Examples of protective groups which may be mentioned, are benzyl protective groups, for example benzyl ethers of hydroxy compounds and benzyl esters of carboxylic acids, from which the benzyl group can be removed by catalytic hydrogenation in the presence of a palladium catalyst, tert-butyl protective groups, for example tert-butyl esters of carboxylic acids, from which the tert-butyl group can be removed by treatment with trifluoroacetic acid, acyl protective groups, for example ester and amides of hydroxy compounds and amino compounds, which can be cleaved again by acidic or basic hydrolysis, or alkoxycarbonyl protective groups, for example tert-butoxycarbonyl derivatives of amino compounds, which can be cleaved again by treatment with trifluoroacetic acid. Compounds of the formula I can also be prepared by solid phase techniques. In such a synthetic approach, the solid phase may also be regarded as having the meaning of a protecting group, and cleavage from the solid phase as removal of the protective group. The use of such techniques is known to a person skilled in the art (cf. Burgess, K. (Ed.), Solid Phase Organic Synthesis, New York, Wiley, 2000). For example, a phenolic hydroxy group can be attached to a trityl-polystyrene resin, which serves as a protecting group, and the molecule cleaved from the resin by treatment with trifluoroacetic acid or another acid at a later stage of the synthesis.

As is usual and applies to all reactions performed in the course of the synthesis of a compound of the formula I, appropriate details of the conditions applied in a specific preparation process, including the solvent, a base or acid, the temperature, the order of addition, the molar ratios and other parameters, are routinely chosen by the skilled person in view of the characteristics of the starting compounds and the target compound and the other particularities of the specific case. As is also known by the skilled person, not all processes described herein will in the same way be suitable for the preparation of all compounds of the formula I and their intermediates, and adaptations have to be made. In all processes for the preparation of the compounds of the formula I, workup of the reaction mixture and the purification of the product is performed according to customary methods known to the skilled person which include, for example, quenching of a reaction mixture with water, adjustment of a certain pH, precipitation, extraction, drying, concentration, crystallization, distillation and chromatography. As further examples of methods applicable in the synthesis of the compounds of the formula I, microwave assistance for speeding-up, facilitating or enabling reactions, as described by Lidstrom, P. et al., Tetrahedron 2001, 57, 9225, for example, may be mentioned, and modern separation techniques like preparative high pressure liquid chromatography (HPLC), which can be used for separating mixtures of positional isomers which may occur in any reactions. Also for the characterization of the products, customary methods are used such as NMR, IR and mass spectroscopy.

Another subject of the present invention are the novel starting compounds and intermediates occurring in the synthesis of the compounds of the formula I, including the compounds of the formulae II to XVII, wherein the groups X, Z, R1 to R3, G1 to G8 and the number n are defined as above, in any of their stereoisomeric forms or a mixture of stereoisomeric forms in any ratio, and their salts, and their use as synthetic intermediates or starting compounds. All general explanations, specifications of embodiments and definitions of numbers and groups given above with respect to the compounds of the formula I apply correspondingly to the said intermediates and starting compounds. A subject of the invention are in particular the novel specific starting compounds and intermediates described herein. Independently thereof whether they are described as a free compound and/or as a specific salt, they are a subject of the invention both in the form of the free compounds and in the form of their salts, and if a specific salt is described, additionally in the form of this specific salt.

The compounds of the present invention are SGK inhibitors, which are capable of inhibiting an exaggerated, or inappropriate, activity of SGK in pathological conditions and are therefore suitable for the prophylaxis and therapy of the diseases mentioned above and below. In particular, they are highly active inhibitors of the SGK-1 enzyme. They are selective SGK-1 inhibitors inasmuch as they do not substantially inhibit or promote the activity of other enzymes and receptors whose activation or inhibition is not desired. The activity of the compounds of the formula I can be determined, for example, in the assays described below or in other in vitro, ex vivo or in vivo assays known to the person skilled in the art. For example, the ability of the compounds to inhibit the SGK enzyme may be measured by methods similar to those described in Perrin, D. et al., Capillary microfluidic electrophoretic mobility shift assays: application to enzymatic assays in drug discovery, Expert Opin. Drug Discov. 2010, 5, 51-63, and by the assay described below. With respect to SGK-1 inhibitory activity, one embodiment of the invention comprises compounds which have an $IC_{50}$ value of <1 µM, in another embodiment of <0.1 µM, in another embodiment of <0.01 µM, for SGK-1 inhibition as determined in the assay described below, and which in a further embodiment do not substantially influence the activity of other enzymes and receptors whose inhibition or activation is not desired. The ability of the compounds to inhibit the SGK-1 mediated glycogen synthase kinase 3beta (GSK3beta) phosphorylation in a cellular setting may be measured by methods similar to those described by Sakoda, H. et al., Differing Roles of Akt and Serum- and Glucocorticoid-regulated Kinase in Glucose Metabolism, DNA Synthesis, and Oncogenic Activity, J. Biol. Chem. 2003, 278, 25802-25807, and by the method described below. The ability of the compounds to inhibit SGK1 dependent activation of epithelial $Na^+$ channel (ENaC) currents in cell monolayers may be measured by methods similar to those described by Alvarez de la Rosa, D. et al., Role of SGK in hormonal regulation of epithelial sodium channel in A6 cells, Am. J. Physiol. Cell Physiol. 2003, 284, C404-C414; Alvarez de la Rosa, D. et al.; Mechanisms of Regulation of Epithelial Sodium Channel by SGK1 in A6 Cells, J. Gen. Physiol. 2004, 124, 395-407, and by the assay described below. The inappropriate SGK-1 activity referred to herein is any SGK-1 activity that deviates from the expected normal SGK-1 activity. Inappropriate SGK-1 activity may take the form of, for example, an abnormal increase in activity, or an aberration in the timing and/or control of SGK-1 activity. Such inappropriate activity may result then, for example, from overexpression or mutation of the protein kinase leading to inappropriate or uncontrolled activation. As SGK-1 inhibitors, the compounds of the formula I and their pharmaceutically acceptable salts are generally suitable for the prophylaxis and/or therapy of conditions in which the inappropriate activity of SGK-1 enzyme plays a role or has an undesired extent, or which can favorably be influenced by inhibiting the SGK-1 enzyme or decreasing the activity, or for the prevention, alleviation or cure of which an inhibition of SGK-1 or a decrease in the activity is desired by the physician.

Because of their pharmacological properties, the compounds of the present invention are suitable for the treatment of all disorders in the progression of which an enhanced activity of SGK enzyme is involved including, for example, the indications described in the introduction. The invention relates in particular to the use of a compound of the formula I or a pharmaceutically acceptable salt thereof for the treatment of degenerative joint disorders and degenerative cartilage changes including osteoarthritis, osteoarthrosis, rheumatoid arthritis, spondylosis, chondrolysis following joint trauma and prolonged joint immobilization after meniscus or patella injuries or ligament tears, connective tissue disorders such as collagenoses, periodontal disorders, wound-healing disturbances, diabetes including diabetes mellitus, diabetic nephropathy, diabetic neuropathy, diabetic angiopathy and microangiopathy, obesity, metabolic syndrome (dyslipidaemia), systemic and pulmonary hypertension, cerebral infarctions, cardiovascular diseases including cardiac fibrosis after myocardial infarction, cardiac hypertrophy and heart failure, arteriosclerosis, renal diseases including glomerulosclerosis, nephrosclerosis, nephritis, nephropathy and electrolyte excretion disorder, any type of fibrosis and inflammatory processes including liver cirrhosis, lung fibrosis, fibrosing pancreatitis, rheumatism, arthritis, gout, Crohn's disease, chronic bronchitis, radiation fibrosis, sclerodermatitis, cystic fibrosis, scar formation, Alzheimer's disease, pain including acute pain like pain following injuries, post-operative pain, pain in association with an acute attack of gout and acute pain following jaw-bone surgery interventions, and chronic pain like pain associated with chronic musculoskeletal diseases, back pain, pain associated with osteoarthritis or rheumatoid arthritis, pain associated with inflammation, amputation pain, pain associated with multiple sclerosis, pain associated with neuritis, pain associated with carcinomas and sarcomas, pain associated with AIDS, pain associated with chemotherapy, trigeminus neuralgia, headache, migraine, cephalalgia, neuropathic pains, post-herpes zoster neuralgia, chronic disorders of the locomotor system such as inflammatory, immunologically or metabolically related acute and chronic arthritides, arthropathies, myalgias and disturbances of bone metabolism, peptic ulcers, especially in forms that are triggered by stress, tinnitus, bacterial infections, glaucoma, cataracts, coagulopathies including dysfibrinogenaemia, hypoproconvertinaemia, haemophilia B, Stuart-Prower defect, prothrombin complex deficiency, consumption coagulopathy, fibrinolysis, immunokoagulopathy or complex coagulopathies, and to the use in tumor therapy including inhibition of tumor growth and tumor metastases, the use in anti-infective therapy, the use for increasing the learning ability and attention, the use for counteracting cellular aging and stress and thus increasing life expectancy and fitness in the elderly, and the use in states of neuronal excitability including epilepsy and progressive myoclonic epilepsy of the Lafora type (Lafora disease). The treatment of diseases is to be understood herein as generally meaning both the therapy of existing pathological changes or malfunctions of the organism or of existing symptoms with the aim of relief, alleviation or cure, and the prophylaxis or prevention of pathological changes or malfunctions of the organism or of symptoms in humans or animals which are susceptible thereto and are in need of such a prophylaxis or prevention, with the aim of a prevention or suppression of their occurrence or of an attenuation in the case of their occurrence. For example, in patients who on account of their disease history are susceptible to myocardial infarction, by means of the prophylactic or preventive medicinal treatment the occurrence or re-occurrence of a myocardial infarct can be prevented or its extent and sequelae decreased. In one embodiment of the invention the treatment of diseases is the therapy of existing pathological changes or malfunctions, in another embodiment it is the prophylaxis or prevention of pathological changes or malfunctions The treatment of diseases can occur both in acute cases and in chronic cases.

The compounds of the formula I and their pharmaceutically acceptable salts can therefore be used in animals, in particular in mammals and specifically in humans, as a pharmaceutical or medicament on their own, in mixtures with one another, or in the form of pharmaceutical compositions. A subject of the present invention also are the compounds of the formula I and their pharmaceutically acceptable salts for use as a pharmaceutical. A subject of the present invention also are pharmaceutical compositions and medicaments which comprise at least one compound of the formula I and/or a pharmaceutically acceptable salt thereof as an active ingredient, in an effective dose for the desired use, and a pharmaceutically acceptable carrier, i.e. one or more pharmaceutically innocuous, or nonhazardous, vehicles and/or excipients, and optionally one or more other pharmaceutical active compounds.

A subject of the present invention also are the compounds of the formula I and their pharmaceutically acceptable salts for use in the treatment of the diseases mentioned above or below, including the treatment of any one of the mentioned diseases, for example the treatment of degenerative joint disorders, degenerative cartilage changes, diabetes, cardiovascular diseases, fibrosis, inflammatory processes, epilepsy, pain, tumors or cerebral infarctions, wherein treatment of diseases comprises their therapy and prophylaxis as mentioned above, or for use as an inhibitor of serum and glucocorticoid regulated kinase (SGK). A subject of the present invention also are the use of the compounds of the formula I and their pharmaceutically acceptable salts for the manufacture of a medicament for the treatment of the diseases mentioned above or below, including the treatment of any one of the mentioned diseases, for example the treatment of degenerative joint disorders, degenerative cartilage changes, diabetes, cardiovascular diseases, fibrosis, inflammatory processes, epilepsy, pain, tumors or cerebral infarctions, wherein treatment of diseases comprises their therapy and prophylaxis as mentioned above, or a medicament for inhibition of serum and glucocorticoid regulated kinase (SGK). A subject of the present invention also are methods for the treatment of the diseases mentioned above or below, including the treatment of any one of the mentioned diseases, for example the treatment of degenerative joint disorders, degenerative cartilage changes, diabetes, cardiovascular diseases, fibrosis, inflammatory processes, epilepsy, pain, tumors or cerebral infarctions, wherein treatment of diseases comprises their therapy and prophylaxis as mentioned above, and a method for inhibiting serum and glucocorticoid regulated kinase (SGK), which comprise administering an efficacious amount of at least one compound of the formula I and/or a pharmaceutically acceptable salt thereof to a human or an animal which is in need thereof.

The compounds of the formula I and their pharmaceutically acceptable salts, and pharmaceutical compositions and medicaments comprising them, can be administered enterally, for example by oral or rectal administration in the form of pills, tablets, lacquered tablets, coated tablets, granules, hard and soft gelatin capsules, solutions, syrups, emulsions, suspensions, aerosol mixtures or suppositories, or parenterally. Parenteral administration can be carried out, for example, intravenously, intraarticularly, intraperitoneally, intramuscularly or subcutaneously, in the form of injection solutions or infusion solutions, microcapsules, implants or rods, or percutaneously, transdermally or topically, for example in the form of ointments, solutions or tinctures, or in other ways, for example in the form of aerosols or nasal sprays. The preferred form of administration depends on the particulars of the specific case.

Pharmaceutical formulations adapted for transdermal administration can be administered as plasters for extended, close contact with the epidermis of the recipient. For topical administration, formulations such as ointments, creams, suspensions, lotions, powders, solutions, pastes, gels, sprays, aerosols or oils can be used. For the treatment of the eye or other external tissue, for example mouth and skin, suitable formulations are topical ointments or creams, for example. In the case of ointments, the active ingredient can be employed either with a paraffinic or a water-miscible cream base. Alternatively, the active ingredient can be formulated to give a cream with an oil-in-water cream base or a water-in-oil base. Pharmaceutical formulations adapted for topical application to the eye include eye drops, in which the active ingredient is dissolved or suspended in a suitable carrier, in particular an aqueous solvent.

The pharmaceutical compositions according to the invention are prepared in a manner known per se and familiar to the person skilled in the art by admixing one or more pharmaceutically acceptable inert inorganic and/or organic vehicles and excipients with one or more compounds of the formula I and/or pharmaceutically acceptable salts thereof, and bringing them into a suitable form for dosage and administration, which can then be used in human medicine or veterinary medicine. For the production of pills, tablets, coated tablets and hard gelatin capsules it is possible to use, for example, lactose, cornstarch or derivatives thereof, talc, stearic acid or its salts. For the production of gelatin capsules and suppositories fats, waxes, semisolid and liquid polyols, natural or hardened oils, for example, can be used. For the production of solutions, for example injection solutions, or of emulsions or syrups water, saline, alcohols, glycerol, polyols, sucrose, invert sugar, glucose, vegetable oils, for example, can be used, and for the production of microcapsules, implants or rods copolymers of glycolic acid and lactic acid, for example, can be used. The pharmaceutical compositions normally contain from about 0.5% to 90% by weight of the compounds of the formula I and/or their pharmaceutically acceptable salts. The amount of the active ingredient of the formula I and/or its pharmaceutically acceptable salts in the pharmaceutical compositions normally is from about 0.5 mg to about 1000 mg, preferably from about 1 mg to about 500 mg per unit dose. Depending on the kind of the pharmaceutical composition and other particulars of the specific case, the amount may deviate from the indicated ones.

In addition to the active ingredients of the formula I and/or their pharmaceutically acceptable salts and to vehicles, or carrier substances, the pharmaceutical compositions can contain excipients, or auxiliaries or additives, such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I, and/or their pharmaceutically acceptable salts. In case a pharmaceutical composition contains two or more compounds of the formula I, the selection of the individual compounds can aim at a specific overall pharmacological profile of the pharmaceutical composition. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds.

When using the compounds of the formula I, the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches known to the person skilled in the art. In general, the daily dose for achieving the desired results in an adult weighing about 75 kg is from about 0.01 mg/kg to about 100 mg/kg, preferably from about 0.1 mg/kg to about 50 mg/kg, in particular from about 0.1 mg/kg to about 10 mg/kg, in each case in mg per kg of body weight. The daily dose can be divided, in particular in the case of the administration of relatively large amounts, into several, for example 2, 3 or 4, part administrations. As usual, depending on individual behavior it may be necessary to deviate upwards or downwards from the daily dose indicated.

The compounds of the present invention are also useful as standard or reference compounds, for example as a quality standard or control, in tests or assays involving the inhibition of the SGK enzyme. For such use, for example in pharmaceutical research involving the SGK enzyme, the compounds may be provided in a commercial kit. For example, a compound of the present invention can be used as a reference in an assay to compare its known activity to a compound with an unknown activity. Furthermore, the compounds of the formula I can be used as synthesis intermediates for the preparation of other compounds, in particular of other pharmaceutical active compounds, which may be obtained from the compounds of the formula I by introduction of substituents or modification of functional groups, for example.

The following examples illustrate the present invention.

EXAMPLES

When in the final step of the synthesis of an example compound an acid such as trifluoroacetic acid or acetic acid was used, for example when trifluoroacetic acid was employed to remove an acid-labile protecting group containing a tert-butyl group, or when a compound was purified by chromatography using an eluent which contained such an acid, as is usual in HPLC (High Performance Liquid Chromatography) purifications on reversed phase columns, in some cases, depending on the work-up procedure, for example the details of a freeze-drying process, the compound was obtained partially or completely in the form of a salt of the acid used, for example in the form of the acetic acid salt or trifluoroacetic acid salt. In the names of the example compounds and the structural formulae such contained trifluoroacetic acid or acetic acid is not specified. Likewise, the acid component of other acid addition salts, such as hydrochlorides, for example, in the form of which example compounds have in part been isolated, is not specified in the names and formulae.

The prepared compounds were in general characterized by spectroscopic data and chromatographic data, in particular mass spectra (MS) and/or nuclear magnetic resonance (NMR) spectra. ¹H-NMR spectra were generally recorded at 400 MHz. In the NMR characterization, the chemical shift δ (in ppm), the number of hydrogen atoms (H), the coupling constant J (in Hz) and the multiplicity (s: singlet, d: doublet, dd: double doublet, t: triplet, dt: double triplet, m: multiplet; br: broad) of the peaks are given. In the MS characterization, the mass number (m/e) of the peak of the molecular ion (M) or of a related ion such as the ion (M+1), i.e. the protonated molecular ion (M+H), or the ion (M−1), which was formed depending on the ionization method used, is given. Generally, the ionization method was electrospray ionization (ES+ or ES−).

ABBREVIATIONS

BDFP 1,1'-Bis(diphenylphosphino)ferrocene-palladium(II) dichloride (Pd(dppf)₂Cl₂)
DCM Dichloromethane
Diox [1,4]Dioxane
DMF N,N-Dimethylformamide
DMSO Dimethyl sulfoxide
EtOAc Ethyl acetate
Hep n-Heptane
iPrOH Isopropanol
MeCN Acetonitrile
RT Room temperature (20° C. to 25° C.)
TFA Trifluoroacetic acid
THF Tetrahydrofuran Example 1

2,5-Dichloro-N-[4-(3-methyl-1H-pyrazolo[3,4-d]pyrimidin-6-yl)-phenyl]-benzenesulfonamide

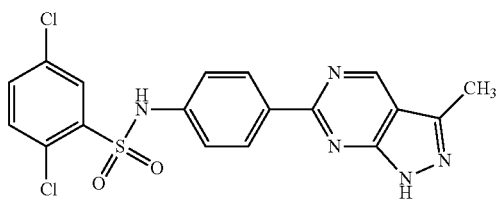

(i) 2,5-Dichloro-N-[4-(4,4,5,5-tetramethyl-[1,3,2]dioxaborolan-2-yl)-phenyl]-benzenesulfonamide 2,5-Dichloro-benzenesulfonyl chloride (11.7 g) and 4-(4,4,5,5-tetramethyl-[1,3,2]dioxaborolan-2-yl)phenylamine (10.0 g) were added to a reaction vessel containing a magnetic stirring bar, followed by 200 ml dry DCM and 4.1 ml pyridine. The reaction mixture was stirred at RT for 20 h before being cooled on an ice-bath and quenched with 1M aqueous sodium hydroxide solution. The organic phase was separated and the aqueous phase acidified with 2M aqueous hydrochloric acid and extracted three times with EtOAc. The combined organic phases were washed with brine and dried over sodium sulfate and evaporated to afford the crude product. Purification by flash chromatography on silica gel using a mixture of EtOAc and Hep as the eluent afforded 2,5-dichloro-N-[4-(4,4,5,5-tetramethyl-[1,3,2]dioxaborolan-2-yl)-phenyl]-benzenesulfonamide as a colorless solid after evaporation of the solvents under reduced pressure. Yield: 13.67 g (70%).

MS (ES−): m/e=426.2 (M−H), chloro pattern.

(ii) 2,5-Dichloro-N-[4-(3-methyl-1H-pyrazolo[3,4-d]pyrimidin-6-yl)-phenyl]-benzenesulfonamide 2,5-Dichloro-N-[4-(4,4,5,5-tetramethyl-[1,3,2]dioxaborolan-2-yl)-phenyl]-benzenesulfonamide (514 mg) was added to a reaction vessel containing a magnetic stirring bar together with 6-chloro-3-methyl-1-(tetrahydro-pyran-2-yl)-1H-pyrazolo[3,4-d]pyrimidine (303 mg) (prepared from 6-chloro-3-methyl-1H-pyrazolo[3,4-d]pyrimidine (WO 2005/121107) analogously to the procedure described in example 3 (i)), BDFP (70 mg) and cesium carbonate (1.17 g), followed by 12 ml Diox and 2 ml water, and the mixture heated to 100° C. under stirring. After 3 h the reaction mixture was cooled to RT and quenched with a saturated aqueous sodium hydrogencarbonate solution (100 ml) and extracted with EtOAc (3×200 ml). The combined aqueous phases were dried over sodium sulfate, filtered and evaporated to afford the crude product as a brown oil. The crude product was dissolved in a mixture of 4M HCl in Diox (6 ml) and iPrOH (6 ml) and stirred for 2 h at RT before evaporation of the solvent. The crude product was purified by preparative HPLC (C18 reversed phase column, elution with a water/MeCN gradient with 0.1% TFA). The fractions containing the product were lyophilized to yield pure 2,5-dichloro-N-[4-(3-methyl-1H-pyrazolo[3,4-d]pyrimidin-6-yl)-phenyl]-benzenesulfonamide. Yield: 83 mg (16%).

¹H-NMR (DMSO-d₆): δ (ppm)=2.55 (s, 3H), 7.27 (d, J=8.8 Hz, 2H), 7.69 (d, J=8.5 Hz, 1H), 7.74 (dd, J=2.5, 8.5

Hz, 1H), 8.07 (d, J=2.5 Hz, 1H), 8.34 (d, J=8.8 Hz, 2H), 9.31 (s, 1H), 11.12 (s, 1H), 13.56 (s, 1H).

MS (ES+): m/e=434.1 (M+H), chloro pattern.

Example 2

2,5-Dichloro-N-[4-(4-morpholin-4-yl-1H-pyrazolo[3,4-d]pyrimidin-6-yl)-phenyl]-benzenesulfonamide

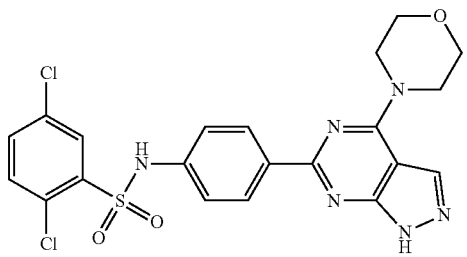 [SMILES: O=S(=O)(Nc1ccc(-c2nc(N3CCOCC3)c3cn[nH]c3n2)cc1)c1cc(Cl)ccc1Cl]

(i) 6-Chloro-4-morpholin-4-yl-1H-pyrazolo[3,4-d]pyrimidine

Morpholine (1.19 ml) was added to a reaction vessel at RT equipped with a magnetic stirring bar and containing a solution of commercially available 4,6-dichloro-1H-pyrazolo[3,4-d]pyrimidine (2.46 g) in DCM (100 ml) and triethylamine (3.61 ml). The reaction mixture was stirred at RT for 2 h during which a white precipitate was formed, and then evaporated to dryness. The residue was stirred in water (100 ml) for 1 h, filtered and the solid washed with water and dried under vacuum to afford 2.84 g 6-chloro-4-morpholin-4-yl-1H-pyrazolo[3,4-d]pyrimidine as a colorless solid (91%).

MS (ES+): m/e=240.1 (M+H), chloro pattern.

(ii) 6-Chloro-4-morpholin-4-yl-1-(tetrahydro-pyran-2-yl)-1H-pyrazolo[3,4-d]pyrimidine 6-Chloro-4-morpholin-4-yl-1H-pyrazolo[3,4-d]pyrimidine (1.2 g) was dissolved in THF (30 ml) followed by addition of 3,4-dihydro-2H-pyran (2.29 ml) and pyridinium 4-toluenesulfonate (63 mg) at RT. The reaction mixture was heated to 60° C. for 3 h and allowed to cool down before evaporation of the volatiles. The residue was dissolved in DCM (80 ml) and washed with a saturated aqueous sodium hydrogencarbonate solution (3×50 ml), dried over sodium sulfate, filtered and evaporated to afford 6-chloro-4-morpholin-4-yl-1-(tetrahydro-pyran-2-yl)-1H-pyrazolo[3,4-d]pyrimidine in quantitative yield.

MS (ES+): m/e=324.1 (M+H), chloro pattern.

(iii) 2,5-Dichloro-N-[4-(4-morpholin-4-yl-1H-pyrazolo[3,4-d]pyrimidin-6-yl)-phenyl]-benzenesulfonamide 2,5-Dichloro-N-[4-(4,4,5,5-tetramethyl-[1,3,2]dioxaborolan-2-yl)-phenyl]-benzenesulfonamide (343 mg) was added to a reaction vessel containing a magnetic stirring bar together with 6-chloro-4-morpholin-4-yl-1-(tetrahydro-pyran-2-yl)-1H-pyrazolo[3,4-d]pyrimidine (259 mg), BDFP (47 mg) and cesium carbonate (782 mg), followed by 8 ml Diox and 2 ml water, and the mixture heated to 100° C. under stirring. After 3 h the reaction mixture was cooled to RT and quenched with a saturated aqueous sodium hydrogencarbonate solution (100 ml) and extracted with EtOAc (3×200 ml). The combined aqueous phases were dried over sodium sulfate, filtered and evaporated to afford the crude product as a brown oil. The crude product was dissolved in a mixture of 4M HCl in Diox (6 ml) and iPrOH (6 ml) and stirred for 2 h at RT before evaporation of the solvent. The crude product was purified by preparative HPLC (C18 reversed phase column, elution with a water/MeCN gradient with 0.1% TFA). The fractions containing the product were lyophilized to yield pure 2,5-dichloro-N-[4-(4-morpholin-4-yl-1H-pyrazolo[3,4-d]pyrimidin-6-yl)-phenyl]-benzenesulfonamide. Yield: 163 mg (40%).

$^1$H-NMR (DMSO-$d_6$): δ (ppm)=3.76-3.79 (m, 2H), 4.00 (br, 2H), 7.24 (d, J=8.8 Hz, 2H), 7.69 (d, J=8.6 Hz, 1H), 7.74 (dd, J=2.5, 8.6 Hz, 1H), 8.06 (d, J=2.5 Hz, 1H), 8.26 (d, J=8.8 Hz, 2H), 8.39 (br, 1H), 11.12 (br s, 1H).

MS (ES+): m/e=505.3 (M+H), chloro pattern.

Example 3

5-Chloro-2-fluoro-N-{4-[4-(4-hydroxy-cyclohexyloxy)-1H-pyrazolo[3,4-d]pyrimidin-6-yl]-phenyl}-benzenesulfonamide

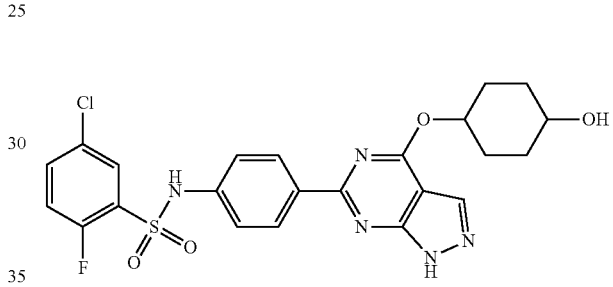

(i) 4,6-Dichloro-1-(tetrahydro-pyran-2-yl)-1H-pyrazolo[3,4-d]pyrimidine

Commercially available 4,6-dichloro-1H-pyrazolo[3,4-d]pyrimidine (30 g) was dissolved in THF (400 ml) in a reaction vessel containing a magnetic stirring bar, followed by addition of 3,4-dihydro-2H-pyran (72.5 ml) and pyridinium 4-toluenesulfonate (1.99 g) at RT. The reaction mixture was heated to 60° C. for 2 h and allowed to cool down before evaporation of the volatiles. The residue was dissolved in EtOAc (200 ml) and washed with a saturated aqueous sodium hydrogencarbonate solution (3×100 ml), dried over sodium sulfate, filtered and evaporated to afford 4,6-dichloro-1-(tetrahydro-pyran-2-yl)-1H-pyrazolo[3,4-d]pyrimidine in quantitative yield.

(ii) 4-[6-Chloro-1-(tetrahydro-pyran-2-yl)-1H-pyrazolo[3,4-d]pyrimidin-4-yloxy]-cyclohexanol 1,4-Cyclohexanediol (1.91 g, cis-trans mixture) was dissolved in 25 ml dry THF in a reaction vessel containing a magnetic stirring bar under a argon atmosphere, and the mixture cooled on an ice bath. Then sodium hydride (132 mg, 60% suspension in mineral oil) was added and the mixture stirred on an ice bath for approximately 30 min before addition of 4,6-dichloro-1-(tetrahydro-pyran-2-yl)-1H-pyrazolo[3,4-d]pyrimidine (948 mg) dissolved in 10 ml THF. The ice bath was removed and the mixture stirred at RT until complete conversion of the starting material as monitored by HPLC/MS. Then the reaction mixture was quenched with water (50 ml) and extracted with EtOAc (3×100 ml) and the combined organic phases dried over sodium sulfate, filtered and evaporated. The crude product was purified by flash chromatography on silica gel using a mixture of EtOAc and Hep as the eluent to afford 4-[6-chloro-1-(tetrahydro-pyran-2-yl)-1H-pyrazolo[3,4-d]pyrimidin-4-yloxy]-cyclohexanol as a colorless oil after evaporation. Yield: 755 mg (65%).

MS (ES+): m/e=353.0 (M+H), chloro pattern.

(iii) 5-Chloro-2-fluoro-N-{4-[4-(4-hydroxy-cyclohexyloxy)-1H-pyrazolo[3,4-d]pyrimidin-6-yl]-phenyl}-benzenesulfonamide 5-Chloro-2-fluoro-N-[4-(4,4,5,5-tetramethyl-[1,3,2]dioxaborolan-2-yl)-phenyl]-benzenesulfonamide (205 mg) was added to a reaction vessel containing a magnetic stirring bar together with 4-[6-chloro-1-(tetrahydro-pyran-2-yl)-1H-pyrazolo[3,4-d]pyrimidin-4-yloxy]-cyclohexanol (177 mg), BDFP (29 mg) and cesium carbonate (489 mg), followed by 5 ml Diox and 1 ml water, and the mixture heated to 100° C. under stirring. After 3 h the reaction mixture was cooled to RT and quenched with a saturated aqueous sodium hydrogencarbonate solution (50 ml) and extracted with EtOAc (3×75 ml). The combined aqueous phases were dried over sodium sulfate, filtered and evaporated to afford the crude product as a brown oil. The crude product was dissolved in a mixture of 4M HCl in Diox (6 ml) and iPrOH (6 ml) and stirred for 2 h at RT before evaporation of the solvent. The crude product was purified by preparative HPLC (C18 reversed phase column, elution with a water/MeCN gradient with 0.1% TFA). The fractions containing the product were lyophilized to yield pure 5-chloro-2-fluoro-N-{4-[4-(4-hydroxy-cyclohexyloxy)-1H-pyrazolo[3,4-d]pyrimidin-6-yl]-phenyl}-benzenesulfonamide. Yield: 49 mg (19%).

$^1$H-NMR (DMSO-$d_6$): δ (ppm)=1.39-2.20 (m, 8H), 3.55-3.63 (m, 0.67H), 3.66-3.72 (m, 0.33H), 4.55 (br, 0.33H), 4.63 (br, 0.67H), 5.40-5.48 (m, 0.67H), 5.50-5.55 (m, 0.33H), 7.26-7.31 (m, 2H), 7.49-7.54 (m, 1H), 7.77-7.81 (m, 1H), 7.86-7.89 (m, 1H), 8.11 (br s, 0.67H), 8.14 (br s, 0.33H), 8.29-8.34 (m, 2H), 11.10 (br s, 0.33H), 11.11 (br s, 0.67H), 13.86 (br s, 1H).

MS (ES+): m/e=518.1 (M+H), chloro pattern.

Example 4

2-Cyano-N-{4-[4-(4-hydroxy-cyclohexyloxy)-1H-pyrazolo[3,4-d]pyrimidin-6-yl]-phenyl}-5-methyl-benzenesulfonamide

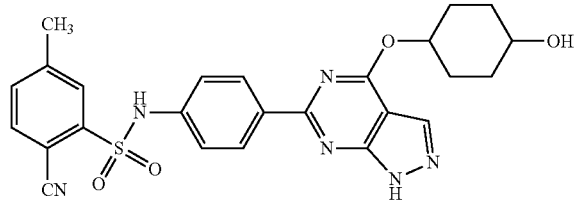 [SMILES: Cc1ccc(C#N)c(S(=O)(=O)Nc2ccc(-c3nc(OC4CCC(O)CC4)c4cn[nH]c4n3)cc2)c1]

(i) 4-[6-(4-Amino-phenyl)-1H-pyrazolo[3,4-d]pyrimidin-4-yloxy]-cyclohexanol

4-[6-Chloro-1-(tetrahydro-pyran-2-yl)-1H-pyrazolo[3,4-d]pyrimidin-4-yloxy]-cyclohexanol (2.0 g) (example 3, step (ii)) was added to a reaction vessel containing a magnetic stirring bar together with 4-(4,4,5,5-tetramethyl-[1,3,2]dioxaborolan-2-yl)-phenylamine (1.24 g), BDFP (331 mg) and cesium carbonate (5.5 g), followed by 50 ml Diox and 5 ml water, and the mixture heated to 100° C. under stirring. After 1 h the reaction mixture was cooled to RT and quenched with a saturated aqueous sodium hydrogencarbonate solution (50 ml) and extracted with EtOAc (3×75 ml). The combined aqueous phases were dried over sodium sulfate, filtered and evaporated to afford the crude product as a brown oil. The crude product was purified by flash chromatography on silica gel using a mixture of EtOAc and Hep as the eluent to afford 4-[6-(4-amino-phenyl)-1H-pyrazolo[3,4-d]pyrimidin-4-yloxy]-cyclohexanol as a brown foam. Yield: 1.1 g (47%).

MS (ES+): m/e=410.2 (M+H).

(ii) 2-Cyano-N-{4-[4-(4-hydroxy-cyclohexyloxy)-1H-pyrazolo[3,4-d]pyrimidin-6-yl]-phenyl}-5-methyl-benzenesulfonamide 4-[6-(4-Amino-phenyl)-1H-pyrazolo[3,4-d]pyrimidin-4-yloxy]-cyclohexanol (280 mg) was dissolved in pyridine (3 ml) and 2-cyano-5-methyl-benzenesulfonyl chloride (147 mg) was added and the mixture heated to 100° C. for 1 h and allowed to cool down before evaporation of the volatiles. The crude product was purified by preparative HPLC (C18 reversed phase column, elution with a water/MeCN gradient with 0.1% TFA). The fractions containing the product were lyophilized to yield pure 2-cyano-N-{4-[4-(4-hydroxy-cyclohexyloxy)-1H-pyrazolo[3,4-d]pyrimidin-6-yl]-phenyl}-5-methyl-benzenesulfonamide. Yield: 166.7 mg (48%).

$^1$H-NMR (DMSO-$d_6$): δ (ppm)=1.39-1.50 (m, 2H), 1.55-1.66 (m, 2H), 1.87-1.95 (m, 2H), 2.11-2.20 (m, 2H), 3.56-3.62 (m, 1H), 5.41-5.47 (m, 1H), 7.27 (d, J=8.7 Hz, 2H), 7.64 (d, J=7.8 Hz, 1H), 7.97 (d, J=7.8 Hz, 1H), 7.97 (s, 1H), 8.12 (s, 1H), 8.30 (d, J=8.7 Hz, 2H), 11.13 (s, 1H), 13.87 (br s, 1H).

MS (ES+): m/e=505.2 (M+H).

Example 5

2,5-Dichloro-N-[4-(4-pyridin-3-yl-1H-pyrazolo[3,4-d]pyrimidin-6-yl)-phenyl]-benzenesulfonamide

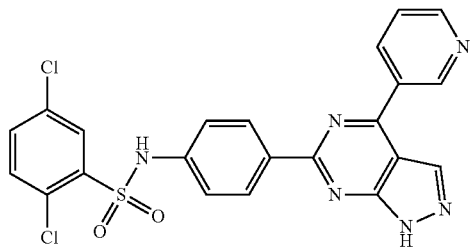 [SMILES: O=S(=O)(Nc1ccc(-c2nc(-c3cccnc3)c3cn[nH]c3n2)cc1)c1cc(Cl)ccc1Cl]

(i) 6-Chloro-4-pyridin-3-yl-1-(tetrahydro-pyran-2-yl)-1H-pyrazolo[3,4-d]pyrimidine In a reaction vessel containing a magnetic stirrer bar, 4,6-dichloro-1-(tetrahydro-pyran-2-yl)-1H-pyrazolo[3,4-d]pyrimidine (1.0 g) (example 3, step (i)) was dissolved in dry toluene (50 ml) before adding lithium chloride (434 mg), tetrakis(triphenylphosphine)palladium (338 mg) and 3-(tributylstannyl)pyridine (1.17 ml). The reaction mixture was heated to 100° C. for 20 h before being cooled to RT and quenched with a saturated aqueous sodium hydrogencarbonate solution (50 ml) and extracted with EtOAc (3×100 ml). The combined aqueous phases were dried over sodium sulfate, filtered and evaporated to afford the crude product that was purified by flash chromatography on silica gel using a mixture of EtOAc and Hep as the eluent to afford pure 6-chloro-4-pyridin-3-yl-1-(tetrahydro-pyran-2-yl)-1H-pyrazolo[3,4-d]pyrimidine. Yield: 45 mg (4%).

MS (ES+): m/e=316.1 (M+H), chloro pattern.

(ii) 2,5-Dichloro-N-[4-(4-pyridin-3-yl-1H-pyrazolo[3,4-d]pyrimidin-6-yl)-phenyl]-benzenesulfonamide 2,5-Dichloro-N-[4-(4,4,5,5-tetramethyl-[1,3,2]dioxaborolan-2-yl)-phenyl]-benzenesulfonamide (67.1 mg) was added to a reaction vessel containing a magnetic stirring bar together with 6-chloro-4-pyridin-3-yl-1-(tetrahydro-pyran-2-yl)-1H-pyrazolo[3,4-d]pyrimidine (45 mg), BDFP (8 mg) and cesium carbonate (140 mg), followed by 3 ml Diox and 0.5 ml water, and the mixture heated to 100° C. under stirring. After 20 h the reaction mixture was cooled to RT and quenched with a saturated aqueous sodium hydrogencarbonate solution (25 ml) and extracted with EtOAc (3×25 ml). The combined aqueous phases were dried over sodium sulfate, filtered and evaporated to afford the crude product as a brown oil. The crude product was dissolved in a mixture of 4M HCl in Diox (6 ml) and iPrOH (6 ml) and stirred for 2 h at RT before evaporation of the solvent. The crude product was purified by preparative HPLC (C18 reversed phase column, elution with a water/MeCN gradient with 0.1% TFA). The fractions containing the product were lyophilized to yield pure 2,5-dichloro-N-[4-(4-pyridin-3-yl-1H-pyrazolo[3,4-d]pyrimidin-6-yl)-phenyl]-benzenesulfonamide. Yield: 15.7 mg (21%).

$^1$H-NMR (DMSO-$d_6$): δ (ppm)=7.33 (d, J=8.9 Hz, 2H), 7.70 (d, J=8.5 Hz, 1H), 7.75 (dd, J=2.5, 8.5 Hz, 1H), 7.83-7.88 (m, 1H), 8.09 (d, J=2.5 Hz, 1H), 8.50 (d, J=8.9 Hz, 2H), 8.78 (s, 1H), 8.92 (d, J=5.0 Hz, 1H), 8.98 (d, J=7.8 Hz, 1H), 9.63 (d, J=2.0 Hz, 1H), 11.19 (s, 1H).

MS (ES−): m/e=495.3 (M−H), chloro pattern.

Example 6

5-Chloro-2-fluoro-N-[4-(4-methyl-1H-pyrazolo[3,4-d]pyrimidin-6-yl)-phenyl]-benzenesulfonamide

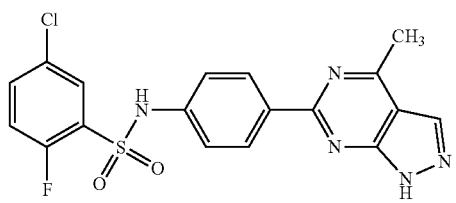 [SMILES: Cc1nc(-c2ccc(NS(=O)(=O)c3cc(Cl)ccc3F)cc2)nc2[nH]ncc12]

(i) 6-Chloro-4-methyl-1-(tetrahydro-pyran-2-yl)-1H-pyrazolo[3,4-d]pyrimidine 4,6-Dichloro-1-(tetrahydro-pyran-2-yl)-1H-pyrazolo[3,4-d]pyrimidine (1.0 g) (example 3, step (i)) was dissolved in dry THF (20 ml) under an argon atmosphere in a reaction vessel containing a magnetic stirrer bar. The solution was cooled on a dry ice acetone bath and methylmagnesium bromide (1.22 ml, 3M in diethyl ether) was added slowly by syringe and the cooling bath was removed. Incomplete conversion was observed at RT and another equivalent methylmagnesium bromide (1.22 ml, 3M in diethyl ether) was added. After 2 h the reaction mixture was quenched with a saturated aqueous sodium hydrogencarbonate solution (50 ml) and extracted with EtOAc (3×100 ml). The combined aqueous phases were dried over sodium sulfate, filtered and evaporated to afford the 6-chloro-4-methyl-1-(tetrahydro-pyran-2-yl)-1H-pyrazolo[3,4-d]pyrimidine. Yield: 920 mg (99%).

MS (ES+): m/e=253.1 (M+H), chloro pattern.

(ii) 5-Chloro-2-fluoro-N-[4-(4-methyl-1H-pyrazolo[3,4-d]pyrimidin-6-yl)-phenyl]-benzenesulfonamide 5-Chloro-2-fluoro-N-[4-(4,4,5,5-tetramethyl-[1,3,2]dioxaborolan-2-yl)-phenyl]-benzenesulfonamide (325 mg) was added to a reaction vessel containing a magnetic stirring bar together with 6-chloro-4-methyl-1-(tetrahydro-pyran-2-yl)-1H-pyrazolo[3,4-d]pyrimidine (200 mg), BDFP (46 mg) and cesium carbonate (773 mg), followed by 6 ml Diox and 1.0 ml water, and the mixture heated to 100° C. under stirring. After 4 h the reaction mixture was cooled to RT and quenched with a saturated aqueous sodium hydrogencarbonate solution (35 ml) and extracted with EtOAc (3×75 ml). The combined aqueous phases were dried over sodium sulfate, filtered and evaporated to afford the crude product as a brown oil. The crude product was dissolved in a mixture of 4M HCl in Diox (6 ml) and iPrOH (6 ml) and stirred for 2 h at RT before evaporation of the solvent. The crude product was purified by preparative HPLC (C18 reversed phase column, elution with a water/MeCN gradient with 0.1% TFA). The fractions containing the product were lyophilized to yield pure 5-chloro-2-fluoro-N-[4-(4-methyl-1H-pyrazolo[3,4-d]pyrimidin-6-yl)-phenyl]-benzenesulfonamide. Yield: 48.3 mg (15%).

$^1$H-NMR (DMSO-$d_6$): δ (ppm)=2.98 (s, 3H), 7.29 (d, J=8.8 Hz, 2H), 7.51 (d, J=8.9 Hz, 1H), 7.76-7.81 (m, 1H), 7.88 (dd, J=2.5, 6.0 Hz, 1H), 8.35 (d, J=8.8 Hz, 2H), 8.40 (s, 1H), 11.11 (s, 1H), 13.56 (s, 1H).

MS (ES+): m/e=417.9 (M+H), chloro pattern.

Example 7

N-[4-(3-Amino-4-methoxy-1H-pyrazolo[3,4-d]pyrimidin-6-yl)-phenyl]-5-chloro-2-fluoro-benzenesulfonamide

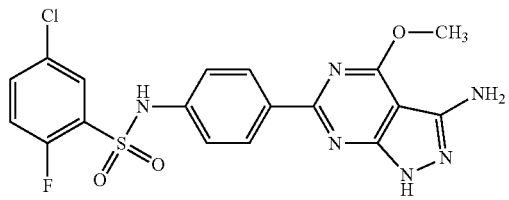 [SMILES: COc1nc(-c2ccc(NS(=O)(=O)c3cc(Cl)ccc3F)cc2)nc2[nH]nc(N)c12]

(i) 6-Chloro-4-methoxy-1H-pyrazolo[3,4-d]pyrimidine

To commercially available 4,6-dichloro-1H-pyrazolo[3,4-d]pyrimidine (5.0 g) dissolved in dry THF (100 ml) was added cesium carbonate (17.2 g) and methanol (60 ml) and the mixture heated to 60° C. After 30 min the reaction mixture was quenched with water and extracted three times with EtOAc. The combined organic phases were dried over sodium sulfate, filtered and evaporated to afford 6-chloro-4-methoxy-1H-pyrazolo[3,4-d]pyrimidine as a brown solid. Yield: 3.34 g (68%).

MS (ES+): m/e=185.0 (M+H), chloro pattern.

(ii) 6-Chloro-3-iodo-4-methoxy-1H-pyrazolo[3,4-d]pyrimidine

To 6-chloro-4-methoxy-1H-pyrazolo[3,4-d]pyrimidine (2.45 g) dissolved in dry DMF (60 ml) was added N-iodo-succinimide (3.45 g) and the reaction mixture heated to 80° C. under stirring. After 3 h the reaction mixture was cooled to RT and the DMF removed by rotary evaporation. Water was added to the residue which was then extracted three times with tert-butyl methyl ether. The combined organic phases were washed with water and brine and dried over sodium sulfate, filtered and evaporated to afford 6-chloro-3-iodo-4-methoxy-1H-pyrazolo[3,4-d]pyrimidine as a brown solid. Yield: 4.13 g (100%).

MS (ES+): m/e=310.9 (M+H), chloro pattern.

(iii) 6-Chloro-3-iodo-4-methoxy-1-(tetrahydro-pyran-2-yl)-1H-pyrazolo[3,4-d]pyrimidine 6-Chloro-3-iodo-4-methoxy-1H-pyrazolo[3,4-d]pyrimidine (4.1 g) was dissolved in THF (60 ml), in a reaction vessel containing a magnetic stirring bar, followed by addition of 3,4-dihydro-2H-pyran (11.4 ml) and pyridinium 4-toluenesulfonate (170 mg) at RT. The reaction mixture was heated to 60° C. for 3 h and allowed to cool down before evaporation of the volatiles. The residue was dissolved in EtOAc (200 ml) and washed with a saturated aqueous sodium hydrogencarbonate solution (3×100 ml), dried over sodium sulfate, filtered and evaporated to afford 6-chloro-3-iodo-4-methoxy-1-(tetrahydro-pyran-2-yl)-1H-pyrazolo[3,4-d]pyrimidine in quantitative yield.

MS (ES+): m/e=395.0 (M+H), chloro pattern.

(iv) Benzhydrylidene-[6-chloro-4-methoxy-1-(tetrahydro-pyran-2-yl)-1H-pyrazolo[3,4-d]pyrimidin-3-yl]-amine To a mixture of palladium acetate (305 mg) and 9,9-dimethyl-4,5-bis(diphenylphosphino)xanthene (923 mg) was added Diox (40 ml) and benzophenone imine (2.98 g) under argon, and the mixture heated to 100° C. for 5 min and then cooled to RT. Then cesium carbonate (13.1 g) and 6-chloro-3-iodo-4-methoxy-1-(tetrahydro-pyran-2-yl)-1H-pyrazolo[3,4-d]pyrimidine (5.25 g) in 90 ml Diox was added and the reaction mixture heated to 100° C. for 3 h. The reaction mixture was cooled, evaporated and diluted with water (400 ml) and extracted three times with tert-butyl methyl ether. The combined organic phases were washed with water and brine and dried over sodium sulfate, filtered and evaporated to afford the crude product that was purified by flash chromatography on silica gel using a mixture of EtOAc and Hep as the eluent to afford pure benzhydrylidene-[6-chloro-4-methoxy-1-(tetrahydro-pyran-2-yl)-1H-pyrazolo[3,4-d]pyrimidin-3-yl]-amine. Yield: 3.23 g (54%).

MS (ES+): m/e=448.3 (M+H), chloro pattern.

(v) N-{4-[3-(Benzhydrylidene-amino)-4-methoxy-1-(tetrahydro-pyran-2-yl)-1H-pyrazolo[3,4-d]pyrimidin-6-yl]-phenyl}-5-chloro-2-fluoro-benzenesulfonamide To a reaction vessel containing 5-chloro-2-fluoro-N-[4-(4,4,5,5-tetramethyl-[1,3,2]dioxaborolan-2-yl)-phenyl]-benzenesulfonamide (288 mg) a magnetic stirring bar and benzhydrylidene-[6-chloro-4-methoxy-1-(tetrahydro-pyran-2-yl)-1H-pyrazolo[3,4-d]pyrimidin-3-yl]-amine (313 mg) was added BDFP (41 mg) and cesium carbonate (688 mg), followed by 6 ml Diox and 1.0 ml water, and the mixture heated to 80° C. under stirring. After 3 h the reaction mixture was cooled to RT and quenched with a saturated aqueous sodium hydrogencarbonate solution (35 ml) and extracted with EtOAc (3×75 ml). The combined aqueous phases were dried over sodium sulfate, filtered and evaporated to afford the crude product that was purified by flash chromatography on silica gel using a mixture of EtOAc and Hep as the eluent to afford pure N-{4-[3-(benzhydrylidene-amino)-4-methoxy-1-(tetrahydro-pyran-2-yl)-1H-pyrazolo[3,4-d]pyrimidin-6-yl]-phenyl}-5-chloro-2-fluoro-benzenesulfonamide. Yield: 430 mg (88%).

MS (ES+): m/e=697.2 (M+H), chloro pattern.

(vi) N-[4-(3-Amino-4-methoxy-1H-pyrazolo[3,4-d]pyrimidin-6-yl)-phenyl]-5-chloro-2-fluoro-benzenesulfonamide N-{4-[3-(Benzhydrylidene-amino)-4-methoxy-1-(tetrahydro-pyran-2-yl)-1H-pyrazolo[3,4-d]pyrimidin-6-yl]-phenyl}-5-chloro-2-fluoro-benzenesulfonamide (430 mg) was dissolved in a mixture of 4M HCl in Diox (6 ml) and iPrOH (6 ml) and stirred for 2 h at RT before evaporation of the solvent. The crude product was purified by preparative HPLC (C18 reversed phase column, elution with a water/MeCN gradient with 0.1% TFA). The fractions containing the product were lyophilized to yield pure N-[4-(3-amino-4-methoxy-1H-pyrazolo[3,4-d]pyrimidin-6-yl)-phenyl]-5-chloro-2-fluoro-benzenesulfonamide. Yield: 45 mg (13%).

$^1$H-NMR (DMSO-d$_6$): δ (ppm)=4.12 (s, 3H), 5.39 (br s, 2H), 7.26 (d, J=8.7 Hz, 2H), 7.49-7.54 (m, 1H), 7.76-7.81 (m, 1H), 7.87 (dd, J=2.6, 6.0 Hz, 1H), 8.30 (d, J=8.8 Hz, 2H), 11.10 (s, 1H), 12.35 (s, 1H).

MS (ES+): m/e=449.1 (M+H), chloro pattern.

Analogously to the procedures described in the examples above, the example compounds of the formula Ib

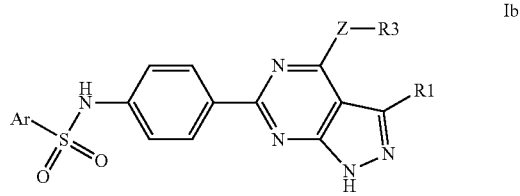

listed in Table 1 were synthesized. In the formulae of the groups —Z—R3 in Table 1 the line crossed with the symbol ⁓ represents the free bond via which the group —Z—R3 is bonded to the carbon atom in the 4-position of the pyrazolo[3,4-d]pyrimidine ring system. I.e., in the formula of the complete molecule the terminal endpoint of the line crossed with the said symbol ends at the carbon atom in the 4-position of the pyrazolo[3,4-d]pyrimidine ring system. If the respective starting compound of the formula H—Z—R3 contained two primary or secondary amino groups, in the employed starting material one of them was protected by a tert-butoxycarbonyl group. If the respective starting compound of the formula H—Z—R3 contained a hydroxy group and a primary or secondary amino group, and a reaction at the hydroxy group was intended, in the employed starting material the amino group was protected by a tert-butoxycarbonyl group. Deprotections were generally performed using either hydrogen chloride in Diox and/or iPrOH or TFA in DCM, for example a 1:1 mixture or TFA and DCM. In the column "Synthesis" the number of the example is specified in analogy to which the synthesis was performed, and in parentheses a reference to footnotes. The ionization method in the MS characterization was ES+ if the specified ion is M+H, and ES− if the specified ion is M−H. CP means chloro pattern, BP means bromo pattern in the mass spectrum.

TABLE 1

Example compounds of the formula Ib

| Example no. | Ar | R1 | —Z—R3 | Synthesis | Yield (%) | MS (m/e) |
|---|---|---|---|---|---|---|
| 8 | 5-chloro-2-fluoro-phenyl | H | —N(morpholine) | 2 | 2 | 489.2 (M + H), CP |
| 9 | 2,3-dichloro-phenyl | H | —N(morpholine) | 2 | 49 | 505.2 (M + H), CP |
| 10 | 5-chloro-2-fluoro-phenyl | CH$_3$ | —H | 1 | 40 | 418.2 (M + H), CP |
| 11 | 2,3-dichloro-phenyl | CH$_3$ | —H | 1 | 35 | 434.1 (M + H), CP |
| 12 | 2,3-dichloro-phenyl | H | —N(piperazine)N—CH$_3$ | 2 | 41 | 518.3 (M + H), CP |
| 13 | 5-chloro-2-fluoro-phenyl | H | —N(piperazine)N—CH$_3$ | 2 | 19 | 502.2 (M + H), CP |
| 14 | 2,5-dichloro-phenyl | H | —N(piperazine)N—CH$_3$ | 2 | 40 | 518.3 (M + H), CP |
| 15 | 2,3-dichloro-phenyl | H | —N(piperazine)NH | 2 | 66 | 502.2 (M − H), CP |
| 16 | 5-chloro-2-fluoro-phenyl | H | —N(piperazine)NH | 2 | 56 | 486.3 (M − H), CP |
| 17 | 2,5-dichloro-phenyl | H | —N(piperazine)NH | 2 | 65 | 502.1 (M − H), CP |
| 18 | 2,3-dichloro-phenyl | H | —NH—CH$_2$-(2-pyridyl) | 2 | 88 | 526.3 (M + H), CP |

TABLE 1-continued

Example compounds of the formula Ib

| Example no. | Ar | R1 | —Z—R3 | Synthesis | Yield (%) | MS (m/e) |
|---|---|---|---|---|---|---|
| 19 | 5-chloro-2-fluoro-phenyl | H | 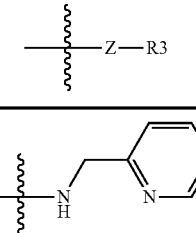 | 2 | 14 | 510.3 (M + H), CP |
| 20 | 5-chloro-2-fluoro-phenyl | H | 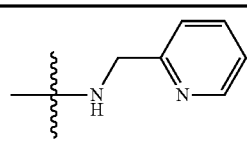 | 2 | 31 | 510.1 (M + H), CP |
| 21 | 2,5-dichloro-phenyl | H | 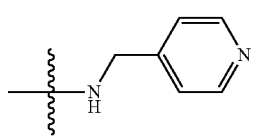 | 2 | 22 | 526.1 (M + H), CP |
| 22 | 5-chloro-2-fluoro-phenyl | H | 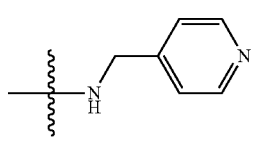 | 2 | 22 | 510.1 (M + H), CP |
| 23 | 5-chloro-2-fluoro-phenyl | H | 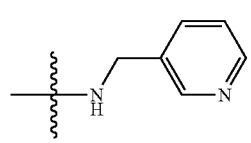 [SMILES: *NCc1cccnc1] | 3 | 18 | 497.1 (M + H), CP |
| 24 | 2,5-dichloro-phenyl | H | 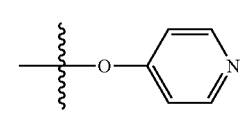 | 3 | 11 | 513.0 (M + H), CP |
| 25 | 2,5-dichloro-phenyl | H | 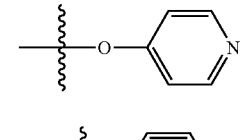 | 5 | 7 | 497.1 (M + H), CP |
| 26 | 5-chloro-2-fluoro-phenyl | H | 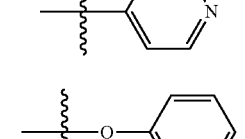 | 3 | 11 | 495.3 (M − H), CP |
| 27 | 2,5-dichloro-phenyl | H | 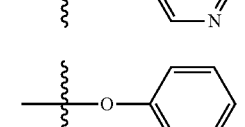 | 3 | 20 | 511.1 (M − H), CP |
| 28 | 2,3-dichloro-phenyl | H | 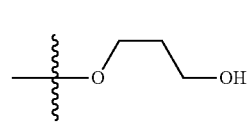 | 3 | 51 | 492.3 (M − H), CP |
| 29 | 5-chloro-2-fluoro-phenyl | H | 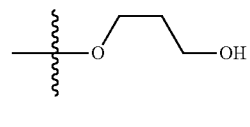 | 3 | 49 | 476.2 (M − H), CP |
| 30 | 2,5-dichloro-phenyl | H | 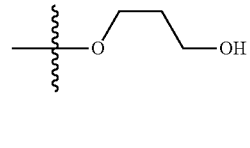 | 3 | 62 | 494.1 (M + H), CP |

TABLE 1-continued

Example compounds of the formula Ib

| Example no. | Ar | R1 | –Z–R3 | Synthesis | Yield (%) | MS (m/e) |
|---|---|---|---|---|---|---|
| 31 | 2,3-dichloro-phenyl | H | –O–CH₂CH₂–OH | 3 | 64 | 480.1 (M + H), CP |
| 32 | 5-chloro-2-fluoro-phenyl | H | –O–CH₂CH₂–OH | 3 | 84 | 464.1 (M + H), CP |
| 33 | 2,5-dichloro-phenyl | H | –O–CH₂CH₂–OH | 3 | 53 | 480.1 (M + H), CP |
| 34 | 2,3-dichloro-phenyl | H | –O–(CH₂)₃–OH | 3 | 60 | 508.1 (M + H), CP |
| 35 | 5-chloro-2-fluoro-phenyl | H | –O–(CH₂)₃–OH | 3 | 72 | 492.1 (M + H), CP |
| 36 | 2,5-dichloro-phenyl | H | –O–(CH₂)₃–OH | 3 | 69 | 508.1 (M + H), CP |
| 37 | 5-chloro-2-fluoro-phenyl | H | –O–(4-hydroxyphenyl) | 3 | 5 | 512.1 (M + H), CP |
| 38 | 5-chloro-2-fluoro-phenyl | H | imidazol-1-yl | 3 | 22 | 470.1 (M + H), CP |
| 39 | 2,5-dichloro-phenyl | H | imidazol-1-yl | 3 | 20 | 486.0 (M + H), CP |
| 40 | 5-chloro-2-fluoro-phenyl | H | 1,2,4-triazol-1-yl | 3 | 13 | 471.1 (M + H), CP |
| 41 | 2,5-dichloro-phenyl | H | 1,2,4-triazol-1-yl | 3 | 7 | 487.1 (M + H), CP |
| 42 | 5-chloro-2-fluoro-phenyl | H | –NH–(CH₂)₃–OH | 2 | 18 | 477.1 (M + H), CP |
| 43 | 2,5-dichloro-phenyl | H | –NH–(CH₂)₃–OH | 2 | 6 | 493.1 (M + H), CP |

TABLE 1-continued

Example compounds of the formula Ib

| Example no. | Ar | R1 | —Z—R3 | Synthesis | Yield (%) | MS (m/e) |
|---|---|---|---|---|---|---|
| 44 | 2,3-dichloro-phenyl | H | 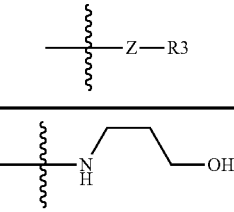 | 2 | 15 | 493.1 (M + H), CP |
| 45 | 2,3-dichloro-phenyl | H | 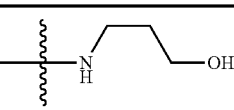 | 2 | 29 | 478.0 (M + H), CP |
| 46 | 5-chloro-2-fluoro-phenyl | H | 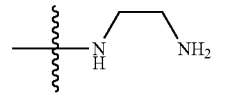 | 2 | 29 | 476.1 (M + H), CP |
| 47 | 5-chloro-2-fluoro-phenyl | H | 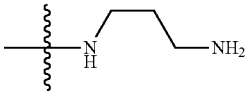 | 2 | 14 | 463.1 (M + H), CP |
| 48 | 2,5-dichloro-phenyl | H | 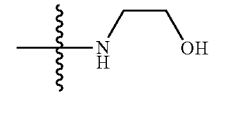 | 2 | 24 | 479.1 (M + H), CP |
| 49 | 2,3-dichloro-phenyl | H | 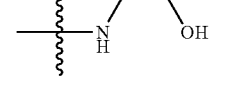 | 2 | 13 | 479.0 (M + H), CP |
| 50 | 5-chloro-2-fluoro-phenyl | H | 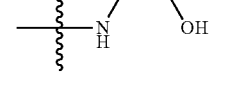 | 2 | 32 | 462.0 (M + H), CP |
| 51 | 2,5-dichloro-phenyl | H | 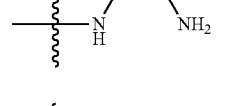 | 2 | 22 | 478.0 (M + H), CP |
| 52 | 2,5-dichloro-phenyl | H | 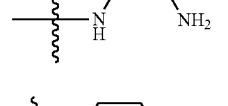 | 2 | 21 | 492.0 (M + H), CP |
| 53 | 2,3-dichloro-phenyl | H | 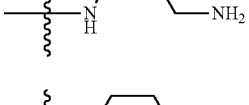 | 2 | 23 | 492.0 (M + H), CP |
| 54 | 5-chloro-2-fluoro-phenyl | H | 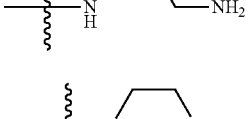 | 3 | 10 | 461.2 (M − H), CP |
| 55 | 2,5-dichloro-phenyl | H | 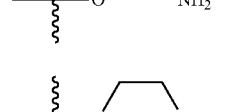 | 3 | 9 | 477.0 (M − H), CP |
| 56 | 2,3-dichloro-phenyl | H | 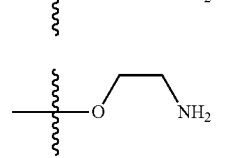 | 3 | 10 | 477.1 (M − H), CP |

TABLE 1-continued

Example compounds of the formula Ib

| Example no. | Ar | R1 | –Z–R3 | Synthesis | Yield (%) | MS (m/e) |
|---|---|---|---|---|---|---|
| 57 | 5-chloro-2-fluoro-phenyl | H | 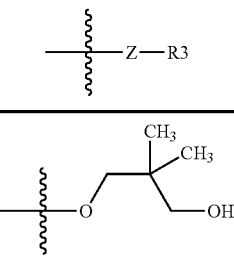 | 3 | 14 | 506.1 (M + H), CP |
| 58 | 2,5-dichloro-phenyl | H | 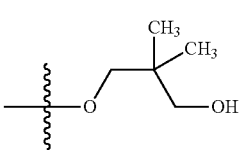 | 3 | 22 | 522.2 (M + H), CP |
| 59 | 2,3-dichloro-phenyl | H | 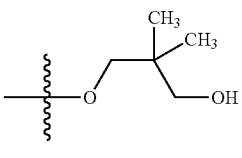 [SMILES: *OCC(C)(C)CO] | 3 | 23 | 522.0 (M + H), CP |
| 60 | 2,5-dichloro-phenyl | H | 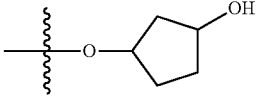 | 3 | 25 | 520.0 (M + H), CP |
| 61 | 2,5-dichloro-phenyl | H | 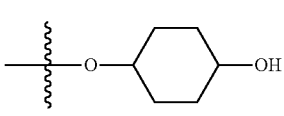 [SMILES: *OC1CCC(O)CC1] | 3 | 10 | 534.0 (M + H), CP |
| 62 | 5-chloro-2-fluoro-phenyl | H | 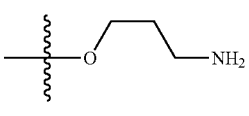 | 3 | 25 | 477.0 (M + H), CP |
| 63 | 2,5-dichloro-phenyl | H | 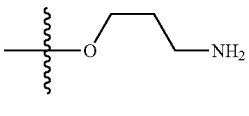 | 3 | 23 | 493.0 (M + H), CP |
| 64 | 2,3-dichloro-phenyl | H | 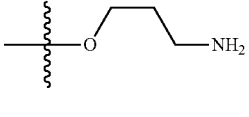 | 3 | 22 | 493.0 (M + H), CP |
| 65 | 5-chloro-2-fluoro-phenyl | H | 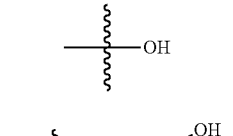 | 3 | 8 | 420.0 (M + H), CP |
| 66 | 5-chloro-2-fluoro-phenyl | H | 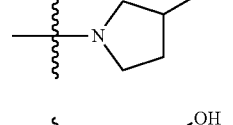 | 2 | 24 | 489.0 (M + H), CP |
| 67 | 2,5-dichloro-phenyl | H | 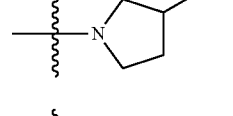 | 2 | 27 | 505.0 (M + H), CP |
| 68 | 5-chloro-2-fluoro-phenyl | H | 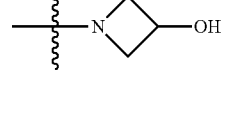 | 2 | 57 | 475.0 (M + H), CP |

TABLE 1-continued

Example compounds of the formula Ib

| Example no. | Ar | R1 | —Z—R3 | Synthesis | Yield (%) | MS (m/e) |
|---|---|---|---|---|---|---|
| 69 | 2,5-dichlorophenyl | H | 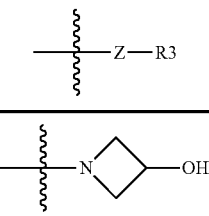 | 2 | 40 | 491.0 (M + H), CP |
| 70 | 5-chloro-2-fluoro-phenyl | H | 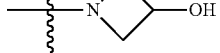 | 3 | 15 | 546.1 (M + H), CP |
| 71 | 5-chloro-2-fluoro-phenyl | H | 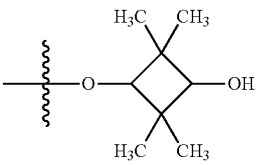 | 2 | 53 | 503.0 (M + H), CP |
| 72 | 2,5-dichlorophenyl | H | 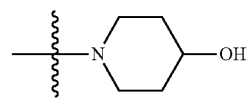 [SMILES: *N1CCC(O)CC1] | 2 | 16 | 517.0 (M − H), CP |
| 73 | 5-chloro-2-fluoro-phenyl | H | 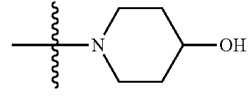 [SMILES: *N1CCC(O)CC1] | 2 | 47 | 512.0 (M + H), CP |
| 74 | 2,5-dichlorophenyl | H | 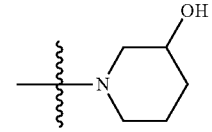 [SMILES: *N1CCCC(O)C1] | 2 | 14 | 519.0 (M + H), CP |
| 75 | 5-chloro-2-fluoro-phenyl | H | 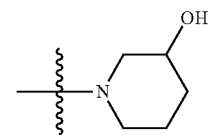 | 3 | 45 | 504.0 (M + H), CP |
| 76 | 2,5-dichlorophenyl | H | 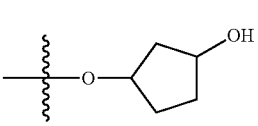 [SMILES: *OC1CCC(O)C1] | 6 | 20 | 433.9 (M + H), CP |
| 77 | 5-chloro-2-fluoro-phenyl | H | 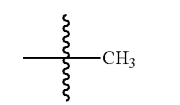<br>trans configuration | 2 | 32 | 517.0 (M + H), CP |
| 78 | 2,5-dichlorophenyl | H | 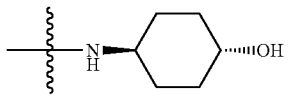 [SMILES: *N[C@H]1CC[C@H](O)CC1]<br>trans configuration | 2 | 18 | 533.0 (M + H), CP |
| 79 | 5-chloro-2-fluoro-phenyl | H | 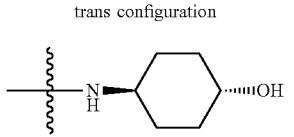<br>trans configuration | 3 | 54 | 518.0 (M + H), CP |

TABLE 1-continued

Example compounds of the formula Ib

| Example no. | Ar | R1 | —Z—R3 | Synthesis | Yield (%) | MS (m/e) |
|---|---|---|---|---|---|---|
| 80 | 2,5-dichloro-phenyl | H | 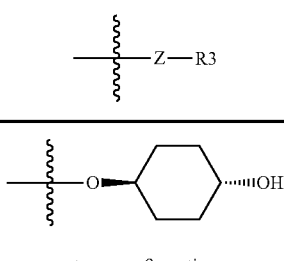<br>trans configuration | 3 | 43 | 534.0 (M + H), CP |
| 81 | 5-chloro-2-fluoro-phenyl | H | 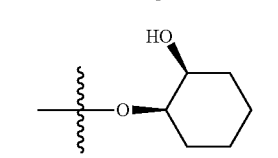 [SMILES: *O[C@@H]1CCCC[C@@H]1O]<br>cis configuration, racemic | 3 | 48 | 518.0 (M + H), CP |
| 82 | 2,5-dichloro-phenyl | H | 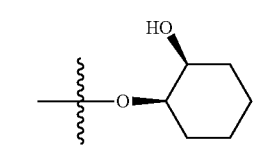 [SMILES: *O[C@@H]1CCCC[C@@H]1O]<br>cis configuration, racemic | 3 | 39 | 534.0 (M + H), CP |
| 83 | 5-chloro-2-cyano-phenyl | H | 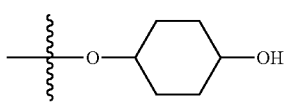 [SMILES: *OC1CCC(O)CC1] | 3 | 44 | 525.0 (M + H), CP |
| 84 | 5-chloro-2-fluoro-phenyl | H | 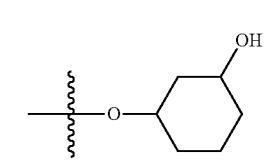 [SMILES: *OC1CCCC(O)C1] | 3 | 48 | 518.0 (M + H), CP |
| 85 | 2,5-dichloro-phenyl | H | 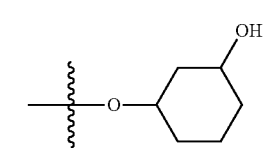 | 3 | 50 | 534.0 (M + H), CP |
| 86 | 5-chloro-2-fluoro-phenyl | H | 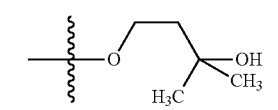 | 3 | 46 | 506.0 (M + H), CP |
| 87 | 5-chloro-2-fluoro-phenyl | H | 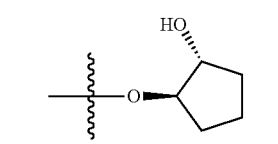 [SMILES: *O[C@@H]1CCC[C@H]1O]<br>trans, R,R-configuration | 3 | 47 | 504.0 (M + H), CP |
| 88 | 2,5-dichloro-phenyl | H | 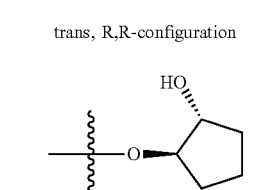<br>trans, R,R-configuration | 3 | 45 | 520.0 (M + H), CP |

TABLE 1-continued

Example compounds of the formula Ib

| Example no. | Ar | R1 | —Z—R3 | Synthesis | Yield (%) | MS (m/e) |
|---|---|---|---|---|---|---|
| 89 | 2,5-dichloro-phenyl | H | 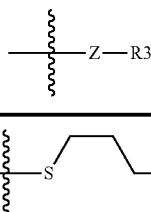 | 3 (a) | 19 | 510.0 (M + H), CP |
| 90 | 2-chloro-5-methoxy-phenyl | H | 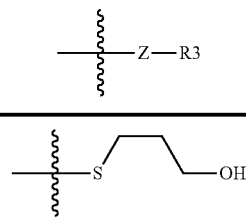 | 3 | 9 | 530.0 (M + H), CP |
| 91 | 2-chloro-5-methoxy-phenyl | H | 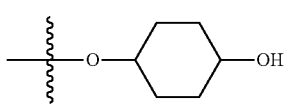 | 3 | 49 | 516.0 (M + H), CP |
| 92 | 2-fluoro-5-methyl-phenyl | H | 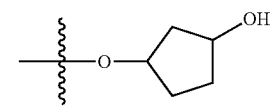 [SMILES: *OC1CCC(O)C1] | 4 | 36 | 496.3 (M − H) |
| 93 | 2-cyano-5-methyl-phenyl | $CH_3$ | 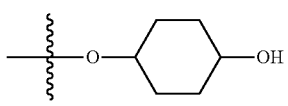 | 1 | 66 | 405.2 (M + H) |
| 94 | 5-chloro-1,3-dimethyl-1H-pyrazol-4-yl | $CH_3$ | 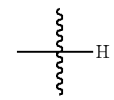 | 1 | | 418.2 (M + H), CP |
| 95 | 2-fluoro-5-methyl-phenyl | $CH_3$ | 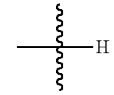 [SMILES: *[H]] | 1 | 90 | 398.2 (M + H) |
| 96 | 2-cyano-5-methyl-phenyl | $CH_3$ | 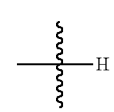 | 3 | 35 | 519.3 (M + H) |
| 97 | 2-cyano-5-methyl-phenyl | $CH_3$ | 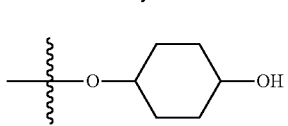 | 3 | 42 | 505.3 (M + H) |
| 98 | 2-cyano-5-methyl-phenyl | $CH_3$ | 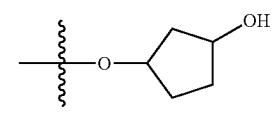 [SMILES: *OC1CCC(O)C1] trans configuration | 2 | 38 | 518.3 (M + H) |
| 99 | 2-cyano-5-methyl-phenyl | $CH_3$ | 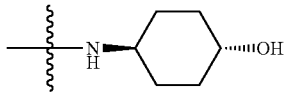 | 3 | 15 | 519.3 (M + H) |
| 100 | 5-chloro-2-cyano-phenyl | $CH_3$ | 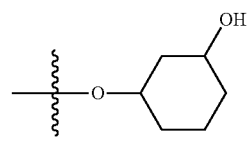 [SMILES: *OC1CCCC(O)C1] | 3 | 15 | 539.3 (M + H), CP |

TABLE 1-continued

Example compounds of the formula Ib

| Example no. | Ar | R1 | –Z–R3 | Synthesis | Yield (%) | MS (m/e) |
|---|---|---|---|---|---|---|
| 101 | 2-fluoro-5-methyl-phenyl | CH₃ | –O–cyclohexyl–OH | 3 | 34 | 512.3 (M + H) |
| 102 | 2-chloro-5-methoxy-phenyl | CH₃ | –O–cyclohexyl–OH | 3 | 40 | 544.3 (M + H), CP |
| 103 | 7-chloro-2,3-dihydro-benzo[1,4]dioxin-6-yl | CH₃ | –H | 4 | 67 | 458.1 (M + H), CP |
| 104 | 2-fluoro-4,5-dimethoxy-phenyl | CH₃ | –H | 4 | 80 | 444.2 (M + H) |
| 105 | 2-bromo-4,5-dimethoxy-phenyl | CH₃ | –H | 4 | 53 | 504.1 (M + H), BP |
| 106 | 4,5-dimethoxy-2-methyl-phenyl | CH₃ | –H | 4 | 54 | 440.2 (M + H) |
| 107 | 2-fluoro-5-methyl-phenyl | H | –O–CH₂–(pyrrolidin-2-one-4-yl) | 3 | 24 | 497.2 (M + H) |
| 108 | 2-fluoro-5-methyl-phenyl | H | –OH | 3 (b) | 19 | 399.2 (M + H) |
| 109 | 2-fluoro-5-methyl-phenyl | H | –N(azetidine)–CH₂OH | 2 | 21 | 469.2 (M + H) |
| 110 | 2-chloro-5-methoxy-phenyl | H | –N(azetidine)–CH₂OH | 2 | 10 | 501.2 (M + H), CP |
| 111 | 5-chloro-2-cyano-phenyl | H | –N(azetidine)–CH₂OH | 2 | 9 | 496.2 (M + H), CP |
| 112 | 2-fluoro-5-methyl-phenyl | H | –O–CH₂CH₂–C(O)NH₂ | 3 | 38 | 485.2 (M + H) |
| 113 | 2-chloro-5-methoxy-phenyl | H | –O–CH₂CH₂–C(O)NH₂ | 3 | 25 | 517.2 (M + H), CP |

TABLE 1-continued

Example compounds of the formula Ib

| Example no. | Ar | R1 | —Z—R3 | Synthesis | Yield (%) | MS (m/e) |
|---|---|---|---|---|---|---|
| 114 | 5-chloro-2-cyano-phenyl | H | 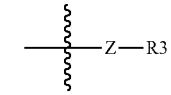 | 3 | 20 | 512.2 (M + H), CP |
| 115 | 5-chloro-2-cyano-phenyl | H | 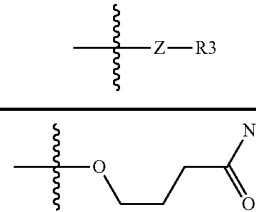 | 3 | 29 | 498.1 (M + H), CP |
| 116 | 2-fluoro-5-methyl-phenyl | H | 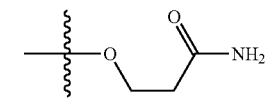 [SMILES: *OCCC(N)=O] | 3 | 21 | 471.2 (M + H) |
| 117 | 2-chloro-5-methoxy-phenyl | H | 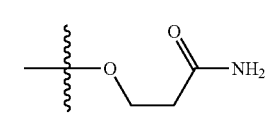 | 3 | 23 | 503.2 (M + H), CP |
| 118 | 2-cyano-5-methyl-phenyl | H |  | 3 | 12 | 478.2 (M + H) |
| 119 | 2-fluoro-5-methyl-phenyl | H | 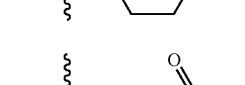 all-cis configuration | 3 | 67 | 514.2 (M + H) |
| 120 | 2-cyano-5-methyl-phenyl | H | 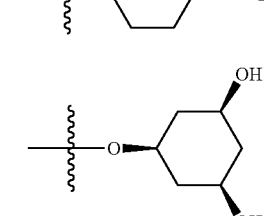 all-cis configuration | 3 | 23 | 521.3 (M + H) |
| 121 | 2-fluoro-5-methyl-phenyl | H | 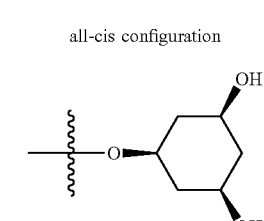 | 3 | 30 | 480.2 (M + H) |
| 122 | 2-cyano-5-methyl-phenyl | H | 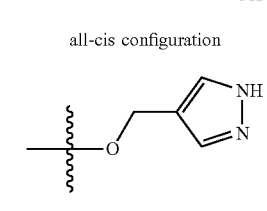 | 3 | 28 | 487.3 (M + H) |
| 123 | 2-fluoro-5-methyl-phenyl | H | 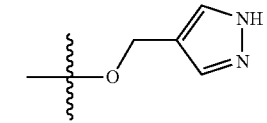 | 3 | 52 | 562.2 (M + H) |

TABLE 1-continued

Example compounds of the formula Ib

| Example no. | Ar | R1 | —Z—R3 | Synthesis | Yield (%) | MS (m/e) |
|---|---|---|---|---|---|---|
| 124 | 2-cyano-5-methyl-phenyl | H | pyranose (CH2O-linked tetrahydroxy pyran) | 3 | 18 | 569.2 (M + H) |
| 125 | 2-cyano-5-methyl-phenyl | H | -OCH2-(pyrrolidin-2-one-4-yl) | 3 | 4 | 504.2 (M + H) |
| 126 | 2-chloro-5-methoxy-phenyl | H | -OH | 3 (b) | | 432.1 (M + H), CP |
| 127 | 5-chloro-2-cyano-phenyl | H | -OCH2-(pyrrolidin-2-one-4-yl) | 3 | 1 | 524.2 (M + H), CP |
| 128 | 5-cyano-2-fluoro-phenyl | CH3 | -O-(4-hydroxycyclohexyl) | 3 | 42 | 523.3 (M + H) |
| 129 | 2-fluoro-5-methoxy-phenyl | CH3 | -O-(4-hydroxycyclohexyl) | 3 | 40 | 528.3 (M + H) |
| 130 | 2-cyano-5-methoxy-phenyl | CH3 | -O-(4-hydroxycyclohexyl) | 3 | 40 | 528.3 (M + H) |
| 131 | 2-cyano-5-fluoro-phenyl | CH3 | -CH2-O-(4-hydroxycyclohexyl) | 3 | 5 | 523.3 (M + H) |
| 132 | 5-cyano-2-fluoro-phenyl | H | -CH2-O-(4-hydroxycyclohexyl) | 3 | 21 | 509.3 (M + H) |
| 133 | 2-fluoro-5-methoxy-phenyl | H | -CH2-O-(4-hydroxycyclohexyl) | 3 | 23 | 514.3 (M + H) |
| 134 | 2-cyano-5-methoxy-phenyl | H | -CH2-O-(4-hydroxycyclohexyl) | 3 | 16 | 521.3 (M + H) |
| 135 | 2-cyano-5-methyl-phenyl | H | -O-CH(CH3)- | 3 | 3 | 421.2 (M + H) |

TABLE 1-continued

Example compounds of the formula Ib

| Example no. | Ar | R1 | —Z—R3 | Synthesis | Yield (%) | MS (m/e) |
|---|---|---|---|---|---|---|
| 136 | 5-chloro-2-fluoro-phenyl | H | —O—CH3 | 3 | 13 | 434.1 (M + H), CP |
| 137 | 2-fluoro-5-methyl-phenyl | H | —O—CH3 | 3 | 35 | 414.1 (M + H) |
| 138 | 5-chloro-2-cyano-phenyl | H | —O—CH3 | 3 | 49 | 441.1 (M + H), CP |
| 139 | 2,5-dichloro-phenyl | H | —O—CH3 | 3 | 48 | 450.0 (M + H), CP |
| 140 | 2-fluoro-5-methyl-phenyl | H | —O—CH3 | 3 | 27 | 429.1 (M + H) |
| 141 | 2-fluoro-5-methyl-phenyl | H | cyclopropyl | 6 | 59 | 424.1 (M + H) |
| 142 | 5-chloro-2-fluoro-phenyl | H | cyclopropyl | 6 | 42 | 444.1 (M + H) |
| 143 | 2-chloro-5-methoxy-phenyl | H | —O—CH3 | 3 | 82 | 444.1 (M − H), CP |
| 144 | 2-fluoro-5-methoxy-phenyl | H | —O—CH3 | 3 | 84 | 430.0 (M + H) |
| 145 | 2-cyano-5-methyl-phenyl | H | cyclopropyl | 6 | 5 | 431.3 (M + H) |
| 146 | 2-cyano-5-methyl-phenyl | H | —CH2CH2Cl | 6 | 10 | 467.2 (M + H), CP |
| 147 | 2-fluoro-5-methoxy-phenyl | H | cyclopropyl | 6 | 5 | 440.2 (M + H) |
| 148 | 2-fluoro-5-methoxy-phenyl | H | —CH2CH2Cl | 6 | 12 | 476.2 (M + H), CP |

TABLE 1-continued

Example compounds of the formula Ib

| Example no. | Ar | R1 | ⸺Z⸺R3 | Synthesis | Yield (%) | MS (m/e) |
|---|---|---|---|---|---|---|
| 149 | 2-cyano-5-methyl-phenyl | NH$_2$ | 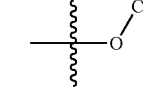 | 7 | 7 | 436.2 (M + H) |
| 150 | 2-chloro-5-methoxy-phenyl | NH$_2$ | 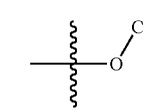 | 7 | 12 | 461.2 (M + H), CP |
| 151 | 5-chloro-2-cyano-phenyl | NH$_2$ |  | 7 | 12 | 456.1 (M + H), CP |
| 152 | 2-fluoro-5-methoxy-phenyl | NH$_2$ | 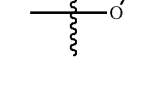 | 7 | 15 | 445.2 (M + H) |
| 153 | 2,5-dichloro-phenyl | NH$_2$ | 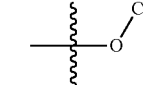 | 7 | 29 | 465.1 (M + H), CP |
| 154 | 2-fluoro-5-methyl-phenyl | H | 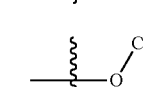 | 6 | 2 | 469.2 (M + H) |
| 155 | 2-chloro-5-methoxy-phenyl | H |  | 6 | 4 | 501.2 (M + H), CP |
| 156 | 2,5-dichloro-phenyl | H | 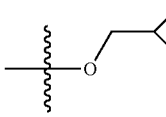 | 6 | 1 | 505.1 (M + H), CP |
| 157 | 2-cyano-5-methyl-phenyl | H |  | 6 | 1 | 476.2 (M + H) |
| 158 | 2-fluoro-5-methyl-phenyl | H | 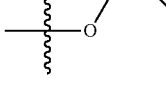 | 6 | 36 | 482.1 (M + H) |
| 159 | 2-chloro-5-methoxy-phenyl | H | 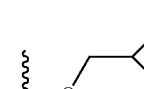 | 6 | 42 | 514.1 (M + H), CP |
| 160 | 5-chloro-2-fluoro-phenyl | H | 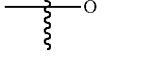 | 6 | 32 | 502.1 (M + H), CP |

TABLE 1-continued

Example compounds of the formula Ib

| Example no. | Ar | R1 | —Z—R3 | Synthesis | Yield (%) | MS (m/e) |
|---|---|---|---|---|---|---|
| 161 | 2,5-dichloro-phenyl | H | —O—CF₃ | 6 | 13 | 518.1 (M + H), CP |
| 162 | 5-chloro-2-cyano-phenyl | H | —O—CF₃ | 6 | 27 | 509.1 (M + H), CP |
| 163 | 2-cyano-5-methyl-phenyl | H | —O—CF₃ | 6 | 40 | 489.1 (M + H) |
| 164 | 2-chloro-4-fluoro-phenyl | NH₂ | —CH₃ | 6 | 26 | 433.1 (M + H), CP |
| 165 | 2,4,5-trifluoro-phenyl | NH₂ | —CH₃ | 6 | 19 | 435.1 (M + H) |
| 166 | 5-bromo-thiophen-2-yl | NH₂ | —CH₃ | 6 | 21 | 465.0 (M + H), BP |
| 167 | 5-chloro-thiophen-2-yl | NH₂ | —CH₃ | 6 | 26 | 421.0 (M + H), CP |
| 168 | 4,5-dichloro-thiophen-2-yl | NH₂ | —CH₃ | 6 | 23 | 455.0 (M + H), CP |
| 169 | 2-fluoro-phenyl | NH₂ | —CH₃ | 6 | 25 | 399.1 (M + H) |
| 170 | 2-chloro-4,5-difluoro-phenyl | NH₂ | —CH₃ | 6 | 25 | 451.1 (M + H), CP |
| 171 | 3-chloro-2-fluoro-phenyl | NH₂ | —CH₃ | 6 | 20 | 433.1 (M + H), CP |
| 172 | 4-bromo-thiophen-2-yl | NH₂ | —CH₃ | 6 | 31 | 465.0 (M + H), BP |
| 173 | 4-bromo-thiophen-3-yl | NH₂ | —CH₃ | 6 | 13 | 465.0 (M + H), BP |

TABLE 1-continued

Example compounds of the formula Ib

| Example no. | Ar | R1 | —Z—R3 | Synthesis | Yield (%) | MS (m/e) |
|---|---|---|---|---|---|---|
| 174 | 4-chloro-thiophen-3-yl | NH$_2$ | —CH$_3$ | 6 | 30 | 419.1 (M − H), CP |
| 175 | 2,5-dichloro-thiophen-3-yl | NH$_2$ | —CH$_3$ | 6 | 31 | 454.9 (M + H), CP |
| 176 | 3-chloro-2-cyano-phenyl | H | —O—CH$_3$ | 3 | 21 | 441.1 (M + H), CP |
| 177 | 2-chloro-3,5-difluoro-phenyl | H | —O—CH$_3$ | 3 | 31 | 452.0 (M + H), CP |
| 178 | 5-chloro-2,4-difluoro-phenyl | H | —O—CH$_3$ | 3 | 37 | 452.0 (M + H), CP |
| 179 | 2,4,5-trifluoro-phenyl | H | —O—CH$_3$ | 3 | 38 | 436.1 (M + H) |
| 180 | 2-chloro-4-fluoro-phenyl | H | —O—CH$_3$ | 3 | 33 | 434.0 (M + H), CP |
| 181 | 3-chloro-2-fluoro-phenyl | H | —O—CH$_3$ | 3 | 42 | 434.0 (M + H), CP |
| 182 | 2-chloro-4,5-difluoro-phenyl | H | —O—CH$_3$ | 3 | 38 | 452.0 (M + H), CP |
| 183 | 4,5-dichloro-thiophen-2-yl | H | —O—CH$_3$ | 3 | 28 | 455.9 (M + H), CP |
| 184 | 2,5-dichloro-thiophen-3-yl | H | —O—CH$_3$ | 3 | 18 | 455.9 (M + H), CP |
| 185 | 2,5-dichloro-phenyl | H | —O—CH$_2$CH$_2$—N(pyrrolidin-2-one) | 3 | 35 | 547.1 (M + H), CP |
| 186 | 5-chloro-2-fluoro-phenyl | H | —O—CH$_2$CH$_2$—N(pyrrolidin-2-one) | 3 | 46 | 531.1 (M + H), CP |

TABLE 1-continued

Example compounds of the formula Ib

| Example no. | Ar | R1 | —Z—R3 | Synthesis | Yield (%) | MS (m/e) |
|---|---|---|---|---|---|---|
| 187 | 5-chloro-2-cyano-phenyl | H | 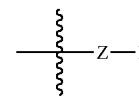 | 3 | 24 | 538.1 (M + H), CP |
| 188 | 2-cyano-5-methyl-phenyl | H | 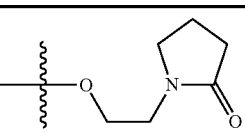 | 3 | 12 | 462.1 (M + H) |
| 189 | 2-chloro-5-methoxy-phenyl | H | 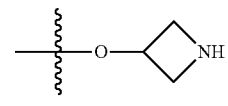 | 3 | 13 | 487.1 (M + H), CP |
| 190 | 2,5-dichloro-phenyl | H | 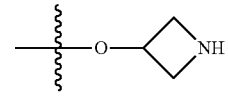 | 3 | 12 | 490.9 (M + H), CP |
| 191 | 5-chloro-2-cyano-phenyl | H | 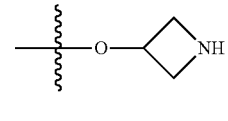 | 3 | 10 | 482.1 (M + H), CP |
| 192 | 2-fluoro-5-methoxy-phenyl | H | 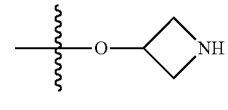 [SMILES: *OC1CNC1] | 3 | 12 | 471.1 (M + H) |
| 193 | 2-cyano-5-methyl-phenyl | NH$_2$ | 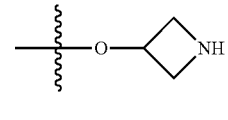 [SMILES: *OC1CNC1] | 7 (c) | 9 | 504.1 (M + H) |
| 194 | 2-chloro-5-methoxy-phenyl | NH$_2$ | 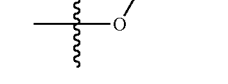 | 7 (c) | 12 | 529.0 (M + H), CP |
| 195 | 2,5-dichloro-phenyl | NH$_2$ | 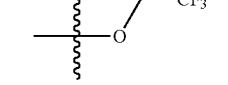 | 7 (c) | 13 | 533.0 (M + H), CP |
| 196 | 5-chloro-2-cyano-phenyl | NH$_2$ | 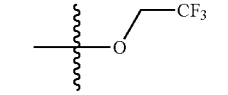 | 7 (c) | 11 | 524.0 (M + H), CP |
| 197 | 2-fluoro-5-methoxy-phenyl | NH$_2$ | 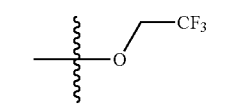 | 7 (c) | 13 | 513.0 (M + H) |
| 198 | 5-chloro-2-fluoro-phenyl | H | 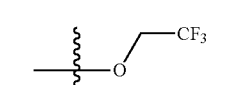 | 3 | 5 | 489.1 (M + H), CP |
| 199 | 2,5-difluoro-phenyl | H | 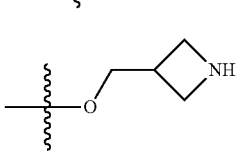 | 3 | 1 | 461.1 (M + H) |

TABLE 1-continued

Example compounds of the formula Ib

| Example no. | Ar | R1 | —Z—R3 | Synthesis | Yield (%) | MS (m/e) |
|---|---|---|---|---|---|---|
| 200 | 2,5-difluoro-phenyl | H | 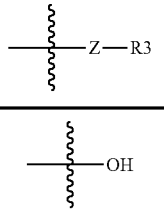 —OH | 3 (b) | 10 | 404.1 (M + H) |
| 201 | 2-fluoro-phenyl | H | 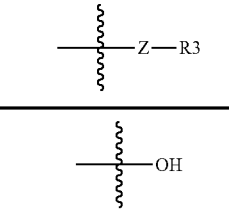 —O—NH2 | 3 | 7 | 443.2 (M + H) |
| 202 | 2-fluoro-phenyl | H | 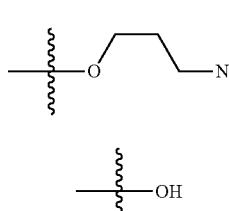 —OH | 3 | 18 | 386.1 (M + H) |
| 203 | 2-chloro-5-methoxy-phenyl | H | 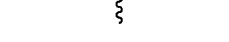 —O—NH2 | 3 | 5 | 489.1 (M + H), CP |
| 204 | 2-fluoro-5-methyl-phenyl | H | 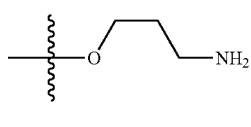 —O—NH2 | 3 | 42 | 457.2 (M + H) |
| 205 | 2,5-difluoro-phenyl | H | 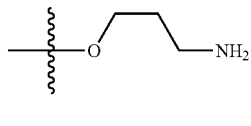 | 6 | 30 | 428.1 (M + H) |
| 206 | 2-fluoro-phenyl | H | 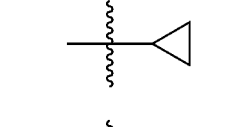 | 6 | 35 | 410.1 (M + H) |
| 207 | 2-fluoro-5-methyl-phenyl | CH3 | 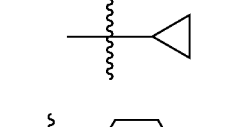 —O—NH2 | 3 | 59 | 471.1 (M + H) |
| 208 | 2,5-difluoro-phenyl | CH3 | 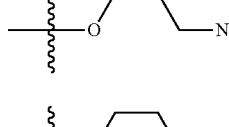 —O—NH2 | 3 | 58 | 475.1 (M + H) |
| 209 | 5-chloro-2-fluoro-phenyl | CH3 | 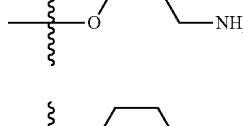 —O—NH2 | 3 | 67 | 491.1 (M + H), CP |
| 210 | 2,5-dichloro-phenyl | CH3 | 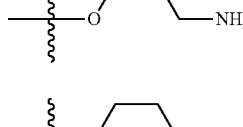 —O—NH2 | 3 | 78 | 505.0 (M − H), CP |
| 211 | 2-fluoro-phenyl | CH3 | 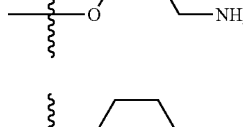 —O—NH2 | 3 | 52 | 457.1 (M + H) |
| 212 | 2-chloro-5-methoxy-phenyl | CH3 | 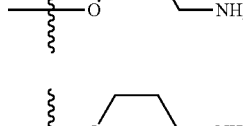 —O—NH2 | 3 | 78 | 503.1 (M + H), CP |

TABLE 1-continued

Example compounds of the formula Ib

| Example no. | Ar | R1 | —Z—R3 | Synthesis | Yield (%) | MS (m/e) |
|---|---|---|---|---|---|---|
| 213 | 2-cyano-5-methyl-phenyl | CH$_3$ | 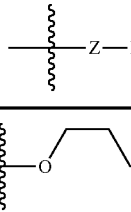 | 3 | 57 | 478.1 (M + H) |
| 214 | 2,5-dichloro-phenyl | CH$_3$ | 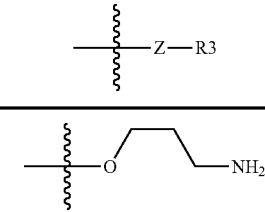 | 3 | 53 | 548.0 (M + H), CP |
| 215 | 5-chloro-2-fluoro-phenyl | CH$_3$ | 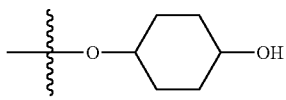 [SMILES: *OC1CCC(O)CC1] | 3 | 70 | 532.1 (M + H), CP |
| 216 | 2-fluoro-phenyl | CH$_3$ | 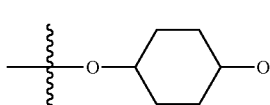 | 3 | 51 | 498.2 (M + H) |
| 217 | 2,5-difluoro-phenyl | CH$_3$ | 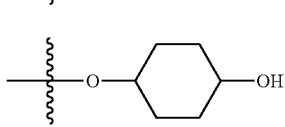 | 3 | 38 | 516.2 (M + H) |
| 218 | 2-fluoro-5-methoxy-phenyl | CH$_3$ | 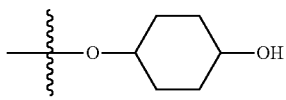 [SMILES: *OC1CCC(O)CC1] | 3 | 74 | 487.1 (M + H) |
| 219 | 2-fluoro-5-methoxy-phenyl | H | 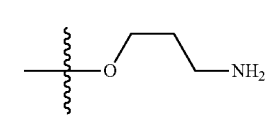 | 3 | 25 | 473.1 (M + H) |
| 220 | 5-chloro-2-cyano-phenyl | CH$_3$ | 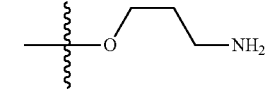 | 3 | 3 | 498.1 (M + H), CP |
| 221 | 2-fluoro-5-methyl-phenyl | H | 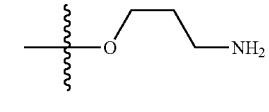 [SMILES: *OCCCN] | 3 | 40 | 483.2 (M + H) |
| 222 | 2,5-difluoro-phenyl | H | 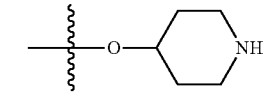 | 3 | 62 | 487.1 (M + H) |
| 223 | 2-chloro-5-methoxy-phenyl | H | 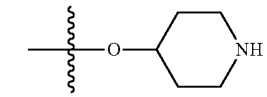 | 3 | 68 | 515.1 (M + H), CP |
| 224 | 5-chloro-2-fluoro-phenyl | H | 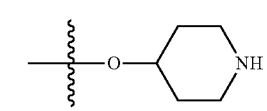 | 3 | 70 | 503.1 (M + H), CP |
| 225 | 2,5-dichloro-phenyl | H | 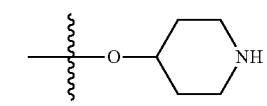 | 3 | 10 | 517.0 (M − H), CP |

TABLE 1-continued

Example compounds of the formula Ib

| Example no. | Ar | R1 | ⸺Z—R3 | Synthesis | Yield (%) | MS (m/e) |
|---|---|---|---|---|---|---|
| 226 | 2-cyano-5-methyl-phenyl | H | 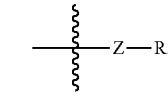 | 3 | 42 | 490.2 (M + H) |
| 227 | 2-fluoro-5-methoxy-phenyl | H | 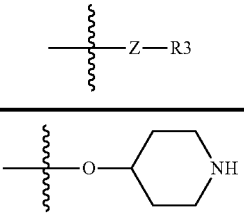 | 3 | 78 | 499.2 (M + H) |
| 228 | 2-fluoro-phenyl | H | 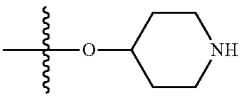 | 3 | 42 | 469.1 (M + H) |
| 229 | 2,5-difluoro-phenyl | H | 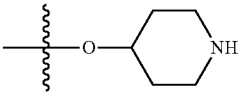 | 3 | 7 | 503.2 (M + H) |
| 230 | 2-fluoro-5-methyl-phenyl | H | 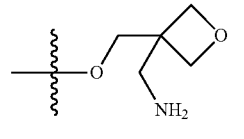 | 3 | 23 | 499.2 (M + H) |
| 231 | 2-fluoro-phenyl | H | 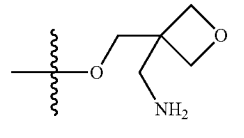 | 3 | 22 | 485.2 (M + H) |
| 232 | 5-chloro-2-fluoro-phenyl | H | 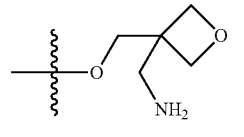 | 3 | 24 | 519.2 (M + H), CP |
| 233 | 2-chloro-5-methoxy-phenyl | H | 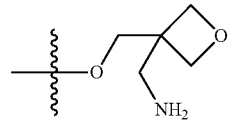 | 3 | 10 | 531.2 (M + H), CP |
| 234 | 2-fluoro-5-methoxy-phenyl | H | 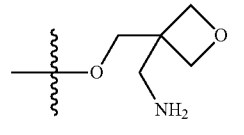 | 3 | 18 | 515.2 (M + H) |
| 235 | 5-chloro-2-cyano-phenyl | H | 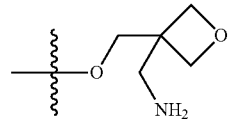 | 3 | 7 | 526.2 (M + H), CP |
| 236 | 2,5-dichloro-phenyl | H | 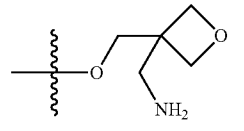 | 3 | 8 | 535.1 (M + H), CP |

TABLE 1-continued
Example compounds of the formula Ib
| Example no. | Ar | R1 | ⸎—Z—R3 | Synthesis | Yield (%) | MS (m/e) |
|---|---|---|---|---|---|---|
| 237 | 2-cyano-5-methyl-phenyl | H | 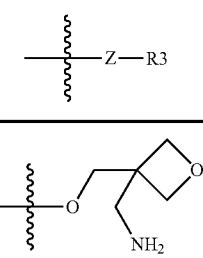 | 3 | 11 | 506.2 (M + H) |
| 238 | 2-fluoro-phenyl | H | 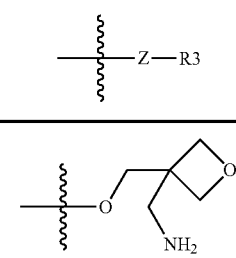 | 3 | 35 | 483.2 (M + H) |
| 239 | 2,5-dichloro-phenyl | H | 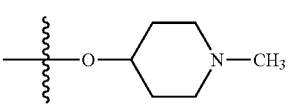 | 3 | 58 | 533.1 (M + H) |
| 240 | 2,5-difluoro-phenyl | H | 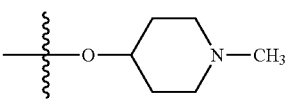 | 3 | 68 | 523.1 (M + H) |
| 241 | 2-fluoro-phenyl | H | 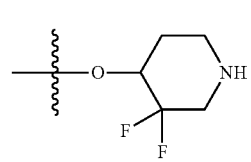 | 3 | 66 | 505.1 (M + H) |
| 242 | 2-fluoro-5-methyl-phenyl | H | 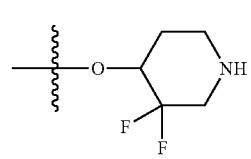 [SMILES: *OC1CCNCC1(F)F] | 3 | 70 | 519.2 (M + H) |
| 243 | 5-chloro-2-fluoro-phenyl | H | 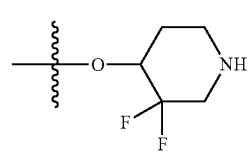 [SMILES: *OC1CCNCC1(F)F] | 3 | 60 | 539.1 (M + H), CP |
| 244 | 2-fluoro-5-methoxy-phenyl | H | 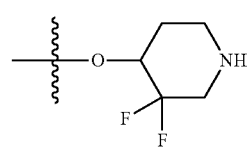 | 3 | 65 | 535.2 (M + H) |
| 245 | 2-chloro-5-methoxy-phenyl | H | 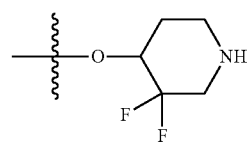 | 3 | 71 | 551.1 (M + H), CP |
| 246 | 5-chloro-2-cyano-phenyl | H | 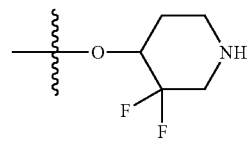 [SMILES: *OC1CCNCC1(F)F] | 3 | 18 | 546.1 (M + H), CP |

TABLE 1-continued

Example compounds of the formula Ib

| Example no. | Ar | R1 | —Z—R3 | Synthesis | Yield (%) | MS (m/e) |
|---|---|---|---|---|---|---|
| 247 | 2,5-dichloro-phenyl | H | 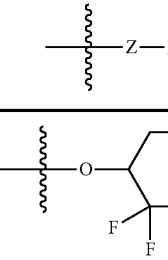 | 3 | 11 | 555.1 (M + H), CP |
| 248 | 2-cyano-5-methyl-phenyl | H |  | 3 | 64 | 526.2 (M + H) |
| 249 | 2-fluoro-5-methoxy-phenyl | H |  | 3 | 50 | 513.2 (M + H) |
| 250 | 2,5-difluoro-phenyl | H |  | 3 | 89 | 501.2 (M + H) |
| 251 | 2-fluoro-5-methoxy-phenyl | H |  | 3 | 19 | 499.2 (M + H) |
| 252 | 2-fluoro-5-methyl-phenyl | CH$_3$ |  | 3 | 17 | 533.2 (M + H) |
| 253 | 2,5-difluoro-phenyl | CH$_3$ |  | 3 | 17 | 537.2 (M + H) |
| 254 | 2-fluoro-phenyl | CH$_3$ |  | 3 | 39 | 519.2 (M + H) |
| 255 | 5-chloro-2-fluoro-phenyl | CH$_3$ |  | 3 | 40 | 571.1 (M + H), CP |
| 256 | 2-fluoro-5-methoxy-phenyl | CH$_3$ |  | 3 | 56 | 549.2 (M + H) |

TABLE 1-continued

Example compounds of the formula Ib

| Example no. | Ar | R1 | —Z—R3 | Synthesis | Yield (%) | MS (m/e) |
|---|---|---|---|---|---|---|
| 257 | 2-chloro-5-methoxy-phenyl | CH₃ | 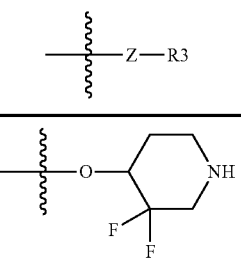 | 3 | 61 | 565.2 (M + H), CP |
| 258 | 5-chloro-2-cyano-phenyl | CH₃ | 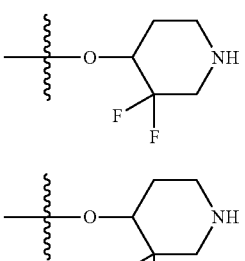 | 3 | 25 | 560.1 (M + H), CP |
| 259 | 2-cyano-5-methyl-phenyl | CH₃ | 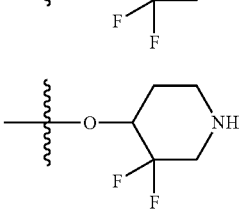 | 3 | 27 | 540.2 (M + H) |
| 260 | 2,5-dichloro-phenyl | CH₃ |  | 3 | 14 | 569.1 (M + H), CP |
| 261 | 5-chloro-2-fluoro-phenyl | CH₃ | 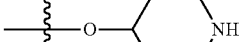 | 3 | 41 | 553.1 (M + H), CP |
| 262 | 2,5-difluoro-phenyl | H | 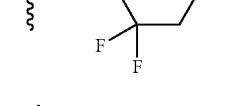 | 3 | 59 | 487.2 (M + H) |
| 263 | 2-fluoro-phenyl | H | 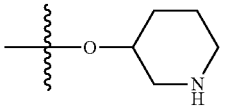 | 3 | 23 | 469.2 (M + H) |
| 264 | 2-fluoro-5-methyl-phenyl | H | 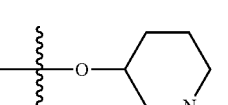 | 3 | 55 | 483.2 (M + H) |
| 265 | 5-chloro-2-fluoro-phenyl | H | 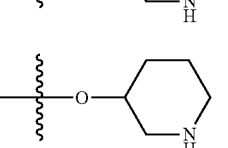 | 3 | 71 | 517.2 (M + H), CP |
| 266 | 2,5-dichloro-phenyl | H | 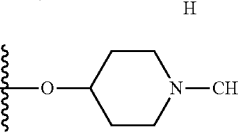 | 3 | 3 | 519.2 (M + H), CP |
| 267 | 2-fluoro-5-methoxy-phenyl | CH₃ | 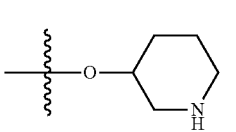 | 3 | 73 | 513.3 (M + H) |

TABLE 1-continued

Example compounds of the formula Ib

| Example no. | Ar | R1 | —Z—R3 | Synthesis | Yield (%) | MS (m/e) |
|---|---|---|---|---|---|---|
| 268 | 2,5-difluoro-phenyl | CH₃ | 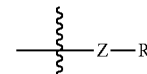 | 3 | 99 | 501.2 (M + H) |
| 269 | 5-chloro-2-fluoro-phenyl | H | 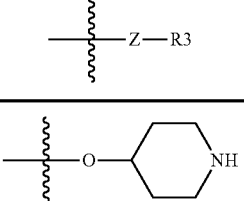 | 3 | 59 | 503.2 (M + H), CP |
| 270 | 2-fluoro-5-methyl-phenyl | CH₃ | 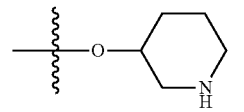 | 3 | 8 | 497.3 (M + H) |
| 271 | 2-fluoro-5-methyl-phenyl | H | 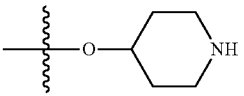 | 3 | 4 | 497.2 (M + H) |
| 272 | 2,5-difluoro-phenyl | CH₃ | 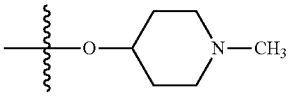 | 3 | 34 | 515.3 (M − H) |
| 273 | 2-cyano-5-methyl-phenyl | CH₃ | 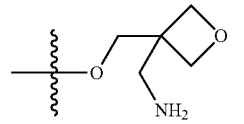 [SMILES: *OCC1(CN)COC1] | 3 | 30 | 518.3 (M − H) |
| 274 | 2-fluoro-5-methyl-phenyl | CH₃ | 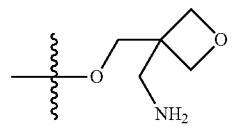 | 3 | 32 | 511.3 (M − H) |
| 275 | 5-chloro-2-fluoro-phenyl | CH₃ | 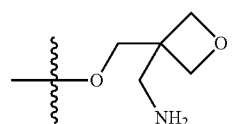 | 3 | 35 | 531.2 (M − H), CP |
| 276 | 2-fluoro-5-methoxy-phenyl | CH₃ | 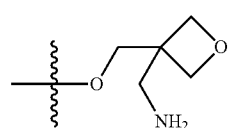 | 3 | 34 | 527.2 (M − H) |
| 277 | 2-chloro-5-methoxy-phenyl | CH₃ | 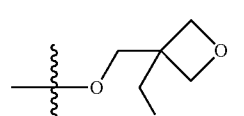 | 3 | 35 | 543.2 (M − H), CP |
| 278 | 2,5-dichloro-phenyl | CH₃ | 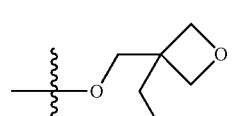 | 3 | 23 | 547.2 (M − H), CP |

TABLE 1-continued

Example compounds of the formula Ib

| Example no. | Ar | R1 | —Z—R3 | Synthesis | Yield (%) | MS (m/e) |
|---|---|---|---|---|---|---|
| 279 | 5-chloro-2-cyano-phenyl | CH₃ | —O—CH₂—C(CH₂NH₂)(CH₂—O—) (oxetane) | 3 | 23 | 538.2 (M − H), CP |
| 280 | 2-fluoro-phenyl | CH₃ | —O-(4-piperidinyl) | 3 | 6 | 483.2 (M + H) |
| 281 | 2,5-dichloro-phenyl | CH₃ | —O-(4-piperidinyl) | 3 | 2 | 533.1 (M + H), CP |
| 282 | 5-chloro-2-fluoro-phenyl | CH₃ | —O-(4-piperidinyl) | 3 | 70 | 517.2 (M + H), CP |
| 283 | 2-chloro-5-methoxy-phenyl | H | —O-(3-piperidinyl) | 3 | 76 | 515.2 (M + H), CP |
| 284 | 2-chloro-5-methoxy-phenyl | CH₃ | —O-(4-piperidinyl) | 3 | 74 | 529.2 (M + H), CP |
| 285 | 5-cyano-2-methyl-phenyl | H | —O-(3-piperidinyl) | 3 | 67 | 490.2 (M + H) |
| 286 | 5-cyano-2-methyl-phenyl | CH₃ | —O-(4-piperidinyl) | 3 | 59 | 504.3 (M + H) |
| 287 | 2-chloro-5-methoxy-phenyl | H | —O-(1-methyl-4-piperidinyl) | 3 | 35 | 529.2 (M + H), CP |
| 288 | 2-fluoro-5-methyl-phenyl | CH₃ | —O—CH₂-(2-morpholinyl) | 3 | 55 | 513.3 (M + H) |
| 289 | 2-fluoro-phenyl | CH₃ | —O—CH₂-(2-morpholinyl) | 3 | 91 | 499.3 (M + H) |
| 290 | 2-chloro-5-methoxy-phenyl | CH₃ | —O—CH₂-(2-morpholinyl) | 3 | 59 | 545.3 (M + H), CP |

TABLE 1-continued

Example compounds of the formula Ib

| Example no. | Ar | R1 | Z—R3 | Synthesis | Yield (%) | MS (m/e) |
|---|---|---|---|---|---|---|
| 291 | 5-chloro-2-fluoro-phenyl | CH$_3$ | 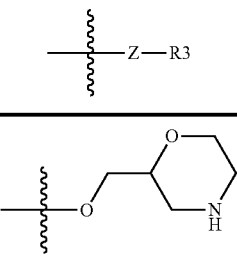 | 3 | 23 | 533.2 (M + H), CP |
| 292 | 2,5-difluoro-phenyl | CH$_3$ | 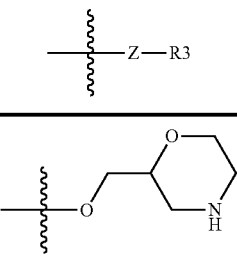 | 3 | 92 | 517.3 (M + H), CP |
| 293 | 2-cyano-5-methyl-phenyl | CH$_3$ | 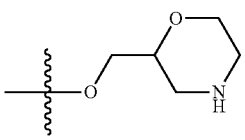 | 3 | 24 | 520.3 (M + H) |
| 294 | 2-fluoro-5-methoxy-phenyl | CH$_3$ | 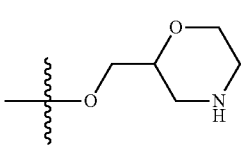 | 3 | 9 | 513.3 (M + H) |
| 295 | 2-fluoro-5-methoxy-phenyl | CH$_3$ | 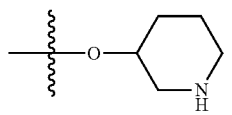 [SMILES: *OC1CCCNC1] | 3 | 5 | 529.3 (M + H) |
| 296 | 2,5-difluoro-phenyl | CH$_3$ | 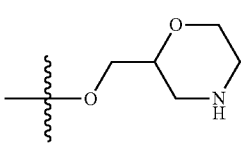 [SMILES: *OCC1CNCCO1] | 3 | 58 | 519.1 (M + H) |
| 297 | 2-fluoro-phenyl | CH$_3$ | 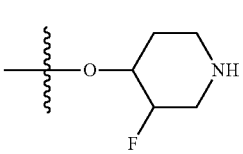 [SMILES: *OC1CCNCC1F] | 3 | 62 | 501.2 (M + H) |
| 298 | 2-fluoro-5-methyl-phenyl | CH$_3$ | 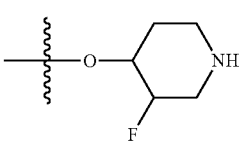 [SMILES: *OC1CCNCC1F] | 3 | 71 | 515.2 (M + H) |
| 299 | 5-chloro-2-cyano-phenyl | CH$_3$ | 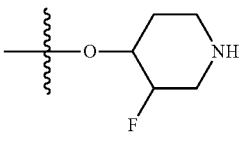 [SMILES: *OC1CCNCC1F] | 3 | 16 | 542.1 (M + H), CP |
| 300 | 2-cyano-5-methyl-phenyl | CH$_3$ | 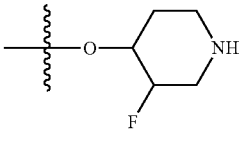 [SMILES: *OC1CCNCC1F] | 3 | 69 | 522.2 (M + H) |

TABLE 1-continued

Example compounds of the formula Ib

| Example no. | Ar | R1 | —Z—R3 | Synthesis | Yield (%) | MS (m/e) |
|---|---|---|---|---|---|---|
| 301 | 5-chloro-2-fluoro-phenyl | CH₃ | 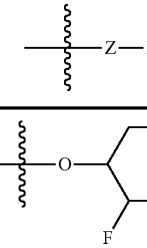 | 3 | 60 | 535.1 (M + H), CP |
| 302 | 2-fluoro-5-methoxy-phenyl | CH₃ | 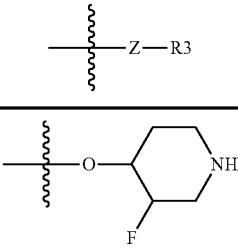 | 3 | 77 | 531.2 (M + H) |
| 303 | 2,5-dichloro-phenyl | CH₃ | 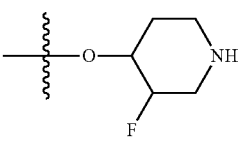 [SMILES: *OC1CCNCC1F] | 3 | 26 | 551.1 (M + H), CP |
| 304 | 2-chloro-5-methoxy-phenyl | CH₃ | 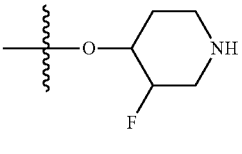 [SMILES: *OC1CCNCC1F] | 3 | 78 | 547.2 (M + H), CP |
| 305 | 5-chloro-2-fluoro-phenyl | H | 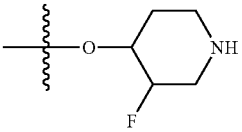 | 3 | | 519.1 (M + H), CP |
| 306 | 2-chloro-5-methoxy-phenyl | H | 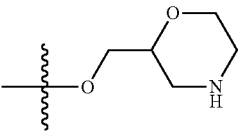 [SMILES: *OCC1CNCCO1] | 3 | 61 | 531.1 (M + H), CP |
| 307 | 2-fluoro-phenyl | H | 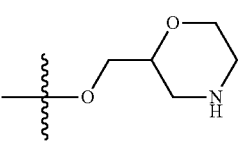 | 3 | 60 | 485.2 (M + H) |
| 308 | 2-fluoro-5-methyl-phenyl | H | 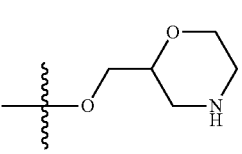 | 3 | 43 | 499.2 (M + H) |
| 309 | 2-fluoro-5-methoxy-phenyl | H | 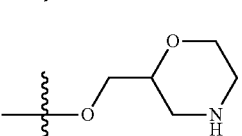 | 3 | 45 | 515.2 (M + H) |
| 310 | 2,5-dichloro-phenyl | NH₂ | 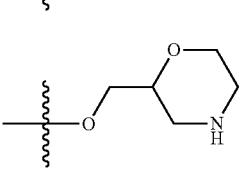 | 7 | 26 | 507.1 (M + H), CP |

TABLE 1-continued

Example compounds of the formula Ib

| Example no. | Ar | R1 | -Z-R3 | Synthesis | Yield (%) | MS (m/e) |
|---|---|---|---|---|---|---|
| 311 | 2,5-difluoro-phenyl | H | 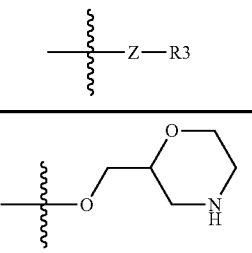 | 3 | 59 | 503.2 (M + H) |
| 312 | 2,5-dichloro-phenyl | H | 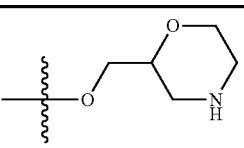 | 3 | 12 | 535.1 (M + H), CP |
| 313 | 2,5-dichloro-phenyl | CH₃ | 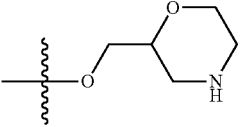 [SMILES: *OCC1CNCCO1] | 3 | 23 | 549.2 (M + H), CP |
| 314 | 2-cyano-5-methyl-phenyl | H | 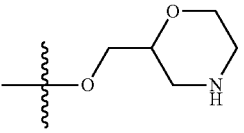 [SMILES: *OCC1CNCCO1] | 3 | 15 | 502.3 (M − H) |
| 315 | 2-cyano-5-methyl-phenyl | H | 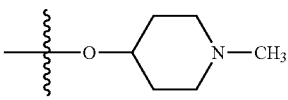 | 3 | 5 | 506.3 (M + H) |
| 316 | 2-chloro-phenyl | NH₂ | 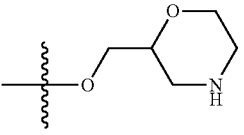 [SMILES: *OCC1CNCCO1] | 7 | 29 | 473.2 (M + H), CP |
| 317 | 2-fluoro-5-methyl-phenyl | NH₂ | 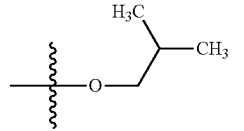 [SMILES: *OCC(C)C] | 7 | 46 | 471.2 (M + H) |
| 318 | 2-chloro-4-fluoro-phenyl | NH₂ | 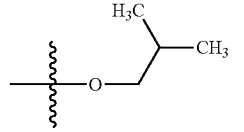 [SMILES: *OCC(C)C] | 7 | 7 | 491.2 (M + H), CP |
| 319 | 2-chloro-5-methoxy-phenyl | CH₃ | 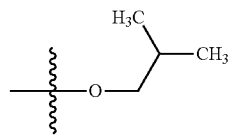 [SMILES: *OCC(C)C] | 3 | 95 | 529.2 (M + H), CP |
| 320 | 2-cyano-5-methyl-phenyl | CH₃ | 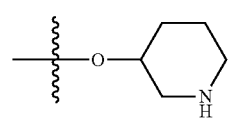 | 3 | 99 | 504.4 (M + H) |
| 321 | 2,5-difluoro-phenyl | CH₃ | 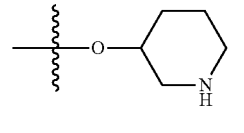 | 3 | 63 | 501.3 (M + H) |

TABLE 1-continued

Example compounds of the formula Ib

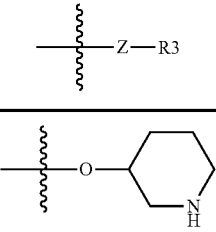

| Example no. | Ar | R1 | Synthesis | Yield (%) | MS (m/e) |
|---|---|---|---|---|---|
| 322 | 2,5-dichloro-phenyl | $CH_3$ | 3 | 74 | 533.3 (M + H), CP |
| 323 | 2-fluoro-phenyl | $CH_3$ | 3 | 68 | 483.3 (M + H) |
| 324 | 2-chloro-3-fluoro-phenyl | $NH_2$ | 7 | 27 | 491.2 (M + H), CP |
| 325 | 2-chloro-4,5-difluoro-phenyl | $NH_2$ | 7 | 38 | 509.2 (M + H), CP |
| 326 | 2-fluoro-5-methoxy-phenyl | $NH_2$ | 7 | 26 | 487.2 (M + H) |
| 327 | 3-chloro-2-fluoro-phenyl | $NH_2$ | 7 | 26 | 491.2 (M + H), CP |
| 328 | 2,5-difluoro-phenyl | $NH_2$ | 7 | 24 | 475.2 (M + H) |
| 329 | 2,4,5-trifluoro-phenyl | $NH_2$ | 7 | 32 | 493.1 (M + H) |
| 330 | 2,5-dichloro-thiophen-3-yl | $NH_2$ | 7 | 3 | 513.1 (M + H), CP |
| 331 | 2-fluoro-phenyl | $NH_2$ | 7 | 26 | 457.2 (M + H) |

TABLE 1-continued

Example compounds of the formula Ib

| Example no. | Ar | R1 | —Z—R3 | Synthesis | Yield (%) | MS (m/e) |
|---|---|---|---|---|---|---|
| 332 | 2-chloro-5-methoxxy-phenyl | NH$_2$ | 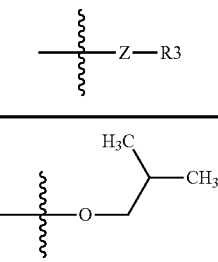 | 7 | 25 | 503.1 (M + H), CP |
| 333 | 2-cyano-5-methyl-phenyl | NH$_2$ | 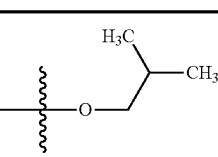 | 7 | 10 | 478.2 (M + H) |
| 334 | 5-chloro-2-fluoro-phenyl | NH$_2$ | 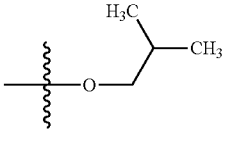 [SMILES: *OCC(C)C] | 7 | 27 | 491.1 (M + H), CP |
| 335 | 2,5-dichloro-phenyl | NH$_2$ | 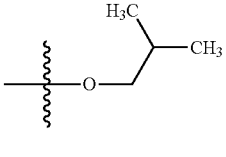 | 7 | 3 | 493.1 (M + H), CP |
| 336 | 2-cyano-5-methoxy-phenyl | NH$_2$ | 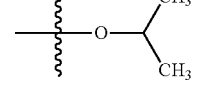 | 7 | 19 | 494.2 (M + H) |
| 337 | 2-chloro-3,5-difluoro-phenyl | NH$_2$ | 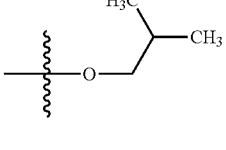 | 7 | 30 | 509.1 (M + H), CP |
| 338 | 2-fluoro-5-methyl-phenyl | CH$_3$ | 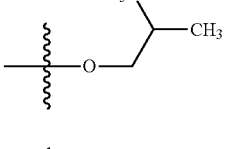 | 3 | 67 | 495.2 (M − H) |
| 339 | 2-fluoro-5-chloro-phenyl | CH$_3$ | 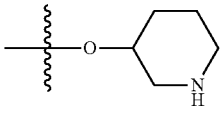 | 3 | 93 | 515.2 (M − H) |
| 340 | 2-fluoro-5-methyl-phenyl | CH$_3$ | 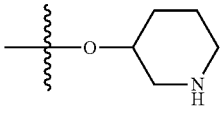 [SMILES: *OC1CCCNC1] | 3 | 10 | 543.4 (M + H) |
| 341 | 2-chloro-5-methoxy-phenyl | CH$_3$ | 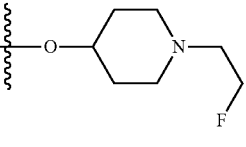 | 3 | 20 | 573.2 (M − H) |

TABLE 1-continued

Example compounds of the formula Ib

| Example no. | Ar | R1 | —Z—R3 | Synthesis | Yield (%) | MS (m/e) |
|---|---|---|---|---|---|---|
| 342 | 2,5-dichloro-phenyl | CH₃ | 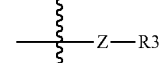 | 3 | 3 | 579.3 (M + H), CP |
| 343 | 2-cyano-5-methyl-phenyl | CH₃ | 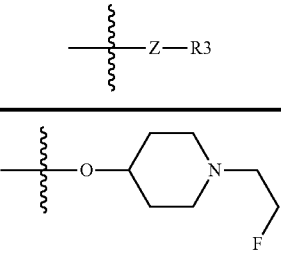 | 3 | 21 | 550.2 (M + H) |
| 344 | 2,5-difluoro-phenyl | CH₃ | 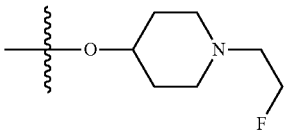 [SMILES: *OC1CCN(CCF)CC1] | 3 | 13 | 547.4 (M + H) |
| 345 | 2-chloro-5-methoxy-phenyl | CH₃ | 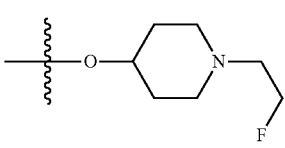 [SMILES: *OC1CCN(CCF)CC1] | 3 | 92 | 571.4 (M + H), CP |
| 346 | 5-chloro-2-fluoro-phenyl | CH₃ | 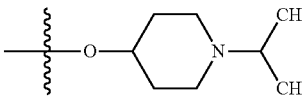 | 3 | 88 | 559.3 (M + H), CP |
| 347 | 2-fluoro-5-methoxy-phenyl | CH₃ | 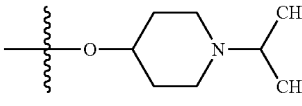 | 3 | 21 | 559.4 (M + H) |
| 348 | 2-fluoro-phenyl | CH₃ | 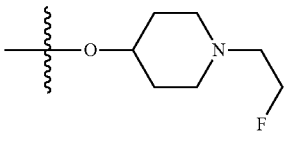 [SMILES: *OC1CCN(CCF)CC1] | 3 | 20 | 529.3 (M + H) |
| 349 | 2,5-difluoro-phenyl | CH₃ | 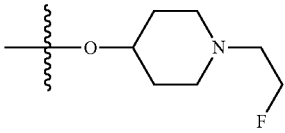 [SMILES: *OC1CCN(CCF)CC1] | 3 | 93 | 543.0 (M + H) |
| 350 | 2-cyano-5-methyl-phenyl | CH₃ | 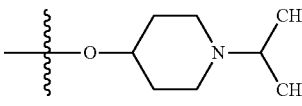 | 3 | 93 | 546.3 (M + H) |
| 351 | 2,5-dichloro-phenyl | CH₃ | 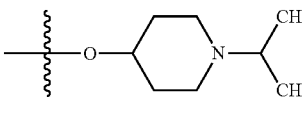 | 3 | 66 | 575.2 (M + H), CP |
| 352 | 2-fluoro-phenyl | CH₃ | 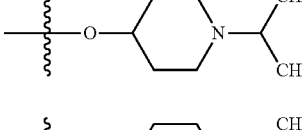 | 3 | 74 | 525.3 (M + H) |

TABLE 1-continued

Example compounds of the formula Ib

| Example no. | Ar | R1 | Z—R3 | Synthesis | Yield (%) | MS (m/e) |
|---|---|---|---|---|---|---|
| 353 | 2-fluoro-5-methyl-phenyl | CH$_3$ | —O-(piperidine-N-CH(CH$_3$)$_2$) | 3 | 91 | 539.3 (M + H) |
| 354 | 5-chloro-2-cyano-phenyl | NH$_2$ | —O—CH$_2$—CH(CH$_3$)$_2$ | 7 | 3 | 498.1 (M + H), CP |
| 355 | 2,5-dichloro-phenyl | NH$_2$ | —O—CH$_2$-cyclopropyl | 7 | 8 | 505.2 (M + H), CP |
| 356 | 5-chloro-2-fluoro-phenyl | CH$_3$ | —O-(piperidine-N-CH$_2$CH$_2$F) | 3 | 5 | 563.3 (M + H), CP |
| 357 | 2-fluoro-5-methoxy-phenyl | CH$_3$ | —O-(piperidine-N-CH(CH$_3$)$_2$) | 3 | 36 | 555.3 (M + H) |
| 358 | 2-chloro-5-methoxy-phenyl | CH$_3$ | —O—CH$_2$—CH(CH$_2$OH)$_2$ | 3 | 19 | 534.2 (M + H) |
| 359 | 5-chloro-2-fluoro-phenyl | CH$_3$ | —O—CH$_2$—CH(CH$_2$OH)$_2$ | 3 | 15 | 522.2 (M + H), CP |
| 360 | 2-fluoro-phenyl | CH$_3$ | —O—CH$_2$—CH(CH$_2$OH)$_2$ | 3 | 13 | 488.2 (M + H) |
| 361 | 2-fluoro-5-methyl-phenyl | CH$_3$ | —O—CH$_2$—CH(CH$_2$OH)$_2$ | 3 | 18 | 502.2 (M + H) |
| 362 | 2-chloro-5-methoxy-phenyl | CH$_3$ | —O—CH$_2$—C(F)$_2$—CH$_2$NH$_2$ | 3 | 8 | 539.2 (M + H), CP |

TABLE 1-continued

Example compounds of the formula Ib

| Example no. | Ar | R1 | —Z—R3 | Synthesis | Yield (%) | MS (m/e) |
|---|---|---|---|---|---|---|
| 363 | 2-fluoro-phenyl | CH₃ | 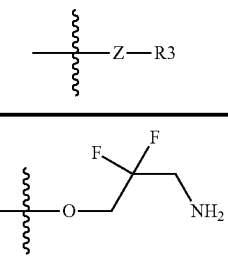 | 3 | 8 | 493.2 (M + H) |
| 364 | 2-fluoro-5-methyl-phenyl | CH₃ |  | 3 | 7 | 507.1 (M + H) |
| 365 | 2-fluoro-5-methoxy-phenyl | CH₃ |  | 3 | 15 | 523.2 (M + H) |
| 366 | 2,5-difluoro-phenyl | CH₃ |  | 3 | 33 | 511.1 (M + H) |
| 367 | 5-chloro-2-fluoro-phenyl | CH₃ |  | 3 | 16 | 527.1 (M + H), CP |
| 368 | 2,5-dichloro-phenyl | CH₃ |  | 3 | 6 | 538.0 (M + H), CP |
| 369 | 2-fluoro-5-methoxy-phenyl | CH₃ |  | 3 | 12 | 518.2 (M + H) |
| 370 | 2,5-difluoro-phenyl | CH₃ |  | 3 | 7 | 506.1 (M + H) |
| 371 | 2-cyano-5-methyl-phenyl | CH₃ |  | 3 | 13 | 509.2 (M + H) |
| 372 | 2,5-difluoro-phenyl | CH₃ |  | 3 | 12 | 499.1 (M + H) |

TABLE 1-continued

Example compounds of the formula Ib

| Example no. | Ar | R1 | —Z—R3 | Synthesis | Yield (%) | MS (m/e) |
|---|---|---|---|---|---|---|
| 373 | 5-chloro-2-fluoro-phenyl | CH₃ | 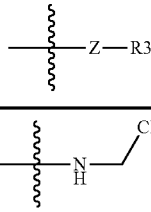 | 3 | 17 | 515.1 (M + H) |
| 374 | 2-fluoro-5-methyl-phenyl | CH₃ | 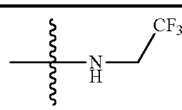 | 3 | 35 | 495.1 (M + H) |
| 375 | 2,5-dichloro-phenyl | CH₃ | 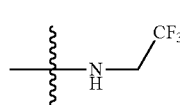 | 3 | 10 | 531.1 (M + H), CP |
| 376 | 2-cyano-5-methyl-phenyl | CH₃ | 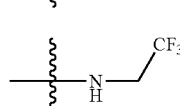 | 3 | 31 | 502.2 (M + H) |
| 377 | 2-fluoro-5-methyl-phenyl | CH₃ | 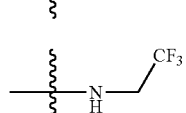 | 3 | 13 | 472.2 (M + H) |
| 378 | 2,5-dichloro-phenyl | CH₃ | 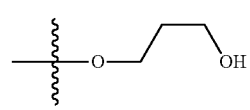 | 3 | 2 | 508.1 (M + H), CP |
| 379 | 2-fluoro-5-methoxy-phenyl | CH₃ | 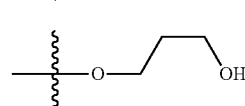 | 3 | 11 | 488.2 (M + H) |
| 380 | 2-cyano-5-methyl-phenyl | CH₃ | 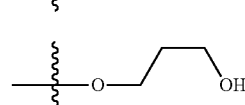 | 3 | 9 | 479.2 (M + H) |
| 381 | 2,5-difluoro-phenyl | CH₃ | 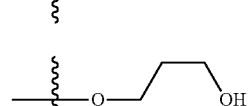 | 3 | 45 | 583.2 (M + H) |
| 382 | 5-chloro-2-fluoro-phenyl | CH₃ | 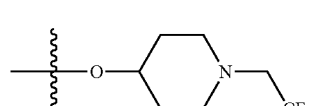 | 3 | 49 | 599.1 (M + H) |
| 383 | 2-chloro-5-methoxy-phenyl | CH₃ | 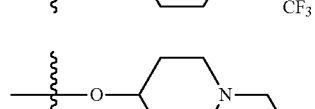 | 3 | 34 | 611.1 (M + H), CP |
| 384 | 2-fluoro-phenyl | CH₃ | 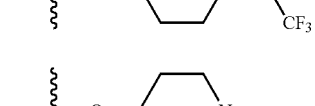 | 3 | 32 | 565.2 (M + H) |
| 385 | 2-fluoro-5-methyl-phenyl | CH₃ | 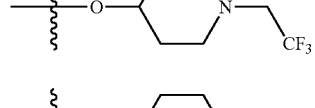 | 3 | 24 | 579.2 (M + H) |

TABLE 1-continued

Example compounds of the formula Ib

| Example no. | Ar | R1 | —Z—R3 | Synthesis | Yield (%) | MS (m/e) |
|---|---|---|---|---|---|---|
| 386 | 2,5-dichloro-phenyl | CH₃ | 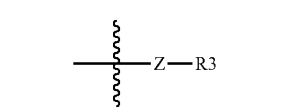 | 3 | 21 | 615.1 (M + H), CP |
| 387 | 2-fluoro-5-methoxy-phenyl | CH₃ | 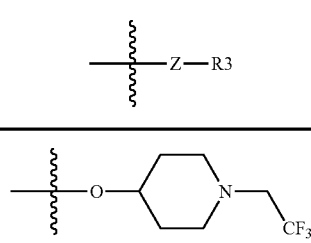 | 3 | 35 | 595.2 (M + H) |
| 388 | 2-cyano-5-methyl-phenyl | CH₃ | 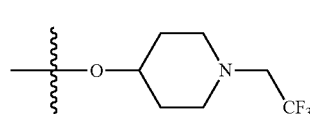 | 3 | 48 | 586.2 (M + H) |
| 389 | 2-fluoro-phenyl | CH₃ | 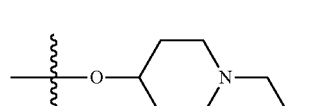 | 3 | 10 | 458.1 (M + H) |
| 390 | 2,5-difluoro-phenyl | CH₃ | 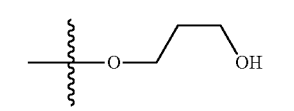 [SMILES: *OCCCO] | 3 | 17 | 476.2 (M + H) |
| 391 | 5-chloro-2-fluoro-phenyl | CH₃ | 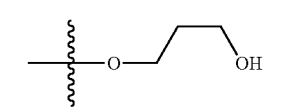 [SMILES: *OCCCO] | 3 | 10 | 492.1 (M + H), CP |
| 392 | 2-chloro-5-methoxy-phenyl | CH₃ | 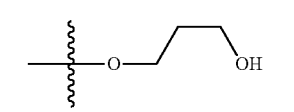 | 3 | 11 | 504.1 (M + H), CP |
| 393 | 2,5-difluoro-phenyl | H | 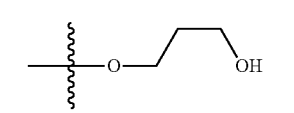 | 3 | 22 | 541.2 (M + H) |
| 394 | 2,5-difluoro-phenyl | H | 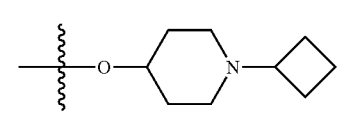 [SMILES: *OC1CCN(C2CCC2)CC1] | 3 | 29 | 559.2 (M + H) |
| 395 | 2,5-difluoro-phenyl | H | 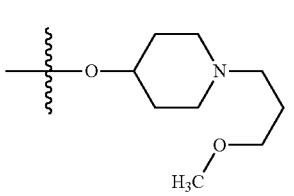 | 3 | 13 | 559.1 (M + H) |
| 396 | 2,5-difluoro-phenyl | H | 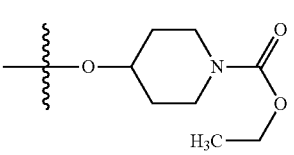 | 3 | 5 | 527.1 (M + H) |

TABLE 1-continued

Example compounds of the formula Ib

| Example no. | Ar | R1 | ⸹⸹—Z—R3 | Synthesis | Yield (%) | MS (m/e) |
|---|---|---|---|---|---|---|
| 397 | 2,5-difluoro-phenyl | CH₃ | 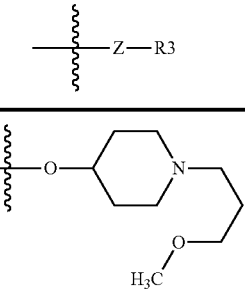 | 3 | 20 | 573.1 (M + H) |
| 398 | 2,5-difluoro-phenyl | CH₃ | 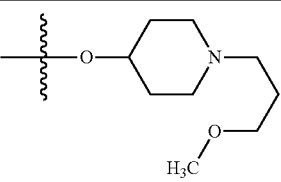 | 3 | 27 | 555.1 (M + H) |
| 399 | 5-chloro-2-fluoro-phenyl | CH₃ | 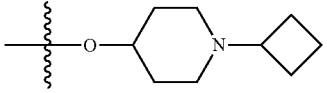 [SMILES: *OC1CCN(C2CCC2)CC1] | 3 | 21 | 545.1 (M + H) |
| 400 | 2,5-difluoro-phenyl | CH₃ | 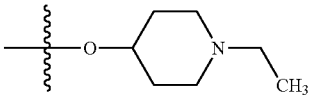 | 3 | 37 | 529.1 (M + H) |
| 401 | 2-chloro-5-methoxy-phenyl | CH₃ | 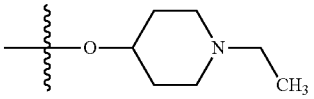 | 3 | 26 | 557.1 (M + H), CP |
| 402 | 2-fluoro-phenyl | CH₃ | 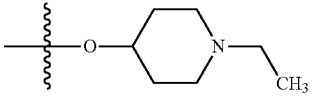 | 3 | 60 | 511.1 (M + H) |
| 403 | 2-fluoro-5-methyl-phenyl | CH₃ | 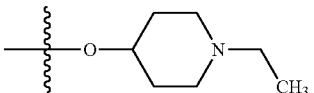 | 3 | 47 | 525.2 (M + H) |
| 404 | 2-fluoro-5-methoxy-phenyl | CH₃ | 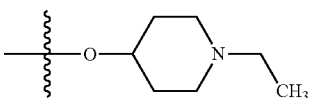 | 3 | 34 | 541.1 (M + H) |
| 405 | 2,5-dichloro-phenyl | CH₃ | 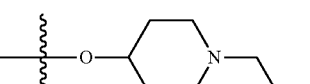 | 3 | 42 | 561.1 (M + H), CP |
| 406 | 5-chloro-2-fluoro-phenyl | CH₃ | 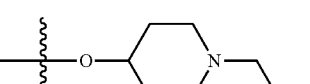 | 3 | 62 | 575.1 (M + H), CP |
| 407 | 2,5-difluoro-phenyl | CH₃ | 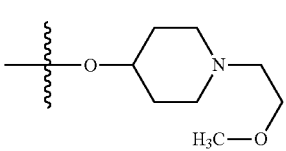 | 3 | 62 | 559.1 (M + H) |

TABLE 1-continued

Example compounds of the formula Ib

| Example no. | Ar | R1 | —Z—R3 | Synthesis | Yield (%) | MS (m/e) |
|---|---|---|---|---|---|---|
| 408 | 2-fluoro-5-methyl-phenyl | CH$_3$ | —O-(4-piperidinyl)-N-CH$_2$CH$_2$-O-CH$_3$ | 3 | 63 | 555.2 (M + H) |
| 409 | 2-fluoro-phenyl | CH$_3$ | —O-(4-piperidinyl)-N-CH$_2$CH$_2$-O-CH$_3$ | 3 | 31 | 541.1 (M + H) |
| 410 | 2-fluoro-5-methoxy-phenyl | CH$_3$ | —O-(4-piperidinyl)-N-CH$_2$CH$_2$-O-CH$_3$ | 3 | 49 | 571.2 (M + H) |
| 411 | 5-chloro-2-cyano-phenyl | CH$_3$ | —O-(4-piperidinyl)-N-CH$_2$CH$_2$-O-CH$_3$ | 3 | 45 | 582.1 (M + H), CP |
| 412 | 2,5-difluoro-phenyl | CH$_3$ | —O-(4-piperidinyl)-N-C(=O)-O-CH$_3$ | 3 | 8 | 573.1 (M + H) |
| 413 | 2,5-difluoro-phenyl | NH$_2$ | —O-CH$_2$-CH$_3$ | 7 | 37 | 447.0 (M + H) |
| 414 | 5-chloro-2-fluoro-phenyl | NH$_2$ | —O-CH$_2$CH$_2$-CH$_3$ | 7 | 28 | 477.0 (M + H), CP |
| 415 | 2,5-difluoro-phenyl | NH$_2$ | —O-CH$_2$CH$_2$-CH$_3$ | 7 | 57 | 461.0 (M + H) |
| 416 | 5-chloro-2-fluoro-phenyl | NH$_2$ | —O-CH$_2$-CH$_3$ | 7 | 18 | 463.0 (M + H), CP |
| 417 | 2-cyano-5-methyl-phenyl | CH$_3$ | —O-(4-piperidinyl)-N-CH$_3$ | 3 | 41 | 532.1 (M + H) |
| 418 | 5-chloro-2-fluoro-phenyl | CH$_3$ | —O-(3-piperidinyl), N-CH$_3$ | 3 | 27 | 545.1 (M + H), CP |

TABLE 1-continued

Example compounds of the formula Ib

| Example no. | Ar | R1 | —Z—R3 | Synthesis | Yield (%) | MS (m/e) |
|---|---|---|---|---|---|---|
| 419 | 2-chloro-5-methoxy-phenyl | CH$_3$ | 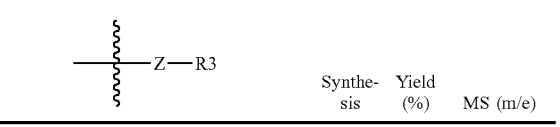 | 3 | 12 | 557.1 (M + H), CP |
| 420 | 2-fluoro-phenyl | CH$_3$ | 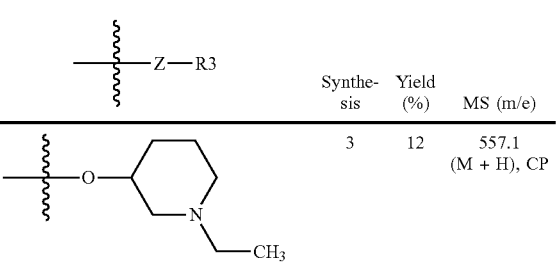 | 3 | 25 | 511.1 (M + H) |
| 421 | 2-fluoro-5-methyl-phenyl | CH$_3$ | 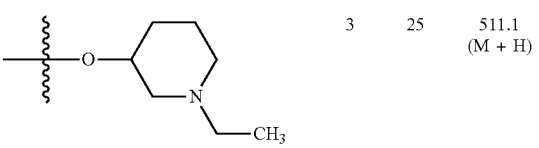 | 3 | 30 | 525.2 (M + H) |
| 422 | 2,5-dichloro-phenyl | CH$_3$ | 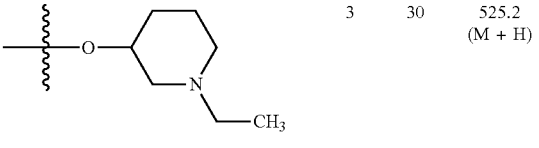 | 3 | 10 | 561.0 (M + H), CP |
| 423 | 2,5-difluoro-phenyl | CH$_3$ | 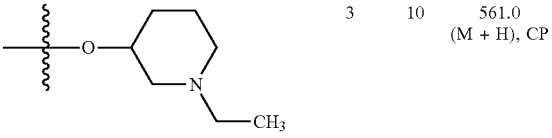 | 3 | 20 | 529.1 (M + H) |
| 424 | 2-fluoro-5-methoxy-phenyl | CH$_3$ | 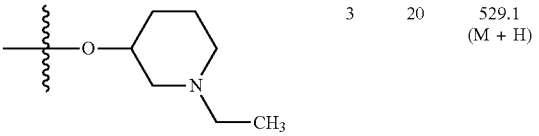 | 3 | 3 | 541.1 (M + H) |
| 425 | 2,5-dichloro-phenyl | NH$_2$ | 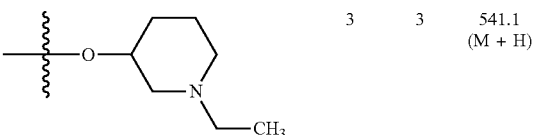 | 7 | 23 | 493.0 (M + H), CP |
| 426 | 2,5-dichloro-phenyl | NH$_2$ | 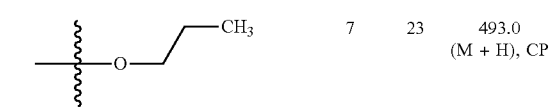 | 7 | 12 | 479.0 (M + H), CP |
| 427 | 2-cyano-5-methyl-phenyl | CH$_3$ | 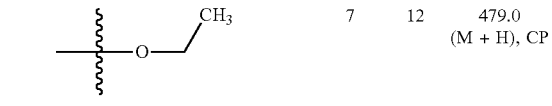 | 3 | 6 | 532.1 (M + H) |
| 428 | 2-fluoro-5-methoxy-phenyl | CH$_3$ | 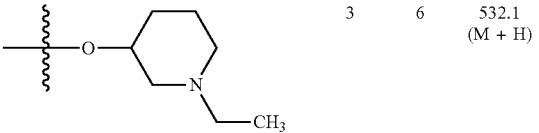 | 3 | 20 | 553.1 (M + H) |
| 429 | 5-chloro-2-fluoro-phenyl | CH$_3$ | 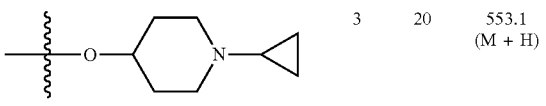 | 3 | 32 | 557.1 (M + H), CP |

TABLE 1-continued

Example compounds of the formula Ib

| Example no. | Ar | R1 | —Z—R3 | Synthesis | Yield (%) | MS (m/e) |
|---|---|---|---|---|---|---|
| 430 | 2-chloro-5-methoxy-phenyl | CH₃ | —O—piperidine-N-cyclopropyl | 3 | 23 | 569.1 (M + H), CP |
| 431 | 2-fluoro-5-methyl-phenyl | CH₃ | —O—piperidine-N-cyclopropyl | 3 | 17 | 537.1 (M + H) |
| 432 | 2,5-dichloro-phenyl | CH₃ | —O—piperidine-N-cyclopropyl | 3 | 29 | 573.0 (M + H), CP |
| 433 | 2,5-difluoro-phenyl | CH₃ | —O—piperidine-N-cyclopropyl | 3 | 40 | 541.1 (M + H) |

(a) Cesium carbonate was employed instead of sodium hydride.
(b) Water was employed as starting material.
(c) Benzhydrylidene-[6-chloro-1-(tetrahydro-pyran-2-yl)-4-(2,2,2-trifluoro-ethoxy)-1H-pyrazolo[3,4-d]pyrimidin-3-yl]-amine was employed.

Exemplary NMR Data of Example Compounds

Example 346

$^1$H-NMR (DMSO-d$_6$): δ (ppm)=1.31 (d, J=6.6 Hz, 6H), 2.02-2.14 (m, 1H), 2.24-2.34 (m, 2H), 2.57 (s, 2H), 3.12-3.41 (m, 3H), 3.45-3.57 (m, 3H), 5.56-5.86 (m, 1H), 7.27 (dd, J=3.8, 8.8 Hz, 2H), 7.52 (t, J=8.8 Hz, 1H), 7.76-7.82 (m, 1H), 7.84-7.89 (m, 1H), 8.33 (dd, J=8.7, 11.3 Hz, 2H), 9.73-10.01 (m, 1H), 11.13 (d, J=5.6 Hz, 1H), 13.48 (br, 1H).

Example 429

$^1$H-NMR (DMSO-d$_6$): δ (ppm)=0.87 (br, s, 2H), =0.98 (br, s, 2H), 1.83-1.96 (m, 1H), 2.07-2.18 (m, 1H), 2.29-2.39 (m, 1H), 2.50 (s, 3H), 2.61 (br, 2H), 2.83-3.15 (m, 1H), 3.30-3.42, 3.45-3.59 (m, 1H), 3.61-3.68 (m, 1H), 5.59-5.79 (m, 1H), 7.27 (d, J=8.5 Hz, 2H), 7.52 (t, J=9.2 Hz, 1H), 7.77-7.83 (m, 1H), 7.87 (dd, J=2, 7, 6.0 Hz, 1H), 8.30 (d, J=8.3 Hz, 2H), 9.01 (br, 1H), 11.13 (s, 1H), 13.47 (br, 1H)

Example 433

$^1$H-NMR (DMSO-d$_6$): δ (ppm)=0.87 (br, s, 2H), 0.97 (br, s, 2H), 1.82-1.96 (m, 1H), 2.05-2.18 (m, 1H), 2.29-2.39 (m, 1H), 2.50 (s, 3H), 2.61 (br, 1H), 2.83-3.15 (m, 1H), 3.45-3.71 (m, 3H), 5.58-5.78 (m, 1H), 7.26 (d, J=8.4 Hz, 2H), 7.49-7.56 (m, 1H), 7.57-7.64 (m, 1H), 7.69-7.75 (m, 1H), 8.30 (d, J=8.3 Hz, 2H), 8.92 (br, 1H), 11.12 (s, 1H), 13.46 (s, 1H).

Analogously to the procedures described in the examples above, the example compounds of the formula Ic

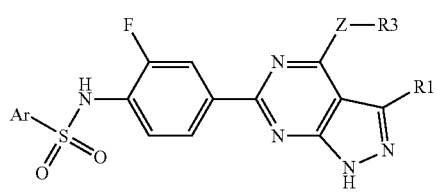

Ic listed in Table 2 were synthesized, employing 2-fluoro-4-(4,4,5,5-tetramethyl-[1,3,2]dioxaborolan-2-yl)-phenylamine instead of 4-(4,4,5,5-tetramethyl-[1,3,2]dioxaborolan-2-yl)-phenylamine as starting material. In the formulae of the groups —Z—R3 in Table 2 the line crossed with the symbol ∼∼ represents the free bond via which the group —Z—R3 is bonded to the carbon atom in the 4-position of the pyrazolo[3,4-d]pyrimidine ring system. I.e., in the formula of the complete molecule the terminal endpoint of the line crossed with the said symbol ends at the carbon atom in the 4-position of the pyrazolo[3,4-d]pyrimidine ring system. In example 442, 3-hydroxy-azetidine-1-carboxylic acid tert-butyl ester was employed as starting material. Deprotections were generally performed using either hydrogen chloride in Diox and/or iPrOH or TFA in DCM, for example a 1:1 mixture of TFA and DCM. In the column "Synthesis" the number of the example is specified in analogy to which the synthesis was performed. The ionization method in the MS characterization was ES+. CP means chloro pattern in the mass spectrum.

TABLE 2
Example compounds of the formula Ic
| Example No. | Ar | R1 | Z—R3 | Synthesis | Yield (%) | MS (m/e) |
|---|---|---|---|---|---|---|
| 434 | 2,5-dichloro-phenyl | CH₃ | 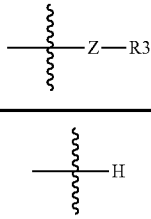 | 1 | 35 | 452.0 (M + H), CP |
| 435 | 5-chloro-2-fluoro-phenyl | H | 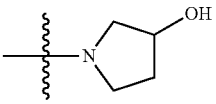 [SMILES: *N1CCC(O)C1] | 2 | 21 | 507.0 (M + H), CP |
| 436 | 5-chloro-2-fluoro-phenyl | H | 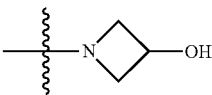 [SMILES: *N1CC(O)C1] | 2 | 30 | 493.0 (M + H), CP |
| 437 | 2,5-dichloro-phenyl | H | 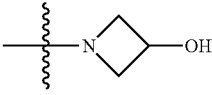 | 2 | 11 | 508.9 (M + H), CP |
| 438 | 2,5-dichloro-phenyl | H | 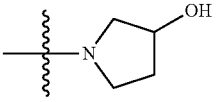 | 2 | 22 | 523.0 (M + H), CP |
| 439 | 2,5-dichloro-phenyl | H | 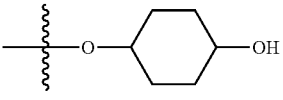 | 3 | 42 | 551.9 (M + H), CP |
| 440 | 5-chloro-2-fluoro-phenyl | H | 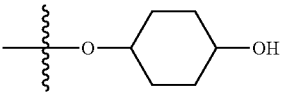 [SMILES: *OC1CCC(O)CC1] | 3 | 42 | 536.0 (M + H), CP |
| 441 | 5-chloro-2-fluoro-phenyl | H | 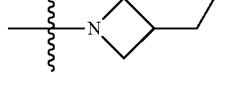 | 2 | 14 | 507.2 (M + H), CP |
| 442 | 5-chloro-2-fluoro-phenyl | H | 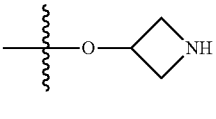 [SMILES: *OC1CNC1] | 3 | 13 | 493.0 (M + H), CP |
| 443 | 5-chloro-2-fluoro-phenyl | H | 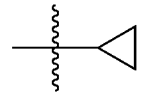 [SMILES: *C1CC1] | 6 | 27 | 462.0 (M + H), CP |

Example 444

N-[4-(3-Amino-4-isopropoxy-1H-pyrazolo[3,4-d]pyrimidin-6-yl)-2-fluoro-phenyl]-5-chloro-2-fluoro-benzenesulfonamide

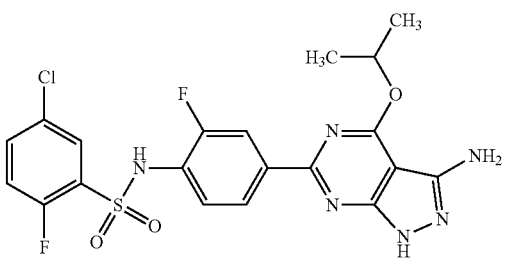 [SMILES: CC(C)Oc1nc(-c2ccc(NS(=O)(=O)c3cc(Cl)ccc3F)c(F)c2)nc2[nH]nc(N)c12]

The title compound was prepared in 29% yield analogously to the procedure described in example 7 employing benzhydrylidene-[6-chloro-1-(tetrahydro-pyran-2-yl)-4-(2,2,2-trifluoro-ethoxy)-1H-pyrazolo[3,4-d]pyrimidin-3-yl]-amine and 5-chloro-2-fluoro-N-[2-fluoro-4-(4,4,5,5-tetramethyl-[1,3,2]dioxaborolan-2-yl)-phenyl]-benzenesulfonamide in step (v). Replacement of the 2,2,2-trifluoro-ethoxy group by an isopropoxy group occurred in the course of the treatment with isopropanol in step (vi).

MS (ES+): m/e=495.09 (M+H), chloro pattern.

Example 445

N-[4-(3-Amino-1H-pyrazolo[3,4-d]pyrimidin-6-yl)-phenyl]-5-chloro-2,4-difluoro-benzenesulfonamide

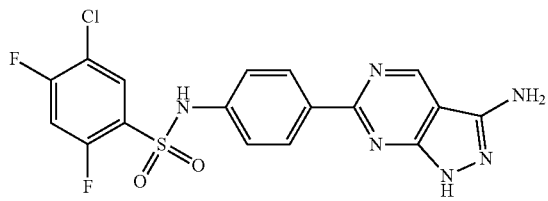 [SMILES: Nc1n[nH]c2nc(-c3ccc(NS(=O)(=O)c4cc(Cl)c(F)cc4F)cc3)ncc12]

(i) 4-Hydroxy-2-(4-nitrophenyl)pyrimidine-5-carbonitrile

To a solution of 3.14 g of 2-cyano-3-ethoxy-acrylic acid ethyl ester (U.S. Pat. No. 2,824,121) and 3 g of 4-nitrobenzimidamide in 50 ml of ethanol, 14 ml of a sodium ethoxide solution (20% in ethanol) were slowly added. The reaction mixture was heated to reflux for 1 h. After cooling to RT and dilution with water, the reaction mixture was acidified with half-concentrated aqueous hydrochloric acid to pH 1. The organic solvents were removed under reduced pressure and the precipitating product was collected by filtration as a brown solid. Yield: 3.0 g.

(ii) 4-Chloro-2-(4-nitrophenyl)pyrimidine-5-carbonitrile

To a solution of 3.0 g of 4-hydroxy-2-(4-nitrophenyl)pyrimidine-5-carbonitrile in 18 ml of phosphorus oxychloride, 1.6 ml of dimethyl-phenyl-amine were added. The reaction mixture was heated to reflux for 1 h, then cooled to RT and concentrated under reduced pressure. After addition of ice water and dilution with DCM, saturated aqueous sodium hydrogencarbonate solution was added and the mixture was extracted with DCM (3×200 ml). The combined organic layers were dried over magnesium sulfate and the solvents were removed under reduced pressure. The crude product was purified by chromatography on silica gel eluting with a gradient of Hep/EtOAc. The fractions containing the product were combined and the solvent evaporated under reduced pressure. Yield: 3.2 g.

(iii) 6-(4-Nitrophenyl)-1H-pyrazolo[3,4-d]pyrimidin-3-amine

To a solution of 1.5 g of 4-chloro-2-(4-nitrophenyl)pyrimidine-5-carbonitrile in 10 ml of iPrOH, 12.7 ml of a hydrazine solution (35% in iPrOH) were added and the reaction mixture was heated for 25 min to 80° C. by using microwave irradiation (Biotage® Initiator apparatus). The reaction mixture was cooled to RT and diluted with acetic acid (20%). The precipitated product was collected by filtration and used in the next reaction step without further purification. Yield: 867 mg.

(iv) tert-Butyl 3-(bis(tert-butoxycarbonyl)amino)-6-(4-nitrophenyl)pyrazolo[3,4-d]pyrimidine-1-carboxylate To a suspension of 867 mg of 6-(4-nitrophenyl)-1H-pyrazolo[3,4-d]pyrimidin-3-amine in 10 ml of DCM, 2.3 g of di-tert-butyl dicarbonate, 1.4 ml of triethylamine and 4 mg of dimethyl-pyridin-4-yl-amine were added. The mixture was stirred for 16 h at RT, then quenched by the addition of water and diluted with DCM. After separation of the organic layer, the aqueous layer was extracted with DCM (3×200 ml). The combined organic layers were dried over magnesium sulfate and the solvents were removed under reduced pressure. The crude product was purified by chromatography on silica gel eluting with a gradient of Hep/EtOAc. The fractions containing the product were combined and the solvent evaporated under reduced pressure. Yield: 1.4 g.

(v) tert-Butyl 6-(4-aminophenyl)-3-(bis(tert-butoxycarbonyl)amino)pyrazolo[3,4-d]pyrimidine-1-carboxylate To a solution of 1.4 g of tert-butyl 3-(bis(tert-butoxycarbonyl)amino)-6-(4-nitrophenyl)pyrazolo[3,4-d]pyrimidine-1-carboxylate obtained in the preceding step in 50 ml of EtOAc, 347 mg of Pd/C (10%) were added under argon and the suspension was stirred under an atmosphere of hydrogen (2 bar) for 16 h. The suspension was filtered over a plug of Celite® and washed with EtOAc. The crude product was obtained after evaporation of the solvent as a brown solid and was dried under reduced pressure. Yield: 3.3 g.

(vi) N-[4-(3-Amino-1H-pyrazolo[3,4-d]pyrimidin-6-yl)-phenyl]-5-chloro-2,4-difluoro-benzenesulfonamide To a solution of 150 mg of tert-butyl 6-(4-aminophenyl)-3-(bis(tert-butoxycarbonyl)amino)pyrazolo[3,4-d]pyrimidine-1-carboxylate in 2.5 ml DCM and 25 μl pyridine, 140 mg of 5-chloro-2,4-difluoro-benzenesulfonyl chloride were added. After stirring the reaction mixture for 16 h at RT, the solvents were removed under reduced pressure. The residue was dissolved in 2 ml DCM and 0.5 ml of TFA and stirred for 6 h at RT. Then toluene was added and the solvents were removed under reduced pressure to yield a brown solid. This crude product was purified by preparative HPLC (C18 reverse phase column, elution with a water/MeCN gradient with 0.1% TFA). The fractions containing the product were lyophilized to yield the pure title compound in the form of its salt with trifluoroacetic acid. This solid was dissolved in 1 ml of a water/MeCN mixture, then 0.5 ml of a 1 M aqueous hydrochloric acid were added and the solution was again lyophilized to yield the title compound in the form of N-[4-(3-amino-1H-pyrazolo[3,4-d]pyrimidin-6-yl)-phenyl]-5-chloro-2,4-difluoro-benzenesulfonamide hydrochloride. Yield: 87 mg.

$^1$H-NMR (DMSO-$d_6$): δ (ppm)=7.28 (d, J=8.7 Hz, 2H), 7.83 (t, J=10.3 Hz, 1H), 8.10 (t, J=8.5 Hz, 1H), 8.27 (d, J=8.7 Hz, 2H), 9.17 (s, 1H), 11.18 (s, 1H).

MS (ES+): m/e=436.9 (M+H), chloro pattern.

Example 446

N-[4-(3-Amino-1H-pyrazolo[3,4-d]pyrimidin-6-yl)-phenyl]-5-chloro-2-cyano-benzenesulfonamide

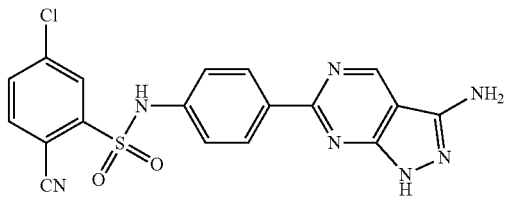 [SMILES: N#Cc1ccc(Cl)cc1S(=O)(=O)Nc1ccc(-c2ncc3c(N)n[nH]c3n2)cc1]

(i) tert-Butyl 3-(bis(tert-butoxycarbonyl)amino)-6-[4-[(5-chloro-2-cyano-phenyl)sulfonylamino]phenyl]pyrazolo[3,4-d]pyrimidine-1-carboxylate To a solution of 3 g of tert-butyl 6-(4-aminophenyl)-3-(bis(tert-butoxycarbonyl)amino)pyrazolo[3,4-d]pyrimidine-1-carboxylate (example 445, step (v)) in 50 ml DCM and 1.4 ml pyridine, 1.4 g of 5-chloro-2-cyano-benzenesulfonyl chloride were added. After stirring the reaction mixture for 16 h at RT, the solvents were removed under reduced pressure. The crude product was purified by chromatography on silica gel eluting with a gradient of Hep/EtOAc. The fractions containing the product were combined and the solvent evaporated under reduced pressure. Yield: 2.7 g.

(ii) N-[4-(3-Amino-1H-pyrazolo[3,4-d]pyrimidin-6-yl)-phenyl]-5-chloro-2-cyano-benzenesulfonamide 1.6 g of tert-butyl 3-(bis(tert-butoxycarbonyl)amino)-6-[4-[(5-chloro-2-cyano-phenyl)sulfonylamino]phenyl]pyrazolo[3,4-d]pyrimidine-1-carboxylate were dissolved in 20 ml DCM and 1.7 ml of TFA. The reaction mixture was stirred for 16 h at RT, then diluted with water and neutralized with a saturated aqueous sodium hydrogencarbonate solution. The precipitated crude product was collected by filtration, washed with EtOAc and recrystallized from ethanol. Yield: 625 mg.

$^1$H-NMR (DMSO-$d_6$): δ (ppm)=7.25 (d, J=8.8 Hz, 2H), 7.59 (d, J=8.5 Hz, 1H), 8.07 (s, 1H), 8.12 (d, J=8.5 Hz, 1H), 8.33 (d, J=8.8 Hz, 2H), 9.13 (s, 1H), 11.19 (s, 1H).

MS (ES−): m/e=424.2 (M−H), chloro pattern.

Example 447

N-[4-(3-Amino-4-methyl-1H-pyrazolo[3,4-d]pyrimidin-6-yl)-phenyl]-5-chloro-2,4-difluoro-benzenesulfonamide

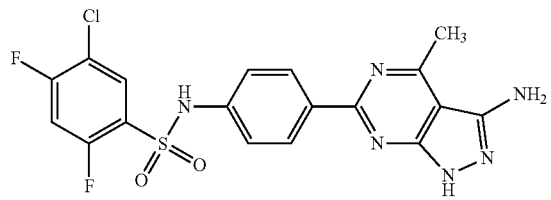 [SMILES: Cc1nc(-c2ccc(NS(=O)(=O)c3cc(Cl)c(F)cc3F)cc2)nc2[nH]nc(N)c12]

(i) 6-Methyl-2-(4-nitro-phenyl)-4-oxo-4,5-dihydro-pyrimidine-5-carbonitrile

To a solution of 5.5 g of 2-cyano-3-ethoxy-but-2-enoic acid ethyl ester (U.S. Pat. No. 2,824,121) and 5 g of 4-nitrobenzimidamide in 200 ml of ethanol, 23.5 ml of a sodium ethoxide solution (20% in ethanol) were slowly added. The reaction mixture was heated to reflux for 1 h. After cooling to RT and dilution with water, the reaction mixture was acidified with half-concentrated aqueous hydrochloric acid to pH 1. The organic solvents were removed under reduced pressure and the precipitating product was collected by filtration as a brown solid. Yield: 7.2 g.

(ii) 4-Chloro-6-methyl-2-(4-nitro-phenyl)-pyrimidine-5-carbonitrile

To a solution of 5.3 g of 6-methyl-2-(4-nitro-phenyl)-4-oxo-4,5-dihydro-pyrimidine-5-carbonitrile in 71 ml of phosphorus oxychloride, 2.6 ml of dimethyl-phenyl-amine were added. The reaction mixture was heated to reflux for 1 h, then cooled to RT and concentrated under reduced pressure. After addition of ice water and dilution with DCM, saturated aqueous sodium hydrogencarbonate solution was added and the mixture was extracted with DCM (3×200 ml). The combined organic layers were dried over magnesium sulfate and the solvents were removed under reduced pressure. The crude product was purified by chromatography on silica gel eluting with a gradient of Hep/EtOAc. The fractions containing the product were combined and the solvent evaporated under reduced pressure. Yield: 3.8 g.

(iii) 4-Methyl-6-(4-nitro-phenyl)-1H-pyrazolo[3,4-d]pyrimidin-3-ylamine

To a solution of 3.9 g of 4-chloro-6-methyl-2-(4-nitro-phenyl)-pyrimidine-5-carbonitrile in 25 ml of iPrOH, 24.5 ml of a hydrazine solution (35% in iPrOH) were added and the reaction mixture was heated for 10 min to 80° C. by using microwave irradiation (Biotage® Initiator apparatus). The reaction mixture was cooled to RT and diluted with acetic acid (20%). The precipitated product was collected by filtration and used in the next reaction step without further purification. Yield: 3.4 g.

(iv) tert-Butyl 3-(bis(tert-butoxycarbonyl)amino)-4-methyl-6-(4-nitrophenyl)pyrazolo[3,4-d]pyrimidine-1-carboxylate To a suspension of 3.4 g of 4-methyl-6-(4-nitro-phenyl)-1H-pyrazolo[3,4-d]pyrimidin-3-ylamine in 105 ml of DCM, 8.3 g of di-tert-butyl dicarbonate, 5.3 ml of triethylamine and 16 mg of dimethyl-pyridin-4-yl-amine were added. The mixture was stirred for 16 h at RT, then quenched by the addition of water and diluted with DCM. After separation of the organic layer, the aqueous layer was extracted with DCM (3×200 ml). The combined organic layers were dried over magnesium sulfate and the solvents were removed under reduced pressure. The crude product was purified by chromatography on silica gel eluting with a gradient of Hep/EtOAc. The fractions containing the product were combined and the solvent evaporated under reduced pressure. Yield: 6.5 g.

(v) tert-Butyl 6-(4-aminophenyl)-3-(bis(tert-butoxycarbonyl)amino)-4-methyl-pyrazolo[3,4-d]pyrimidine-1-carboxylate To a solution of 5.6 g of tert-butyl 3-(bis(tert-butoxycarbonyl)amino)-4-methyl-6-(4-nitrophenyl)pyrazolo[3,4-d]pyrimidine-1-carboxylate obtained in the preceding step in 85 ml of EtOAc, 559 mg of Pd/C (10%) were added under argon and the suspension was stirred under an atmosphere of hydrogen (2 bar) for 16 h. The suspension was filtered over a plug of Celite® and washed with EtOAc. The crude product was obtained after evaporation of the solvent as a brown solid and was dried under reduced pressure. Yield: 5.0 g.

(vi) N-[4-(3-Amino-4-methyl-1H-pyrazolo[3,4-d]pyrimidin-6-yl)-phenyl]-5-chloro-2,4-difluoro-benzenesulfonamide To a solution of 250 mg of tert-butyl 6-(4-aminophenyl)-3-(bis(tert-butoxycarbonyl)amino)-4-methyl-pyrazolo[3,4-d]pyrimidine-1-carboxylate in 2.5 ml DCM and 75 µl pyridine, 114 mg of 5-chloro-2,4-difluoro-benzenesulfonyl chloride were added. After stirring the reaction mixture for 16 h at RT, the solvents were removed under reduced pressure. The residue was dissolved in 2 ml DCM and 0.5 ml of TFA and stirred for 6 h at RT. Then toluene was added and the solvents were removed under reduced pressure to yield a brown solid. This crude product was purified by preparative HPLC (C18 reverse phase column, elution with a water/MeCN gradient with 0.1% TFA). The fractions containing the product were lyophilized to yield the pure title compound in the form of its salt with trifluoroacetic acid. Yield: 65 mg.

$^1$H-NMR (DMSO-d$_6$): δ (ppm)=2.77 (s, 3H), 7.27 (d, J=8.7 Hz, 2H), 7.83 (t, J=10.3 Hz, 1H), 8.09 (t, J=8.5 Hz, 1H), 8.26 (d, J=8.5 Hz, 2H), 11.16 (s, 1H).

MS (ES+): m/e=451.0 (M+H), chloro pattern.

Example 448

N-[4-(3-Amino-4-cyclopropyl-1H-pyrazolo[3,4-d]pyrimidin-6-yl)phenyl]-5-chloro-2,4-difluoro-benzenesulfonamide

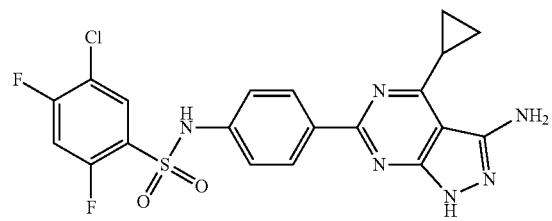 [SMILES: Nc1n[nH]c2nc(-c3ccc(NS(=O)(=O)c4cc(Cl)c(F)cc4F)cc3)nc(C3CC3)c12]

(i) 2-Cyano-3-cyclopropyl-3-hydroxy-acrylic acid ethyl ester

To a solution of 11.0 g of cyano-acetic acid ethyl ester in 100 ml of MeCN, 9.0 g of anhydrous magnesium chloride were added at 0° C. After 10 min, 26.1 ml of triethylamine and after 1 h a solution of 10.0 g of cyclopropanecarbonyl chloride in 30 ml of DCM were added dropwise to the reaction mixture. After stirring for an additional 1 h, the reaction mixture was acidified with half-concentrated aqueous hydrochloric acid to pH 1, and the mixture was extracted with DCM (3×200 ml). The combined organic layers were washed with water, dried over magnesium sulfate and the solvents were removed under reduced pressure. The crude product was purified by crystallization from Hep/EtOAc to yield a crystalline solid. Yield: 10.1 g.

(ii) 2-Cyano-3-cyclopropyl-3-ethoxy-acrylic acid ethyl ester

To a solution of 10.1 g of 2-cyano-3-cyclopropyl-3-hydroxy-acrylic acid ethyl ester in 200 ml of MeCN, 18.1 g of cesium carbonate were added at 0° C., followed by dropwise addition of 7.26 ml of trifluoromethanesulfonic acid ethyl ester. After 1 h the reaction mixture was allowed to warm to RT and stirred for 16 h. Then the reaction mixture was quenched with a saturated aqueous sodium hydrogencarbonate solution (15 ml) and filtered through a Chem Elut® cartridge by eluting with EtOAc. The filtrate was concentrated under reduced pressure and the obtained crude product was used in the next reaction step. Yield: 12 g.

(iii) 4-Cyclopropyl-6-hydroxy-2-(4-nitrophenyl)pyrimidine-5-carbonitrile

To a solution of 9.3 g of 2-cyano-3-cyclopropyl-3-ethoxy-acrylic acid ethyl ester and 3.7 g of 4-nitrobenzimidamide in 200 ml of ethanol, 31 ml of a sodium ethoxide solution (20% in ethanol) were slowly added. The reaction mixture was heated to reflux for 1 h. After cooling to RT and dilution with water, the reaction mixture was acidified with half-concentrated aqueous hydrochloric acid to pH 1. The organic solvents were removed under reduced pressure and the precipitating product was collected by filtration as a brown solid. Yield: 4.1 g.

(iv) 4-Chloro-6-cyclopropyl-2-(4-nitrophenyl)pyrimidine-5-carbonitrile

To a solution of 4.1 g of 4-cyclopropyl-6-hydroxy-2-(4-nitrophenyl)pyrimidine-5-carbonitrile in 24.4 ml of phosphorus oxychloride, 1.9 ml of dimethyl-phenyl-amine were added. The reaction mixture was heated to reflux for 1 h, then cooled to RT and concentrated under reduced pressure. After addition of ice water and dilution with DCM, saturated aqueous sodium hydrogencarbonate solution was added and the mixture was extracted with DCM (3×100 ml). The combined organic layers were dried over magnesium sulfate and the solvents were removed under reduced pressure. The crude product was purified by chromatography on silica gel eluting with a gradient of Hep/EtOAc. The fractions containing the product were combined and the solvent evaporated under reduced pressure. Yield: 2.8 g.

(v) 4-Cyclopropyl-6-(4-nitrophenyl)-1H-pyrazolo[3,4-d]pyrimidin-3-amine

To a solution of 2.0 g of 4-chloro-6-cyclopropyl-2-(4-nitrophenyl)pyrimidine-5-carbonitrile in 18 ml of iPrOH, 18 ml of a hydrazine solution (35% in iPrOH) were added and the reaction mixture was heated for 15 min to 100° C. by using microwave irradiation (Biotage® Initiator apparatus). The reaction mixture was cooled to RT and diluted with acetic acid (20%). The precipitated product was collected by filtration and used in the next reaction step without further purification. Yield: 1.9 g.

(iv) tert-Butyl 3-(bis(tert-butoxycarbonyl)amino)-4-cyclopropyl-6-(4-nitrophenyl)pyrazolo[3,4-d]pyrimidine-1-carboxylate To a suspension of 890 mg of 4-cyclopropyl-6-(4-nitrophenyl)-1H-pyrazolo[3,4-d]pyrimidin-3-amine in 20 ml of DCM, 2 g of di-tert-butyl dicarbonate, 1.2 ml of triethylamine and 4 mg of dimethyl-pyridin-4-yl-amine were added. The mixture was stirred for 16 h at RT, then quenched by the addition of water and diluted with DCM. After separation of the organic layer, the aqueous layer was extracted with DCM (3×200 ml). The combined organic layers were dried over magnesium sulfate and the solvents were removed under reduced pressure. The crude product was purified by chromatography on silica gel eluting with a gradient of Hep/EtOAc. The fractions containing the product were combined and the solvent evaporated under reduced pressure. Yield: 1.3 g.

(v) tert-Butyl 6-(4-aminophenyl)-3-(bis(tert-butoxycarbonyl)amino)-4-cyclopropyl-pyrazolo[3,4-d]pyrimidine-1-carboxylate To a solution of 1.4 g of tert-butyl 3-(bis(tert-butoxycarbonyl)amino)-4-cyclopropyl-6-(4-nitrophenyl)pyrazolo[3,4-d]pyrimidine-1-carboxylate obtained in the preceding step in 8 ml of EtOAc, 139 mg of Pd/C (10%) were added under argon and the suspension was stirred under an atmosphere of hydrogen (2 bar) for 16 h. The suspension was filtered over a plug of Celite® and washed with EtOAc. The crude product was obtained after evaporation of the solvent as a brown solid and was dried under reduced pressure. Yield: 1.3 g.

(vi) N-[4-(3-Amino-4-methyl-1H-pyrazolo[3,4-d]pyrimidin-6-yl)-phenyl]-5-chloro-2,4-difluoro-benzenesulfonamide To a solution of 250 mg of tert-butyl 6-(4-aminophenyl)-3-(bis(tert-butoxycarbonyl)amino)-4-cyclopropyl-pyrazolo[3,4-d]pyrimidine-1-carboxylate in 2 ml DCM and 43 µl pyridine, 67 mg of 5-chloro-2,4-difluoro-benzenesulfonyl chloride were added. After stirring the reaction mixture for 16 h at RT, the solvents were removed under reduced pressure. The residue was dissolved in 2 ml DCM and 1 ml of TFA and stirred for 1 h at RT. Then toluene was added and the solvents were removed under reduced pressure to yield a brown solid. This crude product was purified by preparative HPLC (C18 reverse phase column, elution with a water/MeCN gradient with 0.1% TFA). The fractions containing the product were lyophilized to yield the pure title compound in the form of its salt with trifluoroacetic acid. Yield: 40 mg.

$^1$H-NMR (DMSO-d$_6$): δ (ppm)=1.11 (m, 2H), 1.28 (m, 2H), 2.66 (m, 1H), 7.20 (d, J=8.5 Hz, 2H), 7.79 (t, J=8.5 Hz, 1H), 8.03 (t, J=8.5 Hz, 1H), 8.21 (d, J=8.5 Hz, 2H), 11.02 (s, 1H).

MS (ES+): m/e=477.2 (M+H), chloro pattern.

Example 449

5-Chloro-2,4-difluoro-N-[4-(3-methyl-1H-pyrazolo[3,4-d]pyrimidin-6-yl)-phenyl]-benzenesulfonamide

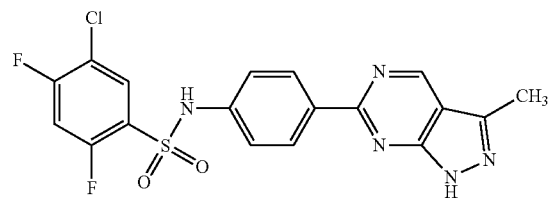 [SMILES: Cc1n[nH]c2nc(-c3ccc(NS(=O)(=O)c4cc(Cl)c(F)cc4F)cc3)ncc12]

(i) 5-Chloro-2,4-difluoro-N-[4-(4,4,5,5-tetramethyl-[1,3,2]dioxaborolan-2-yl)phenyl]benzenesulfonamide To a solution of 500 mg of 4-(4,4,5,5-tetramethyl-[1,3,2]dioxaborolan-2-yl)-phenylamine in 5 ml of DCM and 0.2 ml of pyridine, 564 mg of 5-chloro-2,4-difluoro-benzenesulfonyl chloride were added, and the reaction mixture was stirred for 16 h at RT. Then the solvents were removed under reduced pressure and the crude product was purified by chromatography on silica gel eluting with a gradient of Hep/EtOAc. The fractions containing the product were combined and the solvent evaporated under reduced pressure. Yield: 1.0 g.

(ii) 5-Chloro-2,4-difluoro-N-[4-(3-methyl-1H-pyrazolo[3,4-d]pyrimidin-6-yl)-phenyl]-benzenesulfonamide A solution of 59 mg of 6-chloro-3-methyl-1-tetrahydropyran-2-yl-pyrazolo[3,4-d]pyrimidine, 102 mg 5-chloro-2,4-difluoro-N-[4-(4,4,5,5-tetramethyl-[1,3,2]dioxaborolan-2-yl)phenyl]benzenesulfonamide and 232 mg of cesium carbonate in 1.5 ml of Diox and 0.2 ml of water was purged with argon. Then 13 mg of BDFP were added and the reaction mixture was heated to 100° C. After 2 h, the reaction mixture was cooled to RT and diluted with water. After filtration through a Chem Elut® cartridge by eluting with EtOAc, the solvents were removed under reduced pressure. The residue was dissolved in 2 ml of iPrOH and 2 ml of HCl in Diox (4M) at RT. After 15 min the reaction mixture was diluted with 20 ml of toluene and the solvents were removed under reduced pressure. The residue was purified by preparative HPLC (C18 reverse phase column, elution with a water/MeCN gradient with 0.1% TFA). The fractions containing the product were lyophilized to yield the pure title compound in the form of its salt with trifluoroacetic acid. Yield: 31 mg $^1$H-NMR (DMSO-d$_6$): δ (ppm)=2.56 (s, 3H), 7.28 (d, J=8.7 Hz, 2H), 7.85 (t, J=10.3 Hz, 1H), 8.09 (t, J=8.5 Hz, 1H), 8.36 (d, J=8.5 Hz, 2H), 9.34 (s, 1H), 11.16 (s, 1H).

MS (ES+): m/e=436.0 (M+H), chloro pattern.

Example 450

2,5-Dichloro-N-{4-[3-methyl-4-(2-oxa-6-aza-spiro[3.4]oct-6-yl)-1H-pyrazolo[3,4-d]pyrimidin-6-yl]-phenyl}-benzenesulfonamide

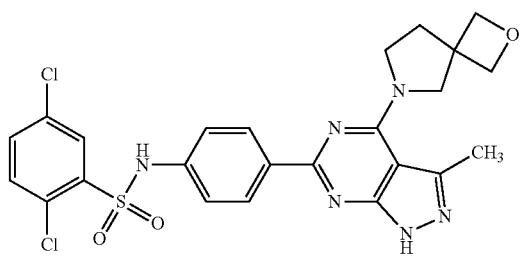 [SMILES: Cc1n[nH]c2nc(-c3ccc(NS(=O)(=O)c4cc(Cl)ccc4Cl)cc3)nc(N3CCC4(COC4)C3)c12]

(i) 2,5-Dichloro-N-[4-(4,4,5,5-tetramethyl-[1,3,2]dioxaborolan-2-yl)-phenyl]benzenesulfonamide To a solution of 10 g of 4-(4,4,5,5-tetramethyl-[1,3,2]dioxaborolan-2-yl)-phenylamine in 100 ml DCM and 4 ml pyridine, 11.7 g of 2,5-dichloro-benzenesulfonyl chloride were added, and the reaction mixture was stirred for 16 h at RT. Then the solvents were removed under reduced pressure and the crude product was purified by chromatography on silica gel eluting with a gradient of Hep/EtOAc. The fractions containing the product were combined and the solvent evaporated under reduced pressure. Yield: 17.9 g.

(ii) 7-(6-Chloro-3-methyl-1-tetrahydropyran-2-yl-pyrazolo[3,4-d]pyrimidin-4-yl)-2-oxa-6-azaspiro[3.4]octane To a solution of 300 mg of 4,6-dichloro-3-methyl-1-tetrahydropyran-2-yl-pyrazolo[3,4-d]pyrimidine (WO 2011/140338) and 0.4 ml triethylamine in 5 ml MeCN, 118 mg of 2-oxa-6-aza-spiro[3.4]octane were added. The reaction mixture was stirred for 5 h at RT, quenched with a saturated aqueous sodium hydrogencarbonate solution (3 ml) and filtered through a Chem Elut® cartridge by eluting with EtOAc. The filtrate was concentrated under reduced pressure and the obtained crude product was used in the next reaction step. Yield: 309 mg.

(iii) 2,5-Dichloro-N-{4-[3-methyl-4-(2-oxa-6-aza-spiro[3.4]oct-6-yl)-1H-pyrazolo[3,4-d]pyrimidin-6-yl]-phenyl}-benzenesulfonamide A solution of 155 mg of 7-(6-chloro-3-methyl-1-tetrahydropyran-2-yl-pyrazolo[3,4-d]pyrimidin-4-yl)-2-oxa-7-azaspiro[3.4]octane, 182 mg 2,5-dichloro-N-[4-(4,4,5,5-tetramethyl-[1,3,2]dioxaborolan-2-yl)-phenyl]-benzenesulfonamide and 415 mg of cesium carbonate in 5 ml of Diox and 1.6 ml of water was purged with argon. Then 28 mg of BDFP were added and the reaction mixture was heated to 100° C. After 3 h, the reaction mixture was cooled to RT and diluted with water. After filtration through a Chem Elut® cartridge by eluting with EtOAc, the solvents were removed under reduced pressure. The residue was dissolved in 3 ml of DCM and 0.5 ml of TFA at RT. After 2 h the reaction mixture was diluted with 20 ml of toluene and the solvents were removed under reduced pressure. The residue was purified by preparative HPLC (C18 reverse phase column, elution with a water/MeCN gradient with 0.1% TFA). The fractions containing the product were lyophilized to yield the pure title compound in the form of its salt with trifluoroacetic acid. Yield: 39 mg.

$^1$H-NMR (DMSO-d$_6$): δ (ppm)=2.33 (t, J=6.6 Hz, 2H), 2.65 (s, 3H), 3.85 (s, 2H), 4.06 (s, 2H), 4.55 (d, J=5.9 Hz, 2H), 4.67 (d, J=5.9 Hz, 2H), 7.21 (d, J=8.5 Hz, 2H), 7.75-7.67 (m, 2H), 8.05 (s, 1H), 8.27 (d, J=8.5 Hz, 2H), 11.16 (s, 1H).

MS (ES+): m/e=545.2 (M+H), chloro pattern.

Analogously to the procedures described in the examples above, the example compounds of the formula Ib

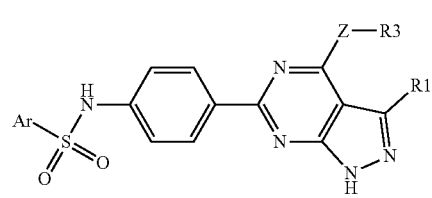

listed in Table 3 were synthesized. In the formulae of the groups —Z—R3 in Table 3 the line crossed with the symbol ~~ represents the free bond via which the group —Z—R3 is bonded to the carbon atom in the 4-position of the pyrazolo[3,4-d]pyrimidine ring system. I.e., in the formula of the complete molecule the terminal endpoint of the line crossed with the said symbol ends at the carbon atom in the 4-position of the pyrazolo[3,4-d]pyrimidine ring system. In the column "Synthesis" the number of the example is specified in analogy to which the synthesis was performed. The ionization method in the MS characterization was ES+ if the specified ion is M+H, and ES− if the specified ion is M−H. CP means chloro pattern, BP means bromo pattern in the mass spectrum.

TABLE 3

Example compounds of the formula Ib

| Example no. | Ar | R1 | Z—R3 | Synthesis | MS (m/e) |
|---|---|---|---|---|---|
| 451 | 5-chloro-2,4-difluoro-phenyl | NH$_2$ | —O—CH(CH$_3$)— | 7 | 481.0 (M + H), CP |
| 452 | 2,5-dichloro-phenyl | NH$_2$ | H | 445 | 435.1 (M + H), CP |
| 453 | 2-cyano-5-methyl-phenyl | NH$_2$ | H | 445 | 406.1 (M + H) |
| 454 | 3-cyano-4-fluoro-phenyl | NH$_2$ | H | 445 | 410.1 (M + H) |
| 455 | 2-fluoro-5-methyl-phenyl | NH$_2$ | H | 445 | 399.1 (M + H) |
| 456 | 3-chloro-2-cyano-phenyl | NH$_2$ | H | 445 | 426.1 (M + H), CP |
| 457 | 3-cyano-phenyl | NH$_2$ | H | 445 | 392.1 (M + H) |
| 458 | 8-chloro-3,4-dihydro-2H-benzo[b][1,4]dioxepin-7-yl | NH$_2$ | H | 445 | 473.2 (M + H), CP |
| 459 | 8-bromo-3,4-dihydro-2H-benzo[b][1,4]dioxepin-7-yl | NH$_2$ | H | 445 | 517.2 (M + H), BP |
| 460 | 5-chloro-1,3-dimethyl-1H-pyrazol-4-yl | NH$_2$ | H | 445 | 419.1 (M + H), CP |
| 461 | 2-chloro-5-methoxy-phenyl | NH$_2$ | H | 445 | 431.0 (M + H), CP |
| 462 | 2-chloro-3,5-difluoro-phenyl | NH$_2$ | H | 445 | 437.1 (M + H), CP |
| 463 | 2,5-dichloro-thiophen-3-yl | NH$_2$ | H | 445 | 441.1 (M + H), CP |

TABLE 3-continued

Example compounds of the formula Ib

| Example no. | Ar | R1 | Z—R3 | Synthesis | MS (m/e) |
|---|---|---|---|---|---|
| 464 | 2,5-dichloro-phenyl | NH₂ | —CH₃ | 447 | 449.1 (M + H), CP |
| 465 | 5-chloro-2-cyano-phenyl | NH₂ | —CH₃ | 447 | 440.2 (M + H), CP |
| 466 | 5-chloro-2-fluoro-phenyl | NH₂ | —CH₃ | 447 | 433.1 (M + H), CP |
| 467 | 2-chloro-5-methoxy-phenyl | NH₂ | —CH₃ | 447 | 445.0 (M + H), CP |
| 468 | 2-cyano-5-methyl-phenyl | NH₂ | —CH₃ | 447 | 420.2 (M + H) |
| 469 | 3-cyano-4-fluoro-phenyl | NH₂ | —CH₃ | 447 | 424.2 (M + H) |
| 470 | 3-chloro-2-cyano-phenyl | NH₂ | —CH₃ | 447 | 440.2 (M +H), CP |
| 471 | 3-cyano-phenyl | NH₂ | —CH₃ | 447 | 406.1 (M + H) |
| 472 | 2-fluoro-5-methyl-phenyl | NH₂ | —CH₃ | 447 | 413.2 (M + H) |
| 473 | 5-cyano-2-methyl-phenyl | NH₂ | —CH₃ | 447 | 420.2 (M + H) |
| 474 | 2-cyano-3-fluoro-phenyl | NH₂ | —CH₃ | 447 | 424.2 (M + H) |
| 475 | 5-chloro-1,3-dimethyl-1H-pyrazol-4-yl | NH₂ | —CH₃ | 447 | 433.1 (M + H), CP |
| 476 | 8-chloro-3,4-dihydro-2H-benzo[b][1,4]di-oxepin-7-yl | NH₂ | —CH₃ | 447 | 485.2 (M − H), CP |

TABLE 3-continued

Example compounds of the formula Ib

| Example no. | Ar | R1 | —Z—R3 | Synthesis | MS (m/e) |
|---|---|---|---|---|---|
| 477 | 8-bromo-3,4-dihydro-2H-benzo[b][1,4]dioxepin-7-yl | NH₂ | —CH₃ | 447 | 531.1 (M + H), BP |
| 478 | 7-chloro-2,3-dihydro-benzo[1,4]dioxin-6-yl | NH₂ | —CH₃ | 447 | 473.2 (M + H), CP |
| 479 | 2-chloro-3,5-difluoro-phenyl | NH₂ | —CH₃ | 447 | 451.1 (M + H), CP |
| 480 | 2-chloro-3,5-difluoro-phenyl | NH₂ | cyclopropyl | 448 | 477.1 (M + H), CP |
| 481 | 2-chloro-4,5-difluoro-phenyl | NH₂ | cyclopropyl | 448 | 477.1 (M + H), CP |
| 482 | 3-chloro-2-fluoro-phenyl | NH₂ | cyclopropyl | 448 | 459.1 (M + H), CP |
| 483 | 2-chloro-4-fluoro-phenyl | NH₂ | cyclopropyl | 448 | 459.1 (M + H), CP |
| 484 | 2,4,5-trifluoro-phenyl | NH₂ | cyclopropyl | 448 | 461.2 (M + H) |
| 485 | 2-fluoro-phenyl | NH₂ | cyclopropyl | 448 | 425.2 (M + H) |
| 486 | 2,5-difluoro-phenyl | NH₂ | cyclopropyl | 448 | 443.2 (M + H) |
| 487 | 5-chloro-2-fluoro-phenyl | NH₂ | cyclopropyl | 448 | 459.1 (M + H), CP |
| 488 | 2-fluoro-5-methyl-phenyl | NH₂ | cyclopropyl | 448 | 439.2 (M + H) |
| 489 | 2,5-dichloro-phenyl | NH₂ | cyclopropyl | 448 | 475.1 (M + H), CP |

TABLE 3-continued

Example compounds of the formula Ib

| Example no. | Ar | R1 | -Z-R3 | Synthesis | MS (m/e) |
|---|---|---|---|---|---|
| 490 | 2-cyano-phenyl | CH₃ | —H | 449 | 391.0 (M + H) |
| 491 | 2-chloro-5-methoxy-phenyl | CH₃ | —H | 449 | 430.0 (M + H), CP |
| 492 | 5-chloro-2-cyano-phenyl | CH₃ | —H | 449 | 425.0 (M + H), CP |
| 493 | 3-cyano-4-fluoro-phenyl | CH₃ | —H | 449 | 409.0 (M + H) |
| 494 | 3-cyano-phenyl | CH₃ | —H | 449 | 391.3 (M + H) |
| 495 | 5-cyano-2-methyl-phenyl | CH₃ | —H | 449 | 405.2 (M + H) |
| 496 | 2,5-dichloro-phenyl | CH₃ | N-piperidine-oxetane spiro | 450 | 559.2 (M + H), CP |
| 497 | 2,5-dichloro-phenyl | CH₃ | N-azetidine-oxetane spiro | 450 | 531.2 (M + H), CP |
| 498 | 2,5-dichloro-phenyl | CH₃ | N-piperidine-oxetane spiro | 450 | 559.2 (M + H), CP |
| 499 | 5-chloro-2-cyano-phenyl | CH₃ | N-piperidine-oxetane spiro | 450 | 550.4 (M + H), CP |
| 500 | 2,5-dichloro-thiophen-3-yl | NH₂ | cyclopropyl | 448 | 480.9 (M + H), CP |
| 501 | 5-chloro-2,4-difluoro-phenyl | NH₂ | —CH(CH₃)—O—CH₃ | 448 | 495.0 (M + H), CP |

TABLE 3-continued

Example compounds of the formula Ib

| Example no. | Ar | R1 | Z—R3 | Synthesis | MS (m/e) |
|---|---|---|---|---|---|
| 502 | 2-chloro-5-methoxy-phenyl | NH$_2$ | 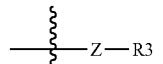 | 448 | 489.1 (M + H), CP |
| 503 | 2-fluoro-5-methyl-phenyl | NH$_2$ | 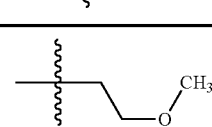 | 448 | 457.1 (M + H) |
| 504 | 2-fluoro-5-methoxy-phenyl | NH$_2$ | 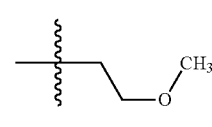 [SMILES: *CCOC] | 448 | 473.1 (M + H) |
| 505 | 2,5-dichloro-phenyl | NH$_2$ | 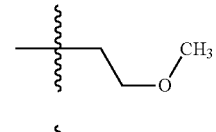 | 448 | 493.0 (M + H), CP |
| 506 | 5-chloro-2-fluoro-phenyl | NH$_2$ | 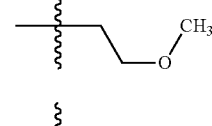 | 448 | 477.0 (M + H), CP |
| 507 | 2-chloro-4-fluoro-phenyl | NH$_2$ | 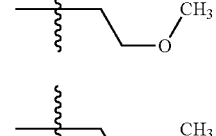 | 448 | 477.0 (M + H), CP |
| 508 | 2,5-difluoro-phenyl | NH$_2$ | 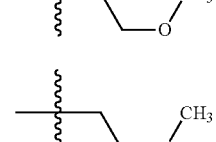 | 448 | 461.1 (M + H) |
| 509 | 2,5-dichloro-thiophen-3-yl | NH$_2$ | 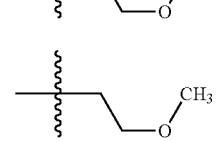 | 448 | 497.1 (M − H), CP |
| 510 | 2-chloro-4,5-difluoro-phenyl | NH$_2$ |  | 448 | 495.0 (M + H), CP |
| 511 | 3-chloro-2-fluoro-phenyl | NH$_2$ | 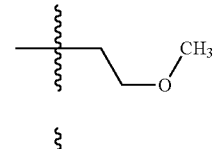 | 448 | 477.0 (M + H), CP |
| 512 | 2-fluoro-phenyl | NH$_2$ | 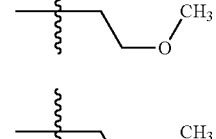 | 448 | 443.1 (M + H) |
| 513 | 2-cyano-5-methyl-phenyl | NH$_2$ | 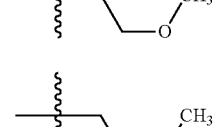 | 448 | 464.1 (M + H) |
| 514 | 2-chloro-4,5-difluoro-phenyl | NH$_2$ | 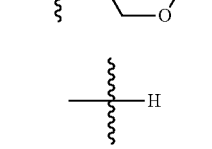 | 445 | 437.0 (M + H), CP |

TABLE 3-continued

Example compounds of the formula Ib

| Example no. | Ar | R1 | Z—R3 | Synthesis | MS (m/e) |
|---|---|---|---|---|---|
| 515 | 3-chloro-2-fluoro-phenyl | NH$_2$ | —H | 445 | 419.0 (M + H), CP |
| 516 | 2,4,5-trifluoro-phenyl | NH$_2$ | —H | 445 | 421.1 (M + H) |
| 517 | 2-fluoro-phenyl | NH$_2$ | —H | 445 | 385.1 (M + H) |
| 518 | 2,4,5-trifluoro-phenyl | NH$_2$ | —CH$_2$—O—CH$_3$ | 448 | 479.1 (M + H) |
| 519 | 2,5-difluoro-phenyl | NH$_2$ | —H | 445 | 403.1 (M + H) |
| 520 | 2-cyano-5-methoxy-phenyl | NH$_2$ | cyclopropyl | 448 | 462.1 (M + H) |
| 521 | 2-cyano-5-methoxy-phenyl | NH$_2$ | —CH$_2$—O—CH$_3$ | 448 | 480.1 (M + H) |
| 522 | 2-cyano-5-methoxy-phenyl | NH$_2$ | —H | 445 | 422.1 (M + H) |
| 523 | 2-chloro-3-fluoro-phenyl | NH$_2$ | —H | 445 | 419.1 (M + H), CP |
| 524 | 2-chloro-phenyl | NH$_2$ | —H | 445 | 401.1 (M + H), CP |
| 525 | 5-chloro-2-fluoro-phenyl | NH$_2$ | —CH$_2$—O—CH$_3$ | 448 | 463.1 (M + H), CP |
| 526 | 2-chloro-4-fluoro-phenyl | NH$_2$ | —H | 445 | 419.0 (M + H), CP |
| 527 | 2-fluoro-5-methoxy-phenyl | NH$_2$ | —H | 445 | 415.1 (M + H) |

TABLE 3-continued

Example compounds of the formula Ib

| Example no. | Ar | R1 | —Z—R3 | Synthesis | MS (m/e) |
|---|---|---|---|---|---|
| 528 | 2-fluoro-5-methyl-phenyl | $NH_2$ | —O—CH2—CH3 | 448 | 457.1 (M + H) |
| 529 | 2,5-dichloro-phenyl | $NH_2$ | —O—CH2—CH3 | 448 | 493.1 (M + H), CP |
| 530 | 3-chloro-2,6-difluoro-phenyl | $NH_2$ | —CH3 | 447 | 451.0 (M + H), CP |
| 531 | 3-chloro-2,6-difluoro-phenyl | $NH_2$ | —H | 445 | 437.0 (M + H), CP |

Exemplary NMR Data of Example Compounds

Example 519

$^1$H-NMR (DMSO-$d_6$): δ (ppm)=7.27 (d, J=8.8 Hz, 2H), 7.52 (m, 1H), 7.51 (m, 1H), 7.70 (m, 1H), 8.27 (d, J=8.8 Hz, 2H), 9.14 (s, 1H), 11.13 (s, 1H).

Example 520

$^1$H-NMR (DMSO-$d_6$): δ (ppm)=1.14 (m, 2H), 1.31 (m, 2H), 2.71 (m, 1H), 3.88 (s, 3H), 7.23 (d, J=8.8 Hz, 2H), 7.33 (m, 1H), 7.52 (d, J=2.5 Hz, 1H), 8.00 (d, J=8.8 Hz), 8.23 (d, J=8.8 Hz, 2H), 11.02 (s, 1H).

Example 527

$^1$H-NMR (DMSO-$d_6$): δ (ppm)=3.88 (s, 3H), 7.21 (m, 1H), 7.26 (d, J=8.8 Hz, 2H), 7.33 (m, 1H), 8.27 (d, J=8.8 Hz, 2H), 9.13 (s, 1H), 11.10 (s, 1H).

Example 531

$^1$H-NMR (DMSO-$d_6$): δ (ppm)=7.30 (d, J=8.8 Hz, 2H), 7.38 (t, J=8.8 Hz, 1H), 7.94 (m, 1H), 8.31 (d, J=8.8 Hz, 2H), 9.14 (s, 1H), 11.24 (s, 1H).

Example 532

2-[4-(3-Methyl-1H-pyrazolo[3,4-d]pyrimidin-6-yl)-phenylsulfamoyl]-benzamide

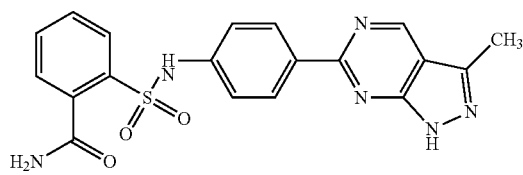 [SMILES: Cc1n[nH]c2nc(-c3ccc(NS(=O)(=O)c4ccccc4C(N)=O)cc3)ncc12]

The title compound was isolated as a further product in example 490.

MS (ES+): m/e=409.0 (M+H).

Example 533

2-Chloro-N-[2-fluoro-4-(3-methyl-1H-pyrazolo[3,4-d]pyrimidin-6-yl)-phenyl]-5-methoxy-benzenesulfonamide

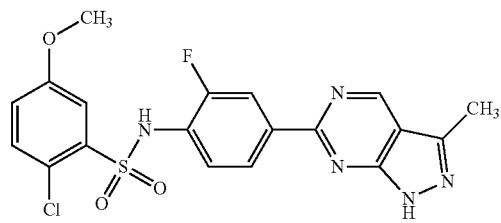 [SMILES: COc1ccc(Cl)c(S(=O)(=O)Nc2ccc(-c3ncc4c(C)n[nH]c4n3)cc2F)c1]

The title compound was prepared analogously to the procedure described in example 449, employing 2-chloro-N-[2-fluoro-4-(4,4,5,5-tetramethyl-[1,3,2]dioxaborolan-2-yl)-phenyl]-5-methoxy-benzenesulfonamide instead of 5-chloro-2,4-difluoro-N-[4-(4,4,5,5-tetramethyl-[1,3,2]dioxaborolan-2-yl)phenyl]benzenesulfonamide.

MS (ES+): m/e=448.0 (M+H), chloro pattern.

Example 534

2,5-Dichloro-N-[2-methoxy-4-(3-methyl-1H-pyrazolo[3,4-d]pyrimidin-6-yl)-phenyl]-benzenesulfonamide

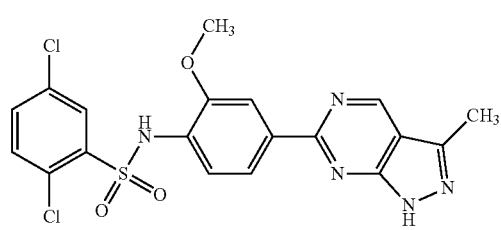 [SMILES: COc1cc(-c2ncc3c(C)n[nH]c3n2)ccc1NS(=O)(=O)c1cc(Cl)ccc1Cl]

The title compound was prepared analogously to the procedure described in example 449, employing 2,5-dichloro-N-[2-methoxy-4-(4,4,5,5-tetramethyl-[1,3,2]dioxaborolan-2-yl)-phenyl]-benzenesulfonamide instead of 5-chloro-2,4-difluoro-N-[4-(4,4,5,5-tetramethyl-[1,3,2]dioxaborolan-2-yl)phenyl]benzenesulfonamide.

MS (ES+): m/e=464.2 (M+H), chloro pattern.

Example 535

2,5-Dichloro-N-[4-(3-methyl-1H-pyrazolo[3,4-d]pyrimidin-6-yl)-2-trifluoromethoxy-phenyl]-benzenesulfonamide

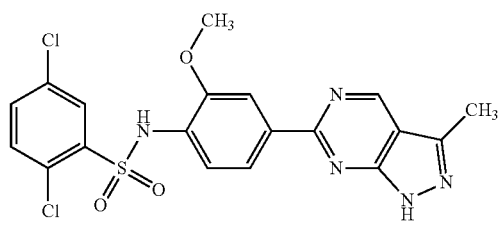 [SMILES: COc1cc(-c2ncc3c(C)n[nH]c3n2)ccc1NS(=O)(=O)c1cc(Cl)ccc1Cl]

The title compound was prepared analogously to the procedure described in example 449, employing 2,5-dichloro-N-[4-(4,4,5,5-tetramethyl-[1,3,2]dioxaborolan-2-yl)-2-trifluoromethoxy-phenyl]-benzenesulfonamide instead of 5-chloro-2,4-difluoro-N-[4-(4,4,5,5-tetramethyl-[1,3,2]dioxaborolan-2-yl)phenyl]benzenesulfonamide.

MS (ES+): m/e=518.0 (M+H), chloro pattern.

Example 536

3-Hydroxy-cyclobutanecarboxylic acid {6-[4-(2,5-dichloro-benzenesulfonylamino)-phenyl]-4-methyl-1H-pyrazolo[3,4-d]pyrimidin-3-yl}-amide

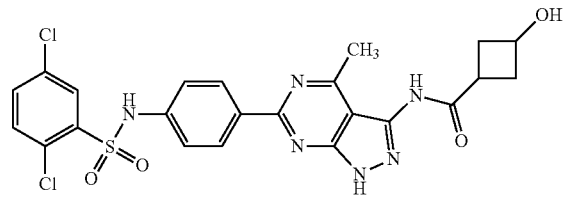 [SMILES: Cc1nc(-c2ccc(NS(=O)(=O)c3cc(Cl)ccc3Cl)cc2)nc2[nH]nc(NC(=O)C3CC(O)C3)c12]

To a solution of 100 mg of N-[4-(3-amino-4-methyl-1H-pyrazolo[3,4-d]pyrimidin-6-yl)-phenyl]-2,5-dichloro-benzenesulfonamide and 23 mg of 3-hydroxycyclobutanecarboxylic acid in 1.5 ml of DMF, 0.1 ml of triethylamine and 45 mg of bis(2-oxo-3-oxazolidinyl)phosphonic chloride (BOP—Cl) were added at RT. After stirring for 16 h the solvents were removed and the residue was purified by preparative HPLC (C18 reverse phase column, elution with a water/MeCN gradient with 0.1% TFA). The fractions containing the product were lyophilized to yield the pure title compound in the form of its salt with trifluoroacetic acid. Yield: 3 mg.

MS (ES+): m/e=547.2 (M+H), chloro pattern.

Analogously to the procedure described in the example 536, the example compounds of the formula Id

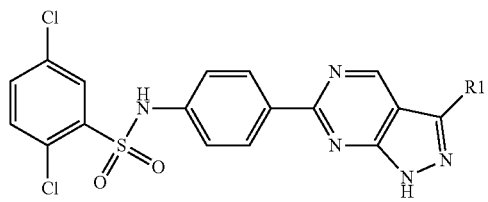

listed in Table 4 were synthesized. In the formulae of the groups —R1 in Table 4 the line crossed with the symbol ∼ represents the free bond via which the group —R1 is bonded to the carbon atom in the 3-position of the pyrazolo[3,4-d]pyrimidine ring system. I.e., in the formula of the complete molecule the terminal endpoint of the line crossed with the said symbol ends at the carbon atom in the 3-position of the pyrazolo[3,4-d]pyrimidine ring system. The ionization method in the MS characterization was ES+. CP means chloro pattern in the mass spectrum.

TABLE 4

Example compounds of the formula Id

| Example no. | R1 | MS (m/e) |
|---|---|---|
| 537 | cyclopropyl-C(O)NH- | 503.1 (M + H), CP |
| 538 | cyclopentyl-C(O)NH- | 531.1 (M + H), CP |
| 539 | cyclohexyl-C(O)NH- | 545.1 (M + H), CP |
| 540 | 2,3-dichlorophenyl-C(O)NH- | 607.0 (M + H), CP |
| 541 | tetrahydropyran-4-yl-C(O)NH- | 547.1 (M + H), CP |
| 542 | 4-chlorophenyl-C(O)NH- | 573.1 (M + H), CP |

TABLE 4-continued

Example compounds of the formula Id

| Example no. | R1 | MS (m/e) |
|---|---|---|
| 543 | 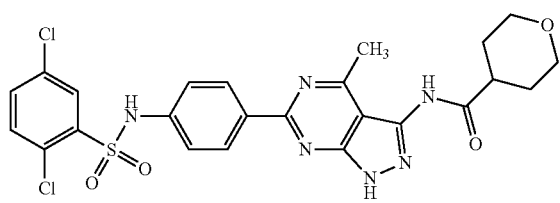 | 553.2 (M + H), CP |
| 544 | | 545.1 (M + H), CP |

Example 545

N-[6-[4-[(2,5-Dichlorophenyl)sulfonylamino]phenyl]-4-methyl-1H-pyrazolo[3,4-d]pyrimidin-3-yl] tetrahydropyran-4-carboxamide

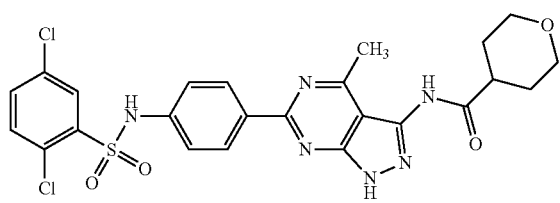 [SMILES: Cc1nc(-c2ccc(NS(=O)(=O)c3cc(Cl)ccc3Cl)cc2)nc2[nH]nc(NC(=O)C3CCOCC3)c12]

To a solution of 100 mg of N-[4-(3-amino-4-methyl-1H-pyrazolo[3,4-d]pyrimidin-6-yl)-phenyl]-2,5-dichloro-benzenesulfonamide in 2 ml pyridine, 26 mg of tetrahydropyran-4-carbonyl chloride were added and the reaction mixture was stirred for 16 h at RT. Then the solvents under reduced pressure and the crude product was purified by preparative HPLC (C18 reversed phase column, elution with a water/MeCN gradient with 0.1% TFA). The fractions containing the product were lyophilized to yield the pure title compound in the form of its salt with trifluoroacetic acid. Yield: 12 mg.

MS (ES+): m/e=561.2 (M+H), chloro pattern.

Example 546

N-[6-[4-[(2,5-Dichlorophenyl)sulfonylamino]phenyl]-1H-pyrazolo[3,4-d]pyrimidin-3-yl]piperidine-4-carboxamide

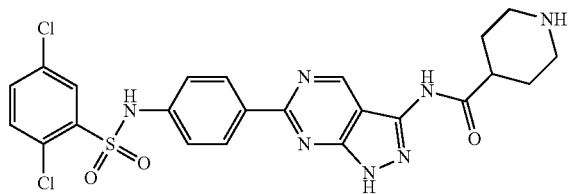 [SMILES: O=C(Nc1n[nH]c2nc(-c3ccc(NS(=O)(=O)c4cc(Cl)ccc4Cl)cc3)ncc12)C1CCNCC1]

The title compound was prepared analogously to the procedure described in example 545, employing 1-tert-butoxycarbonyl-piperidine-4-carboxylic acid in the presence of bis(2-oxo-3-oxazolidinyl)phosphonic chloride (BOP—Cl) as coupling agent instead of tetrahydropyran-4-carbonyl chloride and deprotecting with TFA.

MS (ES+): m/e=546.3 (M+H), chloro pattern.

Example 547

2,5-Dichloro-N-(4-{4-methyl-3-[(tetrahydro-pyran-4-ylmethyl)-amino]-1H-pyrazolo[3,4-d]pyrimidin-6-yl}-phenyl)-benzenesulfonamide

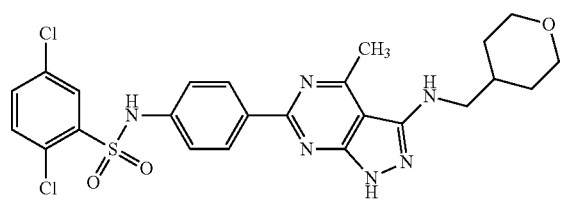 [SMILES: Cc1nc(-c2ccc(NS(=O)(=O)c3cc(Cl)ccc3Cl)cc2)nc2[nH]nc(NCC3CCOCC3)c12]

To a solution of 100 mg of N-[4-(3-amino-4-methyl-1H-pyrazolo[3,4-d]pyrimidin-6-yl)-phenyl]-2,5-dichloro-benzenesulfonamide and 20 mg of tetrahydropyran-4-carbaldehyde in 1 ml of methanol, 22 mg of sodium borohydride and 2 μl of acetic acid were added at RT. After stirring for 16 h, water was added and the reaction mixture was filtered through a Chem Elut® cartridge by eluting with EtOAc. After removal of the solvents under reduced pressure, the residue was purified by preparative HPLC (C18 reversed phase column, elution with a water/MeCN gradient with 0.1% TFA). The fractions containing the product were lyophilized to yield the pure title compound in the form of its salt with trifluoroacetic acid. Yield: 9 mg.

MS (ES+): m/e=547.2 (M+H), chloro pattern.

Example 548

N-{4-[3-(Benzyl-amino)-1H-pyrazolo[3,4-d]pyrimidin-6-yl]-phenyl}-2,5-dichloro-benzenesulfonamide

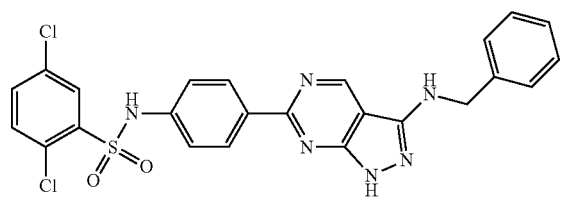 [SMILES: O=S(=O)(Nc1ccc(-c2ncc3c(NCc4ccccc4)n[nH]c3n2)cc1)c1cc(Cl)ccc1Cl]

The title compound was prepared analogously to the procedure described in example 547, employing benzaldehyde instead of tetrahydropyran-4-carbaldehyde.

MS (ES+): m/e=525.2 (M+H), chloro pattern.

Example 549

N-[4-(3-Amino-4-hydroxy-1H-pyrazolo[4,3-c]pyridin-6-yl)phenyl]-5-chloro-2,4-difluoro-benzenesulfonamide

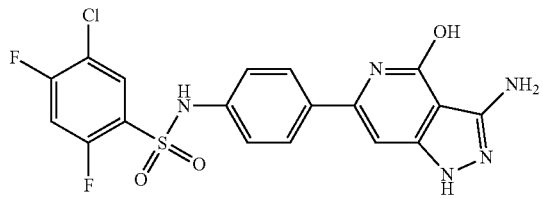 [SMILES: Nc1n[nH]c2cc(-c3ccc(NS(=O)(=O)c4cc(Cl)c(F)cc4F)cc3)nc(O)c12]

(i) tert-Butyl N-[4-[3,3-bis(methylsulfanyl)prop-2-enoyl]phenyl]carbamate

To a suspension of 2.45 g of sodium tert-butylate in 40 ml of toluene, 3 g of tert-butyl N-(4-acetylphenyl)carbamate and 0.77 ml of carbon disulfide were added at 0° C. After 4 h at 0° C., the mixture was stirred for 16 h at RT. Then the solvents were removed under reduced pressure and the residue dissolved in 40 ml of dry methanol. After addition of 1.6 ml of methyl iodide, the reaction mixture was heated under reflux for 30 min, then cooled to RT and quenched by the addition of 50 ml of water. The precipitated product was collected by filtration, dried under reduced pressure and purified by chromatography on silica gel eluting with a gradient of Hep/EtOAc. The fractions containing the product were combined and the solvent evaporated under reduced pressure. Yield: 431 mg.

(ii) tert-Butyl N-[4-(3-cyano-4-methylsulfanyl-2-oxo-3H-pyridin-6-yl)phenyl]carbamate To 3.5 ml of iPrOH, 56 mg of sodium hydride (60% in mineral oil) were added. After 10 min at RT, 431 mg of tert-butyl N-[4-[3,3-bis(methylsulfanyl)prop-2-enoyl]phenyl]carbamate and 107 mg of 2-cyanoacetamide were added and the mixture was heated under reflux for 4 h. Then, after cooling to RT, water was added and the reaction mixture was neutralized by addition of diluted hydrochloric acid. The precipitated product was collected by filtration and dried under reduced pressure. Yield: 386 mg.

(iii) 3-Amino-6-(4-aminophenyl)-1H-pyrazolo[4,3-c]pyridin-4-ol hydrochloride To a solution of 386 mg of tert-butyl N-[4-(3-cyano-4-methylsulfanyl-2-oxo-3H-pyridin-6-yl)phenyl]carbamate in 2 ml of iPrOH, 2 ml of a hydrazine solution (35% in iPrOH) were added and the reaction mixture was heated for 40 min to 110° C. by using microwave irradiation (Biotage® Initiator apparatus). The reaction mixture was cooled to RT and diluted with acetic acid (20%). The precipitated intermediate product tert-butyl N-[4-(3-amino-4-hydroxy-1H-pyrazolo[4,3-c]pyridin-6-yl)phenyl]carbamate was collected by filtration, dried under reduced pressure and dissolved in 10 ml of a ethanolic solution of hydrochloric acid (8M). After stirring for 30 min at RT the reaction mixture was diluted with toluene (100 ml) and the solvents were removed under reduced pressure. The residue was co-distilled additional two times with toluene. After drying under reduced pressure the product was pure enough for the next reaction step. Yield: 319 mg.

(iv) N-[4-(3-Amino-4-hydroxy-1H-pyrazolo[4,3-c]pyridin-6-yl)phenyl]-5-chloro-2,4-difluoro-benzenesulfonamide To a solution of 166 mg of 3-amino-6-(4-aminophenyl)-1H-pyrazolo[4,3-c]pyridin-4-ol hydrochloride in 5 ml of DCM and 145 µl of pyridine, 148 mg of 5-chloro-2,4-difluoro-benzenesulfonyl chloride were added. After stirring the reaction mixture for 16 h at RT, the solvents were removed under reduced pressure. This crude product was purified by preparative HPLC (C18 reverse phase column, elution with a water/MeCN gradient with 0.1% TFA). The fractions containing the product were lyophilized to yield the pure title compound in the form of its salt with trifluoroacetic acid. Yield: 17 mg.

$^1$H-NMR (DMSO-$d_6$): δ (ppm)=6.35 (s, 1H), 7.17 (d, J=8.7 Hz, 2H), 7.62 (d, J=8.7 Hz, 2H), 7.85 (t, J=7.2 Hz, 1H), 8.09 (t, J=7.2 Hz, 1H), 11.16 (s, 1H).

MS (ES−): m/e=450.1 (M−H), chloro pattern.

Example 550

N-[4-(3-Amino-4-hydroxy-1H-pyrazolo[4,3-c]pyridin-6-yl)phenyl]-2,5-dichloro-benzenesulfonamide

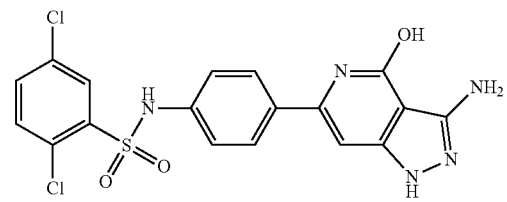

The title compound was prepared analogously to the procedure described in example 549, employing 2,5-dichloro-benzenesulfonyl chloride instead of 5-chloro-2,4-difluoro-benzenesulfonyl chloride.

MS (ES+): m/e=450.1 (M+H), chloro pattern.

Example 551

2,5-Dichloro-N-[6-[4-[(2,5-dichlorophenyl)sulfonylamino]phenyl]-4-hydroxy-1H-pyrazolo[4,3-c]pyridin-3-yl]benzenesulfonamide

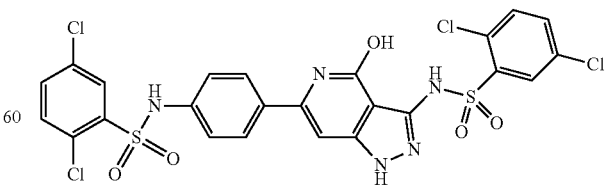

The title compound was isolated as a further product in example 550.

MS (ES−): m/e=656.2, (M−H), chloro pattern.

Example 552

N-[4-(3-Amino-4-hydroxy-1H-pyrazolo[4,3-c]pyridin-6-yl)phenyl]-5-chloro-2-cyano-benzenesulfonamide

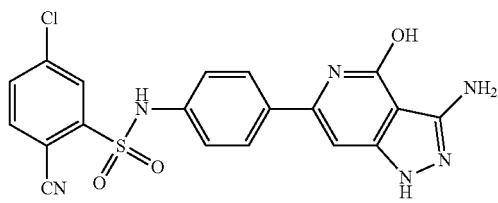 [SMILES: N#Cc1ccc(Cl)cc1S(=O)(=O)Nc1ccc(-c2cc3[nH]nc(N)c3c(O)n2)cc1]

The title compound was prepared analogously to the procedure described in example 549, employing 5-chloro-2-cyano-benzenesulfonyl chloride instead of 5-chloro-2,4-difluoro-benzenesulfonyl chloride.
MS (ES+): m/e=441.1 (M+H), chloro pattern.

Example 553

N-[4-(3-Amino-1H-pyrazolo[4,3-c]pyridin-6-yl)phenyl]-2-cyano-5-methyl-benzenesulfonamide

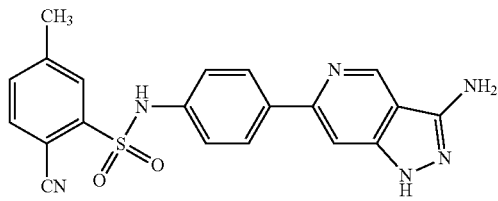 [SMILES: Cc1ccc(C#N)c(S(=O)(=O)Nc2ccc(-c3cc4[nH]nc(N)c4cn3)cc2)c1]

(i) tert-Butyl N-[4-(4-chloro-5-cyano-2-pyridyl)phenyl]carbamate

A solution of 1.0 g of 4,6-dichloropyridine-3-carbonitrile, 1.8 g of tert-butyl N-[4-(4,4,5,5-tetramethyl-[1,3,2]dioxaborolan-2-yl)phenyl]carbamate and 5.6 g of cesium carbonate in 35 ml of Diox and 6 ml of water was purged with argon. Then 338 mg of BDFP were added and the reaction mixture was heated to 100° C. After 5 h, the reaction mixture was cooled to RT and diluted with water. After filtration through a Chem Elut® cartridge by eluting with EtOAc, the solvents were removed under reduced pressure. The crude product was purified by chromatography on silica gel eluting with a gradient of Hep/EtOAc. The fractions containing the product were combined and the solvent evaporated under reduced pressure. Yield: 2.1 g.

(ii) 6-(4-Aminophenyl)-1H-pyrazolo[4,3-c]pyridin-3-amine hydrochloride

To a solution of 2.1 g of tert-butyl N-[4-(4-chloro-5-cyano-2-pyridyl)phenyl]carbamate in 20 ml of iPrOH, 19.4 ml of a hydrazine solution (35% in iPrOH) were added and the reaction mixture was heated for 25 min to 80° C. by using microwave irradiation (Biotage® Initiator apparatus). The reaction mixture was cooled to RT and diluted with acetic acid (20%). The precipitated intermediate product tert-butyl N-[4-(3-amino-1H-pyrazolo[4,3-c]pyridin-6-yl)phenyl]carbamate was collected by filtration, dried under reduced pressure and dissolved in 10 ml of a ethanolic solution of hydrochloric acid (8M). After stirring for 30 min at RT the reaction mixture was diluted with toluene (100 ml) and the solvents were removed under reduced pressure. The residue was co-distilled additional two times with toluene. After drying under reduced pressure the product was pure enough for the next reaction step. Yield: 1.7 g.

(iii) N-[4-(3-amino-1H-pyrazolo[4,3-c]pyridin-6-yl)phenyl]-2-cyano-5-methyl-benzenesulfonamide To a solution of 150 mg of 6-(4-aminophenyl)-1H-pyrazolo[4,3-c]pyridin-3-amine hydrochloride in 3 ml of DCM and 138 µl of pyridine, 123 mg of 2-cyano-5-methyl-benzenesulfonyl chloride were added. After stirring the reaction mixture for 16 h at RT, the solvents were removed under reduced pressure. This crude product was purified by preparative HPLC (C18 reverse phase column, elution with a water/MeCN gradient). The fractions containing the product were lyophilized to yield the pure title compound. Yield: 22 mg.
MS (ES+): m/e=405.2 (M+H).

Analogously to the procedure described in the example 553, the example compounds of the formula Ie

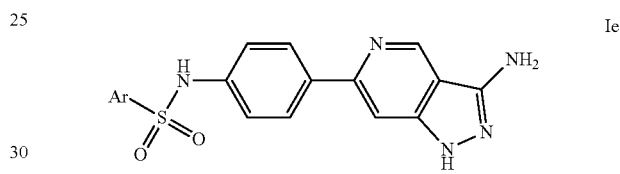

listed in Table 5 were synthesized, employing the respective sulfonyl chloride instead of 2-cyano-5-methyl-benzenesulfonyl chloride. The ionization method in the MS characterization was ES+. CP means chloro pattern in the mass spectrum.

TABLE 5

Example compounds of the formula Ie

| Example no. | Ar | MS (m/e) |
|---|---|---|
| 554 | 5-chloro-2-cyano-phenyl | 425.3 (M + H), CP |
| 555 | 5-chloro-2,4-difluoro-phenyl | 436.1 (M + H), CP |
| 556 | 2,5-dichloro-phenyl | 434.1 (M + H), CP |
| 557 | 2-chloro-3,5-difluoro-phenyl | 436.1 (M + H), CP |
| 558 | 2,5-dichloro-thiophen-3-yl | 440.1 (M + H), CP |
| 559 | 5-chloro-2-fluoro-phenyl | 418.1 (M + H), CP |

Example 560

2,5-Dichloro-N-[6-[4-[(2,5-dichlorophenyl)sulfonylamino]phenyl]-1H-pyrazolo[4,3-c]pyridin-3-yl]benzenesulfonamide

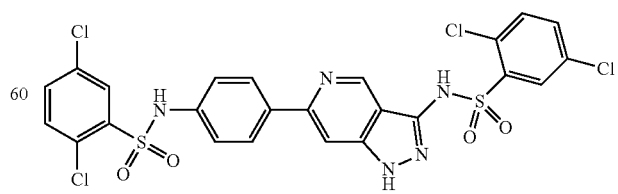

The title compound was isolated as a further product in example 556.
MS (ES+): m/e=642.0 (M+H), chloro pattern.

Example 561

2-Cyano-5-methyl-N-[4-(3-methyl-1H-pyrazolo[4,3-c]pyridin-6-yl)phenyl]benzenesulfonamide

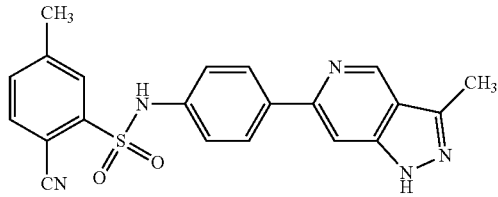

(i) tert-Butyl N-[4-(5-acetyl-4-chloro-2-pyridyl)phenyl]carbamate

A solution of 200 mg of 1-(4,6-dichloro-3-pyridyl)ethanone, 335 mg of tert-butyl N-[4-(4,4,5,5-tetramethyl-[1,3,2]dioxaborolan-2-yl)phenyl]carbamate and 1.0 g of cesium carbonate in 6 ml of Diox and 1 ml of water was purged with argon. Then 62 mg of BDFP were added and the reaction mixture was heated to 100° C. After 2 h, the reaction mixture was cooled to RT and diluted with water. After filtration through a Chem Elut® cartridge by eluting with EtOAc, the solvents were removed under reduced pressure. The crude product was purified by chromatography on silica gel eluting with a gradient of Hep/EtOAc. The fractions containing the product were combined and the solvent evaporated under reduced pressure. Yield: 290 mg.

(ii) 4-(3-Methyl-1H-pyrazolo[4,3-c]pyridin-6-yl)aniline hydrochloride

To a solution of 290 mg of tert-butyl N-[4-(5-acetyl-4-chloro-2-pyridyl)phenyl]carbamate in 3 ml of iPrOH, 2.8 ml of a hydrazine solution (35% in iPrOH) were added and the reaction mixture was heated for 15 min to 80° C. by using microwave irradiation (Biotage® Initiator apparatus). The reaction mixture was cooled to RT and diluted with acetic acid (20%). The precipitated intermediate product tert-butyl N-[4-(3-methyl-1H-pyrazolo[4,3-c]pyridin-6-yl)phenyl]carbamate was collected by filtration, dried under reduced pressure and dissolved in 5 ml of a ethanolic solution of hydrochloric acid (8M). After stirring for 1 h at RT the reaction mixture was diluted with toluene (100 ml) and the solvents were removed under reduced pressure. The residue was co-distilled additional two times with toluene. After drying under reduced pressure the product was pure enough for the next reaction step. Yield: 170 mg.

(iii) 2-Cyano-5-methyl-N-[4-(3-methyl-1H-pyrazolo[4,3-c]pyridin-6-yl)phenyl]benzenesulfonamide To a solution of 170 mg of 6-(4-aminophenyl)-1H-pyrazolo[4,3-c]pyridin-3-amine hydrochloride in 4 ml of DCM and 180 µl of pyridine, 140 mg of 2-cyano-5-methyl-benzenesulfonyl chloride were added. After stirring the reaction mixture for 16 h at RT, the solvents were removed under reduced pressure. This crude product was purified by preparative HPLC (C18 reverse phase column, elution with a water/MeCN gradient). The fractions containing the product were lyophilized to yield the pure title compound. Yield: 44 mg.

$^1$H-NMR (DMSO-d$_6$): δ (ppm)=2.48 (s, 3H), 2.57 (s, 3H), 7.23 (d, J=8.9 Hz, 2H), 7.65 (d, J=8.9 Hz, 1H), 7.86 (s, 1H), 7.96 (d, J=8.9 Hz, 2H), 8.02 (d, J=8.9 Hz, 2H), 9.12 (s, 1H), 10.98 (s, 1H).

MS (ES+): m/e=404.2 (M+H).

Example 562

5-Chloro-2-cyano-N-[4-(3-methyl-1H-pyrazolo[4,3-c]pyridin-6-yl)phenyl]benzenesulfonamide

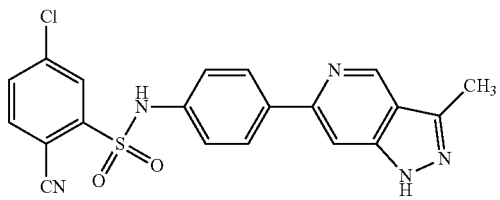 [SMILES: Cc1ccc(C#N)c(S(=O)(=O)Nc2ccc(-c3cc4[nH]nc(C)c4cn3)cc2)c1]

The title compound was prepared analogously to the procedure described in example 561, employing 5-chloro-2-cyano-benzenesulfonyl chloride instead of 2-cyano-5-methyl-benzenesulfonyl chloride.

MS (ES+): m/e=424.1 (M+H), chloro pattern.

Example 563

2,5-Dichloro-N-[4-(1H-pyrazolo[4,3-c]pyridin-6-yl)phenyl]benzenesulfonamide

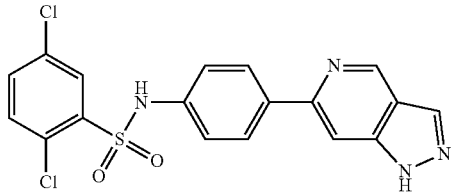

(i) 2,5-Dichloro-N-[4-(4-chloro-5-formyl-2-pyridyl)phenyl]benzenesulfonamide A solution of 60 mg of 4,6-dichloropyridine-3-carbaldehyde, 146 mg of 2,5-dichloro-N-[4-(4,4,5,5-tetramethyl-[1,3,2]dioxaborolan-2-yl)phenyl]benzenesulfonamide and 333 mg of cesium carbonate in 2 ml of Diox and 0.3 ml of water was purged with argon. Then 20 mg of BDFP were added and the reaction mixture was heated to 100° C. After 2 h, the reaction mixture was cooled to RT and diluted with water. After filtration through a Chem Elut® cartridge by eluting with EtOAc, the solvents were removed under reduced pressure. The crude product was used in the next reaction step without further purification. Yield: 190 mg.

(ii) 2,5-Dichloro-N-[4-(1H-pyrazolo[4,3-c]pyridin-6-yl)phenyl]benzenesulfonamide To a solution of 190 mg of 2,5-dichloro-N-[4-(4-chloro-5-formyl-2-pyridyl)phenyl]benzenesulfonamide in 3 ml of iPrOH, 1.45 ml of a hydrazine solution (35% in iPrOH) were added and the reaction mixture was heated for 40 min to 120° C. by using microwave irradiation (Biotage® Initiator apparatus). The reaction mixture was cooled to RT and diluted with acetic acid (20%). The precipitate was collected by filtration and purified by preparative HPLC (C18 reverse phase column, elution with a water/MeCN gradient with 0.1% TFA). The fractions containing the product were lyophilized to yield the pure title compound in the form of its salt with trifluoroacetic acid. Yield: 12 mg.

$^1$H-NMR (DMSO-d$_6$): δ (ppm)=7.30 (d, J=8.7 Hz, 2H), 7.70 (d, J=8.7 Hz, 1H), 7.74 (m, 2H), 7.96 (d, J=8.7 Hz, 2H), 8.03 (s, 1H), 8.12 (s, 1H), 8.40 (s, 1H), 9.33 (s, 1H), 10.98 (s, 1H).

MS (ES+): m/e=419.1 (M+H), chloro pattern.

Example 564

5-Cyano-2-methyl-N-[4-(1H-pyrazolo[4,3-c]pyridin-6-yl)-phenyl]-benzenesulfonamide

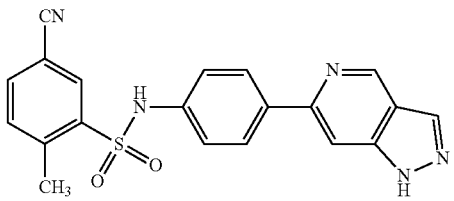 [SMILES: O=S(=O)(Nc1ccc(-c2cc3[nH]ncc3cn2)cc1)c1cc(Cl)ccc1Cl]

The title compound was prepared analogously to the procedure described in example 563, employing 5-cyano-2-methyl-N-[4-(4,4,5,5-tetramethyl-[1,3,2]dioxaborolan-2-yl)-phenyl]-benzenesulfonamide instead of 2,5-dichloro-N-[4-(4,4,5,5-tetramethyl-[1,3,2]dioxaborolan-2-yl)phenyl]benzenesulfonamide.

MS (ES+): m/e=390.2 (M+H).

Example 565

1-[(4-Chloro-phenyl)methyl]-3-[6-[4-[(2,5-dichloro-phenyl)sulfonylamino]phenyl]-1H-pyrazolo[3,4-d]pyrimidin-3-yl]urea

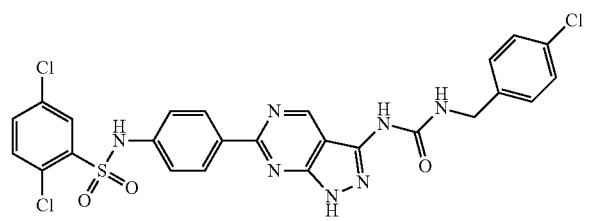 [SMILES: O=C(NCc1ccc(Cl)cc1)Nc1n[nH]c2nc(-c3ccc(NS(=O)(=O)c4cc(Cl)ccc4Cl)cc3)ncc12]

To a solution of 80 mg of N-[4-(3-amino-1H-pyrazolo[3,4-d]pyrimidin-6-yl)-phenyl]-2,5-dichloro-benzenesulfonamide in 2 ml Diox, 31 mg of 1-chloro-4-isocyanatomethylbenzene and 21 mg 1,3-dimethylimidazolidin-2-one were added and the reaction mixture was stirred for 16 h at RT. Then the reaction mixture was concentrated under reduced pressure and the crude product was purified by preparative HPLC (C18 reversed phase column, elution with a water/MeCN gradient with 0.1% TFA). The fractions containing the product were lyophilized to yield the pure title compound in the form of its salt with trifluoroacetic acid. Yield: 102 mg.

MS (ES+): m/e=602.1 (M+H), chloro pattern.

Example 566

1-[6-[4-[(2,5-Dichlorophenyl)sulfonylamino]phenyl]-1H-pyrazolo[3,4-d]pyrimidin-3-yl]-3-(tetrahydropyran-4-ylmethyl)urea

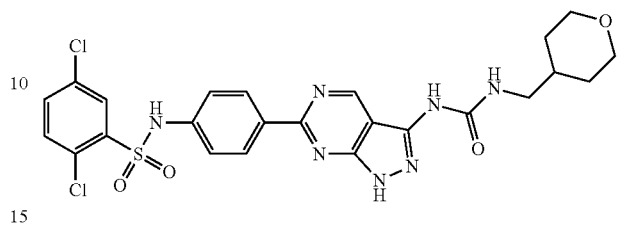

The title compound was prepared analogously to the procedure described in example 565.

MS (ES+): m/e=576.2 (M+H), chloro pattern.

Example 567

2,5-Dichloro-N-[4-[3-(diethylamino)-1H-pyrazolo[3,4-d]pyrimidin-6-yl]phenyl]benzenesulfonamide

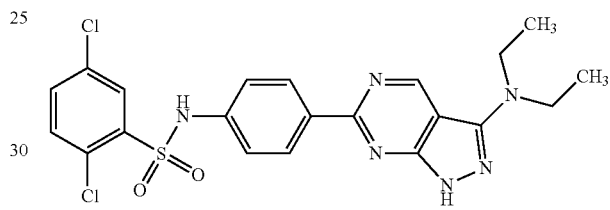

To a solution of 80 mg of N-[4-(3-amino-1H-pyrazolo[3,4-d]pyrimidin-6-yl)-phenyl]-2,5-dichloro-benzenesulfonamide, 41 mg of acetaldehyde in 5 ml of 1,2-dichloroethane, 22 mg of sodium triacetoxyborohydride and 2 μl of acetic acid were added at RT. After stirring for 16 h, water was added and the reaction mixture was filtered through a Chem Elut® cartridge by eluting with EtOAc. After removal of the solvents under reduced pressure, the residue was purified by preparative HPLC (C18 reversed phase column, elution with a water/MeCN gradient with 0.1% TFA). The fractions containing the product were lyophilized to yield the pure title compound in the form of its salt with trifluoroacetic acid. Yield: 15 mg.

MS (ES+): m/e=491.1 (M+H), chloro pattern.

Example 568

N-[4-(3-Amino-4-trifluoromethyl-1H-pyrazolo[3,4-d]pyrimidin-6-yl)-phenyl]-5-chloro-2-fluoro-benzenesulfonamide

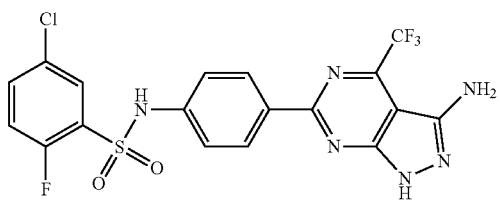 [SMILES: Nc1n[nH]c2nc(-c3ccc(NS(=O)(=O)c4cc(Cl)ccc4F)cc3)nc(C(F)(F)F)c12]

(i) Ethyl 2-cyano-4,4,4-trifluoro-3-hydroxybut-2-enoate

To a solution of 19.2 ml of trifluoroacetic acid anhydride in 300 ml of DCM, 12.3 ml of cyano-acetic acid ethyl ester were added. Then 40 ml of triethylamine were added dropwise at 0° C. and the reaction mixture was allowed to warm to RT and stirred for 1 h. The reaction mixture was acidified with half-concentrated aqueous hydrochloric acid to pH 1, and the mixture was extracted with DCM (3×200 ml). The combined organic layers were washed with water, dried over magnesium sulfate and the solvents were removed under reduced pressure. The crude product was used in the subsequent reaction step. Yield: 30 g.

(ii) Ethyl 3-chloro-2-cyano-4,4,4-trifluorobut-2-enoate

To a solution of 30 g of ethyl 2-cyano-4,4,4-trifluoro-3-hydroxybut-2-enoate in 300 ml of DCM, 64 ml of oxalyl chloride were slowly added dropwise at 0° C. Then the reaction mixture was allowed to warm to RT, stirred for 1 h and 0.3 ml of pyridine were added. The reaction mixture was heated to reflux for 4 h, then cooled to RT and poured into 500 ml of ice water. The organic phase was separated and the aqueous phase was extracted with DCM (2×100 ml). The combined organic layers were dried over magnesium sulfate and the solvents were removed under reduced pressure. The obtained crude product was used in the subsequent reaction step. Yield: 28 g.

(iii) 4-Hydroxy-2-(4-nitrophenyl)-6-(trifluoromethyl)-pyrimidine-5-carbonitrile

To a mixture of 21 g of ethyl 3-chloro-2-cyano-4,4,4-trifluorobut-2-enoate and 7.6 g of 4-nitrobenzimidamide in 300 ml of water, 31 ml of a aqueous sodium hydroxide solution (2M) were added. The reaction mixture was stirred at RT for 4 h, then diluted with 200 ml of water, acidified with half-concentrated aqueous hydrochloric acid to pH 3 and extracted with EtOAc (3×500 ml). The combined organic layers were dried over magnesium sulfate and the solvents were removed under reduced pressure. The crude product was purified by chromatography on silica gel eluting with a gradient of EtOAc/methanol. Yield: 2.7 g.

(iv) 4-Chloro-2-(4-nitrophenyl)-6-(trifluoromethyl)-pyrimidine-5-carbonitrile

To a solution of 660 mg of 4-hydroxy-2-(4-nitrophenyl)-6-(trifluoromethyl)-pyrimidine-5-carbonitrile in 2.92 ml of phosphorus oxychloride, 0.3 ml of dimethyl-phenyl-amine were added. The reaction mixture was heated to reflux for 30 minh, then cooled to RT and concentrated under reduced pressure. After addition of ice water and dilution with DCM, saturated aqueous sodium hydrogencarbonate solution was added and the mixture was extracted with DCM (3×100 ml). The combined organic layers were dried over magnesium sulfate and the solvents were removed under reduced pressure. The obtained crude product was used in the subsequent reaction without further purification. Yield: 700 mg.

(v) 6-(4-Nitrophenyl)-4-(trifluoromethyl)-1H-pyrazolo[3,4-d]pyrimidin-3-amine

To a solution of 700 mg of 4-chloro-2-(4-nitrophenyl)-6-(trifluoromethyl)-pyrimidine-5-carbonitrile in 10 ml of iPrOH, 2.4 ml of hydrazine hydrate (64% in water) were added and the reaction mixture was heated for 4 h to 100° C. The reaction mixture was cooled to RT and diluted with acetic acid (20%). The precipitated product was collected by filtration and purified by preparative HPLC (C18 reverse phase column, elution with a water/MeCN gradient with 0.1% TFA). The fractions containing the product were lyophilized to yield the pure title compound in the form of its salt with trifluoroacetic acid. Yield: 85 mg.

(vi) tert-Butyl 3-(bis(tert-butoxycarbonyl)amino)-6-(4-nitrophenyl)-4-(trifluoromethyl)-pyrazolo[3,4-d]pyrimidine-1-carboxylate To a suspension of 85 mg of 6-(4-nitrophenyl)-4-(trifluoromethyl)-1H-pyrazolo[3,4-d]pyrimidin-3-amine in 30 ml of DCM, 2 g of di-tert-butyl dicarbonate, 0.1 ml of triethylamine and 3 mg of dimethyl-pyridin-4-yl-amine were added. The mixture was stirred for 16 h at RT, then quenched by the addition of water and diluted with DCM. After separation of the organic layer, the aqueous layer was extracted with DCM (3×200 ml). The combined organic layers were dried over magnesium sulfate and the solvents were removed under reduced pressure. The obtained crude product was used without further purification in the next reaction. Yield: 170 mg.

(vii) tert-Butyl 6-(4-aminophenyl)-3-(bis(tert-butoxycarbonyl)amino)-4-(trifluoromethyl)-pyrazolo[3,4-d]pyrimidine-1-carboxylate To a solution of 170 mg of tert-butyl 3-(bis(tert-butoxycarbonyl)amino)-6-(4-nitrophenyl)-4-(trifluoromethyl)-pyrazolo[3,4-d]pyrimidine-1-carboxylate obtained in the preceding step in 40 ml of EtOAc, 30 mg of Pd/C (10%) were added under argon and the suspension was stirred under an atmosphere of hydrogen (2 bar) for 1 h. The suspension was filtered over a plug of Celite® and washed with EtOAc. The crude product was obtained after evaporation of the solvent as a brown solid and was dried under reduced pressure. Yield: 160 mg.

(viii) N-[4-(3-Amino-4-trifluoromethyl-1H-pyrazolo[3,4-d]pyrimidin-6-yl)-phenyl]-5-chloro-2-fluoro-benzenesulfonamide To a solution of 160 mg of tert-butyl 6-(4-aminophenyl)-3-(bis(tert-butoxycarbonyl)amino)-4-trifluoromethyl)-pyrazolo[3,4-d]pyrimidine-1-carboxylate in 5 ml DCM and 43 µl pyridine, 63 mg of 5-chloro-2-fluoro-benzenesulfonyl chloride were added. After stirring the reaction mixture for 16 h at RT, the solvents were removed under reduced pressure. The residue was dissolved in 10 ml DCM and 1 ml of TFA and stirred for 2 h at RT. Then toluene was added and the solvents were removed under reduced pressure to yield a brown solid. This crude product was purified by preparative HPLC (C18 reverse phase column, elution with a water/MeCN gradient with 0.1% TFA). The fractions containing the product were lyophilized to yield the pure title compound in the form of its salt with trifluoroacetic acid. Yield: 23 mg.

MS (ES+): m/e=487.0 (M+H), chloro pattern.

Analogously to the procedure described in example 568, the example compounds of the formula If

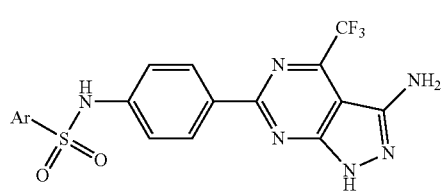

If listed in Table 6 were synthesized, employing the respective sulfonyl chloride instead of 5-chloro-2-fluoro-benzenesulfonyl chloride. The ionization method in the MS characterization was ES+. CP means chloro pattern in the mass spectrum.

TABLE 6

Example compounds of the formula If

| Example no. | Ar | MS (m/e) |
|---|---|---|
| 569 | 2-cyano-5-methyl-phenyl | 474.1 (M + H) |
| 570 | 5-chloro-2-cyano-phenyl | 494.0 (M + H), CP |
| 571 | 2-cyano-5-methoxy-phenyl | 490.1 (M + H) |
| 572 | 2,5-dichloro-thiophen-3-yl | 508.9 (M + H), CP |
| 573 | 2,3,5-trifluoro-phenyl | 489.1 (M + H) |
| 574 | 5-chloro-2,4-difluoro-phenyl | 505.0 (M + H), CP |
| 575 | 2-fluoro-phenyl | 453.1 (M + H) |
| 576 | 2-chloro-3,5-difluoro-phenyl | 505.0 (M + H), CP |
| 577 | 2-chloro-4-fluoro-phenyl | 487.0 (M + H), CP |
| 578 | 3-chloro-2-fluoro-phenyl | 487.0 (M + H), CP |
| 579 | 2,5-dichloro-phenyl | 503.0 (M + H), CP |
| 580 | 2-fluoro-5-methyl-phenyl | 467.1 (M + H) |
| 581 | 2-chloro-5-methoxy-phenyl | 499.0 (M + H), CP |
| 582 | 2,5-difluoro-phenyl | 471.0 (M + H) |
| 583 | 2-chloro-phenyl | 469.0 (M + H), CP |
| 584 | 2,4,5-trifluoro-phenyl | 489.1 (M + H) |

Analogously to the procedures described in the examples above, the example compounds of the formula Ib

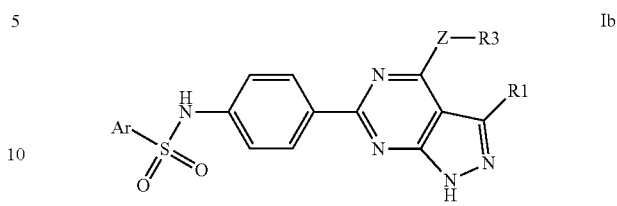

listed in Table 7 were synthesized. In the formulae of the groups —Z—R3 in Table 7 the line crossed with the symbol ~~~ represents the free bond via which the group —Z—R3 is bonded to the carbon atom in the 4-position of the pyrazolo[3,4-d]pyrimidine ring system. I.e., in the formula of the complete molecule the terminal endpoint of the line crossed with the said symbol ends at the carbon atom in the 4-position of the pyrazolo[3,4-d]pyrimidine ring system. In the column "Synthesis" the number of the example is specified in analogy to which the synthesis was performed. The ionization method in the MS characterization was ES+. CP means chloro pattern in the mass spectrum.

TABLE 7

Example compounds of the formula Ib

| Example no. | Ar | R1 | —Z—R3 | Synthesis | Yield (%) | MS (m/e) |
|---|---|---|---|---|---|---|
| 585 | 2-fluoro-phenyl | CH₃ | —O-piperidine-N-cyclopropyl | 3 (a) | 31 | 523.2 (M + H) |
| 586 | 2-cyano-5-methyl-phenyl | CH₃ | —O-piperidine-N-cyclopropyl | 3 (a) | 6 | 544.2 (M + H) |
| 587 | 5-chloro-2-fluoro-phenyl | CH₃ | —O-CH₂-azetidine-N-CH(CH₃)₂ | 3 (a) | 29 | 545.1 (M + H), CP |
| 588 | 2-chloro-5-methoxy-phenyl | CH₃ | —O-CH₂-azetidine-N-CH(CH₃)₂ | 3 (a) | 7 | 557.1 (M + H), CP |
| 589 | 2-fluoro-5-methyl-phenyl | CH₃ | —O-CH₂-azetidine-N-CH(CH₃)₂ | 3 (a) | 25 | 525.1 (M + H) |
| 590 | 2,5-dichloro-phenyl | CH₃ | —O-CH₂-azetidine-N-CH(CH₃)₂ | 3 (a) | 18 | 561.0 (M + H), CP |

TABLE 7-continued

Example compounds of the formula Ib

| Example no. | Ar | R1 | -Z-R3 | Synthesis | Yield (%) | MS (m/e) |
|---|---|---|---|---|---|---|
| 591 | 2-fluoro-phenyl | CH$_3$ | 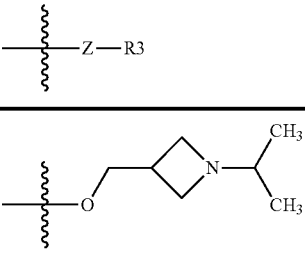 | 3 (a) | 22 | 511.1 (M + H) |
| 592 | 2,5-difluoro-phenyl | CH$_3$ | 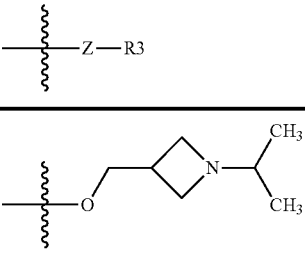 | 3 (a) | 24 | 529.1 (M + H) |
| 593 | 2-fluoro-5-methoxy-phenyl | CH$_3$ | 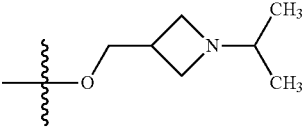 | 3 (a) | 21 | 541.1 (M + H) |
| 594 | 5-chloro-2,4-difluoro-phenyl | NH$_2$ | 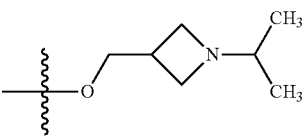 [SMILES: *OCC1CN(C(C)C)C1] | 7 | 28 | 495.0 (M + H), CP |
| 595 | 2-fluoro-5-methyl-phenyl | NH$_2$ | 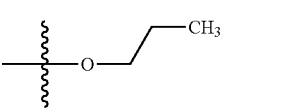 | 7 | 29 | 457.1 (M + H) |
| 596 | 2-fluoro-5-methyl-phenyl | NH$_2$ | 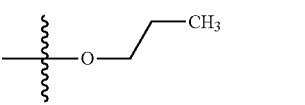 | 7 | 24 | 443.1 (M + H) |
| 597 | 5-chloro-2-fluoro-phenyl | CH$_3$ | 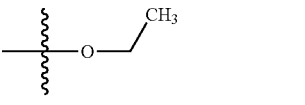 [SMILES: *OCC] | 3 (a) | 13 | 527.0 (M + H), CP |
| 598 | 2-fluoro-phenyl | CH$_3$ | 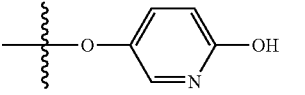 [SMILES: *Oc1ccc(O)nc1] | 3 (a) | 10 | 493.0 (M + H) |
| 599 | 2-chloro-5-methoxy-phenyl | CH$_3$ | 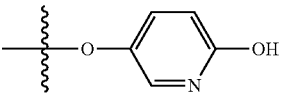 | 3 (a) | 9 | 539.0 M + H), CP |
| 600 | 2-fluoro-5-methyl-phenyl | CH$_3$ | 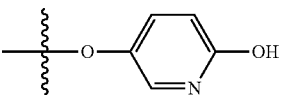 | 3 (a) | 7 | 507.1 (M + H) |
| 601 | 2,5-dichloro-phenyl | CH$_3$ | 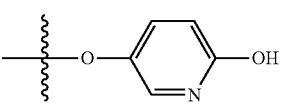 | 3 (a) | 5 | 543.2 (M + H), CP |
| 602 | 2-fluoro-5-methoxy-phenyl | CH$_3$ | 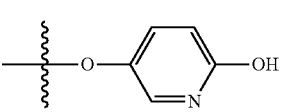 | 3 (a) | 15 | 523.3 (M + H) |

TABLE 7-continued

Example compounds of the formula Ib

| Example no. | Ar | R1 | —Z—R3 | Synthesis | Yield (%) | MS (m/e) |
|---|---|---|---|---|---|---|
| 603 | 2-cyano-5-methyl-phenyl | CH₃ | 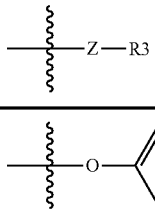 | 3 (a) | 8 | 514.1 (M + H) |
| 604 | 2,5-difluoro-phenyl | CH₃ | 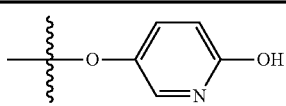 | 3 (a) | 13 | 511.2 (M + H) |
| 605 | 2-chloro-4,5-difluoro-phenyl | NH₂ | 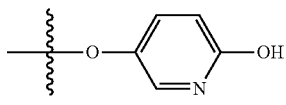 | 7 | 34 | 495.0 (M + H), CP |
| 606 | 2-fluoro-phenyl | NH₂ | 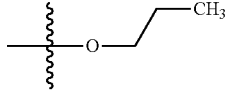 | 7 | 22 | 429.0 (M + H) |
| 607 | 2-fluoro-phenyl | NH₂ | 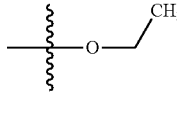 | 7 | 32 | 443.1 (M + H) |
| 608 | 2-fluoro-5-methoxy-phenyl | NH₂ | 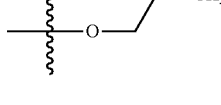 | 7 | 33 | 459.2 (M + H) |
| 609 | 2-fluoro-5-methoxy-phenyl | NH₂ | 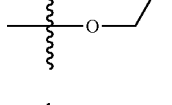 | 7 | 29 | 473.3 (M + H) |
| 610 | 2-chloro-5-methoxy-phenyl | NH₂ | 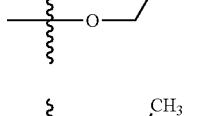 | 7 | 36 | 475.3 (M + H), CP |
| 611 | 2-chloro-5-methoxy-phenyl | NH₂ | 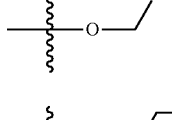 | 7 | 34 | 489.2 (M + H), CP |
| 612 | 2,4,5-trifluoro-phenyl | NH₂ | 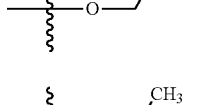 | 7 | 32 | 465.0 (M + H) |
| 613 | 2,4,5-trifluoro-phenyl | NH₂ | 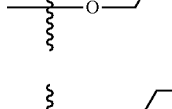 | 7 | 46 | 479.0 (M + H) |
| 614 | 2-chloro-4,5-difluoro-phenyl | NH₂ | 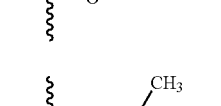 | 7 | 35 | 481.1 (M + H), CP |
| 615 | 5-chloro-2-fluoro-phenyl | CH₃ | 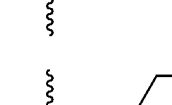 | 3 (a) | 37 | 518.2 (M + H), CP |

TABLE 7-continued
Example compounds of the formula Ib
| Example no. | Ar | R1 | —Z—R3 | Synthesis | Yield (%) | MS (m/e) |
|---|---|---|---|---|---|---|
| 616 | 2-fluoro-phenyl | CH₃ | 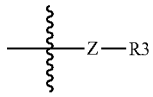 | 3 (a) | 53 | 484.2 (M + H) |
| 617 | 2,5-dichloro-phenyl | CH₃ | 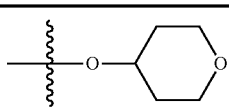 | 3 (a) | 24 | 534.2 (M + H), CP |
| 618 | 5-chloro-2-fluoro-phenyl | CH₃ | 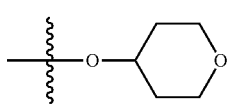 | 3 (a) | 29 | 587.3 (M + H), CP |
| 619 | 2-fluoro-phenyl | CH₃ | 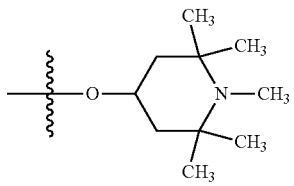 [SMILES: *OC1CC(C)(C)N(C)C(C)(C)C1] | 3 (a) | 36 | 553.4 (M + H) |
| 620 | 2,5-dichloro-phenyl | CH₃ | 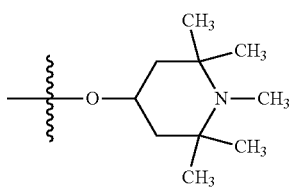 | 3 (a) | 36 | 603.3 (M + H), CP |
| 621 | 2,5-difluoro-phenyl | CH₃ | 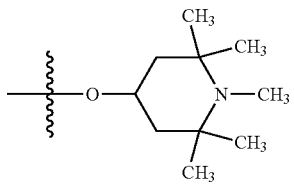 | 3 (a) | 36 | 571.3 (M + H) |
| 622 | 2,5-difluoro-phenyl | CH₃ | 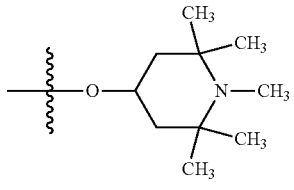 [SMILES: *OC1CC(C)(C)N(C)C(C)(C)C1] | 3 (a) | 28 | 525.2 (M + H) |
| 623 | 2,5-dichloro-phenyl | CH₃ | 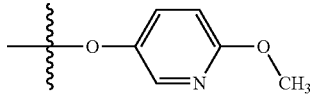 | 3 (a) | 10 | 557.2 (M + H), CP |
| 624 | 2-fluoro-phenyl | CH₃ | 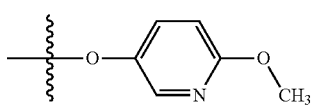 | 3 (a) | 37 | 507.3 (M + H) |
| 625 | 2,5-difluoro-phenyl | CH₃ | 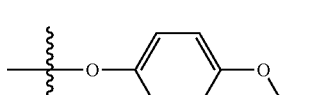 | 3 (a) | 54 | 502.2 (M + H) |

TABLE 7-continued
Example compounds of the formula Ib
| Example no. | Ar | R1 | —Z—R3 | Synthesis | Yield (%) | MS (m/e) |
|---|---|---|---|---|---|---|
| 626 | 5-chloro-2-fluoro-phenyl | CH₃ | 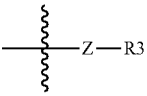 | 3 (a) | 5 | 573.3 (M + H), CP |
| 627 | 2-fluoro-phenyl | CH₃ | 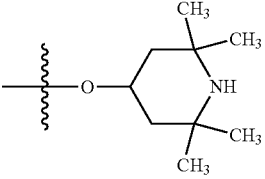 | 3 (a) | 4 | 539.3 (M + H) |
| 628 | 2-chloro-5-methoxy-phenyl | CH₃ | 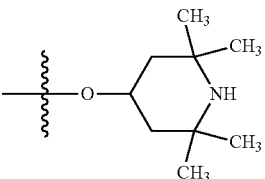 | 3 (a) | 9 | 585.3 (M + H), CP |
| 629 | 2,5-dichloro-phenyl | CH₃ | 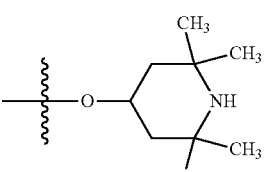 | 3 (a) | 41 | 589.3 (M + H), CP |
| 630 | 2-fluoro-5-methoxy-phenyl | CH₃ | 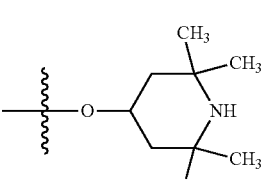 | 3 (a) | 3 | 569.4 (M + H) |
| 631 | 2-fluoro-5-methyl-phenyl | CH₃ | 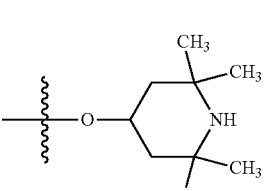 | 3 (a) | 37 | 567.4 (M + H) |
| 632 | 2-chloro-5-methoxy-phenyl | CH₃ | 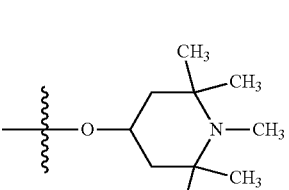 | 3 (a) | 36 | 599.4 (M + H), CP |

TABLE 7-continued

Example compounds of the formula Ib

| Example no. | Ar | R1 | —Z—R3 | Synthesis | Yield (%) | MS (m/e) |
|---|---|---|---|---|---|---|
| 633 | 2-fluoro-5-methoxy-phenyl | CH₃ | 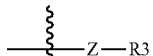 | 3 (a) | 31 | 583.4 (M + H) |
| 634 | 5-chloro-2-fluoro-phenyl | CH₃ | 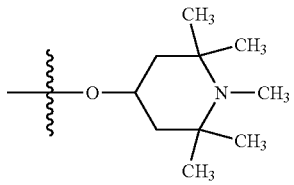 [SMILES: *OC1CC(C)(C)N(C)C(C)(C)C1] | 3 (a) | 2 | 541.2 (M + H), CP |
| 635 | 2,5-dichloro-phenyl | CH₃ | 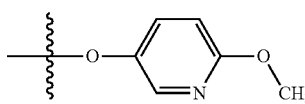 | 3 | 23 | 587.2 (M + H), CP |
| 636 | 5-chloro-2,4-difluoro-phenyl | CH₃ | 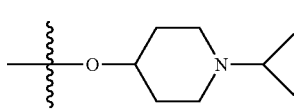 | 3 | 25 | 589.3 (M + H), CP |
| 637 | 5-chloro-2-fluoro-phenyl | CH₃ | 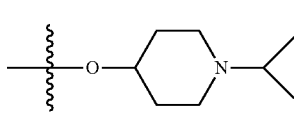 | 3 | 24 | 571.3 (M + H), CP |
| 638 | 2-chloro-3,5-difluoro-phenyl | CH₃ | 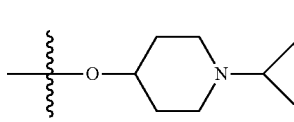 | 3 | 22 | 589.3 (M + H), CP |
| 639 | 2,4,5-trifluoro-phenyl | CH₃ | 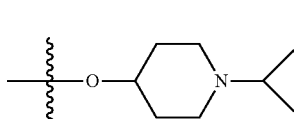 | 3 | 28 | 573.3 (M + H) |
| 640 | 2-chloro-4,5-difluoro-phenyl | CH₃ | 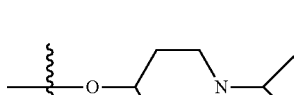 | 3 | 30 | 589.3 (M + H), CP |
| 641 | 2-cyano-5-methoxy-phenyl | CH₃ | 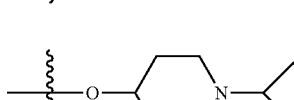 | 3 | 12 | 574.3 (M + H) |
| 642 | 2-fluoro-5-methoxy-phenyl | CH₃ |  | 3 | 23 | 567.3 (M + H) |
| 643 | 2-chloro-5-methoxy-phenyl | CH₃ | 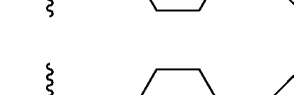 | 3 | 17 | 583.3 (M + H), CP |

TABLE 7-continued

Example compounds of the formula Ib

| Example no. | Ar | R1 | —Z—R3 | Synthesis | Yield (%) | MS (m/e) |
|---|---|---|---|---|---|---|
| 644 | 2,5-difluoro-phenyl | CH$_3$ | 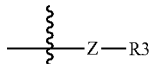 | 3 (a) | 28 | 557.3 (M + H) |
| 645 | 2-cyano-5-methyl-phenyl | CH$_3$ | 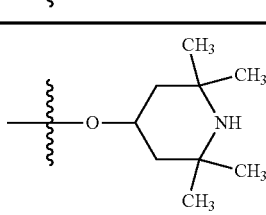 | 3 (a) | 9 | 574.3 (M + H) |
| 646 | 5-chloro-2-fluoro-phenyl | CH$_3$ | 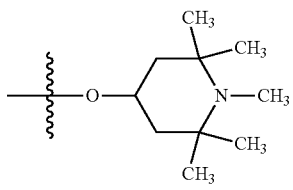 | 3 (a) | 12 | 559.3 (M + H), CP |
| 647 | 2-cyano-5-methyl-phenyl | CH$_3$ | 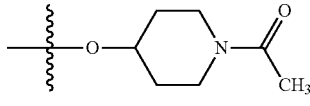 | 3 (a) | 8 | 560.4 (M + H) |
| 648 | 2-fluoro-5-methyl-phenyl | CH$_3$ | 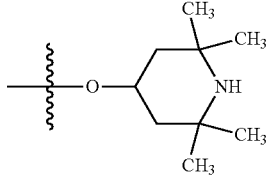 [SMILES: *OC1CC(C)(C)NC(C)(C)C1] | 3 (a) | 12 | 553.4 (M + H) |
| 649 | 5-chloro-2-fluoro-phenyl | CH$_3$ | 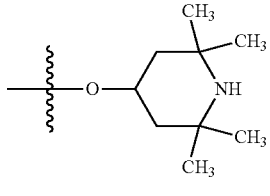 | 3 (a) | 12 | 530.2 (M + H), CP |
| 650 | 2,5-dichloro-phenyl | CH$_3$ | 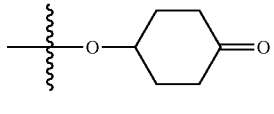 | 3 (a) | 21 | 546.2 (M + H), CP |
| 651 | 2-chloro-5-methoxy-phenyl | CH$_3$ | 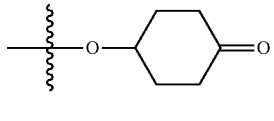 | 3 (a) | 12 | 553.3 (M + H), CP |
| 652 | 2-cyano-5-methyl-phenyl | CH$_3$ | 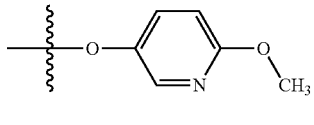 | 3 (a) | 4 | 528.3 (M + H) |
| 653 | 2-fluoro-5-methoxy-phenyl | CH$_3$ | 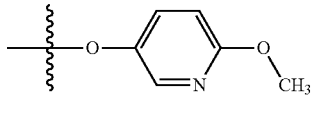 | 3 (a) | 9 | 537.3 (M + H) |

TABLE 7-continued

Example compounds of the formula Ib

| Example no. | Ar | R1 | —Z—R3 | Synthesis | Yield (%) | MS (m/e) |
|---|---|---|---|---|---|---|
| 654 | 2-fluoro-5-methyl-phenyl | CH$_3$ | 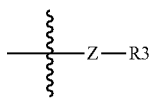 | 3 (a) | 13 | 521.3 (M + H) |
| 655 | 2-fluoro-phenyl | CH$_3$ | 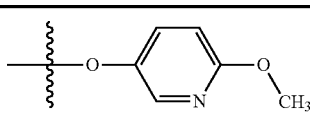 | 3 (a) | 3 | 493.2 (M + H) |
| 656 | 2-fluoro-5-methyl-phenyl | CH$_3$ | 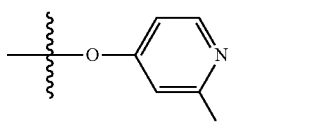 | 3 (a) | 6 | 507.2 (M + H) |
| 657 | 2-cyano-5-methyl-phenyl | CH$_3$ | 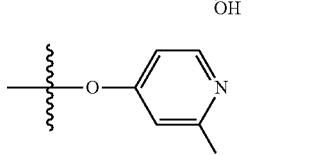 | 3 (a) | 5 | 514.3 (M + H) |
| 658 | 2-fluoro-5-methoxy-phenyl | CH$_3$ | 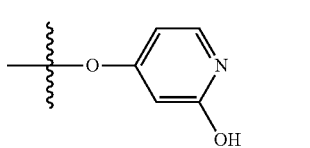 [SMILES: *Oc1ccnc(O)c1] | 3 (a) | 4 | 555.3 (M + H) |
| 659 | 2-cyano-5-methyl-phenyl | CH$_3$ | 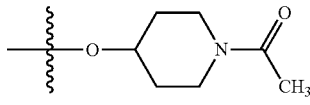 [SMILES: *OC1CCN(C(C)=O)CC1] | 3 (a) | 7 | 546.3 (M + H) |
| 660 | 2-chloro-5-methoxy-phenyl | CH$_3$ | 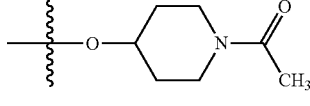 [SMILES: *OC1CCN(C(C)=O)CC1] | 3 (a) | 26 | 571.3 (M + H), CP |
| 661 | 2,5-difluoro-phenyl | CH$_3$ | 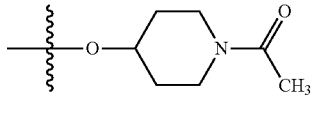 | 3 (a) | 2 | 543.3 (M + H) |
| 662 | 2-fluoro-5-methoxy-phenyl | CH$_3$ | 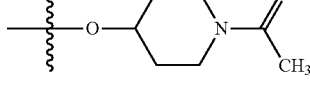 | 3 (a) | 4 | 458.3 (M + H) |
| 663 | 2-fluoro-phenyl | CH$_3$ | 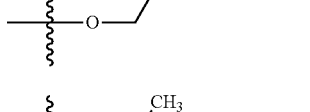 | 3 (a) | 9 | 428.3 (M + H) |
| 664 | 2,5-dichloro-phenyl | CH$_3$ | 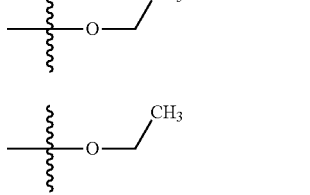 | 3 (a) | 4 | 478.2 (M + H), CP |
| 665 | 2-fluoro-5-methoxy-phenyl | CH$_3$ |  | 3 (a) | 33 | 537.3 (M + H) |

TABLE 7-continued

Example compounds of the formula Ib

| Example no. | Ar | R1 | —Z—R3 | Synthesis | Yield (%) | MS (m/e) |
|---|---|---|---|---|---|---|
| 666 | 5-chloro-2-fluoro-phenyl | CH₃ | —O-(4-pyridyl-2-OCH₃) | 3 (a) | 21 | 541.3 (M + H), CP |
| 667 | 2-cyano-5-methyl-phenyl | CH₃ | —O-(4-pyridyl-2-OCH₃) | 3 (a) | 12 | 528.4 (M + H) |
| 668 | 2,5-difluoro-phenyl | CH₃ | —O-(4-pyridyl-2-OCH₃) | 3 (a) | 34 | 525.3 (M + H) |
| 669 | 2,5-dichloro-phenyl | CH₃ | —O-(4-pyridyl-2-OCH₃) | 3 (a) | 3 | 557.2 (M + H), CP |
| 670 | 2-chloro-5-methoxy-phenyl | CH₃ | —O-(4-pyridyl-2-OCH₃) | 3 (a) | 3 | 553.3 (M + H), CP |
| 671 | 2-fluoro-phenyl | CH₃ | —O-(4-pyridyl-2-OCH₃) | 3 (a) | 4 | 505.4 (M + H) |
| 672 | 2-fluoro-5-methyl-phenyl | CH₃ | —O-(4-pyridyl-2-OCH₃) | 3 (a) | 4 | 519.4 (M + H) |
| 673 | 2-cyano-5-methyl-phenyl | CH₃ | —O—CH₂CH₃ | 3 (a) | 3 | 449.3 (M + H) |
| 674 | 2,5-difluoro-phenyl | CH₃ | —O—CH₂CH₃ | 3 (a) | 2 | 446.2 (M + H) |
| 675 | 2-chloro-5-methoxy-phenyl | CH₃ | —O—CH₂CH₃ | 3 (a) | 5 | 474.2 (M + H), CP |
| 676 | 5-chloro-2-fluoro-phenyl | CH₃ | —O—CH₂CH₃ | 3 (a) | 6 | 462.2 (M + H), CP |

TABLE 7-continued

Example compounds of the formula Ib

| Example no. | Ar | R1 | —Z—R3 | Synthesis | Yield (%) | MS (m/e) |
|---|---|---|---|---|---|---|
| 677 | 2-fluoro-5-methyl-phenyl | CH₃ | 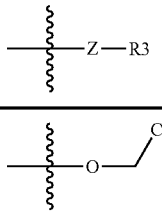 | 3 (a) | 4 | 442.2 (M + H) |
| 678 | 2-fluoro-5-methoxy-phenyl | CH₃ | 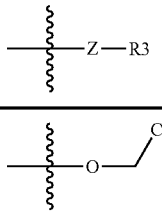 | 3 (a) | 35 | 522.2 (M + H) |
| 679 | 5-chloro-2-fluoro-phenyl | CH₃ | 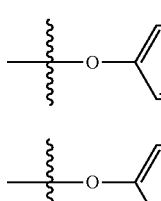 | 3 (a) | 30 | 526.2 (M + H), CP |
| 680 | 2-fluoro-phenyl | CH₃ | 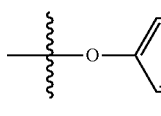 | 3 (a) | 28 | 492.2 (M + H) |
| 681 | 2-chloro-5-methoxy-phenyl | CH₃ | 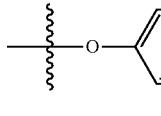 | 3 (a) | 36 | 538.2 (M + H), CP |
| 682 | 2,5-difluoro-phenyl | CH₃ | 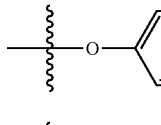 | 3 (a) | 17 | 510.2 (M + H) |
| 683 | 2-fluoro-5-methyl-phenyl | CH₃ | 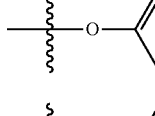 | 3 (a) | 34 | 506.2 (M + H) |
| 684 | 2,5-dichloro-phenyl | CH₃ | 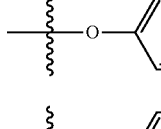 | 3 (a) | 12 | 542.2 (M + H), CP |
| 685 | 2-cyano-5-methyl-phenyl | CH₃ | 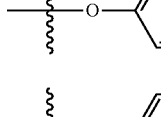 | 3 (a) | 20 | 513.3 (M + H) |
| 686 | 2-fluoro-5-methyl-phenyl | CH₃ | 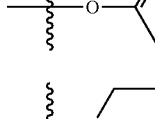 | 3 (a) | 37 | 513.3 (M + H) |
| 687 | 5-chloro-2-fluoro-phenyl | CH₃ | 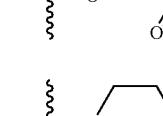 | 3 (a) | 21 | 533.2 (M + H), CP |
| 688 | 2-fluoro-phenyl | CH₃ | 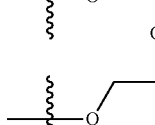 | 3 (a) | 46 | 499.3 (M + H) |
| 689 | 2-chloro-5-methoxy-phenyl | CH₃ | 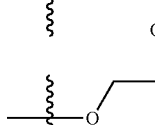 | 3 (a) | 25 | 545.3 (M + H), CP |

TABLE 7-continued

Example compounds of the formula Ib

| Example no. | Ar | R1 | —Z—R3 | Synthesis | Yield (%) | MS (m/e) |
|---|---|---|---|---|---|---|
| 690 | 2,5-dichloro-phenyl | CH$_3$ | 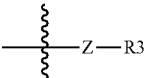 | 3 (a) | 26 | 549.2 (M + H), CP |
| 691 | 2,5-difluoro-phenyl | CH$_3$ | 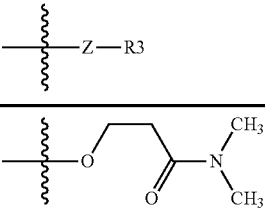 | 3 (a) | 54 | 517.2 (M + H) |
| 692 | 2-fluoro-5-methoxy-phenyl | CH$_3$ | 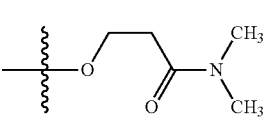 | 3 (a) | 37 | 529.3 (M + H) |
| 693 | 2-fluoro-5-methyl-phenyl | CH$_3$ | 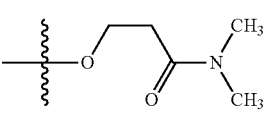 | 3 (a) | 28 | 534.3 (M + H) |
| 694 | 5-chloro-2-fluoro-phenyl | CH$_3$ | 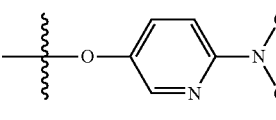 | 3 (a) | 40 | 554.2 (M + H), CP |
| 695 | 2-fluoro-phenyl | CH$_3$ | 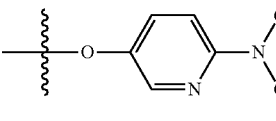 | 3 (a) | 60 | 520.2 (M + H) |
| 696 | 2,5-dichloro-phenyl | CH$_3$ | 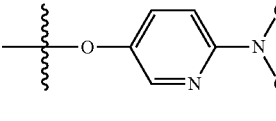 | 3 (a) | 39 | 570.2 (M + H), CP |
| 697 | 2,5-difluoro-phenyl | CH$_3$ | 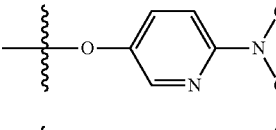 | 3 (a) | 43 | 538.2 (M + H) |
| 698 | 2-fluoro-5-methoxy-phenyl | CH$_3$ | 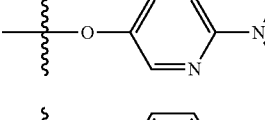 | 3 (a) | 55 | 550.2 (M + H) |
| 699 | 2-chloro-5-methoxy-phenyl | CH$_3$ | 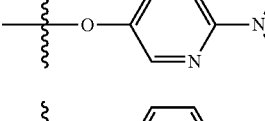 | 3 (a) | 49 | 566.2 (M + H), CP |

(a) In step (ii) of the procedure of example 3, potassium hydroxide and dimethyl sulfoxide were employed instead of sodium hydride and tetrahydrofuran.

Exemplary NMR Data of Example Compounds

Example 597

$^1$H-NMR (DMSO-d$_6$): δ (ppm)=2.54 (s, 1H), 2.60 (s, 3H), 6.44-6.50 (m, 1H), 7.22 (d, J=8.8 Hz, 2H), 7.49 (t, J=9.5 Hz, 1H), 7.60-7.67 (m, 2H), 7.74-7.79 (m, 1H), 7.87 (dd, J=2.7, 6.0 Hz, 1H), 8.08 (d, J=8.8 Hz, 2H), 11.11 (s, 1H), 13.63 (s, 1H).

Example 600

$^1$H-NMR (DMSO-d$_6$): δ (ppm)=2.32 (s, 3H), 2.54 (s, 1H), 2.60 (s, 3H), ), 6.44-6.49 (m, 1H), 7.20 (d, J=8.8 Hz, 2H), 7.27 (dd, J=8.4, 10.3 Hz, 1H), 7.44-7.48 (m, 1H), 7.60-7.65 (m, 2H), 7.71 (dd, J=2.1, 6.9 Hz, 1H), 8.05 (d, J=8.8 Hz, 2H), 10.92 (s, 1H), 13.61 (s, 1H).

Example 646

$^1$H-NMR (DMSO-d$_6$): δ (ppm)=1.70-1.91 (m, 2H), 1.94-2.14 (m, 2H), 2.05 (s, 3H), 2.51 (s, 3H), 3.48-3.72 (m, 4H), 5.69-5.76 (m, 1H), 7.27 (d, J=8.8 Hz, 2H), 7.51 (t, J=9.2 Hz, 1H), 7.76-7.82 (m, 1H), 7.87 (dd, J=2.6, 6.0 Hz, 1H), 8.31 (d, J=8.8 Hz, 2H), 11.10 (s, 1H), 13.42 (br, 1H).

Example 658

$^1$H-NMR (DMSO-d$_6$): δ (ppm)=1.70-1.90 (m, 2H), 1.95-2.12 (m, 2H), 2.05 (s, 3H), 2.52 (s, 3H), 3.49-3.72 (m, 4H), 3.78 (s, 3H), 5.68-5.75 (m, 1H), 7.20-7.25 (m, 1H), 7.26 (d, J=8.8 Hz, 2H), 7.31-7.38 (m, 2H), 8.29 (d, J=8.8 Hz, 2H), 10.96 (s, 1H), 13.41 (br, 1H).

Example 661

$^1$H-NMR (DMSO-d$_6$): δ (ppm)=1.70-1.90 (m, 2H), 1.95-2.13 (m, 2H), 2.05 (s, 3H), 2.51 (s, 3H), 3.50-3.72 (m, 4H), 5.69-5.75 (m, 1H), ), 7.27 (d, J=8.8 Hz, 2H), 7.52 (dt, J=4.2, 9.2 Hz, 1H), 7.56-7.63 (m, 1H), 7.69-7.74 (m, 1H), 8.29 (d, J=8.8 Hz, 2H), 11.10 (s, 1H), 13.42 (s, 1H).

Pharmacological Testing

The ability of the compounds of the invention to inhibit SGK-1 was assessed in an enzymatic activity assay by determining their effect on the ability of the isolated SGK enzyme to catalyze the transfer of phosphate from adenosine triphosphate (ATP) to serine/threonine residues in a labeled substrate peptide, and in cellular assays by determining their effect on cellular function. In one of the cellular assays, the SGK-1 dependent phosphorylation of glycogen synthase kinase 3beta (GSK3beta) in U2OS cells was measured, in another one, a functional electrophysiological assay, the SGK-1 dependent activation of epithelial Na$^+$ channel (ENaC) currents in A6 cell monolayers, and in another one chondrocyte hypertrophic differentiation in mouse chondrogenic ATDC5 cells.

A) Enzymatic Activity Assay

The compounds were tested for serum and glucocorticoid-regulated kinase 1 (SGK-1) inhibitory activity in a substrate phosphorylation assay designed to measure the ability of the isolated enzyme to catalyze the transfer of phosphate from ATP to serine/threonine residues in a fluorescein-labeled substrate peptide, using recombinant human SGK-1 enzyme produced in a baculovirus system (Biomol, Hamburg, Germany, Cat. No. 4-331). The synthesized fluorescent labeled peptide substrate contained (5(6)-Carboxyfluorescein)-RPRAATF-NH$_2$. The phosphorylated substrate peptide and non-phosphorylated substrate peptide were separated with caliper life science's lab-chip technology based on a micro fluidics method. All fluid flow was established on the chip by applying a vacuum of a few psi to the waste well transporting fluid from various sources through interconnecting channels. Because the phosphoryl group is doubly negatively charged, under the pressure-driven hydrodynamic flow and the voltage-driven flow within the electric field, the fluorescent labeled peptide substrate and its phosphorylation product appear at different times in the detection window to the detection point. Substrate turnover can thus be determined as the ratio of the product peak area and the sum of substrate peak area and product peak area.

The enzyme reaction was carried out in a buffer containing 25 mM Tris-HCl (pH 7.4), 5 mM MgCl$_2$, 2 mM MnCl$_2$, 2 mM DTT, and 0.03% bovine serum albumine. The enzyme was pre-incubated with the test compound for 30 min at 24° C. The kinase reaction was initiated by addition of the substrate mixture containing the peptide substrate (final concentration 1 μM) and ATP (final concentration 10 μM).

After 60 min incubation at 37° C., the enzyme reaction was terminated by adding a buffer containing 100 mM Hepes (pH 7.4) and 35 mM EDTA.

For the determination of the compound dose response, a 10 mM DMSO stock solution was diluted and tested in a ten-point, three-fold dilution series run in duplicate beginning at 30 μM final concentration. Data were analyzed using a four-parameter curve fit with a fixed minimum and maximum experimentally defined as the average positive and negative controls on each plate. IC$_{50}$ values (in μM (micromol/liter)) for inhibition of SGK-1 determined in this assay are given in Table 8.

TABLE 8

IC$_{50}$ values for inhibition of SGK-1 enzymatic activity by example compounds

| Example no. | IC$_{50}$ [μM] |
|---|---|
| 1 | <0.0012 |
| 2 | 0.0057 |
| 3 | <0.0012 |
| 4 | <0.0015 |
| 5 | <0.0012 |
| 6 | 0.0065 |
| 7 | <0.0015 |
| 8 | 0.0089 |
| 10 | <0.0012 |
| 11 | 0.0019 |
| 12 | 0.051 |
| 13 | 0.0064 |
| 14 | 0.0063 |
| 15 | <0.0012 |
| 16 | <0.0012 |
| 17 | <0.0012 |
| 19 | 0.0091 |
| 20 | 0.039 |
| 21 | 0.0015 |
| 22 | 0.080 |
| 23 | <0.0012 |
| 24 | <0.0012 |
| 25 | <0.0012 |
| 26 | <0.0012 |
| 27 | <0.0012 |
| 31 | 0.0023 |
| 32 | 0.0051 |
| 34 | 0.0036 |
| 35 | 0.0032 |
| 36 | <0.0012 |
| 37 | 0.0045 |
| 39 | <0.0012 |
| 40 | <0.0012 |
| 41 | <0.0012 |
| 42 | 0.0014 |
| 43 | <0.0015 |
| 44 | 0.0079 |
| 45 | 0.0025 |
| 46 | <0.0012 |
| 47 | 0.020 |
| 48 | 0.0042 |
| 49 | 0.19 |
| 50 | <0.0012 |
| 51 | <0.0012 |
| 52 | <0.0012 |
| 53 | 0.0034 |
| 54 | 0.014 |
| 55 | 0.0024 |
| 56 | 0.032 |
| 57 | 0.0083 |
| 58 | 0.0071 |
| 59 | 0.12 |
| 60 | 0.0040 |
| 61 | <0.0012 |
| 62 | <0.0012 |
| 63 | <0.0012 |
| 64 | 0.0042 |
| 65 | 0.074 |
| 66 | 0.018 |

TABLE 8-continued

IC$_{50}$ values for inhibition of SGK-1 enzymatic activity by example compounds

| Example no. | IC$_{50}$ [μM] |
| --- | --- |
| 67 | 0.014 |
| 68 | 0.017 |
| 69 | 0.016 |
| 70 | 0.058 |
| 71 | 0.16 |
| 72 | 0.083 |
| 73 | 0.0067 |
| 74 | 0.0055 |
| 75 | 0.0048 |
| 76 | 0.0057 |
| 77 | 0.0039 |
| 78 | 0.0036 |
| 79 | <0.0015 |
| 80 | <0.0015 |
| 81 | 0.011 |
| 82 | 0.012 |
| 83 | 0.0020 |
| 84 | 0.0032 |
| 85 | 0.0041 |
| 86 | 0.011 |
| 87 | 0.0068 |
| 88 | 0.0067 |
| 89 | <0.0015 |
| 90 | 0.0022 |
| 91 | <0.0015 |
| 92 | 0.0021 |
| 93 | 2.4 |
| 94 | 8.1 |
| 95 | <0.0015 |
| 96 | <0.0015 |
| 97 | 0.0020 |
| 98 | 0.0017 |
| 99 | 0.0014 |
| 100 | 0.0011 |
| 101 | 0.0021 |
| 102 | 0.0017 |
| 103 | 0.0023 |
| 104 | 0.085 |
| 105 | 0.14 |
| 106 | 2.7 |
| 107 | 0.0025 |
| 108 | 0.025 |
| 109 | 0.016 |
| 110 | 0.014 |
| 111 | 0.029 |
| 112 | 0.0033 |
| 113 | 0.0030 |
| 114 | 0.0077 |
| 115 | 0.0037 |
| 116 | <0.0015 |
| 117 | 0.0023 |
| 118 | 0.0025 |
| 119 | <0.0015 |
| 120 | <0.0015 |
| 121 | <0.0015 |
| 122 | <0.0015 |
| 123 | 0.0099 |
| 124 | 0.024 |
| 125 | 0.0020 |
| 126 | 0.046 |
| 127 | 0.0043 |
| 128 | 0.0027 |
| 129 | <0.0015 |
| 130 | 0.013 |
| 131 | 0.0049 |
| 132 | 0.017 |
| 133 | <0.0015 |
| 134 | <0.0015 |
| 135 | 0.012 |
| 136 | 0.041 |
| 137 | 0.018 |
| 138 | 0.044 |
| 139 | 0.082 |
| 140 | 0.0015 |
| 141 | 0.0065 |
| 142 | 0.0012 |
| 143 | 0.010 |
| 144 | 0.0035 |
| 145 | 0.0041 |
| 146 | 0.047 |
| 147 | 0.0015 |
| 148 | 0.017 |
| 149 | <0.0015 |
| 150 | <0.0015 |
| 151 | <0.0015 |
| 152 | <0.0015 |
| 153 | <0.0015 |
| 154 | 0.0016 |
| 155 | <0.0015 |
| 156 | <0.0015 |
| 157 | <0.0015 |
| 158 | 0.0074 |
| 159 | 0.0061 |
| 160 | 0.010 |
| 161 | 0.019 |
| 162 | 0.018 |
| 163 | 0.0085 |
| 164 | 0.040 |
| 165 | 0.11 |
| 166 | 4.5 |
| 167 | 2.7 |
| 168 | 0.38 |
| 169 | 0.11 |
| 170 | 0.054 |
| 171 | 0.040 |
| 172 | 0.86 |
| 173 | 0.33 |
| 174 | 0.46 |
| 175 | 0.019 |
| 176 | 2.1 |
| 178 | 0.35 |
| 179 | 2.2 |
| 181 | 23 |
| 182 | 2.1 |
| 183 | 6.5 |
| 184 | 1.2 |
| 185 | 0.87 |
| 186 | 1.9 |
| 187 | 6.2 |
| 188 | 0.0034 |
| 189 | 0.0051 |
| 190 | 0.0047 |
| 191 | 0.021 |
| 192 | 0.0028 |
| 193 | 0.0020 |
| 194 | 0.0023 |
| 195 | 0.0054 |
| 196 | 0.0046 |
| 197 | 0.0030 |
| 198 | <0.0015 |
| 199 | 0.026 |
| 200 | 27 |
| 202 | 15 |
| 203 | <0.0015 |
| 204 | <0.0015 |
| 205 | 0.70 |
| 206 | 1.1 |
| 207 | <0.0015 |
| 208 | 0.0082 |
| 209 | <0.0015 |
| 210 | <0.0015 |
| 211 | 0.0023 |
| 212 | <0.0015 |
| 213 | 0.0064 |
| 214 | 0.069 |
| 215 | <0.0015 |
| 216 | 1.9 |
| 217 | 0.0091 |
| 218 | <0.0015 |
| 219 | <0.0015 |

TABLE 8-continued

IC$_{50}$ values for inhibition of SGK-1 enzymatic activity by example compounds

| Example no. | IC$_{50}$ [μM] |
|---|---|
| 220 | <0.0015 |
| 221 | <0.0015 |
| 222 | 0.0027 |
| 223 | <0.0015 |
| 224 | <0.0015 |
| 225 | 0.0026 |
| 226 | 0.0025 |
| 227 | <0.0015 |
| 228 | 0.0031 |
| 229 | 1.0 |
| 230 | 0.0052 |
| 231 | 1.3 |
| 232 | 0.0095 |
| 233 | 0.00085 |
| 234 | <0.00051 |
| 235 | 0.016 |
| 236 | 0.0050 |
| 237 | 0.016 |
| 238 | 0.18 |
| 239 | 0.0048 |
| 240 | 0.027 |
| 241 | 0.072 |
| 242 | 0.0034 |
| 243 | 0.0034 |
| 244 | 0.0029 |
| 245 | 0.0037 |
| 246 | 0.0068 |
| 247 | 0.0065 |
| 248 | 0.0041 |
| 249 | 0.0030 |
| 250 | 0.026 |
| 251 | 0.0021 |
| 252 | 0.0011 |
| 253 | 0.0017 |
| 254 | 0.0015 |
| 255 | 0.0019 |
| 256 | 0.0013 |
| 257 | 0.0015 |
| 258 | 0.0028 |
| 259 | 0.0013 |
| 260 | 0.0029 |
| 261 | 0.00076 |
| 262 | 0.055 |
| 263 | 0.099 |
| 264 | 0.0012 |
| 265 | 0.00059 |
| 266 | 0.0032 |
| 287 | 0.0045 |
| 288 | 0.0023 |
| 289 | 0.023 |
| 290 | 0.0033 |
| 291 | 0.0025 |
| 292 | 0.014 |
| 293 | 0.0032 |
| 294 | 0.0035 |
| 295 | 0.0026 |
| 296 | 0.0027 |
| 297 | 0.0018 |
| 298 | 0.0023 |
| 299 | 0.0033 |
| 300 | 0.0011 |
| 301 | 0.0015 |
| 302 | 0.0019 |
| 303 | 0.0022 |
| 304 | 0.0023 |
| 305 | 0.010 |
| 306 | 0.0071 |
| 307 | 0.58 |
| 308 | 0.0062 |
| 309 | 0.0028 |
| 310 | 0.13 |
| 311 | 0.24 |
| 312 | 0.0060 |
| 313 | 0.0020 |
| 314 | 0.0045 |

TABLE 8-continued

IC$_{50}$ values for inhibition of SGK-1 enzymatic activity by example compounds

| Example no. | IC$_{50}$ [μM] |
|---|---|
| 315 | 0.0079 |
| 316 | 0.48 |
| 317 | 0.011 |
| 318 | 0.95 |
| 319 | 0.0045 |
| 320 | 0.0037 |
| 321 | 0.0069 |
| 322 | 0.0026 |
| 323 | 0.012 |
| 324 | 0.33 |
| 325 | 1.1 |
| 326 | 0.0091 |
| 327 | 0.42 |
| 328 | 0.17 |
| 329 | 0.69 |
| 330 | 0.10 |
| 331 | 0.29 |
| 332 | 0.027 |
| 333 | 0.014 |
| 334 | 0.020 |
| 335 | 0.0083 |
| 336 | 0.0055 |
| 337 | 1.4 |
| 338 | 0.0016 |
| 339 | 0.0013 |
| 340 | 0.0043 |
| 341 | 0.0049 |
| 342 | 0.0060 |
| 343 | 0.0038 |
| 344 | 0.0050 |
| 345 | 0.0048 |
| 346 | 0.0032 |
| 347 | 0.0034 |
| 348 | 0.0081 |
| 349 | 0.0084 |
| 350 | 0.0049 |
| 351 | 0.0038 |
| 352 | 0.011 |
| 353 | 0.0038 |
| 354 | 0.11 |
| 355 | 0.013 |
| 357 | 0.0036 |
| 358 | 0.0027 |
| 359 | 0.0024 |
| 360 | 0.11 |
| 361 | 0.0018 |
| 362 | 0.0038 |
| 363 | 0.034 |
| 364 | 0.0065 |
| 365 | 0.0027 |
| 366 | 0.022 |
| 367 | 0.0055 |
| 368 | 0.0021 |
| 369 | 0.0023 |
| 370 | 0.020 |
| 371 | 0.0039 |
| 372 | 0.049 |
| 373 | 0.0061 |
| 374 | 0.0046 |
| 375 | 0.010 |
| 376 | 0.0057 |
| 377 | 0.0053 |
| 378 | 0.0058 |
| 379 | 0.0028 |
| 380 | 0.012 |
| 381 | 5.6 |
| 382 | 0.27 |
| 383 | 0.86 |
| 385 | 0.24 |
| 386 | 0.27 |
| 387 | 0.080 |
| 388 | 0.087 |
| 389 | 0.20 |
| 390 | 0.12 |
| 391 | 0.0096 |

TABLE 8-continued

IC$_{50}$ values for inhibition of SGK-1 enzymatic activity by example compounds

| Example no. | IC$_{50}$ [μM] |
| --- | --- |
| 392 | 0.0069 |
| 393 | 1.0 |
| 394 | 0.12 |
| 396 | 0.39 |
| 397 | 0.0082 |
| 398 | 0.025 |
| 399 | 0.0042 |
| 400 | 0.0086 |
| 401 | 0.0053 |
| 402 | 0.013 |
| 403 | 0.0057 |
| 404 | 0.0047 |
| 405 | 0.0041 |
| 406 | 0.0047 |
| 407 | 0.011 |
| 408 | 0.0063 |
| 417 | 0.0086 |
| 418 | 0.040 |
| 419 | 0.026 |
| 420 | 0.74 |
| 421 | 0.028 |
| 422 | 0.040 |
| 423 | 0.66 |
| 424 | 0.013 |
| 425 | 0.048 |
| 426 | 0.011 |
| 434 | 0.0018 |
| 435 | 0.092 |
| 436 | 0.13 |
| 437 | 0.10 |
| 438 | 0.085 |
| 439 | 0.0025 |
| 440 | <0.0015 |
| 441 | 0.021 |
| 442 | 0.029 |
| 443 | 0.094 |
| 444 | 0.0034 |
| 445 | 0.0016 |
| 446 | 0.0016 |
| 447 | <0.0015 |
| 448 | <0.0015 |
| 449 | 0.0018 |
| 450 | 0.012 |
| 451 | 0.00057 |
| 452 | 0.0020 |
| 453 | 0.0016 |
| 454 | 0.14 |
| 455 | <0.0015 |
| 456 | 0.0062 |
| 457 | 0.14 |
| 458 | 0.0068 |
| 459 | 0.0067 |
| 460 | 2.7 |
| 461 | <0.0015 |
| 462 | 0.0047 |
| 463 | 0.0025 |
| 464 | <0.0012 |
| 465 | <0.0015 |
| 466 | <0.0015 |
| 467 | <0.0015 |
| 468 | <0.0015 |
| 469 | 0.091 |
| 470 | 0.011 |
| 471 | 0.097 |
| 472 | 0.0015 |
| 473 | 0.032 |
| 474 | 0.012 |
| 475 | 3.1 |
| 476 | 0.0039 |
| 477 | 0.0048 |
| 478 | <0.0015 |
| 479 | 0.016 |
| 480 | <0.0015 |
| 481 | 0.0031 |
| 482 | 0.0037 |
| 483 | 0.0027 |
| 484 | <0.0015 |
| 485 | <0.0015 |
| 486 | <0.0015 |
| 487 | <0.0015 |
| 488 | <0.0015 |
| 489 | <0.0015 |
| 490 | 0.088 |
| 491 | 0.0018 |
| 492 | 0.0038 |
| 493 | 0.18 |
| 494 | 0.32 |
| 495 | 0.065 |
| 496 | 0.0062 |
| 497 | 0.020 |
| 499 | 0.0089 |
| 500 | 0.0027 |
| 501 | 0.040 |
| 502 | 0.018 |
| 503 | 0.029 |
| 504 | 0.012 |
| 505 | 0.047 |
| 506 | 0.11 |
| 507 | 1.5 |
| 508 | 15 |
| 509 | 0.31 |
| 510 | 1.5 |
| 511 | 1.3 |
| 512 | 1.5 |
| 513 | 0.068 |
| 514 | 0.25 |
| 515 | 0.35 |
| 516 | 0.30 |
| 517 | 0.42 |
| 518 | 3.6 |
| 519 | 0.19 |
| 520 | <0.0015 |
| 521 | 0.065 |
| 522 | 0.0024 |
| 523 | 1.9 |
| 524 | 0.40 |
| 525 | 0.025 |
| 526 | 0.41 |
| 527 | <0.00051 |
| 528 | 0.0051 |
| 529 | 0.0047 |
| 530 | 1.6 |
| 531 | 2.1 |
| 532 | 2.2 |
| 533 | 0.0014 |
| 534 | <0.0015 |
| 536 | 0.0020 |
| 537 | 0.0011 |
| 538 | 0.0030 |
| 539 | 0.0092 |
| 540 | 0.011 |
| 541 | 0.0022 |
| 542 | 0.0068 |
| 543 | 0.027 |
| 544 | 0.0030 |
| 545 | 0.0016 |
| 546 | 0.013 |
| 547 | 0.021 |
| 548 | 0.65 |
| 549 | 0.0077 |
| 550 | 0.0055 |
| 551 | 0.029 |
| 552 | 2.2 |
| 553 | 0.0041 |
| 554 | 0.017 |
| 555 | <0.0015 |
| 556 | 0.0017 |
| 557 | 0.096 |
| 558 | 0.013 |
| 559 | 0.019 |

TABLE 8-continued

IC$_{50}$ values for inhibition of SGK-1 enzymatic activity by example compounds

| Example no. | IC$_{50}$ [μM] |
|---|---|
| 560 | 0.034 |
| 561 | 0.0078 |
| 562 | 0.015 |
| 563 | 0.052 |
| 564 | 1.4 |
| 565 | 0.015 |
| 566 | 0.015 |
| 568 | 0.0015 |
| 569 | 0.0017 |
| 570 | 0.0020 |
| 571 | <0.0015 |
| 572 | 0.0052 |
| 573 | 0.71 |
| 574 | 0.0036 |
| 575 | 0.10 |
| 576 | 0.43 |
| 577 | 0.13 |
| 578 | 0.43 |
| 579 | 0.0038 |
| 580 | 0.0027 |
| 581 | 0.0024 |
| 582 | 0.085 |
| 583 | 0.045 |
| 584 | 0.16 |
| 585 | 0.0025 |
| 586 | 0.0013 |
| 587 | 0.0052 |
| 588 | 0.0067 |
| 589 | <0.0005 |
| 590 | 0.0054 |
| 591 | 0.0025 |
| 592 | 0.0020 |
| 593 | 0.0057 |
| 594 | 0.0015 |
| 595 | 0.0063 |
| 596 | <0.0005 |
| 597 | 0.0021 |
| 598 | 0.0055 |
| 599 | 0.0026 |
| 600 | 0.0021 |
| 601 | 0.0023 |
| 602 | 0.0024 |
| 603 | 0.0040 |
| 604 | 0.0056 |
| 605 | 0.023 |
| 606 | 0.0071 |
| 607 | 0.0094 |
| 608 | 0.0017 |
| 609 | 0.0026 |
| 610 | 0.0032 |
| 611 | 0.0047 |
| 612 | 0.012 |
| 613 | 0.019 |
| 614 | 0.097 |
| 615 | 0.0046 |
| 616 | 0.012 |
| 617 | 0.0073 |
| 618 | 0.0024 |
| 619 | 0.0035 |
| 620 | 0.0039 |
| 621 | 0.0035 |
| 622 | 0.037 |
| 623 | 0.066 |
| 624 | 0.037 |
| 625 | 0.0060 |
| 626 | 0.0029 |
| 627 | 0.0055 |
| 628 | 0.0029 |
| 629 | 0.0018 |
| 630 | 0.0046 |
| 631 | 0.0041 |
| 632 | 0.0037 |
| 633 | 0.0018 |
| 634 | 0.023 |
| 635 | 0.0035 |
| 636 | 0.0028 |
| 637 | 0.0029 |
| 638 | 0.011 |
| 639 | 0.0069 |
| 640 | 0.0054 |
| 641 | 0.0032 |
| 642 | 0.0022 |
| 643 | 0.0037 |
| 644 | 0.0050 |
| 645 | 0.0054 |
| 646 | 0.011 |
| 647 | 0.0040 |
| 648 | 0.0039 |
| 649 | 0.0049 |
| 650 | 0.0071 |
| 651 | 0.025 |
| 652 | 0.017 |
| 653 | 0.030 |
| 654 | 0.037 |
| 655 | 0.0051 |
| 656 | 0.0019 |
| 657 | 0.0029 |
| 658 | 0.0058 |
| 659 | 0.0032 |
| 660 | 0.0058 |
| 661 | 0.0028 |
| 662 | 0.0095 |
| 663 | 0.026 |
| 664 | 0.013 |
| 665 | 0.0070 |
| 666 | 0.025 |
| 667 | 0.011 |
| 668 | 0.061 |
| 669 | 0.031 |
| 670 | 0.025 |
| 671 | 0.067 |
| 672 | 0.021 |
| 673 | 0.0081 |
| 674 | 0.021 |
| 675 | 0.015 |
| 676 | 0.023 |
| 677 | 0.0080 |
| 678 | 0.0023 |
| 679 | 0.0044 |
| 680 | 0.0059 |
| 681 | 0.0066 |
| 682 | 0.0073 |
| 683 | 0.0030 |
| 684 | 0.0060 |
| 685 | 0.0026 |
| 686 | 0.011 |
| 687 | 0.015 |
| 688 | 0.092 |
| 689 | 0.013 |
| 690 | 0.014 |
| 691 | 0.033 |
| 692 | 0.0065 |
| 693 | 0.029 |
| 694 | 0.025 |
| 695 | 0.045 |
| 696 | 0.060 |
| 697 | 0.026 |
| 698 | 0.010 |
| 699 | 0.025 |

B) Determination of the Effect on SGK-1 Dependent Phosphorylation of GSK3beta in U2OS Cells It has been shown that glycogen synthase kinase 3beta (GSK3beta) is a phosphorylation target of SGK-1 (Sakoda, H. et al., Differing Roles of Akt and Serum- and Glucocorticoid-regulated Kinase in Glucose Metabolism, DNA Synthesis, and Oncogenic Activity, J. Biol. Chem. 2003, 278, 25802-25807). The ability of the compounds of the invention to inhibit the enzymatic activity of serum and glucocorticoid-regulated kinase 1 (SGK-1) was determined in a cellular assay which measures the SGK-1 dependent phosphorylation of GSK3beta in U2OS cells (ATCC HTB-96) overexpressing recombinant SGK-1 and GSK3beta after transfection with recombinant BacMam viruses.

U2OS cells were cultured in 1:1 Dulbecco modified Eagle medium/Ham's F12 and 10% heat-inactivated fetal calf serum (FCS Gold) at 37° C., 7% $CO_2$ and 95% relative humidity. Cells were harvested and mixed with BacMam virus containing expression constructs for human SGK-1 (amino acids S61-L431 with serine 422 replaced by aspartate) at an MOI (multiplicity of infection) of 50 and BacMam virus containing expression constructs for human GSK3beta at an MOI of 125. Cell suspension mixed with BacMam viruses was seeded in 96 well pCLEAR plates (Greiner) at $3 \times 10^4$ cells per well in 250 μl medium. To reduce background phosphorylation of GSK3beta by AKT, 1 μl of a selective Akt-inhibitor was added (final concentration 2 μM). 1 μl of a solution of the test compound at 250×final concentration was added. Cells are incubated at 37° C., 7% $CO_2$ and 95% relative humidity. After 6 h, medium was aspirated and 50 μl of fixation solution (3.7% paraformaldehyde in phosphate buffered saline (PBS)) was added for 10 min. After removing the fixation solution, cells were permeabilised by adding 200 μl PBT (0.2% Triton X-100 in PBS) per well for 5 min. After removing PBT, cells were blocked by adding 200 μl of blocking solution (1% bovine serum albumine in PBS) per well. Blocking solution was removed and 50 μl of primary antibody (rabbit anti-phospho-GSK-3beta (Ser9), and mouse anti-GSK-3beta) were added for 1 h. After washing the cells 3 times with PBS, 50 μl of secondary antibody (Alexa Fluor 594 goat anti-rabbit IgG, and Alexa Fluor 488 goat anti-mouse IgG) were added and incubated for 1 h in the dark. After washing the cells 3 times with PBS, 200 μl of PBS were added. Fluorescence signals were measured with the ImageXpress MICRO (Molecular Devices). $IC_{50}$ values (in μM (micromol/l)) were calculated using the ratio of phosphorylated GSK3beta to total GSK3beta to compensate for unspecific effects, and are given in Table 9.

TABLE 9

$IC_{50}$ values for inhibition of SGK-1 dependent phosphorylation of GSK3beta in U2OS cells by example compounds

| Example no. | $IC_{50}$ [μM] |
|---|---|
| 1 | 0.83 |
| 3 | 0.67 |
| 4 | 0.11 |
| 6 | 2.6 |
| 10 | 0.43 |
| 15 | 0.87 |
| 16 | 0.95 |
| 17 | 0.81 |
| 26 | 2.6 |
| 27 | 1.9 |
| 35 | 5.7 |
| 57 | 0.50 |
| 60 | 0.48 |
| 61 | 0.43 |
| 62 | 0.45 |
| 63 | 0.28 |
| 64 | 0.56 |
| 70 | 0.42 |
| 73 | 2.4 |
| 74 | 1.2 |
| 75 | 0.25 |
| 76 | 3.0 |
| 77 | 3.6 |
| 78 | 2.6 |
| 79 | 0.12 |
| 80 | 0.45 |
| 81 | 1.7 |
| 82 | 2.1 |
| 83 | 2.1 |
| 84 | 1.2 |
| 85 | 1.5 |
| 86 | 1.8 |
| 87 | 4.1 |
| 88 | 4.5 |
| 89 | 0.10 |
| 90 | 0.20 |
| 91 | 0.18 |
| 92 | 0.18 |
| 93 | 3.3 |
| 95 | 4.6 |
| 96 | 0.74 |
| 97 | 1.6 |
| 98 | 1.7 |
| 99 | 0.76 |
| 100 | 0.98 |
| 101 | 0.43 |
| 102 | 0.38 |
| 103 | 9.1 |
| 107 | 3.7 |
| 109 | 4.6 |
| 110 | 5.1 |
| 112 | 3.9 |
| 113 | 3.6 |
| 116 | 4.8 |
| 117 | 6.8 |
| 119 | 11 |
| 122 | 5.5 |
| 123 | 30 |
| 125 | 12 |
| 128 | 3.6 |
| 129 | 0.17 |
| 131 | 2.6 |
| 133 | 0.26 |
| 134 | 0.64 |
| 135 | 1.9 |
| 136 | 1.7 |
| 137 | 1.4 |
| 138 | 3.5 |
| 139 | 5.5 |
| 140 | 0.050 |
| 141 | 0.15 |
| 142 | 0.14 |
| 143 | 0.10 |
| 144 | 0.055 |
| 145 | 0.35 |
| 146 | 11 |
| 147 | 0.059 |
| 164 | 0.60 |
| 165 | 0.97 |
| 168 | 2.4 |
| 169 | 0.25 |
| 170 | 0.51 |
| 171 | 0.87 |
| 173 | 0.60 |
| 174 | 0.89 |
| 175 | 0.52 |
| 178 | 0.80 |
| 188 | 0.90 |
| 189 | 0.11 |
| 190 | 0.12 |
| 191 | 2.7 |
| 192 | 0.14 |
| 193 | 0.16 |
| 194 | 0.10 |
| 195 | 0.21 |
| 196 | 0.33 |
| 197 | 0.065 |

TABLE 9-continued

IC$_{50}$ values for inhibition of SGK-1 dependent phosphorylation of GSK3beta in U2OS cells by example compounds

| Example no. | IC$_{50}$ [µM] |
|---|---|
| 198 | 0.51 |
| 199 | 0.64 |
| 203 | 0.16 |
| 204 | 0.13 |
| 207 | 0.14 |
| 209 | 0.10 |
| 210 | 0.098 |
| 211 | 0.080 |
| 212 | 0.11 |
| 213 | 0.19 |
| 214 | 0.13 |
| 217 | 0.19 |
| 218 | 0.085 |
| 219 | 0.23 |
| 220 | 0.17 |
| 287 | 0.021 |
| 288 | 0.061 |
| 289 | 0.20 |
| 290 | 0.015 |
| 291 | 0.076 |
| 292 | 0.93 |
| 293 | 0.63 |
| 294 | 0.27 |
| 295 | 0.025 |
| 296 | 0.060 |
| 297 | 0.080 |
| 298 | 0.043 |
| 299 | 0.41 |
| 300 | 0.092 |
| 301 | 0.060 |
| 302 | 0.086 |
| 303 | 0.057 |
| 304 | 0.13 |
| 305 | 0.089 |
| 306 | 0.019 |
| 308 | 0.010 |
| 309 | 0.16 |
| 310 | 0.22 |
| 311 | 0.092 |
| 312 | 0.13 |
| 313 | 0.047 |
| 314 | 0.25 |
| 315 | 0.60 |
| 316 | 0.27 |
| 317 | 0.21 |
| 319 | 0.031 |
| 320 | 0.057 |
| 321 | 0.038 |
| 322 | 0.026 |
| 323 | 0.10 |
| 324 | 0.33 |
| 326 | 0.16 |
| 327 | 0.43 |
| 328 | 0.15 |
| 330 | 0.23 |
| 331 | 0.24 |
| 332 | 0.19 |
| 333 | 1.3 |
| 334 | 0.72 |
| 335 | 0.35 |
| 336 | 0.19 |
| 338 | 0.044 |
| 339 | 0.045 |
| 340 | 0.010 |
| 341 | 0.063 |
| 342 | 0.28 |
| 343 | 0.068 |
| 434 | 3.5 |
| 437 | 1.8 |
| 438 | 7.8 |
| 439 | 0.11 |
| 440 | 0.24 |
| 441 | 11 |
| 442 | 1.3 |
| 443 | 0.32 |
| 444 | 0.05 |
| 445 | 0.34 |
| 446 | 3.7 |
| 447 | 0.34 |
| 449 | 4.9 |
| 452 | 0.98 |
| 453 | 2.1 |
| 455 | 0.39 |
| 456 | 8.9 |
| 458 | 3.5 |
| 459 | 4.0 |
| 461 | 0.26 |
| 463 | 0.12 |
| 465 | 1.2 |
| 466 | 0.26 |
| 467 | 0.15 |
| 468 | 0.23 |
| 470 | 2.0 |
| 472 | 0.33 |
| 473 | 8.2 |
| 474 | 11 |
| 476 | 3.0 |
| 477 | 4.5 |
| 478 | 1.1 |
| 479 | 0.28 |
| 491 | 2.0 |
| 492 | 4.2 |
| 496 | 7.0 |
| 499 | 8.8 |
| 500 | 0.25 |
| 501 | 0.45 |
| 502 | 0.42 |
| 503 | 0.63 |
| 504 | 0.30 |
| 505 | 0.62 |
| 506 | 0.67 |
| 509 | 2.5 |
| 513 | 0.30 |
| 514 | 0.27 |
| 515 | 0.53 |
| 516 | 0.64 |
| 517 | 0.17 |
| 519 | 0.26 |
| 520 | 0.061 |
| 521 | 0.48 |
| 522 | 0.29 |
| 533 | 1.8 |
| 534 | 0.35 |
| 536 | 3.1 |
| 545 | 0.073 |
| 546 | 1.1 |
| 547 | 4.0 |
| 553 | 6.4 |
| 555 | 3.8 |
| 556 | 1.7 |
| 558 | 0.52 |
| 559 | 0.39 |
| 561 | 2.7 |
| 568 | 0.17 |

C) Functional Electrophysiological Assay for Determination of SGK-1 Dependent Activation of ENaC-Currents in A6 Cell Monolayers SGK-1 is up-regulated in A6 cells in response to induction of a hypoosmotic shock (Alvarez de la Rosa, D. et al.; Mechanisms of Regulation of Epithelial Sodium Channel by SGK1 in A6 Cells, J. Gen. Physiol. 2004, 124, 395-407). As a consequence of SGK-1 induction, ENaC function in the plasma membrane is upregulated and the effect of SGK-1 inhibitors on functional ENaC surface expression can be investigated with Ussing chamber technology.

Materials and methods for Ussing chamber measurement of A6 cells: The renal *Xenopus laevis* cell line A6 (Rafferty, K. A.; Mass culture of amphibia cells: methods and observations concerning stability of cell type, in: Biology of Amphibian Tumors, edited by M. Mizell, New York, Springer-Verlag, 1969, 52-81) was used for the experiments. Cells were grown in cell culture flasks (Nunc) at 28° C. in a humidified atmosphere with 4% $CO_2$. The culture medium contained a 7:3 mixture of Leibovitz's L-15 (Sigma-Aldrich)/Coon's (Sigma-Aldrich) media supplemented with 10% fetal bovine serum (PAA), 20% sterile water, 25 mM $NaHCO_3$ (Sigma-Aldrich), 100 U/ml penicillin (PAA) and 100 µg/ml streptomycin (PAA). The osmolality of the medium was 270 mOsml/kg $H_2O$). Cells were detached with accutase (PAA) and seeded for electrophysiological measurements into transwell filter inserts (polyester 0.4 µm pore size, Corning) at a density of $0.4 \times 10^6$ cells/filter. Cells were cultivated for 7-10 days, and confluent A6 cell monolayers were identified by repetitive resistance measurements in cell culture medium using an $EVOM^2$ ohmmeter (World Precision Instruments). Monolayers with a resistance of >10 kOhm were considered confluent. Filters with confluent A6 cells were transferred into a continuously perfused Ussing-chamber, and electrophysiological parameters were measured under open circuit conditions using a transepithelial clamp amplifier (EP Design). Short circuit current (I'sc) was calculated by Ohm's law. The Ringer solutions for Ussing chamber experiments contained NaCl: 122 mmol/l (isoosmotic=260 mOsml/kg $H_2O$) or 82 mmol/l (hypoosmotic=180 mOsml/kg $H_2O$); $KHCO_3$: 2.5 mmol/l; $CaCl_2$: 1 mmol/l; $MgCl_2$: 1 mmol/l; glucose: 5 mmol/l. The pH was adjusted to 8.2. All measurements were done at room temperature. Amiloride, an inhibitor of epithelial $Na^+$ channel (ENaC)-dependent ion transport, was employed at a concentration of 25 µM.

To evaluate the effects of SGK inhibitors on ENaC-mediated transepithelial currents, A6 monolayers were first equilibrated for 5 min with isoosmotic Ringer solution from both the luminal and basolateral side of the cell layer. Amiloride was applied to the luminal site to establish the basal ENaC-dependent current ($I'sc_{basal}$). Cell layers were then perfused from the basolateral side for 10 min with compounds in isotonic buffer or control isotonic buffer. SGK signaling leading to increased ENaC activity and subsequent increase in I'sc was stimulated by application of hypoosmotic Ringer-solution for 45 min to both sides of the A6 cell layer. ENaC-dependent I'sc after the hypoosmotic shock ($I'sc_{hypo}$) was determined by application of amiloride at the end of the experiment. Total changes of amiloride-sensitive Isc was calculated as $\Delta I'sc = I'sc_{hypo} - I'sc_{basal}$. The experimental protocol allows detecting and excluding compounds with an intrinsic effect on ENaC, however, there was no direct effect on ENaC by the compounds under investigation. The inhibition of $\Delta I'sc$ by the test compounds was determined relative to the $\Delta I'sc$ measured with control monolayers which were not treated with the test compound. $IC_{50}$ values (in µM (micromol/l)) were determined by fitting the data to the general dose-response equation, and are given in Table 10.

TABLE 10

$IC_{50}$ values for inhibition of SGK-1 dependent activation of ENaC-currents in A6 cell monolayers by example compounds

| Example no. | $IC_{50}$ [µM] |
|---|---|
| 3 | 3.4 |
| 4 | 3.2 |
| 61 | 1.4 |
| 83 | 1.9 |
| 310 | 10 |
| 317 | 10 |
| 346 | 2.0 |
| 349 | 3.2 |
| 446 | 0.19 |
| 447 | 0.060 |
| 461 | 0.18 |
| 467 | 0.16 |
| 468 | 0.61 |
| 492 | 1.1 |
| 519 | 1.1 |
| 520 | 0.50 |
| 555 | 0.60 |
| 556 | 2.0 |

D) Determination of the effect on chondrocyte hypertrophic differentiation in mouse chondrogenic ATDC5 cells The ATDC5 cell assay was used as in vitro model to determine the effects of the compounds of the invention on chondrocyte hypertrophic differentiation by monitoring the expression levels of collagen type X (Col10a1) as specific marker of chondrocyte hypertrophy.

Background: ATDC5 cells are a clonal mouse embryonic cell line derived from multipotent AT805 teratocarcinoma cells (Atsumi, T. et al., A chondrogenic cell line derived from a differentiating culture of AT805 teratocarcinoma cells, Cell Differ. Dev. 1990, 30, 109-116). The cells can undergo insulin-dependent chondrogenic cell differentiation entailing distinct differentiation stages starting from an undifferentiated, subconfluent stage, a condensation stage, a cartilage nodule formation stage and a calcification stage within 45 days of in vitro culture. Chondrogenic differentiation can be shown by measuring the expression of the cartilage main collagen (Col2a1) and aggrecan (AGC1) and glycosaminoglycan-staining with Alcian Blue within two weeks after insulin-triggered differentiation, and hypertrophic differentiation can be monitored by the expression of collagen type X (Col10a1), a specific marker of chondrocyte hypertrophy within 21 days of in vitro culture. (Shukunami, C. et al., Chondrogenic Differentiation of Clonal Mouse Embryonic Cell Lne ATDC5 In Vitro: Differentiation-dependent Gene Expression of Parathyroid Hormone (PTH)/PTH-related Peptide Receptor, J. Cell Biol. 1996, 133, 457-468). Growth factor BMP-2 is known to stimulate cell differentiation and can stimulate early and late-phase ATDC5 differentiation (Shukunami, C. et al., Sequential Progression of the Differentiation Program by Bone Morphogenetic Protein-2 in Chondrogenic Cell Line ATDC5, Exp. Cell Res. 1998, 241, 1-11). Thyroid hormone triiodothyronine (T3) promotes hypertrophic differentiation of growth plate chondrocytes (Robson, H. et al., Thyroid Hormone Acts Directly on Growth Plate Chondrocytes to Promote Hypertrophic Differentiation and Inhibit Clonal Expansion and Cell Proliferation, Endocrinology 2000, 141, 3887-3897). Addition of BMP2 and T3 can accelerate ATDC5 hypertrophic differentiation leading to the strong induction Col10a1 expression between 10-14 days. SGK-inhibitors were added to differentiating ATDC5 cells for 14 days and Col10a1 gene expression was quantified to determine effects on chondrocyte hypertrophic differentiation.

Cell assay description: ATDC5 cells were maintained in 300 cm² tissue culture flasks in DMEM/Ham's F12+5% FCS supplemented with 10 µg/ml human transferrin, 30 nM sodium selenite, 50 µg/ml kanamycin and grown at 37° C. in 5% $CO_2$ in 95% air. To initiate cell differentiation, $9.9 \times 10^4$ cells were plated in 24 well plates and grown for 2 days. Medium was exchanged with DMEM/Ham's F12+5% FCS supplemented with 10 µg/ml human transferrin, 30 nM sodium selenite, 50 µg/ml ascorbic acid and 1 µg/ml BMP2. The assay was run in triplicates, compounds were added in 10% DMSO, and medium changed every 2-3 days including supplementation of compound. At day 7 after initiation of cell differentiation, 1 µM T3 was used as additional supplement in the cell culture.

After two weeks of cell culture, RNA was isolated and converted to cDNA for determination of gene expression by quantitative real-time PCR. Cells were lysed in 600 µl of RLT-buffer (Qiagen) and total RNA was isolated using the RNA-easy Mini RNA isolation Kit (Qiagen) which was run on a Qiacube system (Qiagen) according to the supplier's instructions. RNA was isolated in 30 µl of pure water and the RNA content measured by UV-spectroscopy (Nanodrop, Peqlab). For cDNA synthesis 50 ng total RNA was reverse transcribed using the High Capacity cDNA Reverse Transcription Kit (Applied Biosystems, Product Number 4368813) according to the manufacturer's instructions. Briefly, a 20 µl reaction was set up, containing 4 mM dNTPs, random primers, RNAse inhibitor and 1 µl MultiScribe reverse transcriptase and incubated for 10 min at 25° C., 120 min at 37° C., 5 min at 85° C.

Quantitative Real-Time PCR: Taqman Fast PCR reaction was performed in a 20 µl volume using Taqman Fast Advanced Master Mix (Applied Biosystems, product number 4444965) and Taqman Gene expression assays for RPL37a (Applied Biosystems, product number Mm01253851_g1) as housekeeping gene and Col10a1 (Applied Biosystems, product number Mm00487041_m1) for Collagen type X expression. Briefly, 2 µl of the cDNA-reaction was combined with 10 µl 2× Taqman Fast Advanced Master Mix, 1 µl of Taqman Gene Expression Assay containing primers and 5'-Fam-labelled minor groove binding Taqman probe according to the manufacturer's instructions in fast thermal cycling 96 well plates. 40 amplification rounds were run in a Viaa7 Real Time PCR System (Applied Biosystems), with 1 sec at 95° C. for denaturing and 20 sec at 60° C. for annealing/extension. Fluorescence data were collected and converted to Ct-Values and expressed values were calculated based on the comparative Ct method (Schmittgen, T. D. et al., Analyzing real-time PCR data by the comparative C(T) method, Nature Protocols 2008, 3, 1101-1108). $IC_{50}$ values (in µM (micromol/l)) were determined by fitting the data to the general dose-response equation, and are given in Table 11.

TABLE 11

$IC_{50}$ values for the inhibition of collagen type X expression in mouse chondrogenic ATDC5 cells by example compounds

| Example no. | $IC_{50}$ [µM] |
|---|---|
| 3 | 0.052 |
| 4 | 0.0090 |
| 32 | 0.28 |
| 61 | 0.036 |
| 79 | 0.025 |
| 83 | 0.13 |
| 96 | 0.033 |
| 100 | 0.061 |
| 321 | 0.68 |
| 322 | 0.0080 |
| 328 | 0.094 |
| 344 | 0.016 |
| 346 | 0.066 |
| 349 | 0.38 |
| 351 | 0.043 |
| 353 | 0.021 |
| 357 | 0.061 |
| 378 | 0.057 |
| 380 | 0.12 |
| 390 | 0.36 |
| 391 | 0.12 |
| 393 | 0.58 |
| 394 | 0.29 |
| 395 | 0.12 |
| 397 | 0.092 |
| 398 | 0.0072 |
| 409 | 0.10 |
| 410 | 0.034 |
| 411 | 0.018 |
| 413 | 0.022 |
| 415 | 0.045 |
| 416 | 0.019 |
| 418 | 0.030 |
| 422 | 0.11 |
| 424 | 0.062 |
| 425 | 0.14 |
| 426 | 0.060 |
| 428 | 0.11 |
| 429 | 0.047 |
| 430 | 0.036 |
| 439 | 0.044 |
| 440 | 0.081 |
| 446 | 0.55 |
| 447 | 0.33 |
| 451 | 0.01 |
| 453 | 0.55 |
| 465 | 0.70 |
| 467 | 0.053 |
| 468 | 0.87 |
| 492 | 0.66 |
| 496 | 0.14 |
| 519 | 0.26 |
| 520 | 0.030 |
| 589 | 0.081 |
| 599 | 0.090 |
| 609 | 0.011 |
| 610 | 0.010 |
| 611 | 0.037 |
| 618 | 0.054 |
| 635 | 0.45 |
| 636 | 0.29 |
| 637 | 0.027 |
| 641 | 0.024 |
| 642 | 0.021 |
| 643 | 0.088 |
| 646 | 0.34 |
| 659 | 0.12 |
| 660 | 0.016 |
| 661 | 0.043 |
| 662 | 0.27 |

The invention claimed is:

1. A compound of formula I, a stereoisomeric form thereof, or a pharmaceutically acceptable salt of any of the foregoing,

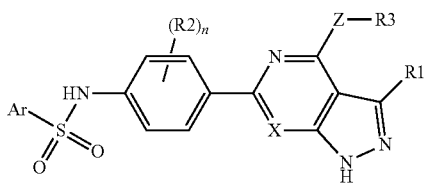

wherein
Ar is selected from the group consisting of phenyl and a 5-membered or 6-membered monocyclic, aromatic, heterocyclic group which comprises 1, 2 or 3 identical or different ring heteroatoms selected from the group consisting of nitrogen, oxygen and sulfur, and is bonded via a ring carbon atom, which all are unsubstituted or substituted by one or more identical or different substituents R5;

n is selected from the group consisting of 0, 1 and 2;

X is selected from the group consisting of N and CH;

Z is selected from the group consisting of a direct bond, O, S and N(R10);

R1 is selected from the group consisting of H, —N(R11)-R12, —N(R13)-C(O)-R14, —N(R13)-S(O)$_2$—R15, —N(R13)-C(O)—NH—R16, ($C_1$-$C_4$)-alkyl and —($C_1$-$C_4$)-alkyl-O—R17;

R2 is selected from the group consisting of halogen, ($C_1$-$C_4$)-alkyl, —O—($C_1$-$C_4$)-alkyl and —CN;

R3 is selected from the group consisting of H, ($C_1$-$C_8$)-alkyl, R30 and —($C_1$-$C_4$)-alkyl-R30, wherein ($C_1$-$C_5$)-alkyl is unsubstituted or substituted by one or more identical or different substituents R31;

R5 is selected from the group consisting of halogen, ($C_1$-$C_4$)-alkyl, ($C_3$-$C_7$)-cycloalkyl, —($C_1$-$C_4$)-alkyl-($C_3$-$C_7$)-cycloalkyl, —O—($C_1$-$C_4$)-alkyl, —O—($C_3$-$C_7$)-cycloalkyl, —O—($C_1$-$C_4$)-alkyl-($C_3$-$C_7$)-cycloalkyl, —C(O)—N(R6)-R7 and —CN, or two groups R5 attached to adjacent ring carbon atoms of Ar, together with the carbon atoms to which they are attached, form a 5-membered to 8-membered monocyclic, unsaturated ring which comprises 0, 1 or 2 identical or different ring heteroatoms selected from the group consisting of nitrogen, oxygen and sulfur, and which is unsubstituted or substituted by one or more identical or different substituents R8;

R6 and R7 are independently selected from the group consisting of H and ($C_1$-$C_4$)-alkyl;

R8 is selected from the group consisting of halogen, ($C_1$-$C_4$)-alkyl, —O—($C_1$-$C_4$)-alkyl and —CN;

R10 is selected from the group consisting of H and ($C_1$-$C_4$)-alkyl;

R11 and R12 are independently selected from the group consisting of H, ($C_1$-$C_4$)-alkyl, ($C_3$-$C_7$)-cycloalkyl, —($C_1$-$C_4$)-alkyl-($C_3$-$C_7$)-cycloalkyl, Het1, —($C_1$-$C_4$)-alkyl-Het1 and —($C_1$-$C_4$)-alkyl-phenyl, wherein phenyl is unsubstituted or substituted by one or more identical or different substituents R50, or R11 and R12, together with the nitrogen atom to which they are attached, form a 4-membered to 7-membered monocyclic, saturated, heterocyclic group which, in addition to the nitrogen atom to which R11 and R12 are attached, comprises 0 or 1 further ring heteroatom selected from the group consisting of nitrogen, oxygen and sulfur, and which is unsubstituted or substituted by one or more identical or different substituents selected from the group consisting of fluorine and ($C_1$-$C_4$)-alkyl;

R13 is selected from the group consisting of H, ($C_1$-$C_4$)-alkyl and ($C_3$-$C_7$)-cycloalkyl;

R14 and R16 are independently selected from the group consisting of ($C_1$-$C_8$)-alkyl, ($C_3$-$C_7$)-cycloalkyl, —($C_1$-$C_4$)-alkyl-($C_3$-$C_7$)-cycloalkyl, phenyl, —($C_1$-$C_4$)-alkyl-phenyl, Het2 and —($C_1$-$C_4$)-alkyl-Het2, wherein ($C_1$-$C_8$)-alkyl and ($C_3$-$C_7$)-cycloalkyl all are unsubstituted or substituted by one or more identical or different substituents selected from the group consisting of —OH and —O—($C_1$-$C_4$)-alkyl, and wherein phenyl and Het2 all are unsubstituted or substituted by one or more identical or different substituents R50;

R15 is selected from the group consisting of ($C_1$-$C_8$)-alkyl, phenyl and Het3, wherein phenyl and Het3 all are unsubstituted or substituted by one or more identical or different substituents R50;

R17 is selected from the group consisting of H and ($C_1$-$C_4$)-alkyl;

R30 is a 3-membered to 12-membered monocyclic or bicyclic, saturated or partially unsaturated cyclic group which comprises 0 ring heteroatoms, which is unsubstituted or substituted by one or more identical or different substituents R32, or R30 is a 3-membered to 12-membered monocyclic or bicyclic, saturated, partially unsaturated or aromatic, cyclic group which comprises 1, 2 or 3 identical or different ring heteroatoms selected from the group consisting of nitrogen, oxygen and sulfur, which is unsubstituted or substituted by one or more identical or different substituents R32;

R31 is selected from the group consisting of halogen, —OH, —O—($C_1$-$C_4$)-alkyl, —O—($C_3$-$C_7$)-cycloalkyl, —O—($C_1$-$C_4$)-alkyl-($C_3$-$C_7$)-cycloalkyl, —N(R33)-R34, —CN and —C(O)—N(R35)-R36;

R32 is selected from the group consisting of halogen, ($C_1$-$C_4$)-alkyl, ($C_3$-$C_7$)-cycloalkyl, —($C_1$-$C_4$)-alkyl-($C_3$-$C_7$)-cycloalkyl, —($C_1$-$C_4$)-alkyl-O—R37, —($C_1$-$C_4$)-alkyl-N(R38)-R39, —($C_1$-$C_4$)-alkyl-CN, —C(O)—($C_1$-$C_4$)-alkyl, —CN, —OH, =O, —O—($C_1$-$C_4$)-alkyl, —N(R40)-R41, —C(O)—O—($C_1$-$C_4$)-alkyl and —C(O)—N(R42)-R43;

R33, R34, R35, R36, R37, R38, R39, R40, R41, R42 and R43 are independently selected from the group consisting of H and ($C_1$-$C_4$)-alkyl;

R50 is selected from the group consisting of halogen, ($C_1$-$C_4$)-alkyl, —O—($C_1$-$C_4$)-alkyl and —CN;

Het1 is a 4-membered to 7-membered monocyclic, saturated, heterocyclic group which comprises 1 or 2 identical or different ring heteroatoms selected from the group consisting of nitrogen, oxygen and sulfur, and is bonded via a ring carbon atom, and which is unsubstituted or substituted by one or more identical or different substituents selected from the group consisting of fluorine and ($C_1$-$C_4$)-alkyl;

Het2 is a 4-membered to 7-membered monocyclic, saturated, partially unsaturated or aromatic, heterocyclic group which comprises 1 or 2 identical or different ring heteroatoms selected from the group consisting of nitrogen, oxygen and sulfur, and is bonded via a ring carbon atom; and Het3 is a 5-membered or 6-membered monocyclic, aromatic, heterocyclic group which comprises 1, 2 or 3 identical or different ring heteroatoms selected from the group consisting of nitrogen, oxygen and sulfur, and is bonded via a ring carbon atom;

wherein all cycloalkyl groups, independently of any other substituents which can be present on a cycloalkyl group, can be substituted by one or more identical or different substituents selected from the group consisting of fluorine and $(C_1-C_4)$-alkyl; and wherein all alkyl groups, independently of any other substituents which can be present on an alkyl group, can be substituted by one or more fluorine substituents.

2. The compound of claim 1, a stereoisomeric form thereof, or a pharmaceutically acceptable salt of any of the foregoing, wherein Ar is selected from the group consisting of phenyl and a 5-membered or 6-membered monocyclic, aromatic, heterocyclic group which comprises 1 or 2 identical or different ring heteroatoms selected from the group consisting of nitrogen, oxygen and sulfur, and is bonded via a ring carbon atom, which all are unsubstituted or substituted by one or more identical or different substituents R5;

R1 is selected from the group consisting of H, —N(R11)-R12, —N(R13)-C(O)-R14, —N(R13)-S(O)$_2$—R15, —N(R13)-C(O)—NH—R16 and $(C_1-C_4)$-alkyl;

R5 is selected from the group consisting of halogen, $(C_1-C_4)$-alkyl, $(C_3-C_7)$-cycloalkyl, —O—$(C_1-C_4)$-alkyl, —O—$(C_3-C_7)$-cycloalkyl, —C(O)—N(R6)-R7 and —CN, or two groups R5 attached to adjacent ring carbon atoms of Ar, together with the carbon atoms to which they are attached, form a 5-membered to 8-membered monocyclic, unsaturated ring which comprises 0, 1 or 2 identical or different ring heteroatoms selected from the group consisting of nitrogen, oxygen and sulfur, and which is unsubstituted or substituted by one or more identical or different substituents R8;

R8 is selected from the group consisting of halogen and $(C_1-C_4)$-alkyl;

R11 and R12 are independently selected from the group consisting of H, $(C_1-C_4)$-alkyl, $(C_3-C_7)$-cycloalkyl, —$(C_1-C_4)$-alkyl-$(C_3-C_7)$-cycloalkyl, Het1, —$(C_1-C_4)$-alkyl-Het1 and —$(C_1-C_4)$-alkyl-phenyl, wherein phenyl is unsubstituted or substituted by one or more identical or different substituents R50;

R13 is selected from the group consisting of H and $(C_1-C_4)$-alkyl;

R15 is selected from the group consisting of phenyl and Het3, wherein phenyl and Het3 all are unsubstituted or substituted by one or more identical or different substituents R50;

R31 is selected from the group consisting of halogen, —OH, —O—$(C_1-C_4)$-alkyl, —O—$(C_3-C_7)$-cycloalkyl, —O—$(C_1-C_4)$-alkyl-$(C_3-C_7)$-cycloalkyl, —N(R33)-R34 and —CN; and Het3 is a 5-membered or 6-membered monocyclic, aromatic, heterocyclic group which comprises 1 or 2 identical or different ring heteroatoms selected from the group consisting of nitrogen, oxygen and sulfur, and is bonded via a ring carbon atom.

3. The compound of claim 1, a stereoisomeric form thereof, or a pharmaceutically acceptable salt of any of the foregoing, wherein Ar is selected from the group consisting of phenyl and a 5-membered monocyclic, aromatic, heterocyclic group which comprises 1 or 2 identical or different ring heteroatoms selected from the group consisting of nitrogen and sulfur, and is bonded via a ring carbon atom, which all are unsubstituted or substituted by one or more identical or different substituents R5;

R1 is selected from the group consisting of H, —N(R11)-R12, —N(R13)-C(O)-R14, —N(R13)-S(O)$_2$—R15, —N(R13)-C(O)—NH—R16 and $(C_1-C_4)$-alkyl;

R2 is selected from the group consisting of halogen, $(C_1-C_4)$-alkyl and —O—$(C_1-C_4)$-alkyl;

R5 is selected from the group consisting of halogen, $(C_1-C_4)$-alkyl, $(C_3-C_7)$-cycloalkyl, —O—$(C_1-C_4)$-alkyl, —O—$(C_3-C_7)$-cycloalkyl and —CN, or two groups R5 attached to adjacent ring carbon atoms of Ar, together with the carbon atoms to which they are attached, form a 5-membered to 7-membered monocyclic, unsaturated ring which comprises 0, 1 or 2 oxygen atoms as ring heteroatoms, and which is unsubstituted or substituted by one or more identical or different substituents R8;

R8 is selected from the group consisting of halogen and $(C_1-C_4)$-alkyl;

one of the groups R11 and R12 is selected from the group consisting of hydrogen and $(C_1-C_4)$-alkyl, and the other of the groups R11 and R12 is selected from the group consisting of hydrogen, $(C_1-C_4)$-alkyl, $(C_3-C_7)$-cycloalkyl, —$(C_1-C_4)$-alkyl-$(C_3-C_7)$-cycloalkyl, Het1, —$(C_1-C_4)$-alkyl-Het1 and —$(C_1-C_4)$-alkyl-phenyl;

R13 is selected from the group consisting of H and $(C_1-C_4)$-alkyl;

R15 is phenyl which is unsubstituted or substituted by one or more identical or different substituents R50;

R30 is a 3-membered to 12-membered monocyclic or bicyclic, saturated or partially unsaturated cyclic group which comprises 0 ring heteroatoms, which is unsubstituted or substituted by one or more identical or different substituents R32, or R30 is a 3-membered to 12-membered monocyclic or bicyclic, saturated, partially unsaturated or aromatic, cyclic group which comprises 1, 2 or 3 identical or different ring heteroatoms selected from the group consisting of nitrogen and oxygen, which is unsubstituted or substituted by one or more identical or different substituents R32;

R31 is selected from the group consisting of halogen, —OH, —O—$(C_1-C_4)$-alkyl, —O—$(C_3-C_7)$-cycloalkyl, —O—$(C_1-C_4)$-alkyl-$(C_3-C_7)$-cycloalkyl and —N(R33)-R34;

R32 is selected from the group consisting of halogen, $(C_1-C_4)$-alkyl, $(C_3-C_7)$-cycloalkyl, —$(C_1-C_4)$-alkyl-$(C_3-C_7)$-cycloalkyl, —$(C_1-C_4)$-alkyl-O—R37, —$(C_1-C_4)$-alkyl-N(R38)-R39, —OH, =O, —O—$(C_1-C_4)$-alkyl and —N(R40)-R41; and Het1 is a 4-membered to 7-membered monocyclic, saturated, heterocyclic group which comprises 1 or 2 identical or different ring heteroatoms selected from the group consisting of nitrogen and oxygen, and is bonded via a ring carbon atom, and which is unsubstituted or substituted by one or more identical or different substituents selected from the group consisting of fluorine and $(C_1-C_4)$-alkyl.

4. The compound of claim 1, a stereoisomeric form thereof, or a pharmaceutically acceptable salt of any of the foregoing, wherein Ar is phenyl, which is unsubstituted or substituted by one or more identical or different substituents R5;

n is selected from the group consisting of 0 and 1;

Z is selected from the group consisting of a direct bond, O and N(R10);

R1 is selected from the group consisting of H, —N(R11)-R12, —N(R13)-C(O)-R14 and $(C_1-C_4)$-alkyl;

R2 is selected from the group consisting of halogen and —O—$(C_1-C_4)$-alkyl;

R5 is selected from the group consisting of halogen, $(C_1-C_4)$-alkyl, —O—$(C_1-C_4)$-alkyl and —CN, or two groups R5 attached to adjacent ring carbon atoms of Ar, together with the carbon atoms to which they are attached, form a 5-membered to 7-membered monocyclic, unsaturated ring which comprises 0, 1 or 2 oxygen atoms as ring heteroatoms, and which is unsubstituted or substituted by one or more identical or different substituents R8;

R8 is selected from the group consisting of halogen and $(C_1-C_4)$-alkyl;

one of the groups R11 and R12 is selected from the group consisting of hydrogen and $(C_1-C_4)$-alkyl, and the other of the groups R11 and R12 is selected from the group consisting of hydrogen, $(C_1-C_4)$-alkyl, —$(C_1-C_4)$-alkyl-$(C_3-C_7)$-cycloalkyl and —$(C_1-C_4)$-alkyl-Het1;

R13 is selected from the group consisting of H and $(C_1-C_4)$-alkyl;

R14 is selected from the group consisting of $(C_3-C_7)$-cycloalkyl, phenyl and Het2, wherein $(C_3-C_7)$-cycloalkyl is unsubstituted or substituted by one or more identical or different substituents selected from the group consisting of —OH and —O—$(C_1-C_4)$-alkyl, and wherein phenyl and Het2 all are unsubstituted or substituted by one or more identical or different substituents R50;

R30 is a 3-membered to 10-membered monocyclic or bicyclic, saturated or partially unsaturated cyclic group which comprises 0 ring heteroatoms, which is unsubstituted or substituted by one or more identical or different substituents R32, or R30 is a 3-membered to 10-membered monocyclic or bicyclic, saturated, partially unsaturated or aromatic, cyclic group which comprises 1, 2 or 3 identical or different ring heteroatoms selected from the group consisting of nitrogen and oxygen, which is unsubstituted or substituted by one or more identical or different substituents R32;

R31 is selected from the group consisting of halogen, —OH, —O—$(C_1-C_4)$-alkyl, —O—$(C_3-C_7)$-cycloalkyl and —N(R33)-R34;

R32 is selected from the group consisting of halogen, $(C_1-C_4)$-alkyl, $(C_3-C_7)$-cycloalkyl, —$(C_1-C_4)$-alkyl-O—R37, —$(C_1-C_4)$-alkyl-N(R38)-R39, —OH, =O, —O—$(C_1-C_4)$-alkyl and —N(R40)-R41;

Het1 is a 4-membered to 7-membered monocyclic, saturated, heterocyclic group which comprises 1 or 2 identical or different ring heteroatoms selected from the group consisting of nitrogen and oxygen, and is bonded via a ring carbon atom, and which is unsubstituted or substituted by one or more identical or different substituents selected from the group consisting of fluorine and $(C_1-C_4)$-alkyl; and Het2 is a 4-membered to 7-membered monocyclic, saturated or aromatic, heterocyclic group which comprises 1 or 2 identical or different ring heteroatoms selected from the group consisting of nitrogen, oxygen and sulfur, and is bonded via a ring carbon atom.

5. The compound of claim 1, a stereoisomeric form thereof, or a pharmaceutically acceptable salt of any of the foregoing, wherein Ar is phenyl, which is unsubstituted or substituted by one or more identical or different substituents R5;

n is selected from the group consisting of 0 and 1;

Z is selected from the group consisting of a direct bond and O;

R1 is selected from the group consisting of H, —N(R11)-R12 and $(C_1-C_4)$-alkyl;

R2 is halogen;

R3 is selected from the group consisting of H, R30 and —$(C_1-C_4)$-alkyl-R30;

R5 is selected from the group consisting of halogen, $(C_1-C_4)$-alkyl, —O—$(C_1-C_4)$-alkyl and —CN;

R11 and R12 are independently selected from the group consisting of hydrogen and $(C_1-C_4)$-alkyl;

R30 is a 3-membered to 7-membered monocyclic, saturated cyclic group which comprises 0 ring heteroatoms, which is unsubstituted or substituted by one or more identical or different substituents R32, or R30 is a 3-membered to 7-membered monocyclic, saturated or aromatic, cyclic group which comprises 1 or 2 identical or different ring heteroatoms selected from the group consisting of nitrogen and oxygen, which is unsubstituted or substituted by one or more identical or different substituents R32; and R32 is selected from the group consisting of halogen, $(C_1-C_4)$-alkyl, $(C_3-C_7)$-cycloalkyl, —$(C_1-C_4)$-alkyl-O—R37, —$(C_1-C_4)$-alkyl-N(R38)-R39, —OH and =O.

6. The compound of claim 1, a stereoisomeric form thereof, or a pharmaceutically acceptable salt of any of the foregoing, wherein Z is a direct bond.

7. The compound of claim 1, a stereoisomeric form thereof, or a pharmaceutically acceptable salt of any of the foregoing, wherein Z is O.

8. The compound of claim 1, a stereoisomeric form thereof, or a pharmaceutically acceptable salt of any of the foregoing, wherein X is N.

9. The compound of claim 1, a stereoisomeric form thereof, or a pharmaceutically acceptable salt of any of the foregoing, wherein X is CH.

10. The compound of claim 1, wherein the compound is selected from the group consisting of:

N-[4-(3-Amino-4-cyclopropyl-1H-pyrazolo[3,4-d]pyrimidin-6-yl)-phenyl]-2-cyano-5-methoxy-benzenesulfonamide;

N-[4-(3-Amino-1H-pyrazolo[3,4-d]pyrimidin-6-yl)-phenyl]-2,5-difluoro-benzenesulfonamide;

N-[4-(3-Amino-1H-pyrazolo[3,4-d]pyrimidin-6-yl)-phenyl]-5-chloro-2-cyano-benzenesulfonamide;

2-Chloro-N-{4-[4-(1-ethyl-piperidin-3-yloxy)-3-methyl-1H-pyrazolo[3,4-d]pyrimidin-6-yl]-phenyl}-5-methoxy-benzenesulfonamide;

5-Chloro-N-{4-[4-(1-ethyl-piperidin-3-yloxy)-3-methyl-1H-pyrazolo[3,4-d]pyrimidin-6-yl]-phenyl}-2-fluoro-benzenesulfonamide;

4-{6-[4-(2,5-Difluoro-benzenesulfonylamino)-phenyl]-3-methyl-1H-pyrazolo[3,4-d]pyrimidin-4-yloxy}-piperidine-1-carboxylic acid ethyl ester;

N-[4-(3-Amino-4-propoxy-1H-pyrazolo[3,4-d]pyrimidin-6-yl)-phenyl]-2,5-difluoro-benzenesulfonamide;

N-[4-(3-Amino-4-ethoxy-1H-pyrazolo[3,4-d]pyrimidin-6-yl)-phenyl]-5-chloro-2-fluoro-benzenesulfonamide;

N-[4-(3-Amino-4-propoxy-1H-pyrazolo[3,4-d]pyrimidin-6-yl)-phenyl]-5-chloro-2-fluoro-benzenesulfonamide;

N-[4-(3-Amino-4-ethoxy-1H-pyrazolo[3,4-d]pyrimidin-6-yl)-phenyl]-2,5-difluoro-benzenesulfonamide;

2-Fluoro-N-(4-{4-[1-(2-methoxy-ethyl)-piperidin-4-yloxy]-3-methyl-1H-pyrazolo[3,4-d]pyrimidin-6-yl}-phenyl)-5-methyl-benzenesulfonamide;
2,5-Difluoro-N-(4-{4-[1-(2-methoxy-ethyl)-piperidin-4-yloxy]-3-methyl-1H-pyrazolo[3,4-d]pyrimidin-6-yl}-phenyl)-benzenesulfonamide;
5-Chloro-2-fluoro-N-(4-{4-[1-(2-methoxy-ethyl)-piperidin-4-yloxy]-3-methyl-1H-pyrazolo[3,4-d]pyrimidin-6-yl}-phenyl)-benzenesulfonamide;
N-{4-[4-(1-Ethyl-piperidin-4-yloxy)-3-methyl-1H-pyrazolo[3,4-d]pyrimidin-6-yl]-phenyl}-2-fluoro-5-methoxy-benzenesulfonamide;
2,5-Dichloro-N-{4-[4-(1-ethyl-piperidin-4-yloxy)-3-methyl-1H-pyrazolo[3,4-d]pyrimidin-6-yl]-phenyl}-benzenesulfonamide;
N-{4-[4-(1-Ethyl-piperidin-4-yloxy)-3-methyl-1H-pyrazolo[3,4-d]pyrimidin-6-yl]-phenyl}-2-fluoro-5-methyl-benzenesulfonamide;
N-{4-[4-(1-Ethyl-piperidin-4-yloxy)-3-methyl-1H-pyrazolo[3,4-d]pyrimidin-6-yl]-phenyl}-2-fluoro-benzenesulfonamide;
5-Chloro-N-{4-[4-(1-ethyl-piperidin-4-yloxy)-3-methyl-1H-pyrazolo[3,4-d]pyrimidin-6-yl]-phenyl}-2-fluoro-benzenesulfonamide;
N-{4-[4-(1-Cyclobutyl-piperidin-4-yloxy)-3-methyl-1H-pyrazolo[3,4-d]pyrimidin-6-yl]-phenyl}-2,5-difluoro-benzenesulfonamide;
2,5-Difluoro-N-(4-{4-[1-(3-methoxy-propyl)-piperidin-4-yloxy]-3-methyl-1H-pyrazolo[3,4-d]pyrimidin-6-yl}-phenyl)-benzenesulfonamide;
5-Chloro-2-fluoro-N-{4-[4-(3-hydroxy-propoxy)-3-methyl-1H-pyrazolo[3,4-d]pyrimidin-6-yl]-phenyl}-benzenesulfonamide;
2,5-Difluoro-N-{4-[4-(1-isopropyl-piperidin-4-yloxy)-3-methyl-1H-pyrazolo[3,4-d]pyrimidin-6-yl]-phenyl}-benzenesulfonamide;
2-Fluoro-N-(4-{4-[1-(2-fluoro-ethyl)-piperidin-4-yloxy]-3-methyl-1H-pyrazolo[3,4-d]pyrimidin-6-yl}-phenyl)-benzenesulfonamide;
5-Chloro-2-fluoro-N-{4-[4-(1-isopropyl-piperidin-4-yloxy)-3-methyl-1H-pyrazolo[3,4-d]pyrimidin-6-yl]-phenyl}-benzenesulfonamide;
2,5-Difluoro-N-(4-{4-[1-(2-fluoro-ethyl)-piperidin-4-yloxy]-3-methyl-1H-pyrazolo[3,4-d]pyrimidin-6-yl}-phenyl)-benzenesulfonamide;
N-[4-(3-Amino-4-isopropoxy-1H-pyrazolo[3,4-d]pyrimidin-6-yl)-phenyl]-2,5-dichloro-benzenesulfonamide;
N-[4-(3-Amino-4-isobutoxy-1H-pyrazolo[3,4-d]pyrimidin-6-yl)-phenyl]-2,5-difluoro-benzenesulfonamide;
N-[4-(3-Amino-4-isobutoxy-1H-pyrazolo[3,4-d]pyrimidin-6-yl)-phenyl]-2-fluoro-5-methoxy-benzenesulfonamide;
2,5-Dichloro-N-{4-[3-methyl-4-(piperidin-3-yloxy)-1H-pyrazolo[3,4-d]pyrimidin-6-yl]-phenyl}-benzenesulfonamide;
2,5-Difluoro-N-{4-[3-methyl-4-(piperidin-3-yloxy)-1H-pyrazolo[3,4-d]pyrimidin-6-yl]-phenyl}-benzenesulfonamide;
2-Fluoro-5-methyl-N-{4-[3-methyl-4-(morpholin-2-yl-methoxy)-1H-pyrazolo[3,4-d]pyrimidin-6-yl]-phenyl}-benzenesulfonamide;
N-{4-[4-(3-Aminomethyl-oxetan-3-ylmethoxy)-1H-pyrazolo[3,4-d]pyrimidin-6-yl]-phenyl}-5-chloro-2-fluoro-benzenesulfonamide;
N-[4-(3-Amino-4-ethoxymethyl-1H-pyrazolo[3,4-d]pyrimidin-6-yl)-phenyl]-2-fluoro-5-methyl-benzenesulfonamide;
N-[4-(3-Amino-4-trifluoromethyl-1H-pyrazolo[3,4-d]pyrimidin-6-yl)-phenyl]-2,5-difluoro-benzenesulfonamide;
2-Fluoro-N-{4-[4-(piperidin-4-yloxy)-1H-pyrazolo[3,4-d]pyrimidin-6-yl]-phenyl}-benzenesulfonamide;
N-[4-(3-Amino-1H-pyrazolo[3,4-d]pyrimidin-6-yl)-phenyl]-2-fluoro-5-methoxy-benzenesulfonamide;
N-[4-(3-Amino-4-methoxymethyl-1H-pyrazolo[3,4-d]pyrimidin-6-yl)-phenyl]-5-chloro-2-fluoro-benzenesulfonamide;
N-{4-[4-(3-Amino-propoxy)-3-methyl-1H-pyrazolo[3,4-d]pyrimidin-6-yl]-phenyl}-5-chloro-2-fluoro-benzenesulfonamide;
N-[4-(3-Amino-1H-pyrazolo[3,4-d]pyrimidin-6-yl)-phenyl]-2,5-difluoro-benzenesulfonamide;
N-[4-(3-Amino-1H-pyrazolo[3,4-d]pyrimidin-6-yl)-phenyl]-2,4,5-trifluoro-benzenesulfonamide;
N-[4-(3-Amino-1H-pyrazolo[3,4-d]pyrimidin-6-yl)-phenyl]-2-chloro-4,5-difluoro-benzenesulfonamide;
N-{4-[3-Amino-4-(2,2,2-trifluoro-ethoxy)-1H-pyrazolo[3,4-d]pyrimidin-6-yl]-phenyl}-2-cyano-5-methyl-benzenesulfonamide;
N-[4-(3-Amino-4-trifluoromethyl-1H-pyrazolo[3,4-d]pyrimidin-6-yl)-phenyl]-5-chloro-2-fluoro-benzenesulfonamide;
N-{4-[3-Amino-4-(2-methoxy-ethyl)-1H-pyrazolo[3,4-d]pyrimidin-6-yl]-phenyl}-2-cyano-5-methyl-benzenesulfonamide;
2-Cyano-5-methyl-N-{4-[4-(2,2,2-trifluoro-ethoxy)-1H-pyrazolo[3,4-d]pyrimidin-6-yl]-phenyl}-benzenesulfonamide;
N-[4-(3-Amino-4-cyclopropyl-1H-pyrazolo[3,4-d]pyrimidin-6-yl)-phenyl]-2,4,5-trifluoro-benzenesulfonamide;
N-[4-(3-Amino-4-cyclopropyl-1H-pyrazolo[3,4-d]pyrimidin-6-yl)-phenyl]-2-fluoro-benzenesulfonamide;
N-[4-(3-Amino-4-cyclopropyl-1H-pyrazolo[3,4-d]pyrimidin-6-yl)-phenyl]-2,5-difluoro-benzenesulfonamide;
N-[4-(3-Amino-4-methoxy-1H-pyrazolo[3,4-d]pyrimidin-6-yl)-phenyl]-5-chloro-2-fluoro-benzenesulfonamide;
N-[4-(3-Amino-4-methoxy-1H-pyrazolo[3,4-d]pyrimidin-6-yl)-phenyl]-5-chloro-2-cyano-benzenesulfonamide;
N-[4-(3-Amino-4-methyl-1H-pyrazolo[3,4-d]pyrimidin-6-yl)-phenyl]-2-chloro-3,5-difluoro-benzenesulfonamide;
2-Cyano-N-{4-[4-(4-hydroxy-cyclohexyloxy)-1H-pyrazolo[3,4-d]pyrimidin-6-yl]-phenyl}-5-methoxy-benzenesulfonamide;
N-[4-(3-Amino-1H-pyrazolo[4,3-c]pyridin-6-yl)-phenyl]-5-chloro-2,4-difluoro-benzenesulfonamide;
5-Chloro-2-cyano-N-{4-[4-(4-hydroxy-cyclohexyloxy)-3-methyl-1H-pyrazolo[3,4-d]pyrimidin-6-yl]-phenyl}-benzenesulfonamide;
N-{4-[4-(1-Cyclopropyl-piperidin-4-yloxy)-3-methyl-1H-pyrazolo[3,4-d]pyrimidin-6-yl]-phenyl}-2,5-difluoro-benzenesulfonamide;
5-Chloro-N-{4-[4-(1-cyclopropyl-piperidin-4-yloxy)-3-methyl-1H-pyrazolo[3,4-d]pyrimidin-6-yl]-phenyl}-2-fluoro-benzenesulfonamide;
N-{4-[4-(1-Acetyl-piperidin-4-yloxy)-3-methyl-1H-pyrazolo[3,4-d]pyrimidin-6-yl]-phenyl}-2-fluoro-5-methoxy-benzenesulfonamide;

N-{4-[4-(1-Acetyl-piperidin-4-yloxy)-3-methyl-1H-pyrazolo[3,4-d]pyrimidin-6-yl]-phenyl}-2,5-difluoro-benzenesulfonamide;
N-{4-[4-(1-Acetyl-piperidin-4-yloxy)-3-methyl-1H-pyrazolo[3,4-d]pyrimidin-6-yl]-phenyl}-5-chloro-2-fluoro-benzenesulfonamide;
5-Chloro-2-fluoro-N-{4-[4-(6-hydroxy-pyridin-3-yloxy)-3-methyl-1H-pyrazolo[3,4-d]pyrimidin-6-yl]-phenyl}-benzenesulfonamide,
2-Fluoro-N-{4-[4-(6-hydroxy-pyridin-3-yloxy)-3-methyl-1H-pyrazolo[3,4-d]pyrimidin-6-yl]-phenyl}-5-methyl-benzenesulfonamide;
2,5-Dichloro-N-[4-(3-methyl-1H-pyrazolo[3,4-d]pyrimidin-6-yl)-phenyl]-benzenesulfonamide; and
N-[4-(3-Amino-4-isopropoxy-1H-pyrazolo[3,4-d]pyrimidin-6-yl)-2-fluoro-phenyl]-5-chloro-2-fluoro-benzenesulfonamide,
or a pharmaceutically acceptable salt thereof.

11. A process for the preparation of the compound of formula I according to claim 1,

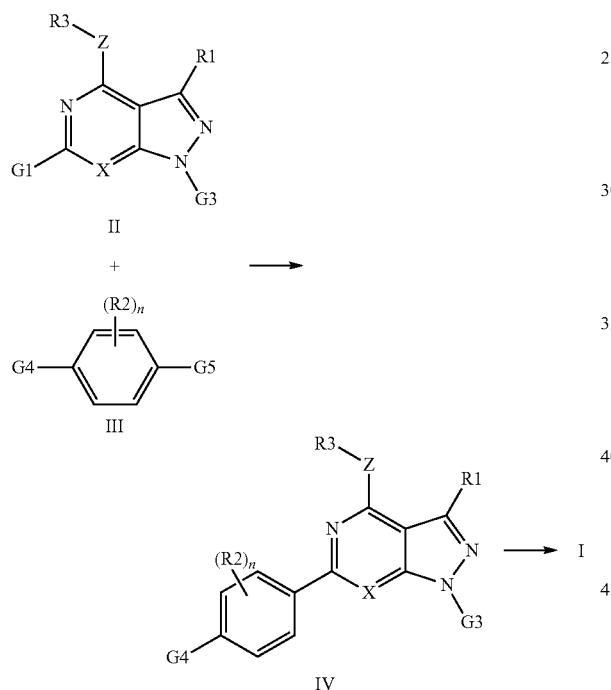

which comprises reacting a compound of formula II and a compound of formula III to give a compound of formula IV, and optionally converting the compound of formula IV into a compound of formula I, wherein X, Z, R1 to R3 and n in the compounds of formulae II, III and IV are defined as in the compound of formula I or functional groups are present in protected form or in the form of a precursor group, the group G1 in the compound of formula II is halogen or a sulfonyloxy group, the group G3 in the compounds of formulae II and IV is hydrogen or a protecting group, the group G4 in the compounds of formulae III and IV is the group of the formula Ar—S(O)$_2$—NH— in which Ar is defined as in the compound of formula I or functional groups are present in protected form or in the form of a precursor group, or G4 is an amino group, a protected amino group or a precursor group of an amino group, and the group G5 in the compound of formula III is a trialkyl-stannyl group or a boronic acid group, a boronic acid ester group or cyclic boronic acid ester group.

12. A pharmaceutical composition comprising the compound of claim 1, a stereoisomeric form thereof or a mixture of stereoisomeric forms thereof in any ratio, or a pharmaceutically acceptable salt of any of the foregoing, and a pharmaceutically acceptable carrier.

13. A method of inhibiting serum and glucocorticoid regulated kinase (SGK) in an individual in need thereof comprising administering to the individual the compound of claim 1, a stereoisomeric form thereof, or a pharmaceutically acceptable salt of any of the foregoing.

14. A method of treating osteoarthritis in an individual in need thereof comprising administering to the individual the compound of claim 1, a stereoisomeric form thereof, or a pharmaceutically acceptable salt of any of the foregoing.

15. A method of inhibiting serum and glucocorticoid regulated kinase (SGK) in an individual in need thereof comprising administering to the individual the composition of claim 12.

16. A method of treating osteoarthritis in an individual in need thereof comprising administering to the individual the composition of claim 12.

17. The compound of claim 1, wherein the compound is of formula Ic,

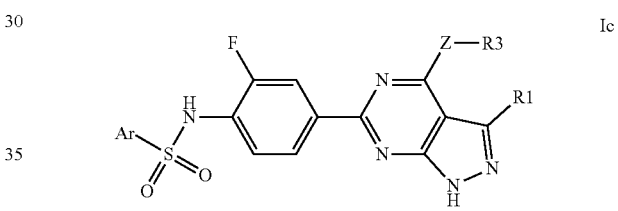

wherein
Ar is 2,5-dichlorophenyl;
R1 is hydrogen; and
-Z-R3 is

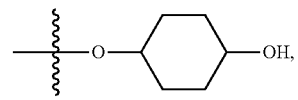

or a pharmaceutically acceptable salt thereof.

18. The compound of claim 1, wherein the compound is of formula If,

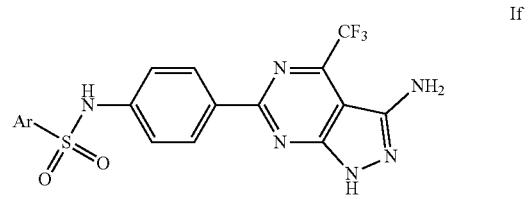

wherein Ar is 2-cyano-5-methoxy-phenyl,
or a pharmaceutically acceptable salt thereof.

19. The compound of claim 1, wherein the compound is of formula Ib,

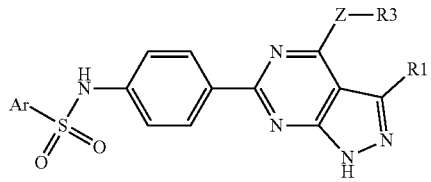

Ib wherein Ar, R1 and -Z-R3 are as follows:

| Ar | R1 | -Z-R3 |
|---|---|---|
| 5-chloro-2-fluoro-phenyl | CH₃ | —H; |
| 2,5-dichloro-phenyl | H | —O—CH₂CH₂CH₂—OH; |
| 2-fluoro-5-methoxy-phenyl | CH₃ | —O—(cyclohexyl)—OH; |
| 5-chloro-2-fluoro-phenyl | CH₃ | —O—(cyclohexyl)—OH; |
| 2-fluoro-5-methoxy-phenyl | CH₃ | —O—CH₂CH₂—OH; |
| 2-chloro-5-methoxy-phenyl | CH₃ | —H; |
| 5-chloro-2-fluoro-phenyl | CH₃ | 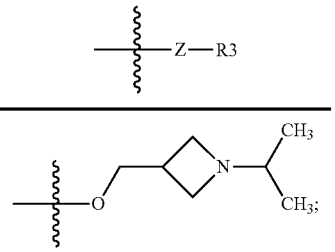 |
| 2,5-dichloro-phenyl | CH₃ | 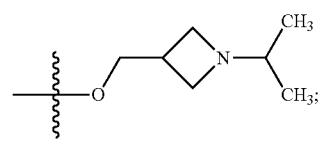 [SMILES: *OCC1CN(C(C)C)C1] |
| 2-fluoro-5-methyl-phenyl | NH₂ | —O—CH₂CH₃; |
| 5-chloro-2-fluoro-phenyl | CH₃ | —O—(tetrahydropyran); |
| 5-chloro-2-fluoro-phenyl | CH₃ | —O—(pyridinyl)—NH₂; or |
| 2-fluoro-5-methyl-phenyl | CH₃ | —O—(pyridinyl)—NH₂, | or a pharmaceutically acceptable salt thereof.

20. The compound of claim 1, a stereoisomeric form thereof, or a pharmaceutically acceptable salt of any of the foregoing, wherein Ar is phenyl, which is substituted by one or more identical or different substituents R5, wherein one of the substituents is in position 2 of the phenyl group.

* * * * *

UNITED STATES PATENT AND TRADEMARK OFFICE
CERTIFICATE OF CORRECTION

PATENT NO. : 9,718,825 B2
APPLICATION NO. : 14/775620
DATED : August 1, 2017
INVENTOR(S) : Marc Nazare et al.

It is certified that error appears in the above-identified patent and that said Letters Patent is hereby corrected as shown below:

In the Claims

At Column 221, Claim number 1, Line numbers 32-33:
Please replace "wherein $(C_1-C_5)$-alkyl" with --wherein $(C_1-C_8)$-alkyl--.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*